US008557776B2

(12) United States Patent
Lehmann et al.

(10) Patent No.: US 8,557,776 B2
(45) Date of Patent: Oct. 15, 2013

(54) COMPOUNDS AND METHODS FOR $^{18}$F LABELED AGENTS

(75) Inventors: Lutz Lehmann, Berlin (DE); Ananth Srinivasan, Berlin (DE); Thomas Brumby, Berlin (DE); Detlef Suelzle, Berlin (DE); Timo Stellfeld, Berlin (DE); Keith Graham, Berlin (DE); Mylene Tania Karramkam, Baie-Mahault (GP); Simon Ametamey, Zurich (CH)

(73) Assignee: Bayer Pharma AG, Berlin (DE)

( * ) Notice: Subject to any disclaimer, the term of this patent is extended or adjusted under 35 U.S.C. 154(b) by 448 days.

(21) Appl. No.: 11/851,910

(22) Filed: Sep. 7, 2007

(65) Prior Publication Data
US 2008/0292548 A1 Nov. 27, 2008

Related U.S. Application Data

(60) Provisional application No. 60/845,163, filed on Sep. 18, 2006.

(30) Foreign Application Priority Data

Sep. 8, 2006 (EP) .................................. 06090166
Apr. 23, 2007 (EP) .................................. 07090079

(51) Int. Cl.
*A61K 38/00* (2006.01)
*A61K 38/16* (2006.01)

(52) U.S. Cl.
USPC ....................................................... 514/17.3

(58) Field of Classification Search
None
See application file for complete search history.

(56) References Cited

U.S. PATENT DOCUMENTS

| | | | |
|---|---|---|---|
| 5,084,555 A | 1/1992 | Coy et al. | |
| 5,723,578 A | 3/1998 | Coy et al. | |
| 6,124,264 A | 9/2000 | Carpino et al. | |
| 6,639,076 B1 | 10/2003 | Hauser et al. | |
| 6,855,715 B1 | 2/2005 | Liebeschuetz et al. | |
| 2004/0034246 A1 | 2/2004 | Mulholland et al. | |
| 2005/0004009 A1 | 1/2005 | Turkson et al. | |
| 2008/0029548 A1 | 2/2008 | De Wree et al. | |

FOREIGN PATENT DOCUMENTS

| | | | |
|---|---|---|---|
| EP | 0309297 A | 3/1989 | |
| WO | 9102746 A | 3/1991 | |
| WO | 9209626 A | 6/1992 | |
| WO | WO 02/44144 A2 | 6/2002 | |
| WO | 03002157 A | 1/2003 | |
| WO | 03087070 A | 10/2003 | |
| WO | WO 2004/018502 A1 * | 3/2004 | |
| WO | WO-2004 080492 | 9/2004 | |
| WO | WO 2006/083424 A2 | 8/2006 | |
| WO | 2008028688 R | 9/2008 | |

OTHER PUBLICATIONS

Seimbille, Y., et al.: "Fluorine-18 labeling of 6,7-distributed anilinoquinazoline derivatives for positron emission tomography (PET) imaging of tyrosine kinase receptors . . . " Journal of Labelled Compounds and Radiopharmaceutecals; Oct. 15, 2005; pp. 829-843; vol. 48, No. 11, from Applicant's IDS.*
Vippagunta, S.R. et al. Adv. Drug Delivery Rev. (2001) 48, pp. 3-26.*
Han, H.-K.. AAPS Pharmsci. (2000) 2(1), Article 6, pp. 1-11.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Muller, Christa E. "Prodrug Approaches for Enhancing the Bioavailability of Drugs with Low Solubility," Chemistry & Biodiversity, vol. 6 (2009), pp. 2071-2083.*
Singh, Yashveer et al, "Recent Trends in Targeted Anticancer Prodrug and Conjugate," DesignCurr Med Chem. 2008 ; 15(18): 1802-1826.*
Ettmayer P. et al. J. Med. Chem. (2004) 47(10), pp. 2393-2404.*
Peptide Crystallization: p. 1 and 2, 2011 from http://www.proteincrystallography.org/crystallisation/peptide_crystallisation.php.*
Li, Zizhong, et al, "Synthesis of Structurally Identical Fluorine-18 and Iodine Isotope," Bioconjugate Chemistry (2003), 14(2), 287-294.*
Sutton,D., et al.; :"Evaluation of 1-fluoro-2-nitro-4-trimethylammoniobenzene iodide . . . "; The Biochemical Journal; Nov. 1972; pp. 589-595; vol. 130, No. 2.
Lemaire, Christian, et al.; "Highly enantioselective synthesis of no-carrier-added . . . "; European Journal of Organic Chemistry; 2004; pp. 2899-2904; vol. 13.
Lang, L., et al.; "Development of fluorine-18-labeled 5-HT1A antagonists"; Journal of Medicinal Chemistry; May 6, 1999; pp. 1576-1586; vol. 42, No. 9.

(Continued)

*Primary Examiner* — Thomas Heard
(74) *Attorney, Agent, or Firm* — Millen, White, Zelano, Branigan, P.C.

(57) ABSTRACT

The present invention relates to novel compounds suitable for or already radiolabeled with $^{18}$F, methods of making such compounds and use of such compounds for diagnostic imaging. Such labeled compounds are characterized by Formula II, wherein the substituents G, Q, L, Y and U have the meaning as defined in the specification and claims.

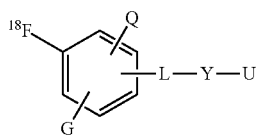

23 Claims, 23 Drawing Sheets

(56) References Cited

OTHER PUBLICATIONS

Oya, Shunichi, et al.: "New PET imaging agent for the serotonin transporter . . . "; Journal of Medicinal Chemistry; Oct. 10, 2002; pp. 4716-4723; vol. 45, No. 21.

Al-Darwich, M.J., et al.; "Enantioselective syntheses of no-carrier-added (n.c.a.) . . . "; Journal of Fluorine Chemistry; Oct. 1996; pp. 117-124; vol. 80, No. 2; Elsevier, Amsterdam, NL.

Seimbille, Y., et al.: "Fluorine-18 labeling of 6,7-distributed anilinoquinazoline derivatives for positron emission tomography (PET) imaging of tyrosine kinase receptors . . . "; Journal of Labelled Compounds and Radiopharmaceuticals; Oct. 15, 2005; pp. 829-843; vol. 48, No. 11.

Ermert, Johannes; "No-carrier-added 18F-labeling of arylaylamines with norephedrine . . . "; Berichte des Forschungszentrums Juelich; 1998; pp. 56-62; vol. Juel-3499.

Andrey, O. et al., "Synthesis of α-(Alkoxysilyl)acetic Esters. A Route to 1,2 Diols," Tetrahedron, 1995, vol. 51, No. 44, pp. 12083-12096.

Bodnar, P. M. et al., "Stereo- and Regioselectivity of Reactions of Siliranes with Aldehydes and Related Substrates," Journal of Organic Chemistry, 1997, vol. 62, pp. 4737-4745.

Mading et al., "Development of Potential Tumor Imaging Agents by 4-[18F] Fluorobenzoylation of Neurotensin Analogues," Journal of Labeled Compounds and Radiopharmaceuticals, 1999, vol. 42, pp. 987-1022.

Schirrmacher, R. et al., "[18]F-Markierung von Peptiden mithilfe eines Organosilicium-Fluoridacceptors," Angew Chem, 2006, vol. 118, pp. 6193-6197.

Sieburth, S. et al., "Silanol Reactivity: Evalution of Silanolate as a Metalation-Directing Group," Journal of Organic Chemistry, 1993, vol. 58, pp. 6314-6318.

Ting, R. et al., "Arylfluoroborates and Alkylfluorosilicates as Potential PET Imaging Agents: High-Yielding Aqueous Biomolecular [18]F-Labeling," Journal of the American Chemical Society, 2005, vol. 127, pp. 13094-13095.

Ushioda, M. et al., "Unique Participation of Unprotected Internucleotide Phosphodiester Residues on Unexpected Cleavage Reaction of the Si-O Bond of the Diisopropysilandiyl Group Used as a Linker for the Solid-Phase Synthesis of 5'-Terminal Guanylated Oligodeoxynucleotides," Helvetica Chimica Acta, 2002, vol. 85, pp. 2930-2945.

Walsh, J. C. et al., "Application of Silicon-Fluoride Chemistry to Fluorine-18 Labeling Agents for Biomolecules: A Preliminary Note," J. Labeled Cpd. Radiopharm., 1999, vol. 42, Suppl. 1.

Wang, M. et al., "Linear and Hyperbranched Poly(silyl ester)s: Synthesis via Cross-Dehydrocoupling-Based Polymerization, Hydrolytic Degradation Properties, and Morphological Analysis by Atomic Force Microscopy," Macromolecules, 2001, vol. 34, pp. 3215-3223.

Zhang et al., "18F-Labeled Bombesin Analogs for Targeting GRP Receptor-Expressing Prostate Cancer," The Journal of Nuclear Medicine, Mar. 2006, vol. 47, No. 3, pp. 492-501.

Zhang, W. et al., "Solution-phase preparation of a 560-Compound Library of Individual Pure Mappicine Analogues by Fluorous Mixture Synthesis," Journal of the American Chemicial Society, 2002, vol. 124, pp. 10443-10450.

* cited by examiner

HPLC of Ia-1 of reaction mixture with co-injection of the cold standard

HPLC of IIA-a-1 (radiometric trace) and IIB-a-1 (UV detector) of reaction mixture with co-injection of the cold standard

IIA-a-1

IIB-a-1

IIA-a-1
(radiometric trace)

IIB-a-1
(UV trace)

HPLC chromatograms of reaction mixture with co-injection of the cold standard of IIA-a-1

Radiometric HPLC of IIA-a-1 incubated in human serum, retention time: 5.018 min

Radiometric HPLC of IIA-a-1 incubated in human serum for 30 min, retention time: 5.005 min Radiometric HPLC of IIA-a-1 incubated in human serum for 90 min, retention time: 5.005 min HPLC chromatograms of reaction mixture with co-injection of the cold standard of IIA-a-1

Radiometric HPLC of IIA-a-1 incubated in human serum, retention time: 5.018 min
3.929 min Radiometric HPLC of IIA-a-1 incubated in human serum for 30 min, retention time: 3.926 min Radiometric HPLC of IIA-a-1 incubated in human serum for 90 min, retention time: 3.918min HPLC chromatograms of reaction mixture with co-injection of the cold standard
[$^{18}$F]-4-Fluoro-3-cyano-benzoyl)-Val-βAla-His(π-Me)-Gly-NH$_2$, (27b).

HPLC chromatograms of reaction mixture with co-injection of the cold standard

Scheme 5

Radioactive Chromatogram

UV Chromatogram

HPLC-chromatogram of reaction mixture with co-injection of the cold standard
F-18 and F-19 fluoro-peptides (23 and 22)

Radioactive Chromatogram

UV Chromatogram

HPLC chromatogram of reaction mixture with co-injection of the cold standard
Methyl 2-Chloro-4-[$^{18}$F]fluorobenzoate HPLC chromatogram of reaction mixture with co-injection of the cold standard Radioactive Chromatogram UV Chromatogram HPLC chromatogram of reaction mixture with co-injection of the cold standard
Example J1. Radiosynthesis of 3-cyano-4-[$^{18}$F]fluorobenzoyl-Val-βAla-His(Me)-Gly-NH$_2$ HPLC chromatogram of reaction mixture with co-injection of the cold standard
3-cyano-4-[$^{18}$F]fluorobenzoyl-Ava-Gln-Trp-Ala-Val-Gly-His-FA01010-Leu-NH$_2$ Radioactive Chromatogram UV Chromatogram HPLC chromatogram of reaction mixture with co-injection of the cold standard
3-cyano-4-[$^{18}$F]fluorobenzoyl-Arg-Ava-Gln-Trp-Ala-Val-Gly-His(3Me)-Sta-Leu-NH$_2$ Radioactive Chromatogram UV Chromatogram Table 1

| Peptide sequence | Bind. Affinity (IC50) | Tumor % ID/g | Panc. % | Blocking | T/B | T/M |
|---|---|---|---|---|---|---|
| 3-CN,4-F-Bz-Ava-Gln-Trp-Ala-Val-Gly-His-FA01010-Leu-NH2 (SEQ ID NO: 29) | 6-10 nM | 1 | 0.34 | >70% | 21.03 | 59.99 |
| 3-CN,4-F-Benzoyl-Arg-Ava-Gln-Trp-Ala-Val-NMeGly-His-Sta-Leu-NH2 (SEQ ID NO: 419) | 1.9-2.7 nM | 1.8 | 1.3 | 40-70% | 6.82 | 12.75 |
| 3-CN,4-F-Benzoyl-Arg-Ava-Gln-Trp-Ala-Val-Gly-His(3Me)-Sta-Leu-NH2 (SEQ ID NO: 420) | 1 nM | 1.38 | 4.16 | 30-90% | 5.65 | 13.84 |
| 3-CF3,4-F-Benzoyl-Arg-Ava-Gln-Trp-Ala-Val-NMeGly-His-Sta-Leu-NH2 (SEQ ID NO: 421) | 0.3-1.8 nM | 1.28 | 1.42 | >70% | 4.56 | 25.3 |
| 4F,3CN-Bnz-Arg-Ava-Gln-Trp-Ala-Val-NMeGly-His(3Me)-Sta-Leu-NH2 (SEQ ID NO: 422) | 2.3 nM | 1.59 | 3.51 | 50-80% | 2.57 | 16.77 |

Fig. 12A

Table 1

X⁻ (CH₃)₃N⁺-(C₆H₄(-G))-L-Y-U (Ia) (-G = 3-cyano, 3-trifluormethyl as indicated; -L- = -O-, X⁻ is triflate)

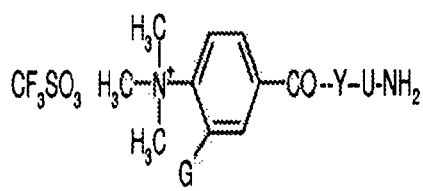

Trimethylammonium-(C₆H₄(-G))-        -L-    -Y-                  -U

Ia-1   4-(Trimethylammonium)-3-cyano-benzoyl-Arg-Ava-Gln-Trp-Ala-Val-NMeGly-His-Sta-Leu-NH₂ (SEQ ID NO: 103)

Ia-2   4-(Trimethylammonium)-3-cyano-benzoyl-Arg-Ava-Gln-Trp-Ala-Val-Gly-His(Me)-Sta-Leu-NH₂ (SEQ ID NO: 109)

Ia-3   4-(Trimethylammonium)-3-cyano-benzoyl-Arg-Ava-Gln-Trp-Ala-Val-NMeGly-His(3Me)-Sta-Leu-NH₂ (SEQ ID NO: 110)

Ia-4   4-(Trimethylammonium)-3-cyano-benzoyl-1,4-cis-Achc-Gln-Trp-Ala-Val-Gly-His(3Me)-Sta-Leu-NH₂ (SEQ ID NO: 111)

Ia-5   4-(Trimethylammonium)-3-cyano-benzoyl-Gln-Trp-Ala-Val-Gly-His(3Me)-Sta-Leu-NH₂ (Y = bond) (SEQ ID NO: 112)

Ia-6   4-(Trimethylammonium)-3-cyano-benzoyl-AOC-Gln-Trp-Ala-Val-Gly-His(3Me)-Sta-Leu-NH₂ (SEQ ID NO: 113)

Ia-7   4-(Trimethylammonium)-3-cyano-benzoyl-Ava-Gln-Trp-Ala-Val-NMeGly-His(3Me)-Sta-Cpa-NH₂ (SEQ ID NO: 114)

Ia-8   4-(Trimethylammonium)-3-cyano-benzoyl-Ava-Gln-Trp-Ala-Val-Gly-His(3Me)-4-Am,5-MeHpA-Leu-NH₂ (SEQ ID NO: 115)

Ia-9   4-(Trimethylammonium)-3-cyano-benzoyl-Ava-Gln-Trp-Ala-Val-Gly-His(3Me)-Sta-Leu-NH₂ (SEQ ID NO: 116)

Ia-10  4-(Trimethylammonium)-3-cyano-benzoyl-Lys(Me)2-βAla-Gln-Trp-Ala-Val-Gly-His(3Me)-Sta-Leu-NH₂ (SEQ ID NO: 117)

Ia-11  4-(Trimethylammonium)-3-cyano-benzoyl-Lys(Me)2-βAla-Gln-Trp-Ala-Val-Gly-His(3Me)-Sta-Leu-NH₂ (SEQ ID NO: 118)

Ia-12  4-(Trimethylammonium)-3-cyano-benzoyl-Arg-Ser-Gln-Trp-Ala-Val-Gly-His(3Me)-4-Am,5-MeHpA-Leu-NH₂ (SEQ ID NO: 119)

Fig. 12B

Ia-13  4-(Trimethylammonium)-3-cyano-benzoyl-Ser-Ser-Gln-Trp-Ala-Val-Gly-His(3Me)-4-Am,5-MeHpA-Leu-NH₂ (SEQ ID NO: 120)

Ia-14  4-(Trimethylammonium)-3-cyano-benzoyl-Lys(Me)2-Ser-Gln-Trp-Ala-Val-Gly-His(3Me)-4-AM-5-MeHpA-Leu-NH2 (SEQ ID NO: 121)

Ia-15  4-(Trimethylammonium)-3-cyano-benzoyl-Arg-Ser-Gln-Trp-Ala-Val-Gly-His(3Me)-Sta-Leu-NH₂ (SEQ ID NO: 122)

Ia-16  4-(Trimethylammonium)-3-cyano-benzoyl-Lys(Me)2-βAla-Gln-Trp-Ala-Val-Gly-His(3Me)-4-Am,5-MeHpA-Leu-NH₂ (SEQ ID NO: 123)

Ia-17  4-(Trimethylammonium)-3-cyano-benzoyl-Ava-Gln-Trp-Ala-Val-Gly-His-4-Am,5-MeHpA- -Leu-NH₂ (SEQ ID NO: 124)

Ia-18  4-(Trimethylammonium)-3-trifluoromethyl-benzoyl-Arg-Ava-Gln-Trp-Ala-Val-Gly-His(3Me)-Sta-Leu-NH₂ (SEQ ID NO: 125)

Ia-19  4-(Trimethylammonium)-3-trifluoromethyl-benzoyl-Arg-Ava-Gln-Trp-Ala-Val-NMeGly-His(3Me)-Sta-Leu-NH₂ (SEQ ID NO: 126)

Ia-20  4-(Trimethylammonium)-3-trifluoromethyl-benzoyl-1,4-cis-Achc-Gln-Trp-Ala-Val-Gly-His(3Me)-Sta-Leu-NH₂ (SEQ ID NO: 127)

Ia-21  4-(Trimethylammonium)-3-trifluoromethyl-benzoyl-Gln-Trp-Ala-Val-Gly-His(3Me)-Sta-Leu-NH₂ (Y = bond) (SEQ ID NO: 128)

Ia-22  4-(Trimethylammonium)-3-trifluoromethyl-benzoyl-Arg-βAla-Gln-Trp-Ala-Val-Gly-His(3Me)-4-Am,5-MeHpA-Leu-NH₂ (SEQ ID NO: 129)

Ia-23  4-(Trimethylammonium)-3-cyano-benzoyl-Ava-Gln-Trp-Ala-Val-NMeGly-His(3Me)-4-Am,5-MeHpA-Cpa-NH₂ (SEQ ID NO: 130)

Ia-24  4-(Trimethylammonium)-3-cyano-benzoyl -Ser-Ser-Gln-Trp-Ala-Val-Gly-His(3Me)-Sta-Leu-NH₂ (SEQ ID NO: 131)

Ia-25  4-(Trimethylammonium)-3-cyano-benzoyl-DOA-Gln-Trp-Ala-Val-Gly-His(3Me)-Sta-Leu-NH₂ (SEQ ID NO: 132)

Fig. 12C

Table 2

[19]F-(C₆H₄(-G))--L--Y--U (IIB-a) (G = 3-cyano, 3-trifluoromethyl or 3-fluoro; -L- = -CO- as indicated)

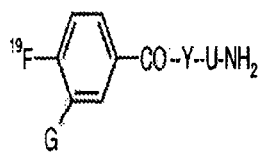

| | [19]F-(C₆H₄(-G))- | -L- | -Y- | -U | K_i(nM) |
|---|---|---|---|---|---|
| IIB-a-1 | 4-[19]-Fluoro-3-cyano-benzoyl-Arg-Ava-Gln-Trp-Ala-Val-NMeGly-His-Sta-Leu-NH₂ (SEQ ID NO: 216) | | | | 0.7 |
| IIB-a-2 | 4-[19]-Fluoro-3-cyano-benzoyl-Arg-Ava-Gln-Trp-Ala-Val-His(Me)-Sta-Leu-NH₂ (SEQ ID NO: 217) | | | | 0.25 |
| IIB-a-3 | 4-[19]-Fluoro-3-cyano-benzoyl-Arg-Ava-Gln-Trp-Ala-Val-NMeGly-His(3Me)-Sta-Leu-NH₂ (SEQ ID NO: 218) | | | | 0.5 |
| IIB-a-4 | 4-[19]-Fluoro-3-cyano-benzoyl-1,4-cis-Achc-Gln-Trp-Ala-Val-Gly-His(3Me)-Sta-Leu-NH₂ (SEQ ID NO: 219) | | | | 0.8 |
| IIB-a-5 | 4-[19]-Fluoro-3-cyano-benzoyl-Gln-Trp-Ala-Val-Gly-His(3Me)-Sta-Leu-NH₂ (Y = bond) (SEQ ID NO: 220) | | | | 0.75 |
| IIB-a-6 | 4-[19]-Fluoro-3-cyano-benzoyl-AOC-Gln-Trp-Ala-Val-Gly-His(3Me)-Sta-Leu-NH₂ (SEQ ID NO: 221) | | | | 0.40 |
| IIB-a-7 | 4-[19]-Fluoro-3-cyano-benzoyl-Ava-Gln-Trp-Ala-Val-NMeGly-His(3Me)-Sta-Cpa-NH₂ (SEQ ID NO: 222) | | | | 200 |
| IIB-a-8 | 4-[19]-Fluoro-3-cyano-benzoyl-Ava-Gln-Trp-Ala-Val-Gly-His(3Me)-4-Am,5-MeHpA-Leu-NH₂ (SEQ ID NO: 223) | | | | 9.6 |
| IIB-a-9 | 4-[19]-Fluoro-3-cyano-benzoyl-Ava-Gln-Trp-Ala-Val-Gly-His(3Me)-Sta-Leu-NH₂ (SEQ ID NO: 224) | | | | 7.0 |
| IIB-a-10 | 4-[19]-Fluoro-3-cyano-benzoyl-Lys(Me)2-βAla-Gln-Trp-Ala-Val-Gly-His(3Me)-Sta-Leu-NH₂ (SEQ ID NO: 225) | | | | 3.0 |
| IIB-a-11 | 4-[19]-Fluoro-3-cyano-benzoyl-Lys(Me)2-βAla-Gln-Trp-Ala-Val-Gly-His(3Me)-Sta-Leu-NH₂ (SEQ ID NO: 226) | | | | 1.6 |
| IIB-a-12 | 4-[19]-Fluoro-3-cyano-benzoyl-Arg-Ser-Gln-Trp-Ala-Val-Gly-His(3Me)-4-Am,5-MeHpA-Leu-NH₂ (SEQ ID NO: 227) | | | | 22.0 |
| IIB-a-13 | 4-[19]-Fluoro-3-cyano-benzoyl-Ser-Ser-Gln-Trp-Ala-Val-Gly-His(3Me)-4-Am,5-MeHpA-Leu-NH₂ (SEQ ID NO: 228) | | | | >25 |

Fig. 12D

| | | |
|---|---|---|
| IIB-a-14 | 4-[19]-Fluoro-3-cyano-benzoyl-Lys(Me)2-Ser-Gln-Trp-Ala-Val-Gly-His(3Me)-4-Am,5-MeHpA-Leu-NH₂ (SEQ ID NO: 229) | NA |
| IIB-a-15 | 4-[19]-Fluoro-3-cyano-benzoyl-Arg-Ser-Gln-Trp-Ala-Val-Gly-His(3Me)-Sta-Leu-NH2 (SEQ ID NO: 230) | 6.4 |
| IIB-a-16 | 4-[19]-Fluoro-3-cyano-benzoyl-Lys(Me)2-ßAla-Gln-Trp-Ala-Val-Gly-His(3Me)-4-Am,5-MeHpA-Leu-NH₂ (SEQ ID NO: 231) | 12.2 |
| IIB-a-17 | 4-[19]-Fluoro-3-cyano-benzoyl-Ava-Gln-Trp-Ala-Val-Gly-His-4-Am,5-MeHpA-Leu-NH₂ (SEQ ID NO: 232) | 1.9 |
| IIB-a-18 | 4-[19]-Fluoro-3-trifluoromethyl-benzoyl-Arg-Ava-Gln-Trp-Ala-Val-Gly-His(3Me)-Sta-Leu-NH₂ (SEQ ID NO: 233) | 0.9 |
| IIB-a-19 | 4-[19]-Fluoro-3-trifluoromethyl-benzoyl-Arg-Ava-Gln-Trp-Ala-Val-NMeGly-His(3Me)-Sta-Leu-NH₂ (SEQ ID NO: 234) | 0.65 |
| IIB-a-20 | 4-[19]-Fluoro-3-trifluoromethyl-benzoyl-1,4-cis-Achc-Gln-Trp-Ala-Val-Gly-His(3Me)-Sta-Leu-NH₂ (SEQ ID NO: 235) | 0.77 |
| IIB-a-21 | 4-[19]-Fluoro-3-trifluoromethyl-benzoyl-Gln-Trp-Ala-Val-Gly-His(3Me)-Sta-Leu-NH₂ (Y = bond) (SEQ ID NO: 236) | 0.6 |
| IIB-a-22 | 4-[19]-Fluoro-3-trifluoromethyl-benzoyl-Arg-ßAla-Gln-Trp-Ala-Val-Gly-His(3Me)-4-Am,5-MeHpA-Leu-NH₂ (SEQ ID NO: 237) | 9.8 |
| IIB-a-23 | 4-[19]-Fluoro-3-cyano-benzoyl-Ava-Gln-Trp-Ala-Val-NMeGly-His(3Me)-4-Am,5-MeHpA-Cpa-NH₂ (SEQ ID NO: 238) | |
| IIB-a-24 | 4-[19]-Fluoro-3-cyano-benzoyl -Ser-Ser-Gln-Trp-Ala-Val-Gly-His(3Me)-Sta-Leu-NH₂ (SEQ ID NO: 239) | |
| IIB-a-25 | 4-[19]-Fluoro-3-cyano-benzoyl-DOA-Gln-Trp-Ala-Val-Gly-His(3Me)-Sta-Leu-NH₂ (SEQ ID NO: 240) | 13.5 |
| IIB-a-26 | 3,4-[19]Difluorobenzoyl-Ava-Gln-Trp-Ala-Val-NMeGly-His-Sta-Leu-NH₂ (SEQ ID NO: 241) | 0.1 |
| IIB-a-27 | 3,4-[19]Difluorobenzoyl-Ava-Gln-Trp-Ala-Val-NMeGly-His-FA02010-Cpa-NH₂ (SEQ ID NO: 242) | 2.4 |
| IIB-a-28 | 3,4-[19]Difluorobenzoyl-Ava-Gln-Trp-Ala-Val-NMeGly-His-4-Am,5-MeHpA-tbuGly-NH₂ (SEQ ID NO: 243) | 2.4 |
| IIB-a-29 | 3,4-[19]Difluorobenzoyl-Ava-Gln-Trp-Ala-Val-NMeGly-His(3Me)-Sta-Leu-NH₂ (SEQ ID NO: 244) | 2.8 |
| IIB-a-30 | 3,4-[19]Difluorobenzoyl-Ava-Gln-Trp-Ala-Val-NMeGly-His(3Me)-Sta-tBuGly-NH₂ (SEQ ID NO: 245) | 2.8 |
| IIB-a-31 | 3,4-[19]Difluorobenzoyl-Ava-Gln-Trp-Ala-Val-Gly-His(3Me)-Sta-Leu-NH₂ (SEQ ID NO: 246) | 4.9 |
| IIB-a-32 | 3,4-[19]Difluorobenzoyl-Ava-Gln-Trp-Ala-Val-NMeGly-His(3Me)-4-Am,5-MeHpA-Leu-NH₂ (SEQ ID NO: 247) | 9.6 |
| IIB-a-33 | 3,4-[19]Difluorobenzoyl-Ava-Gln-DTrp-Ala-Val-Gly-His-4-Am,5-MeHpA-tbuGly-NH₂ (SEQ ID NO: 248) | 30 |
| IIB-a-34 | 3,4-[19]Difluorobenzoyl-Ava-Gln-DTrp-Ala-Val-Gly-His-4-Am-5-MeHxA-Cpa-NH₂ (SEQ ID NO: 249) | 30 |
| IIB-a-35 | 3,4-[19]Difluorobenzoyl-Ava-Gln-Trp-Ala-Val-NMeGly-His(3Me)-Sta-Cpa-NH₂ (SEQ ID NO: 250) | 31 |
| IIB-a-36 | 3,4-[19]Difluorobenzoyl-Ava-Gln-DTrp-Ala-Val-Gly-His-Sta-tbuAla-NH₂ (SEQ ID NO: 251) | >500 |
| IIB-a-37 | 3,4-[19]Difluorobenzoyl-Arg-Ava-Gln-Trp-Ala-Val-NMeGly-His-Sta-Leu-NH₂ (SEQ ID NO: 252) | 0.4 |

Fig. 12E

| | |
|---|---|
| IIB-a-38 3,4-[19]Difluorobenzoyl-Gln-Trp-Ala-Val-Gly-His(3Me)-Sta-Leu--NH$_2$ (SEQ ID NO: 253) | 0.55 |
| IIB-a-39 3,4-[19]Difluorobenzoyl-Arg-Ava-Gln-Trp-Ala-Val-NMeGly-His(3Me)-Sta-Leu-NH$_2$ (SEQ ID NO: 254) | 0.58 |
| IIB-a-40 3,4-[19]Difluorobenzoyl-Arg-Ava-Gln-Trp-Ala-Val-Gly-His(3Me)-Sta-Leu-NH$_2$ (SEQ ID NO: 255) | 1.02 |
| IIB-a-41 3,4-[19]Difluorobenzoyl-Arg-βAla-Arg-Gln-Trp-Ala-Val-Gly-His(3Me)-Sta-Leu-NH$_2$ (SEQ ID NO: 256) | 7.5 |
| IIB-a-42 3,4-[19]Difluorobenzoyl-Ava-Gln-Trp-Ala-Val-Gly-His(3Me)-Sta-Cpa-NH$_2$ (SEQ ID NO: 257) | 14.2 |
| IIB-a-43 3,4-[19]Difluorobenzoyl-Ava-Gln-Trp-Ala-Val-Gly-His(3Me)-Sta-tBuGly-NH$_2$ (SEQ ID NO: 258) | >25 |
| IIB-a-44 3,4-[19]Difluorobenzoyl-Arg-Arg-Gln-Trp-Ala-Val-NMeGly-His(3Me)-Sta-Leu-NH$_2$ (SEQ ID NO: 258) | >25 |
| IIB-a-45 3,4-[19]Difluorobenzoyl-Arg-βAla-Gln-Trp-Ala-Val-NMeGly-His(3Me)-Sta-Leu-NH$_2$ (SEQ ID NO: 260) | >25 |
| IIB-a-46 3,4-[19]Difluorobenzoyl-Gln-Trp-Ala-Val-Gly-His(3Me)-4-Am,5-MeHpA-Leu-NH$_2$ (SEQ ID NO: 261) | >25 |
| IIB-a-47 3,4-[19]Difluorobenzoyl-Ava-Gln-Trp-Ala-Val-NMeGly-His(3Me)-4-Am,5-MeHpA-Cpa-NH$_2$ (SEQ ID NO: 262) | >25 |
| IIB-a-48 3,4-[19]Difluorobenzoyl-Ava-Gln-Trp-Ala-Val-Gly-His(3Me)-4-Am,5-MeHpA-Leu-NH$_2$ (SEQ ID NO: 263) | >25 |
| IIB-a-49 3,4-[19]Difluorobenzoyl-Ava-Gln-Trp-Ala-Val-Gly-NMeHis-4-Am,5-MeHpA-Cpa-NH$_2$ (SEQ ID NO: 264) | >25 |
| IIB-a-49 3,4-[19]Difluorobenzoyl-Ava-Gln-Trp-Ala-Val-Gly-NMeHis(3Me)-4-Am,5-MeHpA-Leu-NH$_2$ (SEQ ID NO: 265) | >25 |
| IIB-a-50 3,4-[19]Difluorobenzoyl-Ava-Gln-Trp-Ala-Val-Gly-NMeHis-4-Am,5-MeHpA-Leu-NH$_2$ (SEQ ID NO: 266) | >25 |
| IIB-a-51 3,4-[19]Difluorobenzoyl-Ava-Gln-Trp-Ala-Val-NMeGly-His-AHMHxA -Leu-NH$_2$ (SEQ ID NO: 267) | >25 |
| IIB-a-52 3,4-[19]Difluorobenzoyl-Ava-Gln-Trp-Ala-Val-βAla-NMeHis-Tha-Cpa-NH$_2$ (SEQ ID NO: 268) | 0.4 |
| IIB-a-53 3,4-[19]Difluorobenzoyl-Ava-Gln-Trp-Ala-Val-βAla-NMeHis-Phe-Cpa-NH$_2$ (SEQ ID NO: 269) | 0.6 |
| IIB-a-54 3,4-[19]Difluorobenzoyl-Ava-Gln-Trp-Ala-Val-βAla-NMeHis-Phe-Leu-NH$_2$ (SEQ ID NO: 270) | 0.4 |
| IIB-a-55 3,4-[19]Difluorobenzoyl-Ava-Gln-Trp-Ala-Val-βAla-DHis-Phe-Leu-NH$_2$ (SEQ ID NO: 271) | 19.0 |
| IIB-a-56 3,4-[19]Difluorobenzoyl-Ava-Gln-Trp-Ala-Val-βAla-His-βhLeu-Leu-NH$_2$ (SEQ ID NO: 272) | 45.0 |
| IIB-a-57 3,4-[19]Difluorobenzoyl-Ava-Gln-Trp-Ala-Val-βAla-His-βhIle-Leu-NH$_2$ (SEQ ID NO: 273) | >50 |
| IIB-a-58 3,4-[19]Difluorobenzoyl-Ava-Gln-Trp-Ala-Val-βAla-His-βhLeu-tbuGly-NH$_2$ (SEQ ID NO: 274) | >50 |
| IIB-a-59 3,4-[19]Difluorobenzoyl-Ava-Gln-Trp-Ala-Val-βAla-His(3Me)-Phe-Tha-NH$_2$ (SEQ ID NO: 275) | >50 |
| IIB-a-60 3,4-[19]Difluorobenzoyl-Ava-Gln-Trp-Ala-Val-βAla-His(3Me)-Phe-Nle-NH$_2$ (SEQ ID NO: 276) | >50 |

Fig. 12F

| | | |
|---|---|---|
| IIB-a-5161 | 3,4-[19]Difluorobenzoyl-Ava-Gln-Trp-Ala-Val-βAla-NMeHis-Phe-tbuGly-NH$_2$ (SEQ ID NO: 277) | NA |
| IIB-a-5262 | 3,4-[19]Difluorobenzoyl-Ava-Gln-Trp-Ala-Val-βAla-NMeHis-Tha-tbuGly-NH$_2$ (SEQ ID NO: 278) | NA |
| IIB-a-5363 | 3,4-[19]Difluorobenzoyl-Ava-Gln-Trp-Ala-Val-βAla-His(3Me)-Tha-tbuGly-NH$_2$ (SEQ ID NO: 279) | NA |
| IIB-a-5464 | 3,4-[19]Difluorobenzoyl-Ava-Gln-Trp-Ala-Val-βAla-His(3Me)-Phe-Cpa-NH$_2$ (SEQ ID NO: 280) | NA |
| IIB-a-5565 | 3,4-[19]Difluorobenzoyl-Ava-Gln-Trp-Ala-NMeVal-βAla-His-Phe-Leu-NH$_2$ (SEQ ID NO: 281) | NA |
| IIB-a-5666 | 3,4-[19]Difluorobenzoyl-Ava-Gln-Trp-Ala-Val-βAla-His-NMePhe-Leu-NH$_2$ (SEQ ID NO: 282) | NA |
| IIB-a-5767 | 3,4-[19]Difluorobenzoyl-Ava-Gln-DTrp-Ala-Val-βAla-His-Phe-Leu-NH$_2$ (SEQ ID NO: 283) | NA |
| IIB-a-5868 | 3,4-[19]Difluorobenzoyl-Ava-Gln-Trp-DAla-Val-βAla-His-Phe-Leu-NH$_2$ (SEQ ID NO: 284) | NA |
| IIB-a-5969 | 3,4-[19]Difluorobenzoyl-Ava-Gln-Trp-Ala-DVal-βAla-His-Phe-Leu-NH$_2$ (SEQ ID NO: 285) | NA |
| IIB-a-6070 | 3,4-[19]Difluorobenzoyl-Ava-Gln-Trp-Ala-Val-βAla-His-DPhe-Leu-NH$_2$ (SEQ ID NO: 286) | NA |
| IIB-a-6171 | 3,4-[19]Difluorobenzoyl-Ava-Gln-Trp-Ala-Val-βAla-His-βhIle-tbuGly-NH$_2$ (SEQ ID NO: 287) | NA |

Fig. 12G

[19]F-(C$_6$H$_4$(-G))--L--Y--U (II) (G = 3-cyano; L = SO$_2$ as indicated)

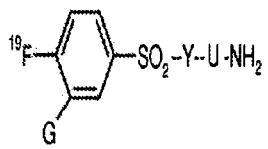

| [19]F-(C$_6$H$_4$(-G))- | -L- | -Y- | -U- | K$_i$(nM) |
|---|---|---|---|---|

IIB-a-6272  4-[19]Fluoro-3-cyano-phenylsulfonyl -Ava-Gln-Trp-Ala-Val-NMeGly-His-4-Am,5-MeHpA-Cpa-NH$_2$ (SEQ ID NO: 288)   0.4

IIB-a-6373  4-[19]Fluoro-3-cyano-phenylsulfonyl -Ava-Gln-Trp-Ala-Val-NMeGly-His-Sta-Cpa-NH$_2$ (SEQ ID NO: 289)   1.1

IIB-a-6474  4-[19]Fluoro-3-cyano-phenylsulfonyl -Ava-Gln-Trp-Ala-Val-NMeGly-His-Sta-tbuAla-NH$_2$ (SEQ ID NO: 290)   2.5

IIB-a-6575  4-[19]Fluoro-3-cyano-phenylsulfonyl -Ava-Gln-Trp-Ala-Val-NMeGly-His-4-Am,5-MeHpA-tbuAla-NH$_2$ (SEQ ID NO: 291)   2.5

Fig. 12H

TABLE 3

[18]F-(C₆H₄(-G))-L₂-Y-U (IIB-a-) (G = 3-cyano or 3-trifluoromethyl, L = CO as indicated)

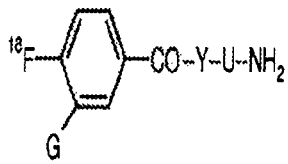

| [18]F-(C₆H₄(-G))- | -L- | -Y- | -U |

IIA-a-1  4-[18]Fluoro-3-cyano-benzoyl-Arg-Ava-Gln-Trp-Ala-Val-NMeGly-His-Sta-Leu-NH₂ (SEQ ID NO: 137)

IIA-a-2  4-[18]Fluoro-3-cyano-benzoyl-Arg-Ava-Gln-Trp-Ala-Val-His(Me)-Sta-Leu-NH₂ (SEQ ID NO: 138)

IIA-a-3  4-[18]Fluoro-3-cyano-benzoyl-Arg-Ava-Gln-Trp-Ala-Val-NMeGly-His(3Me)-Sta-Leu-NH₂ (SEQ ID NO: 139)

IIA-a-4  4-[18]Fluoro-3-cyano-benzoyl-1,4-cis-Achc-Gln-Trp-Ala-Val-Gly-His(3Me)-Sta-Leu-NH₂ (SEQ ID NO: 140)

IIA-a-5  4-[18]Fluoro-3-cyano-benzoyl-Gln-Trp-Ala-Val-Gly-His(3Me)-Sta-Leu-NH₂ (SEQ ID NO: 141) (Y = bond)

IIA-a-6  4-[18]Fluoro-3-cyano-benzoyl-AOC-Gln-Trp-Ala-Val-Gly-His(3Me)-Sta-Leu-NH₂ (SEQ ID NO: 142)

IIA-a-7  4-[18]Fluoro-3-cyano-benzoyl-Ava-Gln-Trp-Ala-Val-NMeGly-His(3Me)-Sta-Cpa-NH₂ (SEQ ID NO: 143)

IIA-a-8  4-[18]Fluoro-3-cyano-benzoyl-Ava-Gln-Trp-Ala-Val-Gly-His(3Me)-FA4-Am,5-MeHpA-Leu-NH₂ (SEQ ID NO: 144)

IIA-a-9  4-[18]Fluoro-3-cyano-benzoyl-Ava-Gln-Trp-Ala-Val-Gly-His(3Me)-Sta-Leu-NH₂ (SEQ ID NO: 145)

IIA-a-10  4-[18]Fluoro-3-cyano-benzoyl-Lys(Me)2-ßAla-Gln-Trp-Ala-Val-Gly-His(3Me)-Sta-Leu-NH₂ (SEQ ID NO: 146)

IIA-a-11  4-[18]Fluoro-3-cyano-benzoyl-Lys(Me)2-ßAla-Gln-Trp-Ala-Val-Gly-His(3Me)-Sta-Leu-NH₂ (SEQ ID NO: 147)

IIA-a-12  4-[18]Fluoro-3-cyano-benzoyl-Arg-Ser-Gln-Trp-Ala-Val-Gly-His(3Me)-4-Am,5-MeHpA-Leu-NH₂ (SEQ ID NO: 148)

Fig. 121

IIA-a-13 4-[18]Fluoro-3-cyano-benzoyl-Ser-Ser-Gln-Trp-Ala-Val-Gly-His(3Me)-4-Am,5-MeHpA-Leu-NH$_2$ (SEQ ID NO: 149)

IIA-a-14 4-[18]Fluoro-3-cyano-benzoyl-Lys(Me)2-Ser-Gln-Trp-Ala-Val-Gly-His(3Me)-4-Am,5-MeHpA-Leu-NH$_2$ (SEQ ID NO: 150)

IIA-a-15 4-[18]Fluoro-3-cyano-benzoyl-Arg-Ser-Gln-Trp-Ala-Val-Gly-His(3Me)-Sta-Leu-NH$_2$ (SEQ ID NO: 151)

IIA-a-16 4-[18]Fluoro-3-cyano-benzoyl-Lys(Me)2-ßAla-Gln-Trp-Ala-Val-Gly-His(3Me)-4-Am,5-MeHpA-Leu-NH$_2$ (SEQ ID NO: 152)

IIA-a-17 4-[18]Fluoro-3-cyano-benzoyl-Ava-Gln-Trp-Ala-Val-Gly-His-4-Am,5-MeHpA-Leu-NH$_2$ (SEQ ID NO: 153)

IIA-a-18 4-[18]Fluoro-3-trifluoromethyl-benzoyl-Arg-Ava-Gln-Trp-Ala-Val-Gly-His(3Me)-Sta-Leu-NH$_2$ (SEQ ID NO: 154)

IIA-a-19 4-[18]Fluoro-3-trifluoromethyl-benzoyl-Arg-Ava-Gln-Trp-Ala-Val-NMeGly-His(3Me)-Sta-Leu-NH$_2$ (SEQ ID NO: 155)

IIA-a-20 4-[18]Fluoro-3-trifluoromethyl-benzoyl-1,4-cis-Achc-Gln-Trp-Ala-Val-Gly-His(3Me)-Sta-Leu-NH$_2$ (SEQ ID NO: 156)

IIA-a-21 4-[18]Fluoro-3-trifluoromethyl-benzoyl-Gln-Trp-Ala-Val-Gly-His(3Me)-Sta-Leu-NH$_2$ (SEQ ID NO: 157) (Y = bond)

IIA-a-22 4-[18]Fluoro-3-trifluoromethyl-benzoyl-Arg-ßAla-Gln-Trp-Ala-Val-Gly-His(3Me)-4-Am,5-MeHpA-Leu-NH$_2$ (SEQ ID NO: 158)

SEQUENCE LISTING

<160> NUMBER OF SEQ ID NOS: 422

<210> SEQ ID NO 1
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 1

Gln Trp Ala Val Gly His Xaa Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 2

Gln Trp Ala Val Gly His Xaa Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 3

Gln Trp Ala Val Gly His Xaa Leu
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 4

Gln Trp Ala Val Gly His Xaa Leu
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 5

Arg Ala Gln Trp Ala Val Gly Xaa Xaa Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 6

Arg Ala Gln Trp Ala Val Gly His Xaa Leu
1               5                   10

<210> SEQ ID NO 7
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 7

Gln Trp Ala Val Gly His Xaa Xaa
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 8

Gln Trp Ala Val Gly His Xaa Leu
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 9
```

```
Arg Ala Gln Trp Ala Val Gly His Xaa Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Cyano-4-(trimethylammonium)-benzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 10

Xaa Gln Trp Ala Val Gly His Xaa Leu
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 11

Arg Ala Gln Trp Ala Val Gly His Xaa Leu
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 12
```

```
Gln Trp Ala Val Gly His Xaa Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 13

Xaa Gln Trp Ala Val Gly His Xaa Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 14

Xaa Gln Trp Ala Val Gly His Xaa Leu
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Trifluormethyl-4-(trimethylammonium)-
      benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
```

```
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 15

Arg Xaa Gln Trp Ala Val Gly His Xaa Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 16

Arg Ala Gln Trp Ala Val Gly His Xaa Leu
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 17

Gln Trp Ala Val Gly His Xaa Leu
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-trifluoromethyl-4-[18F]fluorobenzoyl-Arg
<220> FEATURE:
<221> NAME/KEY: MOD_RES
<222> LOCATION: (2)..(2)
```

```
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 18

Arg Xaa Gln Trp Ala Val Gly His Xaa Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-trifluoromethyl-4-trimethylammoniumbenzoyl-
      Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 19

Arg Xaa Gln Trp Ala Val Gly His Xaa Leu
1               5                   10

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 20

Val Ala Phe Gly
1
```

```
<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 21

Val Ala Phe Gly
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 22

Val Ala Arg Gly
1

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 23

Gln Trp Ala Val Gly His Xaa Xaa
```

```
<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 24

Val Ala Arg Gly
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(Me)
<220> FEATURE:
<223> OTHER INFORMATION: c-term amidation

<400> SEQUENCE: 25

Val Ala His Gly
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 26

Val Ala Arg Gly
1

<210> SEQ ID NO 27
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (7)..(7)
<223> OTHER INFORMATION: (R)-Fmoc-4-amino-5-methyl-hexanoic acid
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 27

Gln Trp Ala Val Gly His Xaa Xaa
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (7)..(7)
<223> OTHER INFORMATION: 4-Am,5-MeHpA
<220> FEATURE:
<221> NAME/KEY: MOD_RES
<222> LOCATION: (8)..(8)
<223> OTHER INFORMATION: tbuGly
<220> FEATURE:
<223> OTHER INFORMATION: c-term amidation

<400> SEQUENCE: 28

Gln Trp Ala Val Gly His Xaa Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Ava
<220> FEATURE:
<221> NAME/KEY: MOD_RES
<222> LOCATION: (8)..(8)
<223> OTHER INFORMATION: (4R,5S)-Fmoc-4-amino-5-methyl-heptanoic acid
<220> FEATURE:
<223> OTHER INFORMATION: c-term amidation

<400> SEQUENCE: 29

Xaa Gln Trp Ala Val Gly His Xaa Leu
1               5

<210> SEQ ID NO 30
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<221> NAME/KEY: MOD_RES
<222> LOCATION: (8)..(8)
<223> OTHER INFORMATION: tBuGly
<220> FEATURE:
<223> OTHER INFORMATION: c-term amidation

<400> SEQUENCE: 30

Gln Trp Ala Val Gly His Xaa Gly
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Ava
<220> FEATURE:
<221> NAME/KEY: MOD_RES
<222> LOCATION: (8)..(8)
<223> OTHER INFORMATION: (4R,5S)-Fmoc-4-amino-5-methyl-heptanoic acid
<220> FEATURE:
<223> OTHER INFORMATION: c-term amidation

<400> SEQUENCE: 31

Xaa Gln Trp Ala Val Gly His Xaa Leu
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 32

Gln Trp Ala Val Gly His Xaa Leu
```

```
<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (7)..(7)
<223> OTHER INFORMATION: 4-Am,5-MeHpA
<220> FEATURE:
<221> NAME/KEY: MOD_RES
<222> LOCATION: (8)..(8)
<223> OTHER INFORMATION: tbuGly
<220> FEATURE:
<223> OTHER INFORMATION: c-term amidation

<400> SEQUENCE: 33

Gln Trp Ala Val Gly His Xaa Gly
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (7)..(7)
<223> OTHER INFORMATION: 4-Am-5-MeHxA
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 34

Gln Trp Ala Val Gly His Xaa Xaa
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<221> NAME/KEY: MOD_RES
```

```
<222> LOCATION: (8)..(8)
<223> OTHER INFORMATION: Cpa
<220> FEATURE:
<223> OTHER INFORMATION: c-term amidation

<400> SEQUENCE: 35

Gln Trp Ala Val Gly His Xaa Xaa
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (7)..(7)
<223> OTHER INFORMATION: Sta
<220> FEATURE:
<221> NAME/KEY: MOD_RES
<222> LOCATION: (8)..(8)
<223> OTHER INFORMATION: tbuAla
<220> FEATURE:
<223> OTHER INFORMATION: c-term amidation

<400> SEQUENCE: 36

Gln Trp Ala Val Gly His Xaa Ala
1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 37

Arg Xaa Gln Trp Ala Val Gly His Xaa Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: 3-cyano-4-trimethylammoniumbenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 38

Arg Xaa Gln Trp Ala Val Gly His Xaa Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 39

Arg Ala Gln Trp Ala Val Gly His Xaa Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation
```

```
<400> SEQUENCE: 40

Arg Ala Gln Trp Ala Val Gly His Xaa Leu
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 41

Xaa Gln Trp Ala Val Gly His Xaa Leu
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 42

Gln Trp Ala Val Gly His Xaa Xaa
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<221> NAME/KEY: MOD_RES
```

```
<222> LOCATION: (8)..(8)
<223> OTHER INFORMATION: tBuGly
<220> FEATURE:
<223> OTHER INFORMATION: c-term amidation

<400> SEQUENCE: 43

Gln Trp Ala Val Gly His Xaa Gly
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 44

Xaa Gln Trp Ala Val Gly His Xaa Leu
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-trifluoromethyl-4-[18F]fluorobenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 45

Arg Xaa Gln Trp Ala Val Gly His Xaa Leu
1               5                   10

<210> SEQ ID NO 46
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 46

Gln Trp Ala Val Gly His Xaa Leu
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: NMeHis(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 47

Gln Trp Ala Val Gly His Xaa Leu
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 48

Gln Trp Ala Val Gly His Xaa Leu
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: NMeHis
<220> FEATURE:
<221> NAME/KEY: MOD_RES
```

```
<222> LOCATION: (7)..(7)
<223> OTHER INFORMATION: 4-Am,5-MeHpA
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 49

Gln Trp Ala Val Gly His Xaa Xaa
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: NMeHis
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 50

Gln Trp Ala Val Gly His Xaa Leu
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (7)..(7)
<223> OTHER INFORMATION: AHMHxA
<220> FEATURE:
<223> OTHER INFORMATION: c-term amidation

<400> SEQUENCE: 51

Gln Trp Ala Val Gly His Xaa Leu
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: NMeHis
<220> FEATURE:
<221> NAME/KEY: MOD_RES
```

```
<222> LOCATION: (7)..(7)
<223> OTHER INFORMATION: Tha
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 52

Gln Trp Ala Val Ala His Xaa Xaa
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: NMeHis
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 53

Gln Trp Ala Val Ala His Phe Xaa
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: NMeHis
<220> FEATURE:
<223> OTHER INFORMATION: c-term amidation

<400> SEQUENCE: 54

Gln Trp Ala Val Ala His Phe Leu
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
```

```
<222> LOCATION: (6)..(6)
<223> OTHER INFORMATION: D-His
<220> FEATURE:
<223> OTHER INFORMATION: c-term amidation

<400> SEQUENCE: 55

Gln Trp Ala Val Ala His Phe Leu
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (7)..(7)
<223> OTHER INFORMATION: beta-hLeu
<220> FEATURE:
<223> OTHER INFORMATION: c-term amidation

<400> SEQUENCE: 56

Gln Trp Ala Val Ala His Leu Leu
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (7)..(7)
<223> OTHER INFORMATION: beta-hIle
<220> FEATURE:
<223> OTHER INFORMATION: c-term amidation

<400> SEQUENCE: 57

Gln Trp Ala Val Ala His Ile Leu
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (7)..(7)
<223> OTHER INFORMATION: beta-hLeu
<220> FEATURE:
<221> NAME/KEY: MOD_RES
<222> LOCATION: (8)..(8)
<223> OTHER INFORMATION: tbuGly
<220> FEATURE:
<223> OTHER INFORMATION: c-term amidation
```

```
<400> SEQUENCE: 58

Gln Trp Ala Val Ala His Leu Gly
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (8)..(8)
<223> OTHER INFORMATION: Tha
<220> FEATURE:
<223> OTHER INFORMATION: c-term amidation

<400> SEQUENCE: 59

Gln Trp Ala Val Ala His Phe Xaa
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (8)..(8)
<223> OTHER INFORMATION: Nle
<220> FEATURE:
<223> OTHER INFORMATION: c-term amidation

<400> SEQUENCE: 60

Gln Trp Ala Val Ala His Phe Xaa
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: NMeHis
<220> FEATURE:
<221> NAME/KEY: MOD_RES
```

```
<222> LOCATION: (8)..(8)
<223> OTHER INFORMATION: tbuGly
<220> FEATURE:
<223> OTHER INFORMATION: c-term amidation

<400> SEQUENCE: 61

Gln Trp Ala Val Ala His Phe Gly
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: NMeHis
<220> FEATURE:
<221> NAME/KEY: MOD_RES
<222> LOCATION: (7)..(7)
<223> OTHER INFORMATION: Tha
<220> FEATURE:
<221> NAME/KEY: MOD_RES
<222> LOCATION: (8)..(8)
<223> OTHER INFORMATION: tbuGly
<220> FEATURE:
<223> OTHER INFORMATION: c-term amidation

<400> SEQUENCE: 62

Gln Trp Ala Val Ala His Xaa Gly
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Tha
<220> FEATURE:
<221> NAME/KEY: MOD_RES
<222> LOCATION: (8)..(8)
<223> OTHER INFORMATION: tbuGly
<220> FEATURE:
<223> OTHER INFORMATION: c-term amidation

<400> SEQUENCE: 63

Gln Trp Ala Val Ala His Xaa Gly
1               5

<210> SEQ ID NO 64
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 64

Gln Trp Ala Val Ala His Phe Xaa
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: NMeVal
<220> FEATURE:
<221> NAME/KEY: MOD_RES
<222> LOCATION: (5)..(5)
<223> OTHER INFORMATION: beta-Ala
<220> FEATURE:
<223> OTHER INFORMATION: c-term amidation

<400> SEQUENCE: 65

Gln Trp Ala Val Ala His Phe Leu
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (7)..(7)
<223> OTHER INFORMATION: NMePhe
<220> FEATURE:
<223> OTHER INFORMATION: c-term amidation

<400> SEQUENCE: 66

Gln Trp Ala Val Ala His Phe Leu
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: D-Trp
<220> FEATURE:
<221> NAME/KEY: MOD_RES
<222> LOCATION: (5)..(5)
<223> OTHER INFORMATION: beta-Ala
<220> FEATURE:
<223> OTHER INFORMATION: c-term amidation

<400> SEQUENCE: 67

Gln Trp Ala Val Ala His Phe Leu
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (5)..(5)
<223> OTHER INFORMATION: beta-Ala
<220> FEATURE:
<223> OTHER INFORMATION: c-term amidation

<400> SEQUENCE: 68

Gln Trp Ala Val Ala His Phe Leu
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Val
<220> FEATURE:
<221> NAME/KEY: MOD_RES
<222> LOCATION: (5)..(5)
<223> OTHER INFORMATION: beta-Ala
<220> FEATURE:
<223> OTHER INFORMATION: c-term amidation

<400> SEQUENCE: 69

Gln Trp Ala Val Ala His Phe Leu
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (7)..(7)
<223> OTHER INFORMATION: D-Phe
<220> FEATURE:
<223> OTHER INFORMATION: c-term amidation
```

```
<400> SEQUENCE: 70

Gln Trp Ala Val Ala His Phe Leu
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-Ala
<220> FEATURE:
<221> NAME/KEY: MOD_RES
<222> LOCATION: (7)..(7)
<223> OTHER INFORMATION: beta-hIle
<220> FEATURE:
<221> NAME/KEY: MOD_RES
<222> LOCATION: (8)..(8)
<223> OTHER INFORMATION: tbuGly
<220> FEATURE:
<223> OTHER INFORMATION: c-term amidation

<400> SEQUENCE: 71

Gln Trp Ala Val Ala His Ile Gly
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (7)..(7)
<223> OTHER INFORMATION: 4-Am,5-MeHpA
<220> FEATURE:
<221> NAME/KEY: MOD_RES
<222> LOCATION: (8)..(8)
<223> OTHER INFORMATION: Cpa
<220> FEATURE:
<223> OTHER INFORMATION: c-term amidation

<400> SEQUENCE: 72

Gln Trp Ala Val Gly His Xaa Xaa
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (7)..(7)
<223> OTHER INFORMATION: Sta
<220> FEATURE:
<221> NAME/KEY: MOD_RES
```

```
<222> LOCATION: (8)..(8)
<223> OTHER INFORMATION: Cpa
<220> FEATURE:
<223> OTHER INFORMATION: c-term amidation

<400> SEQUENCE: 73

Gln Trp Ala Val Gly His Xaa Xaa
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (7)..(7)
<223> OTHER INFORMATION: Sta
<220> FEATURE:
<221> NAME/KEY: MOD_RES
<222> LOCATION: (8)..(8)
<223> OTHER INFORMATION: tbuAla
<220> FEATURE:
<223> OTHER INFORMATION: c-term amidation

<400> SEQUENCE: 74

Gln Trp Ala Val Gly His Xaa Ala
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (7)..(7)
<223> OTHER INFORMATION: 4-Am,5-MeHpA
<220> FEATURE:
<221> NAME/KEY: MOD_RES
<222> LOCATION: (8)..(8)
<223> OTHER INFORMATION: tbuAla
<220> FEATURE:
<223> OTHER INFORMATION: c-term amidation

<400> SEQUENCE: 75

Gln Trp Ala Val Gly His Xaa Ala
1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-trifluoromethyl-4-trimethylammoniumbenzoyl-
      Arg
<220> FEATURE:
```

```
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 76

Arg Xaa Gln Trp Ala Val Gly His Xaa Leu
1               5                   10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 77

Xaa Gln Trp Ala Val Gly His Xaa Xaa
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: (4R,5S)-Fmoc-4-amino-5-methyl-heptanoic acid
<220> FEATURE:
```

<223> OTHER INFORMATION: c-term amidation

<400> SEQUENCE: 78

Xaa Gln Trp Ala Val Gly His Xaa Leu
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 79

Xaa Gln Trp Ala Val Gly His Xaa Leu
1               5

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 80

Arg Ala Gln Trp Ala Val Gly His Xaa Leu
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Me)2
<220> FEATURE:
<221> NAME/KEY: MOD_RES
<222> LOCATION: (2)..(2)
<223> OTHER INFORMATION: beta-Ala
<220> FEATURE:

```
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 81

Lys Ala Gln Trp Ala Val Gly His Xaa Leu
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: FA4-Am,5-MeHpA
<220> FEATURE:
<223> OTHER INFORMATION: c-term amidation

<400> SEQUENCE: 82

Gln Trp Ala Val Gly His Xaa Leu
1               5

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: (4R,5S)-Fmoc-4-amino-5-methyl-heptanoic acid
<220> FEATURE:
<223> OTHER INFORMATION: c-term amidation

<400> SEQUENCE: 83

Arg Ser Gln Trp Ala Val Gly His Xaa Leu
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: (4R,5S)-Fmoc-4-amino-5-methyl-heptanoic acid
<220> FEATURE:
```

<223> OTHER INFORMATION: c-term amidation

<400> SEQUENCE: 84

Ser Ser Gln Trp Ala Val Gly His Xaa Leu
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Me)2
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: (4R,5S)-Fmoc-4-amino-5-methyl-heptanoic acid
<220> FEATURE:
<223> OTHER INFORMATION: c-term amidation

<400> SEQUENCE: 85

Lys Ser Gln Trp Ala Val Gly His Xaa Leu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 86

Arg Ser Gln Trp Ala Val Gly His Xaa Leu
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Me)2
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:

<221> NAME/KEY: MOD_RES
<222> LOCATION: (9)..(9)
<223> OTHER INFORMATION: (4R,5S)-Fmoc-4-amino-5-methyl-heptanoic acid
<220> FEATURE:
<223> OTHER INFORMATION: c-term amidation

<400> SEQUENCE: 87

Lys Ala Gln Trp Ala Val Gly His Xaa Leu
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:
<221> NAME/KEY: MOD_RES
<222> LOCATION: (8)..(8)
<223> OTHER INFORMATION: (4R,5S)-Fmoc-4-amino-5-methyl-heptanoic acid
<220> FEATURE:
<223> OTHER INFORMATION: c-term amidation

<400> SEQUENCE: 88

Xaa Gln Trp Ala Val Gly His Xaa Leu
1               5

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 89

Arg Xaa Gln Trp Ala Val Gly His Xaa Leu
1               5                   10

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:

<223> OTHER INFORMATION: c-term amidation

<400> SEQUENCE: 90

Gln Trp Ala Val Gly His Xaa Leu
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 91

Gln Trp Ala Val Gly His Xaa Leu
1               5

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 92

Arg Xaa Gln Trp Ala Val Gly His Xaa Leu
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:

<223> OTHER INFORMATION: c-term amidation

<400> SEQUENCE: 93

Arg Xaa Gln Trp Ala Val Gly His Xaa Leu
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1,4-cis-Achc
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 94

Xaa Gln Trp Ala Val Gly His Xaa Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 95

Xaa Gln Trp Ala Val Gly His Xaa Xaa
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:

```
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: (4R,5S)-Fmoc-4-amino-5-methyl-heptanoic acid
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 96

Xaa Gln Trp Ala Val Gly His Xaa Xaa
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dioxa
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 97

Xaa Gln Trp Ala Val Gly His Xaa Leu
1               5

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 98

Ser Ser Gln Trp Ala Val Gly His Xaa Leu
1               5                   10

<210> SEQ ID NO 99
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: (4R,5S)-Fmoc-4-amino-5-methyl-heptanoic acid
<220> FEATURE:
<223> OTHER INFORMATION: c-term amidation

<400> SEQUENCE: 99

Arg Ala Gln Trp Ala Val Gly His Xaa Leu
1               5                   10

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 100

Gln Trp Ala Val Gly His Xaa Leu
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am-5-MeHpA
<220> FEATURE:
<221> NAME/KEY: MOD_RES
<222> LOCATION: (8)..(8)
<223> OTHER INFORMATION: 4-amino-5-methylheptanoic acid
<220> FEATURE:
<223> OTHER INFORMATION: c-term amidation

<400> SEQUENCE: 101

Gln Trp Ala Val Gly His Xaa Xaa Leu
1               5

<210> SEQ ID NO 102
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeGly
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am-5-MeHpA
<220> FEATURE:
<221> NAME/KEY: MOD_RES
<222> LOCATION: (8)..(8)
<223> OTHER INFORMATION: 4-amino-5-methylheptanoic acid
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 102

Gln Trp Ala Val Gly His Xaa Xaa Xaa
1               5

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 103

Arg Xaa Gln Trp Ala Val Gly His Xaa Leu
1               5                   10

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: cyclic
<220> FEATURE:
<221> NAME/KEY: MOD_RES
<222> LOCATION: (2)..(2)
<223> OTHER INFORMATION: NMePhe
<220> FEATURE:
```

```
<221> NAME/KEY: MOD_RES
<222> LOCATION: (3)..(3)
<223> OTHER INFORMATION: 1-Nal
<220> FEATURE:
<221> NAME/KEY: MOD_RES
<222> LOCATION: (4)..(4)
<223> OTHER INFORMATION: D-Trp

<400> SEQUENCE: 104

Lys Phe Xaa Trp Lys Thr
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: cyclic
<220> FEATURE:
<221> NAME/KEY: MOD_RES
<222> LOCATION: (1)..(1)
<223> OTHER INFORMATION: NMePhe
<220> FEATURE:
<221> NAME/KEY: MOD_RES
<222> LOCATION: (3)..(3)
<223> OTHER INFORMATION: 1-Nal
<220> FEATURE:
<221> NAME/KEY: MOD_RES
<222> LOCATION: (5)..(5)
<223> OTHER INFORMATION: D-Trp

<400> SEQUENCE: 105

Phe Met Xaa Tyr Trp Lys
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<221> NAME/KEY: MOD_RES
<222> LOCATION: (1)..(1)
<223> OTHER INFORMATION: D-Cys
<220> FEATURE:
<223> OTHER INFORMATION: c-term amidation

<400> SEQUENCE: 106

Cys Leu Ile Thr Arg Cys Arg Tyr
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<221> NAME/KEY: MOD_RES
<222> LOCATION: (1)..(1)
```

```
<223> OTHER INFORMATION: D-Cys
<220> FEATURE:
<223> OTHER INFORMATION: c-term amidation

<400> SEQUENCE: 107

Cys Leu Ile Val Arg Cys Arg Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: (4R,5S)-Fmoc-4-amino-5-methyl-heptanoic acid
<220> FEATURE:
<223> OTHER INFORMATION: c-term amidation

<400> SEQUENCE: 108

Gln Trp Ala Val Gly His Xaa Leu
1               5

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 109

Arg Xaa Gln Trp Ala Val Gly His Xaa Leu
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
```

```
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 110

Arg Xaa Gln Trp Ala Val Gly His Xaa Leu
1               5                   10

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-1,4-
      cis-Achc
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 111

Xaa Gln Trp Ala Val Gly His Xaa Leu
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 112

Gln Trp Ala Val Gly His Xaa Leu
1               5

<210> SEQ ID NO 113
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-AOC
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 113

Xaa Gln Trp Ala Val Gly His Xaa Leu
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 114

Xaa Gln Trp Ala Val Gly His Xaa Xaa
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation
```

-continued

```
<400> SEQUENCE: 115

Xaa Gln Trp Ala Val Gly His Xaa Leu
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 116

Xaa Gln Trp Ala Val Gly His Xaa Leu
1               5

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Lys(Me)2
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 117

Lys Ala Gln Trp Ala Val Gly His Xaa Leu
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Lys(Me)2
<220> FEATURE:
<221> NAME/KEY: MOD_RES
```

```
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 118

Lys Ala Gln Trp Ala Val Gly His Xaa Leu
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Arg
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 119

Arg Ser Gln Trp Ala Val Gly His Xaa Leu
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ser
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 120

Ser Ser Gln Trp Ala Val Gly His Xaa Leu
1               5                   10

<210> SEQ ID NO 121
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Lys(Me)2
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-AM-5-MeHpA
<220> FEATURE:
<223> OTHER INFORMATION: c-term amidation

<400> SEQUENCE: 121

Lys Ser Gln Trp Ala Val Gly His Xaa Leu
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Arg
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 122

Arg Ser Gln Trp Ala Val Gly His Xaa Leu
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Lys(Me)2
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 123

Lys Ala Gln Trp Ala Val Gly His Xaa Leu
```

```
                1               5              10

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 124

Xaa Gln Trp Ala Val Gly His Xaa Leu
1               5

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-trifluoromethyl-
      benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 125

Arg Xaa Gln Trp Ala Val Gly His Xaa Leu
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-trifluoromethyl-
      benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
```

```
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 126

Arg Xaa Gln Trp Ala Val Gly His Xaa Leu
1               5                   10

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-trifluoromethyl-
      benzoyl-1,4-cis-Achc
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 127

Xaa Gln Trp Ala Val Gly His Xaa Leu
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-trifluoromethyl-
      benzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 128

Gln Trp Ala Val Gly His Xaa Leu
1               5

<210> SEQ ID NO 129
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-trifluoromethyl-
      benzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 129

Arg Ala Gln Trp Ala Val Gly His Xaa Leu
1               5                   10

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 130

Xaa Gln Trp Ala Val Gly His Xaa Xaa
1               5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ser
<220> FEATURE:
<221> NAME/KEY: MOD_RES
<222> LOCATION: (8)..(8)
<223> OTHER INFORMATION: His(3Me)
<220> FEATURE:
```

```
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 131

Ser Ser Gln Trp Ala Val Gly His Xaa Leu
1               5                   10

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-DOA
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 132

Xaa Gln Trp Ala Val Gly His Xaa Leu
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: misc_feature
<222> LOCATION: (2)..(7)
<223> OTHER INFORMATION: cyclic
<220> FEATURE:
<221> NAME/KEY: MOD_RES
<222> LOCATION: (3)..(3)
<223> OTHER INFORMATION: NMePhe
<220> FEATURE:
<221> NAME/KEY: MOD_RES
<222> LOCATION: (4)..(4)
<223> OTHER INFORMATION: 1Nal
<220> FEATURE:
<221> NAME/KEY: MOD_RES
<222> LOCATION: (5)..(5)
<223> OTHER INFORMATION: D-Trp

<400> SEQUENCE: 133

Xaa Lys Phe Xaa Trp Lys Thr
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                       peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: MOD_RES
<222> LOCATION: (2)..(2)
<223> OTHER INFORMATION: Dpr
<220> FEATURE:
<221> NAME/KEY: misc_feature
<222> LOCATION: (2)..(7)
<223> OTHER INFORMATION: cyclic
<220> FEATURE:
<221> NAME/KEY: MOD_RES
<222> LOCATION: (4)..(4)
<223> OTHER INFORMATION: NMePhe
<220> FEATURE:
<221> NAME/KEY: MOD_RES
<222> LOCATION: (6)..(6)
<223> OTHER INFORMATION: D-Trp

<400> SEQUENCE: 134

Xaa Xaa Met Phe Tyr Trp Lys
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: MOD_RES
<222> LOCATION: (2)..(2)
<223> OTHER INFORMATION: D-Cys
<220> FEATURE:
<223> OTHER INFORMATION: c-term amidation

<400> SEQUENCE: 135

Xaa Cys Leu Ile Thr Arg Cys Arg Tyr
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(Trimethylammonium)-3-cyano-benzoyl-Ava
<220> FEATURE:
<221> NAME/KEY: MOD_RES
<222> LOCATION: (2)..(2)
<223> OTHER INFORMATION: D-Cys
<220> FEATURE:
<223> OTHER INFORMATION: c-term amidation

<400> SEQUENCE: 136

Xaa Cys Leu Ile Val Arg Cys Arg Tyr
1               5

<210> SEQ ID NO 137
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 137

Arg Xaa Gln Trp Ala Val Gly His Xaa Leu
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 138

Arg Xaa Gln Trp Ala Val Gly His Xaa Leu
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
```

```
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 139

Arg Xaa Gln Trp Ala Val Gly His Xaa Leu
1               5                   10

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-1,4-cis-Achc
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 140

Xaa Gln Trp Ala Val Gly His Xaa Leu
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 141

Gln Trp Ala Val Gly His Xaa Leu
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: 4-[18]Fluoro-3-cyano-benzoyl-AOC
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 142

Xaa Gln Trp Ala Val Gly His Xaa Leu
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 143

Xaa Gln Trp Ala Val Gly His Xaa Xaa
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: FA4-Am,5-MeHpA
<220> FEATURE:
<223> OTHER INFORMATION: c-term amidation

<400> SEQUENCE: 144
```

```
Xaa Gln Trp Ala Val Gly His Xaa Leu
1               5
```

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 145

```
Xaa Gln Trp Ala Val Gly His Xaa Leu
1               5
```

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Lys(Me)2
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 146

```
Lys Ala Gln Trp Ala Val Gly His Xaa Leu
1               5                   10
```

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Lys(Me)2
<220> FEATURE:
<221> NAME/KEY: MOD_RES
<222> LOCATION: (2)..(2)
<223> OTHER INFORMATION: beta-Ala
<220> FEATURE:

```
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 147

Lys Ala Gln Trp Ala Val Gly His Xaa Leu
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Arg
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 148

Arg Ser Gln Trp Ala Val Gly His Xaa Leu
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ser
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 149

Ser Ser Gln Trp Ala Val Gly His Xaa Leu
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: 4-[18]Fluoro-3-cyano-benzoyl-Lys(Me)2
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 150

Lys Ser Gln Trp Ala Val Gly Xaa Xaa Leu
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Arg
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 151

Arg Ser Gln Trp Ala Val Gly His Xaa Leu
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Lys(Me)2
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 152

Lys Ala Gln Trp Ala Val Gly His Xaa Leu
1               5                   10
```

```
<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ava
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 153

Xaa Gln Trp Ala Val Gly His Xaa Leu
1               5

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-trifluoromethyl-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 154

Arg Xaa Gln Trp Ala Val Gly His Xaa Leu
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-trifluoromethyl-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
```

```
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 155

Arg Xaa Gln Trp Ala Val Gly His Xaa Leu
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-trifluoromethyl-benzoyl-1,4-
      cis-Achc
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 156

Xaa Gln Trp Ala Val Gly His Xaa Leu
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-trifluoromethyl-benzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 157

Gln Trp Ala Val Gly His Xaa Leu
1               5

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-trifluoromethyl-benzoyl-Arg
```

```
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 158

Arg Ala Gln Trp Ala Val Gly His Xaa Leu
1               5                   10

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]-Fluoro-3-cyano-benzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 159

Xaa Gln Trp Ala Val Gly His Xaa Xaa
1               5

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]-Fluoro-3-cyano-benzoyl-Ser
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 160
```

```
Ser Ser Gln Trp Ala Val Gly His Xaa Leu
1               5                   10

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]-Fluoro-3-cyano-benzoyl-DOA
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 161

Xaa Gln Trp Ala Val Gly His Xaa Leu
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 162

Xaa Gln Trp Ala Val Gly His Xaa Leu
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: (R)-Fmoc-4-amino-5-methyl-hexanoic acid
```

```
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 163

Xaa Gln Trp Ala Val Gly His Xaa Xaa
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 164

Xaa Gln Trp Ala Val Gly His Xaa Gly
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 165

Xaa Gln Trp Ala Val Gly His Xaa Leu
1               5

<210> SEQ ID NO 166
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: tBuGly
<220> FEATURE:
<223> OTHER INFORMATION: c-term amidation

<400> SEQUENCE: 166

Xaa Gln Trp Ala Val Gly His Xaa Gly
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 167

Xaa Gln Trp Ala Val Gly His Xaa Leu
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
```

```
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 168

Xaa Gln Trp Ala Val Gly His Xaa Leu
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 169

Xaa Gln Trp Ala Val Gly His Xaa Gly
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (8)..(8)
<223> OTHER INFORMATION: 4-Am-5-MeHxA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 170

Xaa Gln Trp Ala Val Gly His Xaa Xaa
1               5

<210> SEQ ID NO 171
<211> LENGTH: 9
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 171

Xaa Gln Trp Ala Val Gly His Xaa Xaa
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: tbuAla
<220> FEATURE:
<223> OTHER INFORMATION: c-term amidation

<400> SEQUENCE: 172

Xaa Gln Trp Ala Val Gly His Xaa Ala
1               5

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Arg
<220> FEATURE:
<221> NAME/KEY: MOD_RES
<222> LOCATION: (2)..(2)
<223> OTHER INFORMATION: Ava
```

```
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 173

Arg Xaa Gln Trp Ala Val Gly His Xaa Leu
1               5                   10

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 174

Gln Trp Ala Val Gly His Xaa Leu
1               5

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 175

Arg Xaa Gln Trp Ala Val Gly His Xaa Leu
1               5                   10
```

```
<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 176

Arg Xaa Gln Trp Ala Val Gly His Xaa Leu
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (9)..(9)
<223> OTHER INFORMATION: His(3Me)
<220> FEATURE:
<221> NAME/KEY: MOD_RES
<222> LOCATION: (10)..(10)
<223> OTHER INFORMATION: Sta
<220> FEATURE:
<223> OTHER INFORMATION: c-term amidation

<400> SEQUENCE: 177

Arg Ala Arg Gln Trp Ala Val Gly His Xaa Leu
1               5                   10

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (7)..(7)
<223> OTHER INFORMATION: His(3Me)
```

```
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 178

Xaa Gln Trp Ala Val Gly His Xaa Xaa
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: tBuGly
<220> FEATURE:
<223> OTHER INFORMATION: c-term amidation

<400> SEQUENCE: 179

Xaa Gln Trp Ala Val Gly His Xaa Gly
1               5

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Arg
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 180

Arg Arg Gln Trp Ala Val Gly His Xaa Leu
1               5                   10
```

```
<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 181

Arg Ala Gln Trp Ala Val Gly His Xaa Leu
1               5                   10

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 182

Gln Trp Ala Val Gly His Xaa Leu
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
```

```
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 183

Xaa Gln Trp Ala Val Gly His Xaa Xaa
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 184

Xaa Gln Trp Ala Val Gly His Xaa Leu
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 185

Xaa Gln Trp Ala Val Gly His Xaa Xaa
1               5
```

-continued

```
<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (7)..(7)
<223> OTHER INFORMATION: NMeHis(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 186

Xaa Gln Trp Ala Val Gly His Xaa Leu
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 187

Xaa Gln Trp Ala Val Gly His Xaa Leu
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: AHMHxA
<220> FEATURE:
<223> OTHER INFORMATION: c-term amidation

<400> SEQUENCE: 188
```

Xaa Gln Trp Ala Val Gly His Xaa Leu
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (8)..(8)
<223> OTHER INFORMATION: Tha
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 189

Xaa Gln Trp Ala Val Ala His Xaa Xaa
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 190

Xaa Gln Trp Ala Val Ala His Phe Xaa
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<223> OTHER INFORMATION: c-term amidation

<400> SEQUENCE: 191

Xaa Gln Trp Ala Val Ala His Phe Leu
1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: D-His
<220> FEATURE:
<223> OTHER INFORMATION: c-term amidation

<400> SEQUENCE: 192

Xaa Gln Trp Ala Val Ala His Phe Leu
1               5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: beta-hLeu
<220> FEATURE:
<223> OTHER INFORMATION: c-term amidation

<400> SEQUENCE: 193

Xaa Gln Trp Ala Val Ala His Leu Leu
1               5

<210> SEQ ID NO 194
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: beta-hIle
<220> FEATURE:
<223> OTHER INFORMATION: c-term amidation

<400> SEQUENCE: 194

Xaa Gln Trp Ala Val Ala His Ile Leu
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: beta-hLeu
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 195

Xaa Gln Trp Ala Val Ala His Leu Gly
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (9)..(9)
<223> OTHER INFORMATION: Tha
```

```
<220> FEATURE:
<223> OTHER INFORMATION: c-term amidation

<400> SEQUENCE: 196

Xaa Gln Trp Ala Val Ala His Phe Xaa
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (9)..(9)
<223> OTHER INFORMATION: Nle
<220> FEATURE:
<223> OTHER INFORMATION: c-term amidation

<400> SEQUENCE: 197

Xaa Gln Trp Ala Val Ala His Phe Xaa
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 198

Xaa Gln Trp Ala Val Ala His Phe Gly
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (8)..(8)
<223> OTHER INFORMATION: Tha
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 199

Xaa Gln Trp Ala Val Ala His Xaa Gly
1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Tha
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 200

Xaa Gln Trp Ala Val Ala His Xaa Gly
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
```

```
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 201

Xaa Gln Trp Ala Val Ala His Phe Xaa
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (5)..(5)
<223> OTHER INFORMATION: NMeVal
<220> FEATURE:
<221> NAME/KEY: MOD_RES
<222> LOCATION: (6)..(6)
<223> OTHER INFORMATION: beta-Ala
<220> FEATURE:
<223> OTHER INFORMATION: c-term amidation

<400> SEQUENCE: 202

Xaa Gln Trp Ala Val Ala His Phe Leu
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: NMePhe
<220> FEATURE:
<223> OTHER INFORMATION: c-term amidation

<400> SEQUENCE: 203

Xaa Gln Trp Ala Val Ala His Phe Leu
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (6)..(6)
<223> OTHER INFORMATION: beta-Ala
<220> FEATURE:
<223> OTHER INFORMATION: c-term amidation

<400> SEQUENCE: 204

Xaa Gln Trp Ala Val Ala His Phe Leu
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: beta-Ala
<220> FEATURE:
<223> OTHER INFORMATION: c-term amidation

<400> SEQUENCE: 205

Xaa Gln Xaa Ala Val Ala His Phe Leu
1               5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (5)..(5)
<223> OTHER INFORMATION: D-Val
<220> FEATURE:
<221> NAME/KEY: MOD_RES
<222> LOCATION: (6)..(6)
<223> OTHER INFORMATION: beta-Ala
<220> FEATURE:
<223> OTHER INFORMATION: c-term amidation

<400> SEQUENCE: 206

Xaa Gln Trp Ala Val Ala His Phe Leu
1               5

<210> SEQ ID NO 207
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: D-Phe
<220> FEATURE:
<223> OTHER INFORMATION: c-term amidation

<400> SEQUENCE: 207

Xaa Gln Trp Ala Val Ala His Phe Leu
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[18]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: beta-hIle
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 208

Xaa Gln Trp Ala Val Ala His Ile Gly
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]-Fluoro-3-cyano-phenylsulfonyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: Cpa
```

```
<220> FEATURE:
<223> OTHER INFORMATION: c-term amidation

<400> SEQUENCE: 209

Xaa Gln Trp Ala Val Gly His Xaa Xaa
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]-Fluoro-3-cyano-phenylsulfonyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 210

Xaa Gln Trp Ala Val Gly His Xaa Xaa
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]-Fluoro-3-cyano-phenylsulfonyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: tbuAla
<220> FEATURE:
<223> OTHER INFORMATION: c-term amidation

<400> SEQUENCE: 211

Xaa Gln Trp Ala Val Gly His Xaa Ala
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 4-[18]-Fluoro-3-cyano-phenylsulfonyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: tbuAla
<220> FEATURE:
<223> OTHER INFORMATION: c-term amidation

<400> SEQUENCE: 212

Xaa Gln Trp Ala Val Gly His Xaa Xaa
1               5

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-(piperidyl-4-
      carbonyl)-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 213

Gln Trp Ala Val Gly His Xaa Leu
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-(piperazin-1-yl-
      acetyl)-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 214

Gln Trp Ala Val Gly His Xaa Leu
```

```
1               5
```

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-1,4-trans-Achc
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 215

```
Xaa Gln Trp Ala Val Gly His Xaa Leu
1               5
```

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 216

```
Arg Xaa Gln Trp Ala Val Gly His Xaa Leu
1               5                   10
```

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES

```
<222> LOCATION: (7)..(7)
<223> OTHER INFORMATION: His(Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 217

Arg Xaa Gln Trp Ala Val His Xaa Leu
1               5

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 218

Arg Xaa Gln Trp Ala Val Gly His Xaa Leu
1               5                   10

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-1,4-cis-Achc
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 219

Xaa Gln Trp Ala Val Gly His Xaa Leu
1               5

<210> SEQ ID NO 220
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 220

Gln Trp Ala Val Gly His Xaa Leu
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-AOC
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 221

Xaa Gln Trp Ala Val Gly His Xaa Leu
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
```

```
<222> LOCATION: (9)..(9)
<223> OTHER INFORMATION: Cpa
<220> FEATURE:
<223> OTHER INFORMATION: c-term amidation

<400> SEQUENCE: 222

Xaa Gln Trp Ala Val Gly His Xaa Xaa
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 223

Xaa Gln Trp Ala Val Gly His Xaa Leu
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 224

Xaa Gln Trp Ala Val Gly His Xaa Leu
1               5

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Lys(Me)2
<220> FEATURE:
<221> NAME/KEY: MOD_RES
```

```
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 225

Lys Ala Gln Trp Ala Val Gly His Xaa Leu
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Lys(Me)2
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 226

Lys Ala Gln Trp Ala Val Gly His Xaa Leu
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Arg
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 227

Arg Ser Gln Trp Ala Val Gly His Xaa Leu
1               5                   10

<210> SEQ ID NO 228
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Ser
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 228

Ser Ser Gln Trp Ala Val Gly His Xaa Leu
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Lys(Me)2
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 229

Lys Ser Gln Trp Ala Val Gly His Xaa Leu
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Arg
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 230

Arg Ser Gln Trp Ala Val Gly His Xaa Leu
```

-continued

```
<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Lys(Me)2
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 231

Lys Ala Gln Trp Ala Val Gly His Xaa Leu
1               5                   10

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Ava
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 232

Xaa Gln Trp Ala Val Gly His Xaa Leu
1               5

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-trifluoromethyl-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
```

```
<222> LOCATION: (9)..(9)
<223> OTHER INFORMATION: Sta
<220> FEATURE:
<223> OTHER INFORMATION: c-term amidation

<400> SEQUENCE: 233

Arg Xaa Gln Trp Ala Val Gly His Xaa Leu
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-trifluoromethyl-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 234

Arg Xaa Gln Trp Ala Val Gly His Xaa Leu
1               5                   10

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-trifluoromethyl-benzoyl-1,4-
      cis-Achc
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 235

Xaa Gln Trp Ala Val Gly His Xaa Leu
1               5

<210> SEQ ID NO 236
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-trifluoromethyl-benzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 236

Gln Trp Ala Val Gly His Xaa Leu
1               5

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-trifluoromethyl-benzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: 4-Am,5-MeHpA
<220> FEATURE:
<223> OTHER INFORMATION: c-term amidation

<400> SEQUENCE: 237

Arg Ala Gln Trp Ala Val Gly His Xaa Leu
1               5                   10

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
```

```
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 238

Xaa Gln Trp Ala Val Gly His Xaa Xaa
1               5

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-Ser
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 239

Ser Ser Gln Trp Ala Val Gly His Xaa Leu
1               5                   10

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-benzoyl-DOA
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 240

Xaa Gln Trp Ala Val Gly His Xaa Leu
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
```

```
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 241

Xaa Gln Trp Ala Val Gly His Xaa Leu
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: (R)-Fmoc-4-amino-5-methyl-hexanoic acid
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 242

Xaa Gln Trp Ala Val Gly His Xaa Xaa
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 243

Xaa Gln Trp Ala Val Gly His Xaa Gly
1               5
```

```
<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 244

Xaa Gln Trp Ala Val Gly His Xaa Leu
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: tBuGly
<220> FEATURE:
<223> OTHER INFORMATION: c-term amidation

<400> SEQUENCE: 245

Xaa Gln Trp Ala Val Gly His Xaa Gly
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
```

```
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 246

Xaa Gln Trp Ala Val Gly His Xaa Leu
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 247

Xaa Gln Trp Ala Val Gly His Xaa Leu
1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 248

Xaa Gln Trp Ala Val Gly His Xaa Gly
1               5
```

```
<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (8)..(8)
<223> OTHER INFORMATION: 4-Am-5-MeHxA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 249

Xaa Gln Trp Ala Val Gly His Xaa Xaa
1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 250

Xaa Gln Trp Ala Val Gly His Xaa Xaa
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
```

```
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: tbuAla
<220> FEATURE:
<223> OTHER INFORMATION: c-term amidation

<400> SEQUENCE: 251

Xaa Gln Trp Ala Val Gly His Xaa Ala
1               5

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 252

Arg Xaa Gln Trp Ala Val Gly His Xaa Leu
1               5                   10

<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 253

Gln Trp Ala Val Gly His Xaa Leu
1               5
```

```
<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 254

Arg Xaa Gln Trp Ala Val Gly His Xaa Leu
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 255

Arg Xaa Gln Trp Ala Val Gly His Xaa Leu
1               5                   10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Arg
<220> FEATURE:
```

```
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (9)..(9)
<223> OTHER INFORMATION: His(3Me)
<220> FEATURE:
<221> NAME/KEY: MOD_RES
<222> LOCATION: (10)..(10)
<223> OTHER INFORMATION: Sta
<220> FEATURE:
<223> OTHER INFORMATION: c-term amidation

<400> SEQUENCE: 256

Arg Xaa Arg Gln Trp Ala Val Gly His Xaa Leu
1               5                   10

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 257

Xaa Gln Trp Ala Val Gly His Xaa Xaa
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: tBuGly
<220> FEATURE:
<223> OTHER INFORMATION: c-term amidation

<400> SEQUENCE: 258
```

```
Xaa Gln Trp Ala Val Gly His Xaa Gly
1               5
```

```
<210> SEQ ID NO 259
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Arg
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 259

Arg Arg Gln Trp Ala Val Gly His Xaa Leu
1               5                   10
```

```
<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 260

Arg Ala Gln Trp Ala Val Gly His Xaa Leu
1               5                   10
```

```
<210> SEQ ID NO 261
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: 3,4-[19]-Difluorobenzoyl-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: 4-Am,5-MeHpA
<220> FEATURE:
<223> OTHER INFORMATION: c-term amidation

<400> SEQUENCE: 261

Gln Trp Ala Val Gly His Xaa Leu
1               5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 262

Xaa Gln Trp Ala Val Gly His Xaa Xaa
1               5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 263
```

```
Xaa Gln Trp Ala Val Gly His Xaa Leu
1               5
```

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 264

```
Xaa Gln Trp Ala Val Gly His Xaa Xaa
1               5
```

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (7)..(7)
<223> OTHER INFORMATION: NMeHis(3Me)
<220> FEATURE:
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 265

```
Xaa Gln Trp Ala Val Gly His Xaa Leu
1               5
```

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (7)..(7)
<223> OTHER INFORMATION: NMeHis
<220> FEATURE:

```
<221> NAME/KEY: MOD_RES
<222> LOCATION: (8)..(8)
<223> OTHER INFORMATION: 4-Am,5-MeHpA
<220> FEATURE:
<223> OTHER INFORMATION: c-term amidation

<400> SEQUENCE: 266

Xaa Gln Trp Ala Val Gly His Xaa Leu
1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: AHMHxA
<220> FEATURE:
<223> OTHER INFORMATION: c-term amidation

<400> SEQUENCE: 267

Xaa Gln Trp Ala Val Gly His Xaa Leu
1               5

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (8)..(8)
<223> OTHER INFORMATION: Tha
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 268

Xaa Gln Trp Ala Val Ala His Xaa Xaa
1               5

<210> SEQ ID NO 269
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 269

Xaa Gln Trp Ala Val Ala His Phe Xaa
1               5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<223> OTHER INFORMATION: c-term amidation

<400> SEQUENCE: 270

Xaa Gln Trp Ala Val Ala His Phe Leu
1               5

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: D-His
<220> FEATURE:
<223> OTHER INFORMATION: c-term amidation

<400> SEQUENCE: 271
```

```
Xaa Gln Trp Ala Val Ala His Phe Leu
1               5
```

```
<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: beta-hLeu
<220> FEATURE:
<223> OTHER INFORMATION: c-term amidation

<400> SEQUENCE: 272

Xaa Gln Trp Ala Val Ala His Leu Leu
1               5
```

```
<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: beta-hIle
<220> FEATURE:
<223> OTHER INFORMATION: c-term amidation

<400> SEQUENCE: 273

Xaa Gln Trp Ala Val Ala His Xaa Leu
1               5
```

```
<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: beta-hLeu
<220> FEATURE:
```

```
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 274

Xaa Gln Trp Ala Val Ala His Leu Gly
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (9)..(9)
<223> OTHER INFORMATION: Tha
<220> FEATURE:
<223> OTHER INFORMATION: c-term amidation

<400> SEQUENCE: 275

Xaa Gln Trp Ala Val Ala His Phe Xaa
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (9)..(9)
<223> OTHER INFORMATION: Nle
<220> FEATURE:
<223> OTHER INFORMATION: c-term amidation

<400> SEQUENCE: 276

Xaa Gln Trp Ala Val Ala His Phe Xaa
1               5

<210> SEQ ID NO 277
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 277

Xaa Gln Trp Ala Val Ala His Phe Gly
1               5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: NMeHis
<220> FEATURE:
<221> NAME/KEY: MOD_RES
<222> LOCATION: (8)..(8)
<223> OTHER INFORMATION: Tha
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 278

Xaa Gln Trp Ala Val Ala His Xaa Gly
1               5

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
```

```
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (8)..(8)
<223> OTHER INFORMATION: Tha
<220> FEATURE:
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 279

Xaa Gln Trp Ala Val Ala His Xaa Gly
1               5

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (7)..(7)
<223> OTHER INFORMATION: His(3Me)
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 280

Xaa Gln Trp Ala Val Ala His Phe Xaa
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (5)..(5)
<223> OTHER INFORMATION: NMeVal
<220> FEATURE:
<221> NAME/KEY: MOD_RES
<222> LOCATION: (6)..(6)
<223> OTHER INFORMATION: beta-Ala
<220> FEATURE:
<223> OTHER INFORMATION: c-term amidation

<400> SEQUENCE: 281

Xaa Gln Trp Ala Val Ala His Phe Leu
1               5
```

```
<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: NMePhe
<220> FEATURE:
<223> OTHER INFORMATION: c-term amidation

<400> SEQUENCE: 282

Xaa Gln Trp Ala Val Ala His Phe Leu
1               5

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (6)..(6)
<223> OTHER INFORMATION: beta-Ala
<220> FEATURE:
<223> OTHER INFORMATION: c-term amidation

<400> SEQUENCE: 283

Xaa Gln Trp Ala Val Ala His Phe Leu
1               5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (6)..(6)
<223> OTHER INFORMATION: beta-Ala
<220> FEATURE:
<223> OTHER INFORMATION: c-term amidation

<400> SEQUENCE: 284
```

```
Xaa Gln Trp Ala Val Ala His Phe Leu
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (5)..(5)
<223> OTHER INFORMATION: D-Val
<220> FEATURE:
<221> NAME/KEY: MOD_RES
<222> LOCATION: (6)..(6)
<223> OTHER INFORMATION: beta-Ala
<220> FEATURE:
<223> OTHER INFORMATION: c-term amidation

<400> SEQUENCE: 285

Xaa Gln Trp Ala Val Ala His Phe Leu
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: D-Phe
<220> FEATURE:
<223> OTHER INFORMATION: c-term amidation

<400> SEQUENCE: 286

Xaa Gln Trp Ala Val Ala His Phe Leu
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3,4-[19]-Difluorobenzoyl-Ava
<220> FEATURE:
<221> NAME/KEY: MOD_RES
<222> LOCATION: (6)..(6)
<223> OTHER INFORMATION: beta-Ala
<220> FEATURE:
<221> NAME/KEY: MOD_RES
<222> LOCATION: (8)..(8)
<223> OTHER INFORMATION: beta-hIle
<220> FEATURE:
```

```
<221> NAME/KEY: MOD_RES
<222> LOCATION: (9)..(9)
<223> OTHER INFORMATION: tbuGly
<220> FEATURE:
<223> OTHER INFORMATION: c-term amidation

<400> SEQUENCE: 287

Xaa Gln Trp Ala Val Ala His Ile Gly
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-phenylsulfonyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 288

Xaa Gln Trp Ala Val Gly His Xaa Xaa
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-phenylsulfonyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: Cpa
<220> FEATURE:
<223> OTHER INFORMATION: c-term amidation

<400> SEQUENCE: 289

Xaa Gln Trp Ala Val Gly His Xaa Xaa
1               5

<210> SEQ ID NO 290
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-phenylsulfonyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: Sta
<220> FEATURE:
<221> NAME/KEY: MOD_RES
<222> LOCATION: (9)..(9)
<223> OTHER INFORMATION: tbuAla
<220> FEATURE:
<223> OTHER INFORMATION: c-term amidation

<400> SEQUENCE: 290

Xaa Gln Trp Ala Val Gly His Xaa Xaa
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]-Fluoro-3-cyano-phenylsulfonyl-Ava
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: 4-Am,5-MeHpA
<220> FEATURE:
<221> NAME/KEY: MOD_RES
<222> LOCATION: (9)..(9)
<223> OTHER INFORMATION: tbuAla
<220> FEATURE:
<223> OTHER INFORMATION: c-term amidation

<400> SEQUENCE: 291

Xaa Gln Trp Ala Val Gly His Xaa Xaa
1               5

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]Fluoro-3-cyano-benzoyl-(piperidyl-4-
      carbonyl)-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
```

```
<220> FEATURE:
<223> OTHER INFORMATION: c-term amidation

<400> SEQUENCE: 292

Gln Trp Ala Val Gly His Xaa Leu
1               5

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]Fluoro-3-cyano-benzoyl-(piperazin-1-yl-
      acetyl)-Gln
<220> FEATURE:
<221> NAME/KEY: MOD_RES
<222> LOCATION: (6)..(6)
<223> OTHER INFORMATION: His(3Me)
<220> FEATURE:
<221> NAME/KEY: MOD_RES
<222> LOCATION: (7)..(7)
<223> OTHER INFORMATION: Sta
<220> FEATURE:
<223> OTHER INFORMATION: c-term amidation

<400> SEQUENCE: 293

Gln Trp Ala Val Gly His Xaa Leu
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]Fluoro-3-cyano-benzoyl-1,4-trans-Achc
<220> FEATURE:
<221> NAME/KEY: MOD_RES
<222> LOCATION: (6)..(6)
<223> OTHER INFORMATION: NMeGly
<220> FEATURE:
<221> NAME/KEY: MOD_RES
<222> LOCATION: (8)..(8)
<223> OTHER INFORMATION: Sta
<220> FEATURE:
<223> OTHER INFORMATION: c-term amidation

<400> SEQUENCE: 294

Xaa Gln Trp Ala Val Gly His Xaa Leu
1               5

<210> SEQ ID NO 295
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ava
<220> FEATURE:
<221> NAME/KEY: misc_feature
<222> LOCATION: (2)..(7)
```

```
<223> OTHER INFORMATION: cyclic
<220> FEATURE:
<221> NAME/KEY: MOD_RES
<222> LOCATION: (3)..(3)
<223> OTHER INFORMATION: NMePhe
<220> FEATURE:
<221> NAME/KEY: MOD_RES
<222> LOCATION: (4)..(4)
<223> OTHER INFORMATION: 1-Nal
<220> FEATURE:
<221> NAME/KEY: MOD_RES
<222> LOCATION: (5)..(5)
<223> OTHER INFORMATION: D-Trp

<400> SEQUENCE: 295

Xaa Lys Phe Xaa Trp Lys Thr
1               5

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ava
<220> FEATURE:
<221> NAME/KEY: MOD_RES
<222> LOCATION: (2)..(2)
<223> OTHER INFORMATION: Dpr
<220> FEATURE:
<221> NAME/KEY: misc_feature
<222> LOCATION: (2)..(7)
<223> OTHER INFORMATION: cyclic
<220> FEATURE:
<221> NAME/KEY: MOD_RES
<222> LOCATION: (4)..(4)
<223> OTHER INFORMATION: NMePhe
<220> FEATURE:
<221> NAME/KEY: MOD_RES
<222> LOCATION: (6)..(6)
<223> OTHER INFORMATION: D-Trp

<400> SEQUENCE: 296

Xaa Xaa Met Phe Tyr Trp Lys
1               5

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]Fluoro-3-cyano-benzoyl-Ava
<220> FEATURE:
<221> NAME/KEY: misc_feature
<222> LOCATION: (2)..(7)
<223> OTHER INFORMATION: cyclic
<220> FEATURE:
<221> NAME/KEY: MOD_RES
<222> LOCATION: (3)..(3)
<223> OTHER INFORMATION: NMePhe
<220> FEATURE:
<221> NAME/KEY: MOD_RES
<222> LOCATION: (4)..(4)
<223> OTHER INFORMATION: 1-Nal
<220> FEATURE:
<221> NAME/KEY: MOD_RES
<222> LOCATION: (5)..(5)
```

```
<223> OTHER INFORMATION: D-Trp

<400> SEQUENCE: 297

Xaa Lys Phe Xaa Trp Lys Thr
1               5

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]Fluoro-3-cyano-benzoyl-Ava
<220> FEATURE:
<221> NAME/KEY: MOD_RES
<222> LOCATION: (2)..(2)
<223> OTHER INFORMATION: Dpr
<220> FEATURE:
<221> NAME/KEY: misc_feature
<222> LOCATION: (2)..(7)
<223> OTHER INFORMATION: cyclic
<220> FEATURE:
<221> NAME/KEY: MOD_RES
<222> LOCATION: (4)..(4)
<223> OTHER INFORMATION: NMePhe
<220> FEATURE:
<221> NAME/KEY: MOD_RES
<222> LOCATION: (6)..(6)
<223> OTHER INFORMATION: D-Trp

<400> SEQUENCE: 298

Xaa Xaa Met Phe Tyr Trp Lys
1               5

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ava
<220> FEATURE:
<221> NAME/KEY: MOD_RES
<222> LOCATION: (2)..(2)
<223> OTHER INFORMATION: D-Cys
<220> FEATURE:
<223> OTHER INFORMATION: c-term amidation

<400> SEQUENCE: 299

Xaa Cys Leu Ile Thr Arg Cys Arg Tyr
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[18]Fluoro-3-cyano-benzoyl-Ava
<220> FEATURE:
<221> NAME/KEY: MOD_RES
<222> LOCATION: (2)..(2)
```

```
<223> OTHER INFORMATION: D-Cys
<220> FEATURE:
<223> OTHER INFORMATION: c-term amidation

<400> SEQUENCE: 300

Xaa Cys Leu Ile Val Arg Cys Arg Tyr
1               5

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]Fluoro-3-cyano-benzoyl-Ava
<220> FEATURE:
<221> NAME/KEY: MOD_RES
<222> LOCATION: (2)..(2)
<223> OTHER INFORMATION: D-Cys
<220> FEATURE:
<223> OTHER INFORMATION: c-term amidation

<400> SEQUENCE: 301

Xaa Cys Leu Ile Thr Arg Cys Arg Tyr
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-[19]Fluoro-3-cyano-benzoyl-Ava
<220> FEATURE:
<221> NAME/KEY: MOD_RES
<222> LOCATION: (2)..(2)
<223> OTHER INFORMATION: D-Cys
<220> FEATURE:
<223> OTHER INFORMATION: c-term amidation

<400> SEQUENCE: 302

Xaa Cys Leu Ile Val Arg Cys Arg Tyr
1               5

<210> SEQ ID NO 303
<211> LENGTH: 40
<212> TYPE: DNA
<213> ORGANISM: Artificial Sequence
<220> FEATURE:
<223> OTHER INFORMATION: Description of DNA/RNA hybrid sequence:
      Synthetic oligonucleotide
<220> FEATURE:
<223> OTHER INFORMATION: Description of Artificial Sequence: Synthetic
      oligonucleotide

<400> SEQUENCE: 303
gggaggacgc gucgccguaa uggauguuuu gcucccuggt                          40

<210> SEQ ID NO 304
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                              peptide
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 304

Arg Xaa Gln Trp Ala Val Gly His Xaa Leu
1               5                   10

<210> SEQ ID NO 305
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2-chloro-benzoyl)-Trp
<220> FEATURE:
<223> OTHER INFORMATION: c-term amidation

<400> SEQUENCE: 305

Trp Ala Val Leu
1

<210> SEQ ID NO 306
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp(BOC)
<220> FEATURE:
<223> OTHER INFORMATION: c-term amidation

<400> SEQUENCE: 306

Trp Ala Val Leu
1

<210> SEQ ID NO 307
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(4-Fluoro-2-chloro-benzoyl)-Trp
<220> FEATURE:
<223> OTHER INFORMATION: c-term amidation

<400> SEQUENCE: 307

Trp Ala Val Leu
1
```

<210> SEQ ID NO 308
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Arg
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 308

Arg Ala His Leu
1

<210> SEQ ID NO 309
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg(Pbf)
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 309

Arg Ala His Leu
1

<210> SEQ ID NO 310
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(4-Fluoro-3-cyano-benzoyl)-Arg
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 310

Arg Ala His Leu
1

<210> SEQ ID NO 311
<211> LENGTH: 4
<212> TYPE: PRT
<213> ORGANISM: Artificial Sequence
<220> FEATURE:
<223> OTHER INFORMATION: Description of Artificial Sequence: Synthetic

```
                                    peptide
<220> FEATURE:
<221> NAME/KEY: MOD_RES
<222> LOCATION: (1)..(1)
<223> OTHER INFORMATION: (4-Trimethylammonium-3-fluoro-benzoyl)-Gly
<220> FEATURE:
<223> OTHER INFORMATION: c-term amidation

<400> SEQUENCE: 311

Gly Thr Tyr Ala
1

<210> SEQ ID NO 312
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr(O-tBu)
<220> FEATURE:
<221> NAME/KEY: MOD_RES
<222> LOCATION: (3)..(3)
<223> OTHER INFORMATION: Tyr(O-tBu)
<220> FEATURE:
<223> OTHER INFORMATION: c-term amidation

<400> SEQUENCE: 312

Gly Thr Tyr Ala
1

<210> SEQ ID NO 313
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (3-Fluoro-4-[18F]-fluoro-benzoyl)-Gly
<220> FEATURE:
<223> OTHER INFORMATION: c-term amidation

<400> SEQUENCE: 313

Gly Thr Tyr Ala
1

<210> SEQ ID NO 314
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2-fluoro-benzoyl)-Lys(N-
      dimethyl)
<220> FEATURE:
<223> OTHER INFORMATION: c-term amidation

<400> SEQUENCE: 314

Lys Ala Gly Leu
1

<210> SEQ ID NO 315
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(N-dimethyl)
<220> FEATURE:
<223> OTHER INFORMATION: c-term amidation

<400> SEQUENCE: 315

Lys Ala Gly Leu
1

<210> SEQ ID NO 316
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (2-Fluoro-4-[18F]-fluoro-benzoyl)-Lys(N-
      dimethyl)
<220> FEATURE:
<223> OTHER INFORMATION: c-term amidation

<400> SEQUENCE: 316

Lys Ala Gly Leu
1

<210> SEQ ID NO 317
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2.3-difluoro-benzoyl)-Val
<220> FEATURE:
<223> OTHER INFORMATION: c-term amidation

<400> SEQUENCE: 317

Val Arg Ser Gly
1

<210> SEQ ID NO 318
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg(Pbf)
<220> FEATURE:
<221> NAME/KEY: MOD_RES
<222> LOCATION: (3)..(3)
<223> OTHER INFORMATION: Ser(O-tBu)
<220> FEATURE:
<223> OTHER INFORMATION: c-term amidation

<400> SEQUENCE: 318
```

Val Arg Ser Gly
1

<210> SEQ ID NO 319
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (2.3-Difluoro-4-[18F]-fluoro-benzoyl)-Val
<220> FEATURE:
<223> OTHER INFORMATION: c-term amidation

<400> SEQUENCE: 319

Val Arg Ser Gly
1

<210> SEQ ID NO 320
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-trifluormethyl-benzoyl)-
      Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 320

Val Ala Phe Gly
1

<210> SEQ ID NO 321
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2.6-difluoro-benzoyl)-Gly
<220> FEATURE:
<223> OTHER INFORMATION: c-term amidation

<400> SEQUENCE: 321

Gly Pro Phe Val
1

<210> SEQ ID NO 322
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidation

<400> SEQUENCE: 322

```
Gly Pro Phe Val
1

<210> SEQ ID NO 323
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (2.6-Difluoro-4-[18F]-fluoro-benzoyl)-Gly
<220> FEATURE:
<223> OTHER INFORMATION: c-term amidation

<400> SEQUENCE: 323

Gly Pro Phe Val
1

<210> SEQ ID NO 324
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2-bromo-benzoyl)-Gly
<220> FEATURE:
<223> OTHER INFORMATION: c-term amidation

<400> SEQUENCE: 324

Gly Phe Ile Gly
1

<210> SEQ ID NO 325
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidation

<400> SEQUENCE: 325

Gly Phe Ile Gly
1

<210> SEQ ID NO 326
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(2-Bromo-4-fluoro-benzoyl)-Gly
<220> FEATURE:
<223> OTHER INFORMATION: c-term amidation

<400> SEQUENCE: 326

Gly Phe Ile Gly
1
```

```
<210> SEQ ID NO 327
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2-nitro-benzoyl)-Ser
<220> FEATURE:
<223> OTHER INFORMATION: c-term amidation

<400> SEQUENCE: 327

Ser Thr Val Gly
1

<210> SEQ ID NO 328
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser(O-tBu)
<220> FEATURE:
<221> NAME/KEY: MOD_RES
<222> LOCATION: (2)..(2)
<223> OTHER INFORMATION: Thr(O-tBu)
<220> FEATURE:
<223> OTHER INFORMATION: c-term amidation

<400> SEQUENCE: 328

Ser Thr Val Gly
1

<210> SEQ ID NO 329
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(2-Nitro-4-fluoro-benzoyl)-Ser
<220> FEATURE:
<223> OTHER INFORMATION: c-term amidation

<400> SEQUENCE: 329

Ser Thr Val Gly
1

<210> SEQ ID NO 330
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2-cyano-benzoyl)-Arg
<220> FEATURE:
<223> OTHER INFORMATION: c-term amidation

<400> SEQUENCE: 330
```

Arg Val Gly Phe
1

<210> SEQ ID NO 331
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg(Pbf)
<220> FEATURE:
<223> OTHER INFORMATION: c-term amidation

<400> SEQUENCE: 331

Arg Val Gly Phe
1

<210> SEQ ID NO 332
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(2-Cyano-4-fluoro-benzoyl)-Arg
<220> FEATURE:
<223> OTHER INFORMATION: c-term amidation

<400> SEQUENCE: 332

Arg Val Gly Phe
1

<210> SEQ ID NO 333
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-methanesulfonyl-
      benzoyl)-Gly
<220> FEATURE:
<223> OTHER INFORMATION: c-term amidation

<400> SEQUENCE: 333

Gly Phe Val Leu
1

<210> SEQ ID NO 334
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidation

<400> SEQUENCE: 334

Gly Phe Val Leu
1

```
<210> SEQ ID NO 335
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(3-Methanesulfonyl-4-fluoro-benzoyl)-Gly
<220> FEATURE:
<223> OTHER INFORMATION: c-term amidation

<400> SEQUENCE: 335

Gly Phe Val Leu
1

<210> SEQ ID NO 336
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-nitro-benzoyl)-Thr
<220> FEATURE:
<223> OTHER INFORMATION: c-term amidation

<400> SEQUENCE: 336

Thr Val Phe Leu
1

<210> SEQ ID NO 337
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr(OtBu)
<220> FEATURE:
<223> OTHER INFORMATION: c-term amidation

<400> SEQUENCE: 337

Thr Val Phe Leu
1

<210> SEQ ID NO 338
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(3-Nitro-4-fluoro-benzoyl)-Thr
<220> FEATURE:
<223> OTHER INFORMATION: c-term amidation

<400> SEQUENCE: 338

Thr Val Phe Leu
1
```

```
<210> SEQ ID NO 339
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 339

Val Ala Phe Gly
1

<210> SEQ ID NO 340
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(3-Trifluormethyl-4-fluoro-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 340

Val Ala Phe Gly
1

<210> SEQ ID NO 341
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2-trifluormethyl-benzoyl)-
      Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 341

Val Ala His Gly
1

<210> SEQ ID NO 342
<211> LENGTH: 4
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 342

Val Ala His Gly
1

<210> SEQ ID NO 343
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ([18F]-4-Fluoro-2-trifluormethyl-benzoyl)-Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 343

Val Ala His Gly
1

<210> SEQ ID NO 344
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-trifluormethoxy-
      benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 344

Val Ala Phe Gly
1

<210> SEQ ID NO 345
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 345

Val Ala Phe Gly
1

<210> SEQ ID NO 346
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ([18F]-4-Fluoro-3-trifluormethoxy-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 346

Val Ala Phe Gly
1

<210> SEQ ID NO 347
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (5-Trimethylammonium-2-trifluormethyl-benzoyl)-
      Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 347

Val Ala Trp Gly
1

<210> SEQ ID NO 348
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: Trp(N-Boc)
<220> FEATURE:
<223> OTHER INFORMATION: c-term amidation

<400> SEQUENCE: 348
```

Val Ala Trp Gly
1

<210> SEQ ID NO 349
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ([18F]-5-Fluoro-2-trifluormethyl-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 349

Val Ala Trp Gly
1

<210> SEQ ID NO 350
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (5-Trimethylammonium-2-bromo-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 350

Val Ala Arg Gly
1

<210> SEQ ID NO 351
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: Arg(Pbf)
<220> FEATURE:
<223> OTHER INFORMATION: c-term amidation

<400> SEQUENCE: 351

Val Ala Arg Gly
1

<210> SEQ ID NO 352
<211> LENGTH: 4
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(2-Bromo-5-fluoro-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 352

Val Ala Arg Gly
1

<210> SEQ ID NO 353
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (5-Trimethylammonium-2-methanesulfonyl-
      benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 353

Val Ala Arg Gly
1

<210> SEQ ID NO 354
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: Arg(Pbf)
<220> FEATURE:
<223> OTHER INFORMATION: c-term amidation

<400> SEQUENCE: 354

Val Ala Arg Gly
1

<210> SEQ ID NO 355
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

<223> OTHER INFORMATION: [18F]-(2-Methanesulfonyl-5-fluoro-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 355

Val Ala Arg Gly
1

<210> SEQ ID NO 356
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (5-Trimethylammonium-2-chloro-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 356

Val Ala Arg Gly
1

<210> SEQ ID NO 357
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: Arg(Pbf)
<220> FEATURE:
<223> OTHER INFORMATION: c-term amidation

<400> SEQUENCE: 357

Val Ala Arg Gly
1

<210> SEQ ID NO 358
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(5-Fluoro-2-chloro-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

```
<400> SEQUENCE: 358

Val Ala Arg Gly
1

<210> SEQ ID NO 359
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (2-Nitro-5-trimethylammonium-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 359

Val Ala Phe Gly
1

<210> SEQ ID NO 360
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 360

Val Ala Phe Gly
1

<210> SEQ ID NO 361
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(5-Fluoro-2-nitro-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 361

Val Ala Phe Gly
1

<210> SEQ ID NO 362
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: (2-Chloro-5-methanesulfonyl-4-
      trimethylammonium-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 362

Val Ala Phe Gly
1

<210> SEQ ID NO 363
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 363

Val Xaa Phe Gly
1

<210> SEQ ID NO 364
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(2-Chloro-4-fluoro-5-methanesulfonyl-
      benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 364

Val Ala Phe Gly
1

<210> SEQ ID NO 365
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (5-Trimethylammonium-2-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
```

<223> OTHER INFORMATION: c-term amidation

<400> SEQUENCE: 365

Val Ala Arg Gly
1

<210> SEQ ID NO 366
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: Arg(Pbf)
<220> FEATURE:
<223> OTHER INFORMATION: c-term amidation

<400> SEQUENCE: 366

Val Ala Arg Gly
1

<210> SEQ ID NO 367
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(5-Fluoro-2-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 367

Val Ala Arg Gly
1

<210> SEQ ID NO 368
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-2-chloro-5-fluoro-
      benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 368

Val Ala Phe Gly
1

```
<210> SEQ ID NO 369
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 369

Val Ala Phe Gly
1

<210> SEQ ID NO 370
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(4-Trimethylammonium-2-chloro-5-fluoro-
      benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 370

Val Ala Phe Gly
1

<210> SEQ ID NO 371
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Gly
<220> FEATURE:
<221> NAME/KEY: MOD_RES
<222> LOCATION: (3)..(3)
<223> OTHER INFORMATION: beta-Ala
<220> FEATURE:
<223> OTHER INFORMATION: c-term amidation

<400> SEQUENCE: 371

Gly Tyr Ala Val
1

<210> SEQ ID NO 372
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: Tyr(OtBu)
<220> FEATURE:
<221> NAME/KEY: MOD_RES
<222> LOCATION: (3)..(3)
<223> OTHER INFORMATION: beta-Ala
<220> FEATURE:
<223> OTHER INFORMATION: c-term amidation

<400> SEQUENCE: 372

Gly Tyr Ala Val
1

<210> SEQ ID NO 373
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Gly
<220> FEATURE:
<221> NAME/KEY: MOD_RES
<222> LOCATION: (3)..(3)
<223> OTHER INFORMATION: beta-Ala
<220> FEATURE:
<223> OTHER INFORMATION: c-term amidation

<400> SEQUENCE: 373

Gly Tyr Ala Val
1

<210> SEQ ID NO 374
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Ava
<220> FEATURE:
<221> NAME/KEY: MOD_RES
<222> LOCATION: (2)..(2)
<223> OTHER INFORMATION: His(pi-Me)
<220> FEATURE:
<221> NAME/KEY: MOD_RES
<222> LOCATION: (3)..(3)
<223> OTHER INFORMATION: Sta
<220> FEATURE:
<223> OTHER INFORMATION: c-term amidation

<400> SEQUENCE: 374

Xaa His Xaa Leu
1

<210> SEQ ID NO 375
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:
<221> NAME/KEY: MOD_RES
<222> LOCATION: (2)..(2)
```

```
<223> OTHER INFORMATION: His(pi-Me)
<220> FEATURE:
<221> NAME/KEY: MOD_RES
<222> LOCATION: (3)..(3)
<223> OTHER INFORMATION: Sta
<220> FEATURE:
<223> OTHER INFORMATION: c-term amidation

<400> SEQUENCE: 375

Xaa His Xaa Leu
1

<210> SEQ ID NO 376
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Ava
<220> FEATURE:
<221> NAME/KEY: MOD_RES
<222> LOCATION: (2)..(2)
<223> OTHER INFORMATION: His(pi-Me)
<220> FEATURE:
<221> NAME/KEY: MOD_RES
<222> LOCATION: (3)..(3)
<223> OTHER INFORMATION: Sta
<220> FEATURE:
<223> OTHER INFORMATION: c-term amidation

<400> SEQUENCE: 376

Xaa His Xaa Leu
1

<210> SEQ ID NO 377
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-NMeGly
<220> FEATURE:
<221> NAME/KEY: MOD_RES
<222> LOCATION: (2)..(2)
<223> OTHER INFORMATION: His(pi-Me)
<220> FEATURE:
<221> NAME/KEY: MOD_RES
<222> LOCATION: (3)..(3)
<223> OTHER INFORMATION: Sta
<220> FEATURE:
<223> OTHER INFORMATION: c-term amidation

<400> SEQUENCE: 377

Gly His Xaa Leu
1

<210> SEQ ID NO 378
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: NMeGly
<220> FEATURE:
<221> NAME/KEY: MOD_RES
<222> LOCATION: (2)..(2)
<223> OTHER INFORMATION: His(Tr)
<220> FEATURE:
<221> NAME/KEY: MOD_RES
<222> LOCATION: (3)..(3)
<223> OTHER INFORMATION: Sta
<220> FEATURE:
<223> OTHER INFORMATION: c-term amidation

<400> SEQUENCE: 378

Gly His Xaa Leu
1

<210> SEQ ID NO 379
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-NMeGly
<220> FEATURE:
<221> NAME/KEY: MOD_RES
<222> LOCATION: (2)..(2)
<223> OTHER INFORMATION: His(pi-Me)
<220> FEATURE:
<221> NAME/KEY: MOD_RES
<222> LOCATION: (3)..(3)
<223> OTHER INFORMATION: Sta
<220> FEATURE:
<223> OTHER INFORMATION: c-term amidation

<400> SEQUENCE: 379

Gly His Xaa Leu
1

<210> SEQ ID NO 380
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 380

Val Ala Arg Gly
1

<210> SEQ ID NO 381
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: beta-Ala
<220> FEATURE:
<221> NAME/KEY: MOD_RES
<222> LOCATION: (3)..(3)
<223> OTHER INFORMATION: Arg(Pbf)
<220> FEATURE:
<223> OTHER INFORMATION: c-term amidation

<400> SEQUENCE: 381

Val Ala Arg Gly
1

<210> SEQ ID NO 382
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 382

Val Ala Arg Gly
1

<210> SEQ ID NO 383
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 383

Val Ala His Gly
1

<210> SEQ ID NO 384
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
```

-continued

```
<223> OTHER INFORMATION: His(pi-Me)
<220> FEATURE:
<223> OTHER INFORMATION: c-term amidation

<400> SEQUENCE: 384

Val Ala His Gly
1

<210> SEQ ID NO 385
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 385

Val Ala His Gly
1

<210> SEQ ID NO 386
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 386

Val Ala His Leu
1

<210> SEQ ID NO 387
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
```

```
<223> OTHER INFORMATION: His(pi-Me)
<220> FEATURE:
<223> OTHER INFORMATION: c-term amidation

<400> SEQUENCE: 387

Val Ala His Leu
1

<210> SEQ ID NO 388
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 388

Val Ala His Leu
1

<210> SEQ ID NO 389
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 389

Val Ala Phe Gly
1

<210> SEQ ID NO 390
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 390

Val Ala Phe Gly
1
```

```
<210> SEQ ID NO 391
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(4-Fluoro-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 391

Val Ala Phe Gly
1

<210> SEQ ID NO 392
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 392

Val Ala Trp Gly
1

<210> SEQ ID NO 393
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: Trp(Boc)
<220> FEATURE:
<223> OTHER INFORMATION: c-term amidation

<400> SEQUENCE: 393

Val Ala Trp Gly
1

<210> SEQ ID NO 394
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
                peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 394

Val Ala Trp Gly
1

<210> SEQ ID NO 395
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 395

Val Ala Tyr Gly
1

<210> SEQ ID NO 396
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: Tyr(OtBu)
<220> FEATURE:
<223> OTHER INFORMATION: c-term amidation

<400> SEQUENCE: 396

Val Ala Tyr Gly
1

<210> SEQ ID NO 397
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Val
<220> FEATURE:
<221> NAME/KEY: MOD_RES
<222> LOCATION: (2)..(2)
```

```
<223> OTHER INFORMATION: beta-Ala
<220> FEATURE:
<223> OTHER INFORMATION: c-term amidation

<400> SEQUENCE: 397

Val Ala Tyr Gly
1

<210> SEQ ID NO 398
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-trifluormethyl-benzoyl)-
      Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 398

Val Ala His Gly
1

<210> SEQ ID NO 399
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 399

Val Ala His Gly
1

<210> SEQ ID NO 400
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
```

```
<222> LOCATION: (3)..(3)
<223> OTHER INFORMATION: His(pi-Me)
<220> FEATURE:
<223> OTHER INFORMATION: c-term amidation

<400> SEQUENCE: 400

Val Ala Xaa Gly
1

<210> SEQ ID NO 401
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 401

Val Ala Lys Gly
1

<210> SEQ ID NO 402
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: Lys(Boc)
<220> FEATURE:
<223> OTHER INFORMATION: c-term amidation

<400> SEQUENCE: 402

Val Ala Lys Gly
1

<210> SEQ ID NO 403
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 403

Val Ala Lys Gly
```

<210> SEQ ID NO 404
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4-Trimethylammonium-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 404

Val Ala Met Gly
1

<210> SEQ ID NO 405
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 405

Val Ala Met Gly
1

<210> SEQ ID NO 406
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-4-Fluoro-3-cyano-benzoyl)-Val
<220> FEATURE:
<221> NAME/KEY: MOD_RES
<222> LOCATION: (2)..(2)
<223> OTHER INFORMATION: beta-Ala
<220> FEATURE:
<223> OTHER INFORMATION: c-term amidation

<400> SEQUENCE: 406

Val Ala Met Gly
1

<210> SEQ ID NO 407
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: (4-Trimethylammonium-3-cyano-benzenesulfonyl)-
      Gly
<220> FEATURE:
<221> NAME/KEY: MOD_RES
<222> LOCATION: (3)..(3)
<223> OTHER INFORMATION: beta-Ala
<220> FEATURE:
<221> NAME/KEY: MOD_RES
<222> LOCATION: (4)..(4)
<223> OTHER INFORMATION: His(pi-Me)
<220> FEATURE:
<223> OTHER INFORMATION: c-term amidation

<400> SEQUENCE: 407

Gly Val Ala His Gly
1               5

<210> SEQ ID NO 408
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 408

Val Ala His Gly
1

<210> SEQ ID NO 409
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: [18F]-(4-Fluoro-3-cyano-benzenesulfonyl)-Val
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(3)
<223> OTHER INFORMATION: His(pi-Me)
<220> FEATURE:
<223> OTHER INFORMATION: c-term amidation

<400> SEQUENCE: 409

Val Ala His Gly
1

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: 3-Cyano-4-(trimethylammonium)-benzoyl-Ava
<220> FEATURE:
<221> NAME/KEY: MOD_RES
<222> LOCATION: (8)..(8)
<223> OTHER INFORMATION: 4-amino-5-metyl-heptanoic acid
<220> FEATURE:
<223> OTHER INFORMATION: c-term amidation

<400> SEQUENCE: 410

Xaa Gln Trp Ala Val Gly His Xaa Leu
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:
<221> NAME/KEY: MOD_RES
<222> LOCATION: (8)..(8)
<223> OTHER INFORMATION: 4-amino-5-metyl-heptanoic acid
<220> FEATURE:
<223> OTHER INFORMATION: c-term amidation

<400> SEQUENCE: 411

Xaa Gln Trp Ala Val Gly His Xaa Leu
1               5

<210> SEQ ID NO 412
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-[18F]fluorobenzoyl-Ava
<220> FEATURE:
<221> NAME/KEY: MOD_RES
<222> LOCATION: (8)..(8)
<223> OTHER INFORMATION: 4-amino-5-metyl-heptanoic acid
<220> FEATURE:
<223> OTHER INFORMATION: c-term amidation

<400> SEQUENCE: 412

Xaa Gln Trp Ala Val Gly His Xaa Leu
1               5

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Ava
<220> FEATURE:
<221> NAME/KEY: MOD_RES
<222> LOCATION: (8)..(8)
<223> OTHER INFORMATION: 4-amino-5-metyl-heptanoic acid
<220> FEATURE:
```

-continued

<223> OTHER INFORMATION: c-term amidation

<400> SEQUENCE: 413

Xaa Gln Trp Ala Val Gly His Xaa Leu
1               5

<210> SEQ ID NO 414
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Cyano-4-(trimethylammonium)-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(pi-Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 414

Arg Xaa Gln Trp Ala Val Gly His Xaa Leu
1               5                   10

<210> SEQ ID NO 415
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(pi-Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 415

Arg Xaa Gln Trp Ala Val Gly His Xaa Leu
1               5                   10

<210> SEQ ID NO 416
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Cyano-4-[18F]fluorobenzoyl-Arg
<220> FEATURE:

```
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(pi-Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 416

Arg Xaa Gln Trp Ala Val Gly His Xaa Leu
1               5                   10

<210> SEQ ID NO 417
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-trimethylammoniumbenzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 417

Arg Xaa Gln Trp Ala Val Gly His Xaa Leu
1               5                   10

<210> SEQ ID NO 418
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Cyano-4-(trimethylammonium)-benzoyl-Arg
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 418
```

Arg Ala Gln Trp Ala Val Gly His Xaa Leu
1               5                   10

<210> SEQ ID NO 419
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-fluoro-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 419

Arg Xaa Gln Trp Ala Val Gly His Xaa Leu
1               5                   10

<210> SEQ ID NO 420
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-cyano-4-fluoro-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 420

Arg Xaa Gln Trp Ala Val Gly His Xaa Leu
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-CF3-4-fluoro-benzoyl-Arg
<220> FEATURE:

```
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 421

Arg Xaa Gln Trp Ala Val Gly His Xaa Leu
1               5                   10

<210> SEQ ID NO 422
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-Fluoro-3-cyano-benzoyl-Arg
<220> FEATURE:
<221> NAME/KEY: MOD_RES
<222> LOCATION: (2)..(2)
<223> OTHER INFORMATION: Ava
<220> FEATURE:
<221> NAME/KEY: MOD_RES
<222> LOCATION: (7)..(7)
<223> OTHER INFORMATION: NMeGly
<220> FEATURE:
<221> NAME/KEY: MOD_RES
<222> LOCATION: (8)..(8)
<223> OTHER INFORMATION: His(3Me)
<220> FEATURE:
<221> NAME/KEY: MOD_RES
<222> LOCATION: (9)..(9)
<223> OTHER INFORMATION: Sta
<220> FEATURE:
<223> OTHER INFORMATION: c-term amidation

<400> SEQUENCE: 422

Arg Xaa Gln Trp Ala Val Gly His Xaa Leu
1               5                   10
```

COMPOUNDS AND METHODS FOR $^{18}$F LABELED AGENTS

This application claims the benefit of the filing date of U.S. Provisional Application Ser. No. 60/845,163 filed Sep. 18, 2006.

SEQUENCE LISTING

The instant application contains a Sequence Listing which has been submitted in ASCII format via EFS-Web and is hereby incorporated by reference in its entirety. Said ASCII copy, created on Jan. 3, 2011, is named SCH-2176.txt and is 183,197 bytes in size.

FIELD OF INVENTION

This invention relates to novel compounds suitable for radiolabeling or already being radiolabeled with halogen, more specifically with $^{18}$F, a method of making such compounds, a composition comprising such compounds, their use for diagnostic imaging, a kit comprising a sealed vial containing a predetermined quantity of such novel compounds, such compounds for use as medicament, as diagnostic imaging agent and most specifically as imaging agent for Positron Emission Tomography.

BACKGROUND ART

Over the last few years, in-vivo scanning using Positron Emission Tomography (PET) has increased. PET is both a medical and research tool. It is used heavily in clinical oncology for medical imaging of tumors and the search for metastasis, and for clinical diagnosis of certain diffuse brain diseases such as those causing various types of dementias. Radiotracers consisting of a radionuclide stably bound to a biomolecule are used for in vivo imaging of disorders.

In designing an effective radiopharmaceutical tracer for use as a diagnostic agent, it is imperative that the drug has appropriate in vivo targeting and pharmacokinetic properties. Fritzberg et al. (*J. Nucl. Med.*, 1992, 33:394) state further that radionuclide chemistry and associated linkages underscore the need to optimize the attachment and labelling of chemical modifications of the biomolecule carrier, diluent, excipient or adjuvant. Hence the type of radionuclide, the type of biomolecule and the method used for linking them to one another may have a crucial effect onto the radiotracer properties.

Peptides are biomolecules that play a crucial role in many physiological processes including actions as neurotransmitters, hormones, and antibiotics. Research has shown their importance in such fields as neuroscience, immunology, pharmacology and cell biology. Some peptides can act as chemical messenger. They bind to receptor on the target cell surface and the biological effect of the ligand is transmitted to the target tissue. Hence the specific receptor binding property of the ligand can be exploited by labelling the ligand with a radionuclide. Theoretically, the high affinity of the ligand for the receptor facilitates retention of the radio labeled ligand in receptor expressing tissues. However, it is still under investigation which peptides can efficiently be labeled and under which conditions the labelling shall occur. It is well known that receptor specificity of ligand peptide may be altered during chemical reaction. Therefore an optimal peptidic construct has to be determined.

Tumors overexpress various receptor types to which peptide bound specifically. Boerman et al. (*Seminar in Nuclear Medicine*, 30(3) July, 2000; pp 195-208) provide a non exhaustive list of peptides binding to receptor involved in tumor, i.e., somatostatin, vasoactive intestinal peptide (VIP), bombesin binding to gastrin-releasing peptide (GRP) receptor, gastrin, cholecystokinin (CCK) and calcitonin.

The radionuclides used in PET scanning are typically isotopes with short half lives such as $^{11}$C (~20 min), $^{13}$N (~10 min), $^{15}$O (~2 min), $^{68}$Ga (~68 min) or $^{18}$F (~110 min). Due to their short half lives, the radionuclides must be produced in a cyclotron which is not too far away in delivery-time from the PET scanner. These radionuclides are incorporated into biologically active compounds or biomolecules that have the function to vehicle the radionuclide into the body though the targeted site, for example a tumor.

The linkage of the radionuclide to the biomolecule is done by various methods resulting in the presence or not of a linker between the radionuclide and the biomolecule. Hence, various linkers are known. C. J. Smith et al. ("*Radiochemical investigations of $^{177}$Lu-DOTA-8-Aoc-BBN[7-14]NH$_2$: an in vitro/in vivo assessment of the targeting ability of this new radiopharmaceutical for PC-3 human prostate cancer cells.*" Nucl. Med. Bio., 30(2):101-9; 2003) disclose radiolabeled bombesin wherein the linker is DOTA-X where X is a carbon tether. However, the radiolabel $^{177}$Lu (half life 6.5 days) does not match the biological half-life of the native bombesin what makes the $^{177}$Lu-DOTA-X-bombesin a non-appropriate radiotracer for imaging tumor.

E. Garcia Garayoa et al. ("*Chemical and biological characterization of new Re(CO)$_3$/[$^{99m}$Tc](CO)3 bombesin Analogues.*" Nucl. Med. Biol., 17-28; 2007) disclose a spacer between the radionuclide [$^{99m}$Tc] and the bombesin wherein the spacer is -β-Ala-β-Ala- and 3,6-dioxa-8-aminooctanoic acid. E. Garcia Garayoa et al. conclude that the different spacer does not have a significant effect on stability or on receptor affinity.

Listed above linkers have been specifically designed for a specific type of radionuclide and determine the type and chemical conditions of the radiobinding method.

More recently, peptides have been conjugated to a macrocyclic chelator for labelling with $^{64}$Cu, $^{86}$Y, and $^{68}$Ga for PET application. However, such radionuclides interact with the in vivo catabolism resulting in unwanted physiologic effects and chelate attachment.

The nucleophilic aromatic $^{18}$F-fluorination reaction is of great importance for $^{18}$F-labeled radiopharmaceuticals which are used as in vivo imaging agents for targeting and visualizing diseases, e.g., solid tumors or diseases of brain. A very important technical goal in using $^{18}$F-labeled radiopharmaceuticals is the quick preparation and administration of the radioactive compound due to the fact that the $^{18}$F isotopes have a short half-life of about only 111 minutes.

$^{18}$F-labeled compounds are gaining importance due to the availability thereof as well as due to the development of methods for labeling biomolecules. It has been shown that some compounds labeled with $^{18}$F produce images of high quality. Additionally, the longer lifetime of $^{18}$F would permit longer imaging times and allow preparation of radiotracer batches for multiple patients and delivery of the tracer to other facilities, making the technique more widely available to clinical investigators. Additionally, it has been observed that the development of PET cameras and availability of the instrumentation in many PET centers is increasing. Hence, it is increasingly important to develop new tracers labeled with $^{18}$F.

The nucleophilic aromatic $^{18}$F-fluorination reaction is of great importance for $^{18}$F-labeled radiopharmaceuticals which are used as in vivo imaging agents targeting and visualizing diseases, e.g., solid tumors.

Various methods of radiofluorination have been published using different precursors or starting material for obtaining $^{18}$F-labeled peptides. Due to the smaller size of peptides, both higher target-to-background ratios and rapid blood clearance can often be achieved with radiolabeled peptides. Hence, short-lived positron emission tomography (PET) isotopes are potential candidates for labelling peptides. Among a number of positron-emitting nuclides, fluorine-18 appears to be the best candidate for labelling bioactive peptides by virtue of its favourable physical and nuclear characteristics. The major disadvantage of labelling peptides with $^{18}$F is the laborious and time-consuming preparation of the $^{18}$F labelling agents. Due to the complex nature of peptides and several functional groups associated with the primary structure, $^{18}$F-labeled peptides are not prepared by direct fluorination. Hence, difficulties associated with the preparation of $^{18}$F-labeled peptide were alleviated with the employment of prosthetic groups as shown below. Several such prosthetic groups have been proposed in the literature, including N-succinimidyl-4-[$^{18}$F]fluorobenzoate, m-maleimido-N-(p-[$^{18}$F]fluorobenzyl)-benzamide, N-(p-[$^{18}$F]fluorophenyl)maleimide, and 4-[$^{18}$F]fluorophenacylbromide. Almost all of the methodologies currently used today for the labeling of peptides and proteins with $^{18}$F utilize active esters of the fluorine labeled synthon.

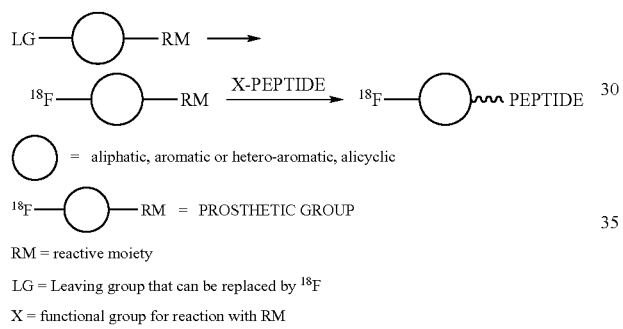

Okarvi et al. ("*Recent progress in fluorine-18 labeled peptide radiopharmaceuticals.*" *Eur. J. Nucl. Med.*, 2001 July; 28(7):929-38)) present a review of the recent developments in $^{18}$F-labeled biologically active peptides used in PET.

Xianzhong Zhang et al. ("*$^{18}$F-labeled bombesin analogs for targeting GRP receptor-expressing prostate cancer.*" *J. Nucl. Med.*, 47(3):492-501 (2006)) relate to the 2-step method detailed above. [Lys3]Bombesin ([Lys3]BBN) and aminocaproic acid-bombesin(7-14) (Aca-BBN(7-14)) were labeled with $^{18}$F by coupling the Lys3 amino group and Aca amino group, respectively, with N-succinimidyl-4-$^{18}$F-fluorobenzoate ($^{18}$F-SFB) under slightly basic condition (pH 8.5). Unfortunately, the obtained $^{18}$F-FB-[Lys3]BBN is metabolically relatively unstable having for result to reduce the extent of use of the $^{18}$F-FB-[Lys3]BBN for reliable imaging of tumor.

Thorsten Poethko et al. ("*Two-step methodology for high-yield routine radiohalogenation of peptides: $^{18}$F-labeled RGD and octreotide analogs.*" *J. Nucl. Med.*, 2004 May; 45(5):892-902) relate to a 2-step method for labelling RGD and octreotide analogs. The method discloses the steps of radiosynthesis of the $^{18}$F-labeled aldehyde or ketone and the chemoselective ligation of the $^{18}$F-labeled aldehyde or ketone to the aminooxy functionalized peptide.

Thorsten Poethko et al. ("*First $^{18}$F-labeled tracer suitable for routine clinical imaging of somatostatin receptor-expressing tumors using positron emission tomography.*" *Clin. Cancer Res.*, 2004 Jun. 1; 10(11):3593-606) apply the 2-step method for the synthesis of $^{18}$F-labeled carbohydrated Tyr (3)-octreotate (TOCA) analogs with optimized pharmacokinetics suitable for clinical routine somatostatin-receptor (sst) imaging.

WO 2003/080544 A1 and WO 2004/080492 A1 relate to radiofluorination methods of bioactive peptides for diagnostics imaging using the 2-step method shown above.

The most crucial aspect in the successful treatment of any cancer is early detection. Likewise, it is crucial to properly diagnose the tumor and metastasis.

Routine application of $^{18}$F-labeled peptides for quantitative in vivo receptor imaging of receptor-expressing tissues and quantification of receptor status using PET is limited by the lack of appropriate radiofluorination methods for routine large-scale synthesis of $^{18}$F-labeled peptides. There is a clear need for radiofluorination method that can be conducted rapidly without loss of receptor affinity by the peptide and leading to a positive imaging (with reduced background), wherein the radiotracer is stable and shows enhanced clearance properties The conversions of mono- (mainly para-) substituted trimethylammonium benzene derivatives (1) to substituted [$^{18}$F]-fluoro-benzene derivatives (2) which may serve as radiopharmaceutical itself or as prosthetic group for the F-18 labeling of small and large molecules have been reported in the literature (We et al. 1982, *Fluorine Chem.*, 27, (1985), 117-191; Haka et al. 1989) (see Scheme 1).

Scheme 1

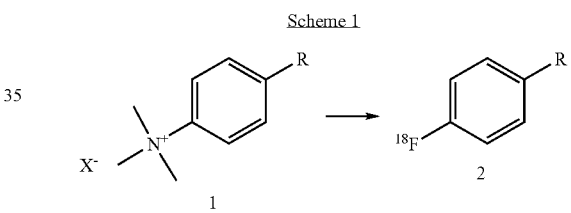

There are only a few publications about nucleophilic aromatic $^{18}$F-fluorination reactions of trimethyl ammonium substituted aromatic derivatives which contain two or more substituents beside the trimethylammonium moiety:

Oya et al. treated [2-Chloro-5-(2-dimethylcarbamoyl-phenylsulfanyl)-4-nitro-phenyl]-trimethyl-ammonium triflate with [$^{18}$F]potassium fluoride and obtained the desired $^{18}$F-labeled compound (*J. Med. Chem.*, 2002, 45(21):4716-4723).

Li et al. report on the $^{18}$F-fluorination reaction of 4-(N,N,N-trimethylammonium)-3-cyano-3'-iodobenzophenone triflate (*Bioconjugate Chemistry*, 2003, 14(2):287-294).

Enas et al. convert (2,2-Dimethyl-1,3-dioxo-indan-5-yl)-trimethyl-ammonium triflate into the desired $^{18}$F-labeled compound (*J. Fluorine Chem.*, 1993, 63(3):233-41).

Seimbille et al. and other groups have labeled (2-Chloro-4-nitro-phenyl)-trimethyl-ammonium triflate successfully with $^{18}$F (*J. Labeled Compd. Radiopharm.*, 2005, 48, 11:829-843).

(2-Benzyloxy-4-formyl-phenyl)-trimethyl-ammonium triflate has successfully been labeled with $^{18}$F at high temperature (130° C.) by Langer et. al. (*Bioorg. Med. Chem.*, EN; 9; 3; 2001:677-694).

Lang et al. have radiolabeled trimethyl-(2-methyl-4-pentamethylphenyl methoxycarbonyl-phenyl)-ammonium triflate by using [$^{18}$F]potassium fluoride (*J. Med. Chem.*, 42, 9, 1999:1576-1586).

Trimethyl-(4-nitro-naphthalen-1-yl)-ammonium triflate has been labeled with $^{18}$F by Amokhtari et al. (*J. Labeled Compd. Radiopharm.; S42*, 1 (1999):S622-S623).

Lemaire et al. have converted (2-formyl-5-methoxy-phenyl)-trimethyl-ammonium triflate into the desired $^{18}$F-labeled product (*J. Labeled Compd. Radiopharm.*, 44, 2001: S857-S859).

VanBrocklin et al. describe the $^{18}$F labeling of (2-bromo-4-nitro-phenyl)-trimethyl-ammonium triflate (*J. Labeled Compd. Radiopharm.*, 44; 2001:S880-S882) and Cetir Centre Medic report on the successful $^{18}$F-labeling of (5-Chloro-8-hydroxy-quinolin-7-yl)-trimethyl-ammonium triflate (EP 1 563 852 A1).

D. A. Sutton et al. (*"Evaluation of 1-fluoro-2-nitro-4-trimethylammoniobenzene iodide, a protein-solubilizing agent"*, *Biochem. J.*, 1972, 130:589-595) disclose model derivatives which consist of a benzene substituted with trimethylammonium, an electron withdrawing nitro group and a glycine, phenylalanine or acetyltyrosine.

C. Lemaire et al. (*"Highly enantioselective synthesis of no-carrier-added 6-[$^{18}$F]fluoro-L-dopa by chiral phase-transfer alkylation"*, *Eur. J. Org. Chem.*, 2004:2899-2904) disclose 2-[$^{18}$F]fluoro-4,5-dimethoxybenzaldehyde to be used to prepare 6-[$^{18}$F]fluoro-L-dopa.

L. Lang et al. (*"Development of fluorine-18-labeled 5-HT$_{1A}$ antagonists"*, *J. Med. Chem.*, 1999, 42(9):1576-1586) disclose conversion of pentamethyl 4-(trimethylammonium trifluormethanesulfonate)benzoate and pentamethyl 3-methyl-4-(trimethylammonium trifluormethansulfonate) benzoate to the respective $^{18}$F substituted benzoyl chloride which is then coupled with WAY 100635 (N-{2-[4-(2-methoxyphenyl)-piperazino]ethyl}-N-(2-pyridyl)cyclohexanecarboxamide).

S. Oya et al. (*"New PET imaging agent for the serotonin transporter: [$^{18}$F]ACF (2-[(-amino-4-chloro-5-fluorophenyl)thio]-N,N-dimethyl-benzenmethanamine)"*, *J. Med. Chem.*, 2002, 45:4716-4723) disclose conversion of [2-chloro-5-(2-dimethylaminocarbonyl-phenylthio)-4-nitro-phenyl]trimethylammonium trifluoromethanesulfonate to the respective $^{18}$F substituted compound.

M. J. Al-Darwich et al. (*"Enantioselective synthesis of non-carrier-added (n.c.a.) (S)-4-chloro-2-[$^{18}$F]fluorophenylalanine and (S)-(α-methyl)-4-chloro-2-[18F]fluorophenylalanine"*, *J. Fluorine Chem.*, 1996, 80:117-124) disclose 4-chloro-2-trimethylammoniumbenzaldehyde triflate to be reacted to 4-chloro-2-[$^{18}$F]fluorobenzaldehyde which are then further reacted to yield the title compounds.

Y. Seimbille et al. (*"Fluorine-18 labeling of 6,7-disubstituted anilinoquinazoline derivatives for positron emission tomography (PET) imaging of tyrosine kinase receptors: synthesis of $^{18}$F-Iressa and related molecular probes"*, *J. Labeled Compd. Radiopharm.*, 2005, 48:829-843, i.a., report on the reaction of 3-chloro-4-trimethylammonium nitrobenzene trifluoro-methanesulfonate to give 3-chloro-4-[$^{18}$F] fluoroaniline via 3-chloro-4-[$^{18}$F]fluoro-nitro-benzene.

WO 2002/44144 A1 relates to nucleophilic reaction for preparing radiolabeled imaging agents using [$^{18}$F]fluoride to react with trimethylammoniumbenzene compounds.

WO 2006/083424 A2 relates to [$^{18}$F]-radiolabeled compounds and the manufacture thereof.

Most of these mentioned $^{18}$F-labeled aromatic derivatives which cannot contain two or more additional substituents cannot be coupled to chemical functionalities like amines, thiols, carboxylic acids, phenols or other chemicals groups of complex molecules like peptides without further transformations.

$^{18}$F labeling of more complex radiopharmaceuticals like peptides takes place in all known publications in a two- or multi-step strategy (see Scheme 2, review article: *Eur. J. Nucl. Med.*, 2001, 28:929-938).

For these kinds of $^{18}$F-labeling also mono-substituted trimethylammonium benzene derivatives are used and react in a first step with [$^{18}$F]potassium fluoride to obtain substituted [$^{18}$F]-fluoro-benzene derivatives. These compounds are then coupled in a second step to larger and more complex molecules like peptides, small molecules or nucleotides (see scheme 2).

Scheme 2

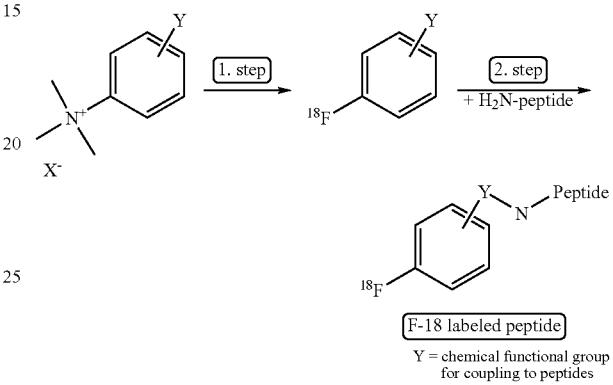

Y = chemical functional group for coupling to peptides

Especially 4-[$^{18}$F]fluorobenzaldehyde has been used in many examples for F-18 labelling of complex molecules (e.g., *J. Nucl. Med.*, 2004, 45(5):892-902). But also N-succinimidyl-8-[4'-[$^{18}$F]fluorobenzylamino]suberate (*Bioconjugate Chem.*, 1991, 2:44-49), 4-[$^{18}$F]fluorophenacyl bromide and 3-[$^{18}$F]fluoro-5-nitrobenzimidate (*J. Nucl. Med.*, 1987, 28:462-470), m-maleimido-N-(p-[$^{18}$F]fluorobenzyl)-benzamide (*J. Labeled Compd. Radiopharm.*, 1989, 26:287-289,), N-{4-[4-[$^{18}$F]fluorobenzylidene(aminooxy)-butyl}-maleimide (*Bioconjugate Chem.*, 2003, 14:1253-1259), [$^{18}$F]N-(4-fluorobenzyl)-2-bromoacetamide (*Bioconjugate Chem.*, 2000, 11:627-636) and [$^{18}$F]-3,5-difluorophenyl azide (and 5 derivatives) (*J. Org. Chem.*, 1995, 60:6680-6681) are known examples. F-18 labeling of peptides via para-[18F]-fluorobenzoates is also a very common method either by coupling of the corresponding acid with additional activating agents (such as 1,3-dicyclohexylcarbodiimide/1-hydroxy-7-azabenzotriazole (DCC/HOAt) or N-[(dimethyl-amino)-1H-1,2, 3-triazolyl[4,5]pyridine-1-yl-methylene]-N-methyl-methanaminium hexafluorophosphate N-oxide (HATU/DIPEA, *Eur. J. Nucl. Med. Mol. Imaging.*, 2002, 29:754-759) or by isolated N-succinimidyl 4-[$^{18}$F]fluorobenzoate (*Nucl. Med. Biol.*, 1996, 23:365).

None of these compounds and none of other published compounds allow a direct (one-step) labeling of peptides with $^{18}$F-fluoride.

Therefore is an object of the present invention the development of a practical and mild technique for $^{18}$F labeling of molecules like, e.g., peptides, oligonucleotides or small molecule targeting agents and to provide radiofluorination methods for obtaining radiotracer based on receptor specific peptides for the detection of tumors.

SUMMARY OF THE INVENTION

The object of the present invention is solved as detailed herein below.

A first aspect of the present invention refers to novel compounds having general chemical Formula A (general chemical Formula I), wherein K=N$^+$(R$^1$)(R$^2$)(R$^3$)X$^-$ and to pharmaceutically acceptable salts of inorganic or organic acids thereof, hydrates, complexes, esters, amides, solvates and prodrugs thereof. These compounds are precursors for a single step labeling more preferably radiolabeling to yield the novel compounds according to the second aspect of the present invention.

A second aspect of the present invention refers to novel compounds (radiopharmaceuticals, labeled $^{18}$F), having general chemical Formula A, wherein K=W (general chemical Formula II) and to pharmaceutically acceptable salts of inorganic or organic acids thereof, hydrates, complexes, esters, amides, solvates and prodrugs thereof.

Compounds having general chemical Formula A, wherein K=N$^+$(R$^1$)(R$^2$)(R$^3$)X$^-$ (general chemical Formula I), can be converted into compounds having general chemical Formula A, wherein K=W (general chemical Formula II), by means of a one-step labeling more preferably radiolabeling reaction with a fluoine isotope, more specifically with $^{18}$F.

A third aspect of the present invention refers to a one-step method of labeling more preferably radiolabeling compounds having general chemical Formula A, wherein K=N$^+$(R$^1$)(R$^2$)(R$^3$)X$^-$, in order to arrive at compounds having general chemical Formula A, wherein K=W.

A fourth aspect of the present invention refers to compositions, more preferably to diagnostic compositions, comprising a compound having general chemical Formula A, wherein K=N$^+$(R$^1$)(R$^2$)(R$^3$)X$^-$, or a pharmaceutically acceptable salts of inorganic or organic acids thereof, hydrates, complexes, esters, amides, solvates and prodrugs thereof and a pharmaceutically acceptable carrier, diluent, excipient or adjuvant. According to this fourth aspect the present invention further refers to compositions, more preferably diagnostic compositions, comprising a radiolabelled compound having general chemical Formula A, wherein K=W, or a pharmaceutically acceptable salts of inorganic or organic acids thereof, hydrates, complexes, esters, amides, solvates and prodrugs thereof and a pharmaceutically acceptable carrier, diluent, excipient or adjuvant.

A fifth aspect, the present invention refers to a method of imaging diseases, the method comprising introducing into a patient a detectable quantity of a labeled compound having general chemical Formula A, wherein K=W, or a pharmaceutically acceptable salts of inorganic or organic acids thereof, hydrates, complexes, esters, amides, solvates and prodrugs thereof.

A sixth aspect of the present invention refers to a kit for preparing a radiopharmaceutical preparation, said kit comprising a sealed vial containing a predetermined quantity of the compound of Formula A, wherein K=N$^+$(R$^1$)(R$^2$)(R$^3$)X$^-$, or a pharmaceutically acceptable salts of inorganic or organic acids thereof, hydrates, complexes, esters, amides, solvates and prodrugs thereof and further optionally an acceptable carrier, diluent, excipient or adjuvant supplied as a mixture with the compound having general chemical Formula I or independently for the manufacture of a compound having general chemical Formula II. More preferably, the present invention relates to a kit comprising a compound or composition, as defined herein above, in powder form, and a container containing an appropriate solvent for preparing a solution of the compound or composition for administration to an animal, including a human.

A seventh aspect of the present invention refers to a compound having general chemical Formula A, wherein K=N$^+$(R$^1$)(R$^2$)(R$^3$)X$^-$ or W, or of a pharmaceutically acceptable salts of inorganic or organic acids thereof, hydrates, complexes, esters, amides, solvates and prodrugs thereof for use as medicament and, if K=W, for use as diagnostic imaging agent and more specifically for use as imaging agent for PET.

An eighth aspect of the present invention refers to a use of a compound having general chemical Formula A, wherein K=N$^+$(R$^1$)(R$^2$)(R$^3$)X$^-$ or W, or of a pharmaceutically acceptable salts of inorganic or organic acids thereof, hydrates, complexes, esters, amides, solvates and prodrugs thereof for the manufacture of a medicament, more specifically for the manufacture of a diagnostic imaging agent and most specifically for the manufacture of a diagnostic imaging agent for imaging tissue at a target site using the imaging agent.

A ninth aspect of the present invention refers to bombesin analogs that bind specifically to human GRP receptors present in prostate tumor, breast tumor and metastasis. In a preferred embodiment, the bombesin analog is a peptide having sequence from Seq ID 1 to Seq ID 102 or those sequences disclosed below.

Further aspects of the present invention are directed to methods and intermediates useful for synthesizing the tumor imaging compounds having general chemical Formulae I and II as described herein below.

DETAILED DESCRIPTION OF THE INVENTION

As used hereinafter in the description of the invention and in the claims, the term "alkyl", by itself or as part of another group, refers to a straight chain or branched chain alkyl group with 1 to 20 carbon atoms such as, for example methyl, ethyl, propyl, isopropyl, butyl, isobutyl, tert-butyl, pentyl, isopentyl, neopentyl, heptyl, hexyl, decyl. Alkyl groups can also be substituted, such as by halogen atoms, hydroxyl groups, $C_1$-$C_4$ alkoxy groups or $C_6$-$C_{12}$ aryl groups (which, intern, can also be substituted, such as by 1 to 3 halogen atoms). More preferably alkyl is $C_1$-$C_{10}$ alkyl, $C_1$-$C_6$ alkyl or $C_1$-$C_4$ alkyl.

As used hereinafter in the description of the invention and in the claims, the term "cycloalkyl" by itself or as part of another group, refers to mono- or bicyclic chain of alkyl group with 3 to 20 carbon atoms such as, for example cyclopropyl, cyclobutyl, cyclopentyl, cyclohexyl or cycloheptyl. More preferably cycloalkyl is $C_3$-$C_{10}$ cycloalkyl or $C_5$-$C_8$ cycloalkyl, most preferably $C_6$ cycloalkyl.

As used hereinafter in the description of the invention and in the claims, the term "heterocycloalkyl", by itself or as part of another group, refers to groups having 3 to 20 mono- or bi-ring atoms of a cycloalkyl; and containing carbon atoms and 1, 2, 3 or 4 oxygen, nitrogen or sulfur heteroatoms. More preferably heterocycloalkyl is $C_3$-$C_{10}$ heterocycloalkyl, $C_5$-$C_8$ heterocycloalkyl or $C_5$-$C_{14}$ heterocycloalkyl, most preferably $C_6$ heterocycloalkyl.

As used hereinafter in the description of the invention and in the claims, the term "aralkyl" refers to aryl-substituted alkyl radicals such as benzyl, diphenylmethyl, triphenylmethyl, phenylethyl, phenylbutyl and diphenylethyl.

As used hereinafter in the description of the invention and in the claims, the terms "aryloxy" refers to aryl groups having an oxygen through which the radical is attached to a nucleus, examples of which are phenoxy.

As used hereinafter in the description of the invention and in the claims, the terms "alkenyl" and "alkynyl" are similarly defined as for alkyl, but contain at least one carbon-carbon double or triple bond, respectively. More preferably $C_2$-$C_6$ alkenyl and $C_2$-$C_6$ alkynyl.

As used hereinafter in the description of the invention and in the claims, the term "lower unbranched or branched alkyl" shall have the following meaning: a substituted or unsubstituted, straight or branched chain monovalent or divalent radical consisting substantially of carbon and hydrogen, containing no unsaturation and having from one to eight carbon atoms, e.g., but not limited to methyl, ethyl, n-propyl, n-pentyl, 1,1-dimethylethyl (t-butyl), n-heptyl and the like.

As used hereinafter in the description of the invention and in the claims, the terms "aralkenyl" refers to aromatic structure (aryl) coupled to alkenyl as defined above.

As used hereinafter in the description of the invention and in the claims, the terms "alkoxy (or alkyloxy), aryloxy, and aralkenyloxy" refer to alkyl, aryl, and aralkenyl groups respectively linked by an oxygen atom, with the alkyl, aryl, and aralkenyl portion being as defined above.

As used hereinafter in the description of the invention and in the claims, the terms "salts of inorganic or organic acids", "inorganic acid" and "organic acid" refer to mineral acids, including, but not being limited to: acids such as carbonic, nitric, phosphoric, hydrochloric, perchloric or sulphuric acid or the acidic salts thereof such as potassium hydrogen sulphate, or to appropriate organic acids which include, but are not limited to: acids such as aliphatic, cycloaliphatic, aromatic, araliphatic, heterocyclic, carboxylic and sulphonic acids, examples of which are formic, acetic, trifluoracetic, propionic, succinic, glycolic, gluconic, lactic, malic, fumaric, pyruvic, benzoic, anthranilic, mesylic, fumaric, salicylic, phenylacetic, mandelic, embonic, methansulfonic, ethanesulfonic, benzenesulfonic, phantothenic, toluenesulfonic, trifluormethansulfonic and sulfanilic acid, respectively.

As used hereinafter in the description of the invention and in the claims, the term "aryl" by itself or as part of another group refers to monocyclic or bicyclic aromatic groups containing from 6 to 12 carbon atoms in the ring portion, preferably 6-10 carbons in the ring portion, such as phenyl, naphthyl or tetrahydronaphthyl.

As used hereinafter in the description of the invention and in the claims, the term "heteroaryl" by itself or as part of another group, refers to groups having 5 to 14 ring atoms; 6, 10 or 14 π (pi) electrons shared in a cyclic array; and containing carbon atoms and 1, 2, 3 or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, carbolinyl, phenanthridinyl, acridinyl, perimidinyl, phenanthrolinyl, phenazinyl, isothiazolyl, phenothiazinyl, isoxazolyl, furazanyl and phenoxazinyl groups).

Whenever the term substituted is used, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a pharmaceutical composition. The substituent groups may be selected from halogen atoms, hydroxyl groups, $C_1$-$C_4$ alkoxy groups or $C_6$-$C_{12}$ aryl groups (which, intern, can also be substituted, such as by 1 to 3 halogen atoms).

As used hereinafter in the description of the invention and in the claims, the term "fluorine isotope" (F) refers to all isotopes of the fluorine atomic element. Fluorine isotope (F) is selected from radioactive or non-radioactive isotope. The radioactive fluorine isotope is selected from $^{18}F$. The non-radioactive "cold" fluorine isotope is selected from $^{19}F$.

As used hereinafter in the description of the invention and in the claims, the term "prodrug" means any covalently bonded compound, which releases the active parent pharmaceutical according to formula II.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmaco-logical Basis of Therapeutics, 8 ed, McGraw-HiM, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs of the compounds of the present invention include those compounds wherein for instance a hydroxy group, such as the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

As used hereinafter in the description of the invention and in the claims, the terms "amino acid sequence" and "peptide" are defined herein as a polyamide obtainable by (poly)condensation of at least two amino acids.

As used hereinafter in the description of the invention and in the claims, the term "amino acid" means any molecule comprising at least one amino group and at least one carboxyl group, but which has no peptide bond within the molecule. In other words, an amino acid is a molecule that has a carboxylic acid functionality and an amine nitrogen having at least one free hydrogen, preferably in alpha position thereto, but no amide bond in the molecule structure. Thus, a dipeptide having a free amino group at the N-terminus and a free carboxyl group at the C-terminus is not to be considered as a single "amino acid" in the above definition. The amide bond between two adjacent amino acid residues which is obtained from such a condensation is defined as "peptide bond". Optionally, the nitrogen atoms of the polyamide backbone (indicated as NH above) may be independently alkylated, e.g., with $C_1$-$C_6$-alkyl, preferably $CH_3$.

An amide bond as used herein means any covalent bond having the structure

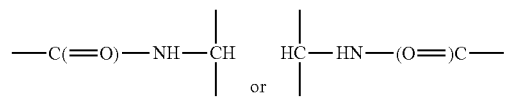

wherein the carbonyl group is provided by one molecule and the NH-group is provided by the other molecule to be joined. The amide bonds between two adjacent amino acid residues which are obtained from such a polycondensation are defined as "peptide bonds". Optionally, the nitrogen atoms of the polyamide backbone (indicated as NH above) may be independently alkylated, e.g., with —$C_1$-$C_6$-alkyl, preferably —$CH_3$.

As used hereinafter in the description of the invention and in the claims, an amino acid residue is derived from the corresponding amino acid by forming a peptide bond with another amino acid.

As used hereinafter in the description of the invention and in the claims, an amino acid sequence may comprise naturally occurring and/or synthetic/artificial amino acid residues, proteinogenic and/or non-proteinogenic amino acid residues. The non-proteinogenic amino acid residues may be further classified as (a) homo analogues of proteinogenic amino acids, (b) β-homo analogues of proteinogenic amino acid residues and (c) further non-proteinogenic amino acid residues.

Accordingly, the amino acid residues may be derived from the corresponding amino acids, e.g., from proteinogenic amino acids, namely Ala, Arg, Asn, Asp, Cys, Gln, Glu, Gly, His, Ile, Leu, Lys, Met, Phe, Pro, Ser, Thr, Trp, Tyr and Val; or non-proteinogenic amino acids, such as homo analogues of proteinogenic amino acids wherein the sidechain has been extended by a methylene group, e.g., homoalanine (Hal), homoarginine (Har), homocysteine (Hcy), homoglutamine (Hgl), homohistidine (Hhi), homoisoleucine (Hil), homoleucine (Hle), homolysine (Hly), homomethionine (Hme), homophenylalanine (Hph), homoproline (Hpr), homoserine (Hse), homothreonine (Hth), homotryptophane (Htr), homotyrosine (Hty) and homovaline (Hva);

β-homo analogues of proteinogenic amino acids wherein a methylene group has been inserted between the α-carbon and the carboxyl group yielding β-amino acids, e.g., β-homoalanine (βHal), β-homoarginine (βHar), β-homoasparagine (βHas), β-homocysteine (βHcy), β-homoglutamine (βHgl), β-homohistidine (βHhi), β-homoisoleucine (βHil), β-homoleucine (βHle), β-homolysine (βHly), β-homomethionine (βHme), β-homophenylalanine (βHph), β-homoproline (βHpr), β-homoserine (βHse), β-homothreonine (βHth), β-homotryptophane (βHtr), β-homotyrosine (βHty) and β-homovaline (βHva);

further non-proteinogenic amino acids, e.g., α-aminoadipic acid (Aad), β-aminoadipic acid (βAad), α-aminobutyric acid (Abu), α-aminoisobutyric acid (Aib), β-alanine (βAla), 4-aminobutyric acid (4-Abu), 5-aminovaleric acid (5-Ava), 6-aminohexanoic acid (6-Ahx), 8-aminooctanoic acid (8-Aoc), 9-aminononanoic acid (9-Anc), 10-aminodecanoic acid (10-Adc), 12-aminododecanoic acid (12-Ado), α-aminosuberic acid (Asu), azetidine-2-carboxylic acid (Aze), β-cyclohexylalanine (Cha), aitrulline (Cit), dehydroalanine (Dha), γ-carboxyglutamic acid (Gla), α-cyclohexylglycine (Chg), propargylglycine (Pra), pyroglutamic acid (Glp), α-tert-butylglycine (Tle), 4-benzoylphenylalanine (Bpa), δ-hydroxylysine (Hyl), 4-hydroxyproline (Hyp), allo-isoleucine (alle), lanthionine (Lan), (1-naphthyl)alanine (1-Nal), (2-naphthyl)alanine (2-Nal), norleucine (Nle), norvaline (Nva), ornithine (Orn), phenylglycin (Phg), pipecolic acid (Pip), sarcosine (Sar), selenocysteine (Sec), statine (Sta), β-thienylalanine (Thi), 1,2,3,4-tetrahydroisochinoline-3-carboxylic acid (Tic), allo-threonine (aThr), thiazolidine-4-carboxylic acid (Thz), γ-aminobutyric acid (GABA), iso-cysteine (iso-Cys), diaminopropionic acid (Dpr), 2,4-diaminobutyric acid (Dab), 3,4-diaminobutyric acid (γβDab), biphenylalanine (Bip), phenylalanine substituted in para-position with —$C_1$-$C_6$ alkyl, -halide, —$NH_2$, —$CO_2H$ or Phe(4-R) (wherein R=—$C_1$-$C_6$ alkyl, -halide, —$NH_2$, or —$CO_2H$); peptide nucleic acids (PNA, cf., P. E. Nielsen, *Acc. Chem. Res.*, 32, 624-30);

or their N-alkylated analogues, such as their N-methylated analogues.

Cyclic amino acids may be proteinogenic or non-proteinogenic, such as Pro, Aze, Glp, Hyp, Pip, Tic and Thz.

For further examples and details reference can be made to, e.g., J. H. Jones, *J. Peptide Sci.*, 2003, 9, 1-8 which is herein incorporated by reference.

As used hereinafter in the description of the invention and in the claims, the terms "non-proteinogenic amino acid" and "non-proteinogenic amino acid residue" also encompass derivatives of proteinogenic amino acids. For example, the side chain of a proteinogenic amino acid residue may be derivatized thereby rendering the proteinogenic amino acid residue "non-proteinogenic". The same applies to derivatives of the C-terminus and/or the N-terminus of a proteinogenic amino acid residue terminating the amino acid sequence.

As used hereinafter in the description of the invention and in the claims, a proteinogenic amino acid residue is derived from a proteinogenic amino acid selected from the group consisting of Ala, Arg, Asn, Asp, Cys, Gln, Glu, Gly, His, Ile, Leu, Lys, Met, Phe, Pro, Ser, Thr, Trp, Tyr and Val either in L- or D-configuration; the second chiral center in Thr and Ile may have either R- or S-configuration. Therefore, for example, any posttranslational modification of an amino acid sequence, such as N-alkylation, which might naturally occur renders the corresponding modified amino acid residue "non-proteinogenic", although in nature said amino acid residue is incorporated in a protein. Preferably modified amino acids are selected from N-alkylated amino acids, β-amino acids, γ-amino acids, lanthionines, dehydro amino acids, and amino acids with alkylated guanidine moieties.

As used hereinafter in the description of the invention and in the claims, the term "peptidomimetic" relates to molecules which are related to peptides, but with different properties. A peptidomimetic is a small protein-like chain designed to mimic a peptide. They typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally.

As used hereinafter in the description of the invention and in the claims, the term "peptide analogs", by itself refers to synthetic or natural compounds which resemble naturally occurring peptides in structure and/or function.

As used hereinafter in the description of the invention and in the claims, the term "pharmaceutically acceptable salt" relates to salts of inorganic and organic acids, such as mineral acids, including, but not limited to, acids such as carbonic, nitric or sulfuric acid, or organic acids, including, but not limited to acids such as aliphatic, cycloaliphatic, aromatic, aralphatic, heterocyclic, carboxylic and sulphonic acids, examples of which are formic, acetic, trifluoroacetic, propionic, succinic, glycolic, gluconic, lactic, malic, fumaric, pyruvic, benzoic, anthranilic, mesylic, salicylic, phenylacetic, mandelic, embonic, methansulfonic, ethanesulfonic, benzenesulfonic, phantothenic, toluenesulfonic and sulfanilic acid.

If a chiral center or another form of an isomeric center is present in a compound having general chemical Formulae A, I, II, III or IV of the present invention, as given hereinafter, all forms of such isomers, including enantiomers and diastereoisomers, are intended to be covered herein. Compounds containing a chiral center may be used as a racemic mixture or as an enantiomerically enriched mixture, or the racemic mixture may be separated using well-known techniques and an individual enantiomer maybe used alone. In cases in which compounds have unsaturated carbon-carbon double bonds, both the cis-isomer and trans-isomers are within the scope of this invention. In cases in which compounds may exist in tautomeric forms, such as keto-enol tautomers, each tautomeric form is contemplated as being included within the scope of the present invention whether existing in equilibrium or predominantly in one form.

As used hereinafter in the description of the invention and in the claims, the term "oligonucleotide" shall have the following meaning: short sequences of nucleotides, typically with twenty or fewer bases. Examples are, but are not limited to, molecules named and cited in the book: "*The aptamers handbook. Functional oligonuclides and their application*" by Svenn Klussmann, Wiley-VCH, 2006. An example for such an oligonucleotide is TTA1 (*J. Nucl. Med.*, 2006, April, 47(4):668-78).

As used hereinafter in the description of the invention and in the claims, the term "aptamer" refers to an oligonucleotide, comprising from 4 to 100 nucleotides, wherein at least two single nucleotides are connected to each other via a phosphodiester linkage. Said aptamers have the ability to bind specifically to a target molecule (see, e.g., M Famulok, G Mayer, "*Aptamers as Tools in Molecular Biology and Immunology*", in: "*Combinatorial Chemistry in Biology, Current Topics in Microbiology and Immunology*" (M Famulok, C H Wong, E L Winnacker, Eds.), Springer Verlag Heidelberg, 1999, Vol. 243, 123-136). There are many ways known to the skilled person of how to generate such aptamers that have specificity for a certain target molecule. An example is given in WO 01/09390 A, the disclosure of which is hereby incorporated by reference. Said aptamers may comprise substituted or non-substituted natural and non-natural nucleotides. Aptamers can be synthesized in vitro using, e.g., an automated synthesizer. Aptamers according to the present invention can be stabilized against nuclease degradation, e.g., by the substitution of the 2'-OH group versus a 2'-fluoro substituent of the ribose backbone of pyrimidine and versus 2'-O-methyl substituents in the purine nucleic acids. In addition, the 3' end of an aptamer can be protected against exonuclease degradation by inverting the 3' nucleotide to form a new 5'-OH group, with a 3' to 3' linkage to a penultimate base.

For the purpose of this invention, the term "nucleotide" refers to molecules comprising a nitrogen-containing base, a 5-carbon sugar, and one or more phosphate groups. Examples of said base comprise, but are not limited to, adenine, guanine, cytosine, uracil, and thymine. Also non-natural, substituted or non-substituted bases are included. Examples of 5-carbon sugar comprise, but are not limited to, D-ribose, and D-2-desoxyribose. Also other natural and non-natural, substituted or non-substituted 5-carbon sugars are included. Nucleotides as used in this invention may comprise from one to three phosphates.

As used hereinafter in the description of the invention and in the claims, the term "halogen" refers to F, Cl, Br and I.

In a first aspect the present invention refers to compounds having general chemical Formula A (general chemical Formula I), wherein $K=N^+(R^1)(R^2)(R^3)X^-$:

wherein:
-G is selected from the group comprising —F, —Cl, —Br, —I, —NO, —NO$_2$, —NR$^4$COCF$_3$, —NR$^4$SO$_2$CF$_3$, —N(R$^4$)SO$_2$R$^5$, —N(CF$_3$)$_2$, —NHCSNHR$^4$, —N(SO$_2$R$^5$)$_2$, —N(O)=NCONH$_2$, —NR$^4$CN, —NHCSR$^5$, —N≡C, —N=C(CF$_3$)$_2$, —N=NCF$_3$, —N=NCN, —NR$^4$COR$^4$, —NR$^4$COOR$^5$, —OSO$_2$CF$_3$, —OSO$_2$C$_6$H$_5$, —OCOR$^5$, —ONO$_2$, —OSO$_2$R$^5$, —O—C=CH$_2$, —OCF$_2$CF$_3$, —OCOCF$_3$, —OCN, —OCF$_3$, —C≡N, —C(NO$_2$)$_3$, —COOR$^4$, —CONR$^4$R$^5$, —C(S)NH$_2$, —CH=NOR$^4$, —CH$_2$SO$_2$R$^4$, —COCF$_3$, —CF$_3$, —CF$_2$Cl—CBr$_3$, —CClF$_2$, —CCl$_3$, —CF$_2$CF$_3$, —C≡CR$^4$, —CH=NSO$_2$CF$_3$, —CH$_2$CF$_3$, —COR$^5$, —CH=NOR$^5$, —CH$_2$CONH$_2$, —CSNHR$^5$, —CH=NNHCSNH$_2$, —CH=NNHCONHNH$_2$, —C≡C—CF$_3$, —CF=CFCF$_3$, —CF$_2$—CF$_2$—CF$_3$, —CR$^4$(CN)$_2$, —COCF$_2$CF$_2$CF$_3$, —C(CF$_3$)$_3$, —C(CN)$_3$, —CR$^4$=C(CN)$_2$, -1-pyrryl, —C(CN)=C(CN)$_2$, —C-pyridyl, —COC$_6$H$_5$, —COOC$_6$H$_5$, —SOCF$_3$, —SO$_2$CF$_3$, —SCF$_3$, —SO$_2$CN, —SCOCF$_3$, —SOR$^5$, —S(OR$^5$), —SC=CR$^4$, —SO$_2$R$^5$, —SSO$_2$R$^5$, —SR$^5$, —SSR$^4$, —SO$_2$CF$_2$CF$_3$, —SCF$_2$CF$_3$, —S(CF$_3$)=NSO$_2$CF$_3$, —SO$_2$C$_6$H$_5$, —SO$_2$N(R$^5$)$_2$, —SO$_2$C(CF$_3$)$_3$, —SC(CF$_3$)$_3$, —SO(CF$_3$)=NSO$_2$CF$_3$, —S(O)(=NH)CF$_3$, —S(O)(=NH)R$^5$, —S—C=CH$_2$, —SCOR$^5$, —SOC$_6$H$_5$, —P(O)C$_3$F$_7$, —PO(OR$^5$)$_2$, —PO(N(R$^5$)$_2$)$_2$, —P(N(R$^5$)$_2$)$_2$, —P(O)R$^5$$_2$, and —PO(OR$^5$)$_2$ or another electron-drawing group wherein the respective substituent can be in ortho, para or meta position in respect of the K group, For the purposes of the present invention, the term "electron-drawing group" or "electron withdrawing group" refers to a chemical moiety (substituent) which is attached to the benzene ring, which is able to decrease the electron density of the benzene ring and which is listed in Chem. Rev. (1991), 91, 165-195, Tablel (and references therein) with values of $\sigma_m$ or $\sigma_p > 0$;

-Q is hydrogen, lower unbranched or branched alkyl, aryl, heteroaryl, —O—(C$_1$-C$_4$ alkyl), —CN, -halogen, —SO$_2$—R$^4$, —NO$_2$ or a condensed aryl or condensed heteroaryl wherein the respective substituent can be in ortho, para or meta position in respect of the K group, wherein R$^4$ is hydrogen or lower unbranched or branched alkyl and R$^5$ is lower unbranched or branched alkyl, -L- is a bond, —CO—, —SO$_2$—, —(CH$_2$)$_d$—CO—, —SO—, —C≡C—CO—, —[CH$_2$]$_m$-E-[CH$_2$]$_n$—

CO—, —[CH$_2$]$_m$-E-[CH$_2$]$_n$—SO$_2$—, —C(═O)—O—, —NR$^{10}$—, —O—, —(S)$_p$—, —C(═O)NR$^{12}$—, —C(═S)NR$^{12}$—, —C(═S)O—, C$_1$-C$_6$ cycloalkyl, alkenyl, heterocycloalkyl, unsubstituted or substituted aryl or unsubstituted or substituted heteroaryl, aralkyl, heteroaralkyl, alkylenoxy, arylenoxy, aralkyloxy, —SO$_2$NR$^{13}$—, —NR$^{13}$SO$_2$—, —NR$^{13}$C(═O)O—, —NR$^{13}$C(═O)NR$^{12}$—, —NH—NH— and —NH—O—, wherein d is an integer of from 1 to 6, m and n, independently, are any integer of from 0 to 5, -E- is a bond, —S—, —O— or —NR$^9$—, wherein R$^9$ is H, C$_1$-C$_{10}$ alkyl, aryl, heteroaryl or aralkyl, p is any integer of from 1 to 3, R$^{10}$, R$^{11}$ and R$^{12}$, independently, are selected from the group comprising H, C$_1$-C$_{10}$alkyl, aryl, heteroaryl or aralkyl and R$^{13}$ is H, substituted or nonsubstituted, linear or branched C$_1$-C$_6$ alkyl, aryl, cycloalkyl, heterocycloalkyl, heteroaryl, aralkyl or heteroaralkyl, —Y— is a bond or a spacer, U is a targeting agent, preferably selected from the group comprising peptides, peptidomimetics, small molecules and oligonucleotides.

K is N$^+$(R$^1$)(R$^2$)(R$^3$)X$^-$,

X$^-$ is CF$_3$S(O)$_2$O$^-$, C$_4$F$_9$S(O)$_2$O$^-$, iodide anion, bromide anion, chloride anion, perchlorate anion (ClO$_4^-$), phosphate anion, trifluoroacetate anion (CF$_3$—C(O)O$^-$), or the anion of another salt of an inorganic or organic acid, wherein R$^1$, R$^2$ and R$^3$ are independently from each other selected from the group comprising substituted or unsubstituted alkyl and aralkyl.

The invention further refers to pharmaceutically acceptable salts of inorganic or organic acids, hydrates, complexes, esters, amides, solvates and prodrugs of the compounds having general chemical Formula I.

In a preferred embodiment of the present invention, in the compounds having general chemical Formula I, -G is selected from the group comprising —F, —Cl, —Br, —NO$_2$, —NR$^4$SO$_2$R$^5$, —NHCSNHR$^4$, —NR$^4$CN, —NR$^4$SO$_2$CF$_3$, —N═C, —NR$^4$COR$^4$, —NR$^4$COOR$^5$, —OSO$_2$R$^5$, —OCF$_3$, —C≡N, —COOR$^4$, —CONR$^4$R$^5$, —COCF$_3$, —CF$_2$CF$_3$, —C≡CR$^4$, —COR$^5$, —CH$_2$CONH$_2$, —CF$_3$, —C≡C—CF$_3$, —CF$_2$—CF$_2$—CF$_3$, —C(CN)═C(CN)$_2$, —COC$_6$H$_5$, —SO$_2$CF$_3$, —SCOCF$_3$, —SO$_2$R$^5$, —SO$_2$CF$_2$CF$_3$, —SO$_2$C$_6$H$_5$, —SO$_2$N(R$^5$)$_2$ and —PO(OR$^5$)$_2$ wherein the respective substituent can be in ortho, para or meta position in respect of the K group.

In a further preferred embodiment of the present invention, in the compounds having general chemical Formula I, -G is selected from the group comprising —F, —Cl, —Br, —NO$_2$, —NR$^4$SO$_2$R$^5$, —NR$^4$COR$^4$, —NR$^4$COOR$^5$, —C≡N, —CONR$^4$R$^5$, —C≡CR$^4$, —COR$^5$, —CF$_3$, —COC$_6$H$_5$, —SO$_2$CF$_3$, —SO$_2$R$^5$, —SO$_2$C$_6$H$_5$ and —SO$_2$N(R$^5$)$_2$ wherein the respective substituent can be in ortho, para or meta position in respect of the K group.

In a further alternative embodiment of the present invention, in the compounds having general chemical Formula I, -G is selected from the group comprising —F, —Cl, —Br, —NO$_2$, —NR$^4$SO$_2$R$^5$, —NR$^4$COR$^4$, —NR$^4$COOR$^5$, —C≡N, —CONR$^4$R$^5$, —C≡CR$^4$, —COR$^5$, —CF$_3$ and —SO$_2$R$^5$ wherein the respective substituent can be in ortho, para or meta position in respect of the K group.

In a further more preferred alternative embodiment of the present invention, in the compounds having general chemical Formula I, -G is selected from a group comprising those members which have a value of the Hammet constant σ≥0.35 (compare Chem. Rev., 1991, 91:165, Table 1; (FIGS. 12A-12C) and which contain a fluoro or a nitrogen atom:

—F, —NO, —NO$_2$, —NR$^4$SO$_2$CF$_3$, —N(CF$_3$)$_2$, —N(SO$_2$R$^5$)$_2$, —N(O)═NCONH$_2$, —N≡C, —N═NCF$_3$, —N═NCN, —NR$^4$COR$^4$, —OSO$_2$CF$_3$, —OCOR$^5$, —ONO$_2$, —OCF$_2$CF$_3$, —OCOCF$_3$, —OCN, —OCF$_3$, —C≡N, —C(NO$_2$)$_3$, —CONR$^4$R$^5$, —CH═NOR$^4$, —COCF$_3$, —CF$_3$, —CF$_2$Cl—CBr$_3$, —CClF$_2$, —CF$_2$CF$_3$, —CH═NSO$_2$CF$_3$, —CH═NNHCSNH$_2$, —CF═CFCF$_3$, —CF$_2$—CF$_2$—CF$_3$, —CR$^4$(CN)$_2$, —COCF$_2$CF$_2$CF$_3$, —C(CF$_3$)$_3$, —C(CN)$_3$, —CR$^4$═C(CN)$_2$, —C(CN)═C(CN)$_2$, —SOCF$_3$, —SO$_2$CF$_3$, —SCF$_3$, —SO$_2$CN, —SCOCF$_3$, —SO$_2$CF$_2$CF$_3$, —SCF$_2$CF$_3$, —S(CF$_3$)═NSO$_2$CF$_3$, —SO$_2$N(R$^5$)$_2$, —SO$_2$C(CF$_3$)$_3$, —SC(CF$_3$)$_3$, —SO(CF$_3$)═NSO$_2$CF$_3$, —S(O)(═NH)CF$_3$, —S(O)(═NH)R$^5$ and —P(O)C$_3$F$_7$ wherein the respective substituent can be in ortho, para or meta position in respect of the K group.

In a further even more preferred alternative embodiment of the present invention, in the compounds having general chemical Formula I, -G is selected from a group comprising those members of the embodiment herein above which have a value of the Hammet constant σ≥0.50 (compare Chem. Rev., 1991, 91:165, Table 1 or which contain a fluoro atom:

—F, —NO, —NO$_2$, —NR$^4$SO$_2$CF$_3$, —N(CF$_3$)$_2$, —N(O)═NCONH$_2$, —N═NCF$_3$, —N═NCN, —OSO$_2$CF$_3$, —ONO$_2$, —OCF$_2$CF$_3$, —OCOCF$_3$, —OCN, —OCF$_3$, —C≡N, —C(NO$_2$)$_3$, —COCF$_3$, —CF$_3$, —CF$_2$Cl—CBr$_3$, —CClF$_2$, —CF$_2$CF$_3$, —CH═NSO$_2$CF$_3$, —CF═CFCF$_3$, —CF$_2$—CF$_2$—CF$_3$, —CR$^4$(CN)$_2$, —COCF$_2$CF$_2$CF$_3$, —C(CF$_3$)$_3$, —C(CN)$_3$, —CR$^4$═C(CN)$_2$, —C(CN)═C(CN)$_2$, —SOCF$_3$, —SO$_2$CF$_3$, —SCF$_3$, —SO$_2$CN, —SCOCF$_3$, —SO$_2$CF$_2$CF$_3$, —SCF$_2$CF$_3$, —S(CF$_3$)═NSO$_2$CF$_3$, —SO$_2$N(R$^5$)$_2$, —SO$_2$C(CF$_3$)$_3$, —SC(CF$_3$)$_3$, —SO(CF$_3$)═NSO$_2$CF$_3$, —S(O)(═NH)CF$_3$ and —P(O)C$_3$F$_7$ wherein the respective substituent can be in ortho, para or meta position in respect of the K group.

In a further even more preferred alternative embodiment of the present invention, in the compounds having general chemical Formula I, -G is selected from a group comprising —F, —NO$_2$, —OCF$_2$CF$_3$—OCF$_3$, —C≡N, —COCF$_3$, —CF$_3$, —CF$_2$CF$_3$, —CF$_2$—CF$_2$—CF$_3$, —COCF$_2$CF$_2$CF$_3$, —SO$_2$CF$_3$, —SO$_2$CN, —SO$_2$CF$_2$CF$_3$, —SO$_2$N(R$^5$)$_2$ and SC(CF$_3$)$_3$ wherein the respective substituent can be in ortho, para or meta position in respect of the K group.

In a further even more preferred alternative embodiment of the present invention, in the compounds having general chemical Formula I, -G is selected from the group comprising those members with a value of the Hammet constant σ≥0.50 (compare Chem. Rev., 1991, 91:165, Table 1 or which contain a sulfur or a fluoro atom:

—F, —NR$^4$SO$_2$CF$_3$, —N(CF$_3$)$_2$, —N═NCF$_3$, —OSO$_2$CF$_3$—OCF$_2$CF$_3$, —OCOCF$_3$, —OCF$_3$, —COCF$_3$, —CF$_3$, —CF$_2$Cl—CBr$_3$, —CClF$_2$, —CF$_2$CF$_3$, —CH═NSO$_2$CF$_3$, —CF═CFCF$_3$, —CF$_2$—CF$_2$—CF$_3$, —COCF$_2$CF$_2$CF$_3$, —C(CF$_3$)$_3$, —SOCF$_3$, —SO$_2$CF$_3$, —SCF$_3$, —SO$_2$CN, —SO$_2$R$^5$, —SCOCF$_3$, —SO$_2$CF$_2$CF$_3$, —SCF$_2$CF$_3$, —S(CF$_3$)═NSO$_2$CF$_3$, —SO$_2$N(R$^5$)$_2$, —SO$_2$C(CF$_3$)$_3$, —SC(CF$_3$)$_3$, —SO(CF$_3$)═NSO$_2$CF$_3$, —S(O)(═NH)CF$_3$ and —P(O)C$_3$F$_7$ wherein the respective substituent can be in ortho, para or meta position in respect of the K group.

In a further even more preferred alternative embodiment of the present invention, in the compounds having general chemical Formula I, -G is selected from the group comprising —F, —NR$^4$SO$_2$CF$_3$, —OSO$_2$CF$_3$—OCF$_2$CF$_3$, —OCF$_3$, —COCF$_3$, —CF$_3$, —SO$_2$CF$_3$, —SO$_2$R$^5$ and —SO$_2$N(R$^5$)$_2$ wherein the respective substituent can be in ortho, para or meta position in respect of the K group.

A positive value of a Hammet constant is a measure of electron deficiency. It seems that certain combinations of substituents with particular atoms (nitrogen, sulfur and/or fluoro) are favourable over others. For example nitrogen or fluoro substituents combined with positive Hammet constants allow a $^{18}$F radiolabeling with relative high radiochemical yields whereas sulfur or fluoro atoms seem to guarantee radiolabeling reactions with only minor side reactions. It is for example known from literature that the choice of substituent can influence the ratio of ring fluorination versus methyl fluoride formation at trimethylammonium benzene derivatives with two substituents in total (review Coenen, "*Fluorine*-18 *Labeling Methods: Features and Possibilities of Basic Reaction*", 2006, in: P. A. Schubiger, M. Friebe, L. Lehmann, (eds), *PET-Chemistry—The Driving Force in Molecular Imaging.* Springer, Berlin Heidelberg, p. 15-50, in particular p. 23-26).

In a further alternative embodiment of the present invention -G is selected from the group comprising —F, —Cl, —Br, —NO$_2$, —OSO$_2$R$^4$, —OCF$_3$, —C≡N, —COOR$^4$, —CONR$^4$R$^5$, —COCF$_3$, —CF$_2$CF$_3$, —COR$^5$, —CF$_3$, —C≡C—CF$_3$, —CF$_2$—CF$_2$—CF$_3$, —COC$_6$H$_5$, —SO$_2$CF$_3$, —SCOCF$_3$, —SO$_2$R$^5$, —SO$_2$CF$_2$CF$_3$, —SO$_2$C$_6$H$_5$, —SO$_2$N(R$^5$)$_2$, and —PO(OR$^5$)$_2$ and more preferably from —F, —Cl, —Br, —NO$_2$, —C≡N, —CF$_3$, —SO$_2$CF$_3$, —SO$_2$R$^5$, —SO$_2$C$_6$H$_5$, or —SO$_2$N(R$^5$)$_2$ wherein the respective substituent can be in ortho, para or meta position in respect of the K group.

In a further preferred embodiment of the present invention, -Q is —H, lower unbranched or branched alkyl, aryl, heteroaryl, —O—(C$_1$-C$_4$alkyl), —CN, -halogen, —SO$_2$—R$^4$—, —NO$_2$ or a condensed aryl or heteroaryl wherein the respective substituent can be in ortho, para or meta position in respect of the K group.

In a more preferred embodiment of the present invention, -Q is —H, —C$_1$-C$_4$ alkyl, —O—(C$_1$-C$_4$ alkyl), —CN, —F, —Cl, —Br or —NO$_2$ wherein the respective substituent can be in ortho, para or meta position in respect of the K group.

In an even more preferred embodiment of the present invention, -Q is —H, —CH$_3$, —O—CH$_3$, —CN, —F, —Cl or —NO$_2$ wherein the respective substituent can be in ortho, para or meta position in respect of the K group.

In an alternative embodiment -Q is —H, —CN, -halogen, —SO$_2$—R$^4$ or —NO$_2$ wherein the respective substituent can be in ortho, para or meta position in respect of the K group.

In a further alternative embodiment of the present invention -Q is selected from —H, —CN, —F, —Cl, —Br or —NO$_2$, more preferably from —H, —CN, —F or —NO$_2$ wherein the respective substituent can be in ortho, para or meta position in respect of the K group.

In a further alternative embodiment of the present invention, in the compounds having general chemical Formula I, -Q is —H, —CN or —F wherein the respective substituent can be in ortho, para or meta position in respect of the K group.

In a very preferred embodiment of the present invention, any of -G and -Q, more preferred -G, is in ortho, or less preferred, in para position relative to K=N$^+$(R$^1$)(R$^2$)(R$^3$)X$^-$.

In a preferred embodiment of compounds of Formula I, -G and -Q are independently from each other selected from —H, —CN, CF$_3$, and —Cl.

In a more preferred embodiment -G and -Q are independently from each other H, —CF$_3$, or CN.

In a even more preferred embodiment in a more preferred embodiment -G and -Q are independently from each other H, —CF$_3$, or —CN, whereas at least -G or -Q is —CF$_3$ or —CN.

In a further preferred embodiment of the present invention, in the compounds having general chemical Formula I, R$^4$ is hydrogen or unbranched or branched C$_1$-C$_6$ alkyl, more preferably C$_1$-C$_4$ alkyl, most preferably hydrogen or methyl.

In a further preferred embodiment of the present invention, in the compounds having general chemical Formula I, R$^5$ is unbranched or branched C$_1$-C$_6$ alkyl, more preferably C$_1$-C$_4$ alkyl, most preferably methyl.

In a preferred embodiment of the present invention, in compounds having general chemical Formula I, R$^1$, R$^2$ and R$^3$ are independently from each other selected from the group comprising lower unbranched (linear) or branched alkyl or aralkyl.

In another preferred embodiment of the present invention, in the compounds having general chemical Formula I, R$^1$, R$^2$ and R$^3$ are independently from each other selected from the group comprising aralkyl or lower alkyl, whereas one of the three moieties (R$^1$, R$^2$, R$^3$) can be resin-bound.

In another preferred embodiment of the present invention, in the compounds having general chemical Formula I, R$^1$, R$^2$ and R$^3$ are independently from each other selected from the group comprising aralkyl or lower alkyl, preferably C$_1$-C$_6$ alkyl, whereas at least two moieties of the three moieties (R$^1$, R$^2$, R$^3$) are alkyl.

In another preferred embodiment of the present invention, in the compounds having general chemical Formula I, R$^1$, R$^2$ and R$^3$ are independently from each other selected from the group comprising C$_1$-C$_6$ alkyl moieties.

In another preferred embodiment of the present invention, in the compounds having general chemical Formula I, R$^1$ is aralkyl and R$^2$ and R$^3$ are each methyl.

In another preferred embodiment of the present invention, in the compounds having general chemical Formula I, R$^1$, R$^2$ and R$^3$ are each methyl.

In a further preferred embodiment of the present invention, in the compound having general chemical Formula I, X$^-$ is CF$_3$—C(O)O$^-$, CF$_3$S(O)$_2$O$^-$, C$_4$F$_9$S(O)$_2$O$^-$.

In an even more preferred embodiment of the present invention, in the compound having general chemical Formula I, X$^-$ is CF$_3$—C(O)O$^-$ or CF$_3$S(O)$_2$O$^-$.

In a further preferred embodiment of the present invention, -L- is a bond, —CO—, —SO$_2$—, —(CH$_2$)$_d$—CO—, —SO—, or —C≡C—CO—, wherein d is an integer of from 1 to 6.

In a more preferred embodiment of the present invention, in the compounds having general chemical Formula I, -L- is —CO—, —SO$_2$— or —C≡C—CO—.

In an even more preferred embodiment of the present invention, in the compounds having general chemical Formula I, -L- is —CO— or —SO$_2$—.

In a further preferred embodiment of the present invention, in the compound having general chemical Formula I, the spacer —Y— is a natural or unnatural amino acid sequence or mixture thereof or a non-amino acid group.

In a more preferred embodiment of the present invention, in the compounds having general chemical Formula I, the spacer —Y— is an amino acid sequence with two (2) to twenty (20) amino acid residues.

In an even more preferred embodiment of the present invention, in the compounds having general chemical Formula I, the spacer —Y— is Arg-Ser, Arg-Ava, Lys(Me)2-β-ala, Lys(Me)-2-ser, Arg-β-ala, Ser-Ser, Ser-Thr, Arg-Thr, S-alkylcysteine, cysteic acid, thioalkylcysteine (S—S-Alkyl) or

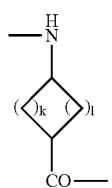

wherein k and l are independently selected in the range of from 0 to 4.

In an even more preferred embodiment of the present invention, in the compounds having general chemical Formula I, the spacer —Y— is a non-amino acid moiety selected from the group comprising —NH—$(CH_2)_p$—CO—, wherein p is an integer of from 2 to 10, —NH—$(CH_2$—$CH_2$—$O)_q$—$CH_2$—$CH_2$—CO—, wherein q is an integer of from 0 to 5.

—NH-cycloalkyl-CO— wherein cycloalkyl is selected from $C_5$-$C_8$ cycloalkyl, more preferably $C_6$ atom cycloalkyl, and —NH-heterocycloalkyl-$(CH_2)_v$—CO— wherein heterocycloalkyl is selected from $C_5$-$C_8$ heterocycloalkyl containing carbon atoms and 1, 2, 3 or 4 oxygen, nitrogen or sulfur heteroatoms more preferably 1 to 2 heteroatom even more preferably 1 heteroatom and v is an integer of from 1 to 4, more preferably v is an integer of from 1 to 2 U is a targeting agent.

For the purposes of the present invention, the term "targeting agent" shall have the following meaning: The targeting agent is a compound or moiety that targets or directs the radionuclide attached to it to a specific site in a biological system. A targeting agent can be any compound or chemical entity that binds to or accumulates at a target site in a mammalian body, i.e., the compound localizes to a greater extent at the target site than to surrounding tissue.

The compounds of this invention are useful for the imaging of a variety of cancers including but not limited to: carcinoma such as bladder, breast, colon, kidney, liver, lung, including small cell lung cancer, esophagus, gall-bladder, ovary, pancreas, stomach, cervix, thyroid, prostate and skin, hematopoetic tumors of lymphoid and myeloid lineage, tumors of mesenchymal origin, tumors of central peripheral nervous systems, other tumors, including melanoma, seminoma, teratocarcinoma, osteosarcoma, xeroderma pigmentosum, keratoxanthoma, thyroid follicular cancer and Karposi's sarcoma. Most preferably, the use is not only for imaging of tumors, but also for imaging of inflammatory and/or neurodegenerative diseases, such as multiple sclerosis or Alzheimer's disease, or imaging of angiogenesis-associated diseases, such as growth of solid tumors, and rheumatoid arthritis.

Preferably the targeting agent U is a peptide, a peptidomimetic, or an oligonucleotide, particularly one which has specificity to target the complex to a specific site in a biological system. Small molecules effective for targeting certain sites in a biological system can also be used as the targeting agent.

Small molecules effective for targeting certain sites in a biological system can be used as the targeting agent U. Smaller organic molecules may be "small chemical entities". As used in this application, the term "small chemical entity" shall have the following meaning: A small chemical entity is a compound that has a molecular mass of from 200 to 800 or of from 150 to 700, more preferably from 200 to 700, more preferably from 250 to 700, even more preferably from 300 to 700, even more preferably from 350 to 700 and most preferably from 400 to 700. A small chemical entity as used herein may further contain at least one aromatic or heteroaromatic ring and may also have a primary or secondary amine, a thiol or hydroxyl group coupled via which the benzene ring structure in the compounds of general chemical Formulae I and II is coupled via -L-Y—. Such targeting moieties are known in the art, so are methods for preparing them.

The small molecule targeting agents may preferably be selected from those described in the following references: P. L. Jager, M. A. Korte, M. N. Lub-de Hooge, A. van Waarde, K. P. Koopmans, P. J. Perik and E. G. E. de Vries, *Cancer Imaging*, (2005) 5, 27-32; W. D. Heiss and K. Herholz, *J. Nucl. Med.*, (2006) 47(2), 302-312; and T. Higuchi and M. Schwaiger, *Curr. Cardiol. Rep.*, (2006) 8(2), 131-138. More specifically examples of small molecule targeting agents are listed hereinafter:

| Name | Abbr. | target |
|---|---|---|
| 18F-2b-Carbomethoxy-3b-(4-fluorophenyl)tropane | CFT | DAT (dopamine transporter) |
| 18F-Fluoroethylspiperone | FESP | D2 (dopamine 2 receptor), 5-$HT_2$ (5-hydroxytryptamine receptor) |
| 18F-Fallypride | | D2 (dopamine 2 receptor) |
| 18F-Altanserin | | 5-HT2A receptor |
| 18F-Cyclofoxy | | Opioid receptors |
| 18F-CPFPX | | Adenosine A1 receptor |
| Batimastat | | MMP |
| Fatty acids and analogues | | |
| Choline analogues (metabolism) | | |
| Flumazenil | | Benzodiazepine receptors |
| Raclopride | | D2 receptors |
| Dihydrotestosteron and analogues | | AR |
| Tamoxifen and analogues | | |
| Deoxyglucose | | |
| Thymidine | | Proliferation marker-thymidine kinase |
| DOPA | | |
| Benzazepines | | $D_1$ antagonists |
| N-methyl spiperone and derivatives thereof | | dopamine receptors |

| Name | Abbr. | target |
|---|---|---|
| Benzamide raclopride; benzamide derivatives, e.g., fallopride, iodo benzamide; clozapine, quietapine | | $D_2$ receptors |
| Nomifensine, substituted analogs of cocaine, e.g., tropane type derivatives of cocaine, methyl phenidate | | DAT |
| 2β-Carboxymethoxy-3β-(4-iodophenyl)tropane | CIT | DAT |
| | CIT-FE, CIT-FM | DAT |
| Altanserin, setoperon, ketanserin | | $5\text{-}HT_{2A}$ |
| | McN5652, 403U76 derivative ADAM, DASP, MADAM | 5-HTT |
| Acetylcholine analogues | MP3A, MP4A, PMP; QNB, TKB, NMPB, | acetylcholine receptors |
| Scopolamine, benztropine | | acetylcholine receptors |
| Flumazenil | | GABA receptor |
| | RO-15-4513, FDG | GABA receptor |
| | PK-11195 | benzodiazepine receptor |
| Xanthine analogues | CPFPX, MPDX | adenosine receptor |
| Carfentanyl, diprenorphine | | opoid receptor |

Further various small molecule targeting agents and the targets thereof are given in Table 1 in W. D. Heiss and K. Herholz, ibid. and in FIG. 1 in T. Higuchi, M. Schwaiger, ibid.

Further preferred biomolecules are sugars, oligosaccharides, polysaccharides, aminoacids, nucleic acids, nucleotides, nucleosides, oligonucleotides, proteins, peptides, peptidomimetics, antibodies, aptamers, lipids, hormones (steroid and nonsteroid), neurotransmitters, drugs (synthetic or natural), receptor agonists and antagonists, dendrimers, fullerenes, virus particles and other targeting molecules/biomolecules (e.g., cancer targeting molecules).

Preferably the targeting agent U is a peptide.

The targeting agent U may be a peptide comprising from 4 to 100 amino acids wherein the amino acids may be selected from natural and non-natural amino acids and also may comprise modified natural and non-natural amino acids.

Examples for peptides as targeting agent targeting agent U are, but are not limited to, somatostatin and derivatives thereof and related peptides, somatostatin receptor specific peptides, neuropeptide Y and derivatives thereof and related peptides, neuropeptide V, and the analogs thereof, bombesin and derivatives thereof and related peptides, gastrin, gastrin releasing peptide and the derivatives thereof and related peptides, epidermal growth factor (EGF of various origin), insulin growth factor (IGF) and IGF-1, integrins ($\alpha_3\beta_1$, $\alpha_v\beta_3$, $\alpha_v\beta_5$, $\alpha IIb_3$), LHRH agonists and antagonists, transforming growth factors, particularly TGF-$\alpha$; angiotensin; cholecystokinin receptor peptides, cholecystokinin (CCK) and the analogs thereof; neurotensin and the analogs thereof, thyrotropin releasing hormone, pituitary adenylate cyclase activating peptide (PACAP) and the related peptides thereof, chemokines, substrates and inhibitors for cell surface matrix metalloproteinase, prolactin and the analogs thereof, tumor necrosis factor, interleukins (IL-1, IL-2, IL-4 or IL-6), interferons, vasoactive intestinal peptide (VIP) and the related peptides thereof. Such peptides comprise from 4 to 100 amino acids, wherein the amino acids are selected from natural and non-natural amino acids and also comprise modified natural and non-natural amino acids. Preferably targeting agent U is not insulin.

More preferably targeting agent U may be selected from the group comprising bombesin and bombesin analogs, preferably those having the sequences listed herein below, somatostatin and somatostatin analogs, preferably those having the sequences listed herein below, neuropeptide $Y_1$ and the analogs thereof, preferably those having the sequences listed herein below, vasoactive intestinal peptide (VIP) and the analogs thereof.

Even more preferably targeting agent U may be selected from the group comprising bombesin, somatostatin, neuropeptide $Y_1$ and the analogs thereof.

Even more preferably targeting agent U may be bombesin and the analogs thereof.

Bombesin is a fourteen amino acid peptide that is an analog of human Gastrin releasing peptide (GRP) that binds with high specificity to human GRP receptors present in prostate tumor, breast tumor and metastasis. Accordingly, as to a ninth aspect of the present invention, bombesin analogs are provided.

In a more preferred embodiment, bombesin analogs have the following sequence having Formula III:

$AA_1$-$AA_2$-$AA_3$-$AA_4$-$AA_5$-$AA_6$-$AA_7$-$AA_8$-$NT_1T_2$ (type A) Formula III, with:
 $T_1$=$T_2$=H or $T_1$=H, $T_2$=OH or $T_1$=$CH_3$, $T_2$=OH
 $AA_1$=Gln, Asn, Phe(4-CO—$NH_2$)
 $AA_2$=Trp, D-Trp
 $AA_3$=Ala, Ser, Val
 $AA_4$=Val, Ser, Thr
 $AA_5$=Gly, (N-Me)Gly
 $AA_6$=His, His(3-Me), (N-Me)His, (N-Me)His(3-Me)
 $AA_7$=Sta, Statine analogs and isomers, 4-Am,5-Me-HpA, 4-Am,5-MeHxA, γ-substituted aminoacids
 $AA_8$=Leu, Cpa, Cba, CpnA, Cha, t-buGly, tBuAla, Met, Nle, iso-Bu-Gly In a more preferred embodiment, bombesin analogs have the following sequence of formula IV:

$AA_1$-$AA_2$-$AA_3$-$AA_4$-$AA_5$-$AA_6$-$AA_7$-$AA_8$-$NT_1T_2$ (type B) Formula IV, with:
 $T_1$=$T_2$=H or $T_1$=H, $T_2$=OH or $T_1$=$CH_3$, $T_2$=OH
 $AA_1$=Gln, Asn or Phe(4-CO—$NH_2$)
 $AA_2$=Trp, D-Trp
 $AA_3$=Ala, Ser, Val
 $AA_4$=Val, Ser. Thr AA$_5$=βAla, β$^2$- and β$^3$-amino acids as shown herein after

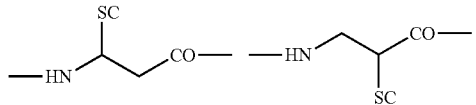

wherein SC represents a side chain found in proteinogenic amino acids and homologs of proteinogenic amino acids,
AA$_6$=His, His(3-Me), (N-Me)His, (N-Me)His(3-Me)
AA$_7$=Phe, Tha, Nal,
AA$_8$=Leu, Cpa, Cba, CpnA, Cha, t-buGly, tBuAla, Met, Nle, iso-Bu-Gly.

Therefore, in an even more preferred embodiment of the present invention targeting agent U may be selected from the group comprising bombesin analogs having sequence III or IV.

In a more preferred embodiment, bombesin analogs have the following sequences:

| Seq ID | P |
|---|---|
| Seq ID 1 | Gln-Trp-Ala-Val-NMeGly-His-Sta-Leu-NH$_2$ |
| Seq ID 2 | Gln-Trp-Ala-Val-Gly-His(Me)-Sta-Leu-NH$_2$ |
| Seq ID 3 | Gln-Trp-Ala-Val-NMeGly-His(3Me)-Sta-Leu-NH$_2$ |
| Seq ID 4 | Gln-Trp-Ala-Val-Gly-His(3Me)-Sta-Leu-NH$_2$ |
| Seq ID 7 | Gln-Trp-Ala-Val-NMeGly-His(3Me)-Sta-Cpa-NH$_2$ |
| Seq ID 8 | Gln-Trp-Ala-Val-Gly-His(3Me)-4-Am,5-MeHpA-Leu-NH$_2$ |
| Seq ID 12 | Gln-Trp-Ala-Val-Gly-His(3Me)-4-Am,5-MeHpA-Leu-NH$_2$ |
| Seq ID 17 | Gln-Trp-Ala-Val-Gly-His-4-Am,5-MeHpA-Leu-NH$_2$ |
| Seq ID 23 | Gln-Trp-Ala-Val-NMeGly-His(3Me)-4-Am,5-MeHpA-Cpa-NH$_2$ |
| Seq ID 27 | Gln-Trp-Ala-Val-NMeGly-His-FA02010-Cpa-NH$_2$ |
| Seq ID 28 | Gln-Trp-Ala-Val-NMeGly-His-4-Am,5-MeHpA-tbuGly-NH$_2$ |
| Seq ID 30 | Gln-Trp-Ala-Val-NMeGly-His(3Me)-Sta-tBuGly-NH$_2$ |
| Seq ID 32 | Gln-Trp-Ala-Val-NMeGly-His(3Me)-4-Am,5-MeHpA-Leu-NH$_2$ |
| Seq ID 33 | Gln-DTrp-Ala-Val-Gly-His-4-Am,5-MeHpA-tbuGly-NH$_2$ |
| Seq ID 34 | Gln-DTrp-Ala-Val-Gly-His-4-Am-5-MeHxA-Cpa-NH$_2$ |
| Seq ID 35 | Gln-Trp-Ala-Val-NMeGly-His(3Me)-Sta-Cpa-NH$_2$ |
| Seq ID 36 | Gln-DTrp-Ala-Val-Gly-His-Sta-tbuAla-NH$_2$ |
| Seq ID 42 | Gln-Trp-Ala-Val-Gly-His(3Me)-Sta-Cpa-NH$_2$ |
| Seq ID 43 | Gln-Trp-Ala-Val-Gly-His(3Me)-Sta-tBuGly-NH$_2$ |
| Seq ID 46 | Gln-Trp-Ala-Val-Gly-His(3Me)-4-Am,5-MeHpA-Leu-NH$_2$ |
| Seq ID 48 | Gln-Trp-Ala-Val-Gly-His(3Me)-4-Am,5-MeHpA-Leu-NH$_2$ |
| Seq ID 49 | Gln-Trp-Ala-Val-Gly-NMeHis-4-Am,5-MeHpA-Cpa-NH$_2$ |
| Seq ID 47 | Gln-Trp-Ala-Val-Gly-NMeHis(3Me)-4-Am,5-MeHpA-Leu-NH$_2$ |
| Seq ID 50 | Gln-Trp-Ala-Val-Gly-NMeHis-4-Am,5-MeHpA-Leu-NH$_2$ |
| Seq ID 51 | Gln-Trp-Ala-Val-NMeGly-His-AHMHxA-Leu-NH$_2$ |
| Seq ID 52 | Gln-Trp-Ala-Val-βAla-NMeHis-Tha-Cpa-NH$_2$ |
| Seq ID 53 | Gln-Trp-Ala-Val-βAla-NMeHis-Phe-Cpa-NH$_2$ |
| Seq ID 54 | Gln-Trp-Ala-Val-βAla-NMeHis-Phe-Leu-NH$_2$ |
| Seq ID 55 | Gln-Trp-Ala-Val-βAla-DHis-Phe-Leu-NH$_2$ |
| Seq ID 56 | Gln-Trp-Ala-Val-βAla-His-βhLeu-Leu-NH$_2$ |
| Seq ID 57 | Gln-Trp-Ala-Val-βAla-His-βhIle-Leu-NH$_2$ |
| Seq ID 58 | Gln-Trp-Ala-Val-βAla-His-βhLeu-tbuGly-NH$_2$ |
| Seq ID 59 | Gln-Trp-Ala-Val-βAla-His(3Me)-Phe-Tha-NH$_2$ |
| Seq ID 60 | Gln-Trp-Ala-Val-βAla-His(3Me)-Phe-Nle-NH$_2$ |
| Seq ID 61 | Gln-Trp-Ala-Val-βAla-NMeHis-Phe-tbuGly-NH$_2$ |
| Seq ID 62 | Gln-Trp-Ala-Val-βAla-NMeHis-Tha-tbuGly-NH$_2$ |
| Seq ID 63 | Gln-Trp-Ala-Val-βAla-His(3Me)-Tha-tbuGly-NH$_2$ |
| Seq ID 64 | Gln-Trp-Ala-Val-βAla-His(3Me)-Phe-Cpa-NH$_2$ |
| Seq ID 65 | Gln-Trp-Ala-NMeVal-βAla-His-Phe-Leu-NH$_2$ |
| Seq ID 66 | Gln-Trp-Ala-Val-βAla-His-NMePhe-Leu-NH$_2$ |
| Seq ID 67 | Gln-DTrp-Ala-Val-βAla-His-Phe-Leu-NH$_2$ |
| Seq ID 68 | Gln-Trp-DAla-Val-βAla-His-Phe-Leu-NH$_2$ |
| Seq ID 69 | Gln-Trp-Ala-DVal-βAla-His-Phe-Leu-NH$_2$ |
| Seq ID 70 | Gln-Trp-Ala-Val-βAla-His-DPhe-Leu-NH$_2$ |

-continued

| Seq ID 71 | Gln-Trp-Ala-Val-βAla-His-βhIle-tbuGly-NH$_2$ |
| Seq ID 72 | Gln-Trp-Ala-Val-NMeGly-His-4-Am,5-MeHpA-Cpa-NH$_2$ |
| Seq ID 73 | Gln-Trp-Ala-Val-NMeGly-His-Sta-Cpa-NH$_2$ |
| Seq ID 74 | Gln-Trp-Ala-Val-NMeGly-His-Sta-tbuAla-NH$_2$ |
| Seq ID 75 | Gln-Trp-Ala-Val-NMeGly-His-4-Am,5-MeHpA-tbuAla-NH$_2$ |
| Seq ID 77 | Gln-Trp-Ala-Val-His(Me)-Sta-Leu-NH$_2$ |
| Seq ID 82 | Gln-Trp-Ala-Val-Gly-His(3Me)-FA4-Am,5-MeHpA-Leu-NH$_2$ |
| Seq ID 90 | Gln-Trp-Ala-Val-Gly-His(3Me)-4-Am,5-MeHpA-Leu-NH$_2$ |
| Seq ID 91 | Gln-Trp-Ala-Val-Gly-His-4-Am,5-MeHpA-Leu-NH$_2$ |
| Seq ID 101 | Gln-Trp-Ala-Val-Gly-His(3Me)-4-Am-5-MeHpA - 4-amino-5-methylheptanoic acid -Leu-NH$_2$ |
| Seq ID 102 | Gln-Trp-Ala-Val-NMeGly-His(3Me)-4-Am-5-MeHpA - 4-amino-5-methylheptanoic acid -Cpa-NH$_2$ |

Thus, the invention also refers to bombesin analogs that bind specifically to human GRP receptors present in prostate tumor, breast tumor and metastasis. In a preferred embodiment, the bombesin analogs are peptides having sequences from Seq ID 1 to Seq ID 102 and preferably have one of them. More preferably a bombesin analog is additionally labeled with a fluorine isotope (F) wherein fluorine isotope (F) is selected from $^{18}$F or $^{19}$F. More preferably the bombesin analog is radiolabeled with $^{18}$F. The bombesin analog is preferably radiolabeled using the radiofluorination method of the present invention.

In a more preferred embodiment, somatostatin analogs have the following sequences:

| SEQ ID 104 | - - - c[Lys-(NMe)Phe-1Nal-D-Trp-Lys-Thr] |
| SEQ ID 105 | - - - c[Dpr-Met-(NMe)Phe-Tyr-D-Trp-Lys] |

In a more preferred embodiment, neuropeptide Y$_1$ analogs have the following sequences:

| SEQ ID 106 | -DCys-Leu-Ile-Thr-Arg-Cys-Arg-Tyr-NH$_2$ |
| SEQ ID 107 | -DCys-Leu-Ile-Val-Arg-Cys-Arg-Tyr-NH$_2$ |

(_indicates disulfide bridge)

In a more preferred embodiment, peptide is tetrapeptide of the following sequences:
valyl-β-alanyl-phenylalanyl-glycine amide
valyl-β-alanyl-histidyl(π-Me)-glycine amide In a further preferred embodiment targeting agent (P) may be selected from the group comprising oligonucleotides comprising from 4 to 100 nucleotides.

In other preferred embodiments the targeting agent U is selected to be an oligonucleotide. In a further preferred embodiment the targeting agent U may be selected from the group comprising oligonucleotides comprising from 4 to 100 nucleotides.

Preferred as targeting agents U are peptides comprising from 4 to 100 amino acids or oligonucleotides comprising from 4 to 100 nucleotides.

Preferred oligonucleotide is TTA1 (see experimental part).

In a further preferred embodiment of the present invention, the targeting agent U may comprise a combination of any of the aforementioned bioactive molecules suitable to bind to a target site together with a reacting moiety which serves the linking between the bioactive molecule and the rest of the compound of the invention (Formulae I, II, III), wherein reacting moiety is selected from —NR$^7$, —NR$^7$—(CH$_2$)$_n$—, —O—(CH$_2$)$_n$— or —S—(CH$_2$)$_n$—, wherein R$^7$ is hydrogen or unbranched or branched alkyl and n is an integer from 1 to 6 and wherein the suitable bioactive molecule is selected from peptide, peptidomimetic, oligonucleotide, or small molecule.

In a preferred embodiment of R$^7$ the alkyl is unbranched or branched C$_1$-C$_6$ alkyl, more preferably a methyl.

In a preferred embodiment U is NR$^7$-peptide, or —(CH$_2$)$_n$-peptide, —O—(CH$_2$)$_n$— peptide or —S—(CH$_2$)$_n$-peptide, NR$^7$-small-molecule, or —(CH$_2$)$_n$-small-molecule, —O—(CH$_2$)$_n$-small-molecule or —S—(CH$_2$)$_n$-small-molecule, NR$^7$-oligonucleotide, or —(CH$_2$)$_n$-oligonucleotide, —O—(CH$_2$)$_n$-oligonucleotide or —S—(CH$_2$)$_n$-oligonucleotide—wherein n is an integer of from 1 to 6.

In a more preferred embodiment U is —NR$^7$-peptide, —(CH$_2$)$_n$-peptide, wherein n is an integer of from 1 to 6.

In another more preferred embodiment U is —NR$^7$-oligonucleotide or —(CH$_2$)$_n$-oligonucleotide, wherein n is an integer of from 1 to 6.

In another more preferred embodiment U is —NR$^7$-small-molecule or —(CH$_2$)$_n$-small molecule, wherein n is an integer of from 1 to 6.

In a preferred embodiment, the precursor for a single step radiolabeling is selected from the following list wherein U is a bombesin analog:

Ia-1 4-(Trimethylammonium)-3-cyano-benzoyl-Arg-Ava-Gln-Trp-Ala-Val-NMeGly-His-Sta-Leu-NH$_2$,
Ia-2 4-(Trimethylammonium)-3-cyano-benzoyl-Arg-Ava-Gln-Trp-Ala-Val-Gly-His(Me)-Sta-Leu-NH$_2$,
Ia-3 4-(Trimethylammonium)-3-cyano-benzoyl-Arg-Ava-Gln-Trp-Ala-Val-NMeGly-His(3Me)-Sta-Leu-NH$_2$,
Ia-4 4-(Trimethylammonium)-3-cyano-benzoyl-1,4-cis-Achc-Gln-Trp-Ala-Val-Gly-His(3Me)-Sta-Leu-NH$_2$,
Ia-5 4-(Trimethylammonium)-3-cyano-benzoyl-Gln-Trp-Ala-Val-Gly-His(3Me)-Sta-Leu-NH$_2$,
Ia-6 4-(Trimethylammonium)-3-cyano-benzoyl-AOC-Gln-Trp-Ala-Val-Gly-His(3Me)-Sta-Leu-NH$_2$,
Ia-7 4-(Trimethylammonium)-3-cyano-benzoyl-Ava-Gln-Trp-Ala-Val-NMeGly-His(3Me)-Sta-Cpa-NH$_2$,
Ia-8 4-(Trimethylammonium)-3-cyano-benzoyl-Ava-Gln-Trp-Ala-Val-Gly-His(3Me)-4-Am,5-MeHpA-Leu-NH$_2$,
Ia-9 4-(Trimethylammonium)-3-cyano-benzoyl-Ava-Gln-Trp-Ala-Val-Gly-His(3Me)-Sta-Leu-NH$_2$,
Ia-10 4-(Trimethylammonium)-3-cyano-benzoyl-Lys(Me)2-βAla-Gln-Trp-Ala-Val-Gly-His(3Me)-Sta-Leu-NH$_2$,
Ia-11 4-(Trimethylammonium)-3-cyano-benzoyl-Lys(Me)2-βAla-Gln-Trp-Ala-Val-Gly-His(3Me)-Sta-Leu-NH$_2$,
Ia-12 4-(Trimethylammonium)-3-cyano-benzoyl-Arg-Ser-Gln-Trp-Ala-Val-Gly-His(3Me)-4-Am,5-MeHpA-Leu-NH$_2$, Ia-13 4-(Trimethylammonium)-3-cyano-benzoyl-Ser-Ser-Gln-Trp-Ala-Val-Gly-His(3Me)-4-Am,5-MeHpA-Leu-NH₂, Ia-14 4-(Trimethylammonium)-3-cyano-benzoyl-Lys(Me)2-Ser-Gln-Trp-Ala-Val-Gly-His(3Me)-4-AM-5-MeHpA-Leu-NH₂, Ia-15 4-(Trimethylammonium)-3-cyano-benzoyl-Arg-Ser-Gln-Trp-Ala-Val-Gly-His(3Me)-Sta-Leu-NH₂, Ia-16 4-(Trimethylammonium)-3-cyano-benzoyl-Lys(Me)2-βAla-Gln-Trp-Ala-Val-Gly-His(3Me)-4-Am,5-MeHpA-Leu-NH₂, Ia-17 4-(Trimethylammonium)-3-cyano-benzoyl-Ava-Gln-Trp-Ala-Val-Gly-His-4-Am,5-MeHpA-Leu-NH₂, Ia-18 4-(Trimethylammonium)-3-trifluoromethyl-benzoyl-Arg-Ava-Gln-Trp-Ala-Val-Gly-His(3Me)-Sta-Leu-NH₂, Ia-19 4-(Trimethylammonium)-3-trifluoromethyl-benzoyl-Arg-Ava-Gln-Trp-Ala-Val-NMeGly-His(3Me)-Sta-Leu-NH₂, Ia-20 4-(Trimethylammonium)-3-trifluoromethyl-benzoyl-1,4-cis-Achc-Gln-Trp-Ala-Val-Gly-His(3Me)-Sta-Leu-NH₂, Ia-21 4-(Trimethylammonium)-3-trifluoromethyl-benzoyl-Gln-Trp-Ala-Val-Gly-His(3Me)-Sta-Leu-NH₂, Ia-22 4-(Trimethylammonium)-3-trifluoromethyl-benzoyl-Arg-βAla-Gln-Trp-Ala-Val-Gly-His(3Me)-4-Am,5-MeHpA-Leu-NH₂, Ia-23 4-(Trimethylammonium)-3-cyano-benzoyl-Ava-Gln-Trp-Ala-Val-NMeGly-His(3Me)-4-Am,5-Me-HpA-Cpa-NH₂, Ia-24 4-(Trimethylammonium)-3-cyano-benzoyl-Ser-Ser-Gln-Trp-Ala-Val-Gly-His(3Me)-Sta-Leu-NH₂, Ia-25 4-(Trimethylammonium)-3-cyano-benzoyl-DOA-Gln-Trp-Ala-Val-Gly-His(3Me)Sta-Leu-NH₂, In a preferred embodiment, the precursor for a single step radiolabeling is selected from the following list wherein U is somatostatin analogs:

1a-66: 4-(Trimethylammonium)-3-cyano-benzoyl-Ava-ε-c[Lys-(NMe)Phe-1Nal-D-Trp-Lys-Thr]

1a-67: 4-(Trimethylammonium)-3-cyano-benzoyl-Ava-β-c[Dpr-Met-(NMe)Phe-Tyr-D-Trp-Lys]

In a preferred embodiment, the precursor for a single step radiolabeling is selected from the following list wherein U is neuropeptide Y₁ analogs:

1a-68: 4-(Trimethylammonium)-3-cyano-benzoyl-Ava-DCys-Leu-Ile-Thr-Arg-Cys-Arg-Tyr-NH₂]

1a-69: 4-(Trimethylammonium)-3-cyano-benzoyl-Ava-DCys-Leu-Ile-Val-Arg-Cys-Arg-Tyr-NH₂]

In a preferred embodiment, the precursor for a single step radiolabeling is selected from the following list wherein U is a small molecule:

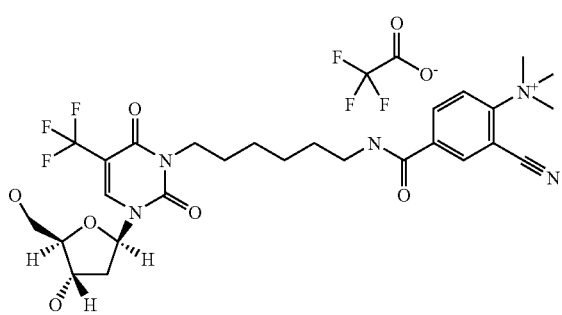

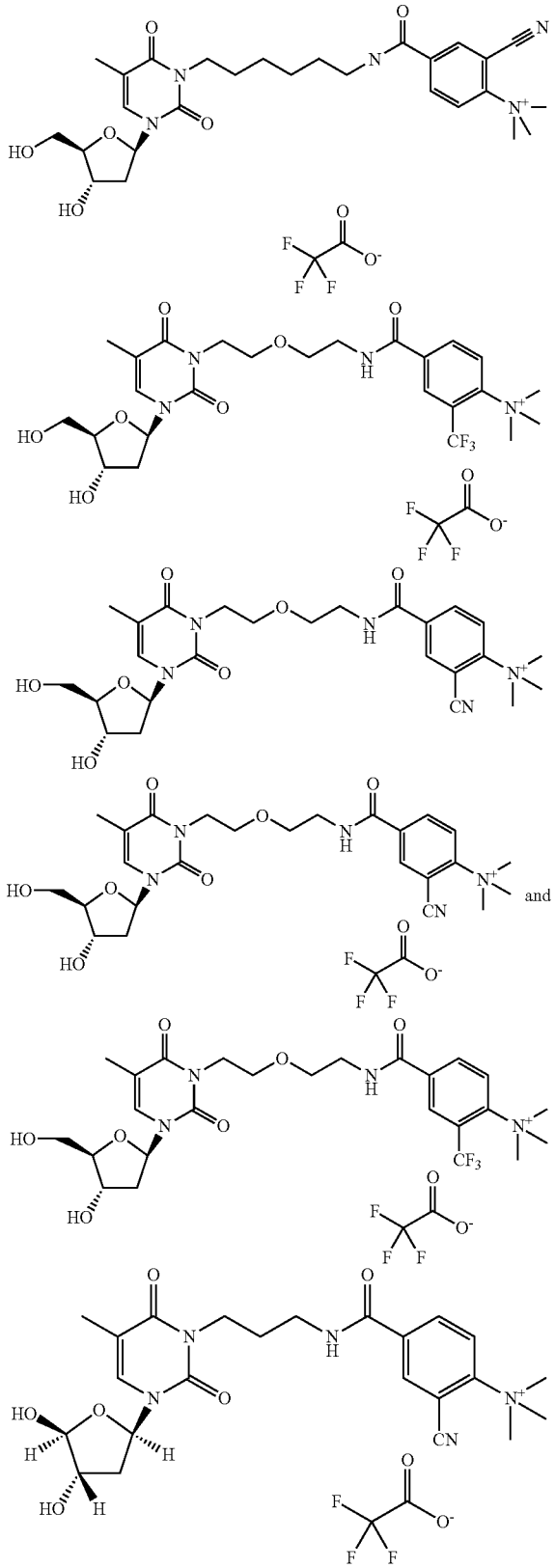

The N⁺(R¹)(R²)(R³)X⁻ group attached to the benzene ring can be displaced with fluorine isotope, to provide a chemically and biologically stable bond, In a second aspect the present invention refers to compounds having general chemical Formula A (general chemical Formula II) wherein K=W:

It has been found that compounds according to Formula I can be $^{18}$F-labeled surprisingly in a one-step radiofluorination reaction in order to arrive at compounds according to Formula A (general chemical Formula II), wherein K=W:

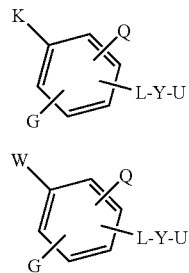

wherein the residues and substituents K, N⁺(R¹)(R²)(R³), X⁻, -G, -Q, -L-, —Y— and -U have the same meaning as depicted above for compounds having general chemical Formula I. This includes in particular all preferred embodiments mentioned above with regard to the residues and substituents K, R¹, R², R³, W, X⁻, -G, -Q, -L-, —Y— and -U and all residues used to define these residues and substituents, such as R⁴, R⁵ and the like.

W is a fluororine isotope, preferably radioactive or non-radioactive ("cold") fluorine isotope, more preferably W is $^{18}$F or $^{19}$F, even more preferably W is $^{18}$F.

Surprisingly, It has been found that when Q or G are selected from the group of substituents listed in Chem Rev. (1999), Vol. 42, No. 9, 165-195, Table 1 and have a σ$_m$ and σ$_p$ value<0 for compound of formula I then one-step labelling is less or not suited for good or high radio-chemical yields.

The invention further refers to pharmaceutically acceptable salts of inorganic or organic acids, hydrates, complexes, esters, amides, solvates and prodrugs of the compounds having general chemical Formula II.

Unless otherwise specified, when referring to the compounds having general chemical Formula I per se as well as to any pharmaceutical composition thereof the present invention includes all of the salts of inorganic or organic acids thereof, hydrates, complexes, esters, amides, solvates and prodrugs of the compounds of the invention.

W is a fluororine isotope, preferably radioactive or non-radioactive ("cold") fluorine isotope, more preferably W is $^{18}$F or $^{19}$F, even more preferably W is $^{18}$F.

If W is $^{18}$F, the compound of the invention having general chemical Formula II being radiopharmaceutically labelled with $^{18}$F has the following general chemical Formula IIA:

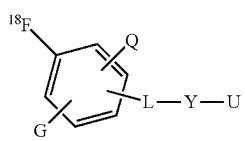

More preferably, when W=$^{19}$F then the compound having general chemical Formula II being radiopharmaceutically labelled with $^{19}$F has general chemical Formula IIB:

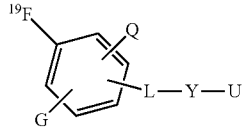

In a preferred embodiment of compounds of Formula II, -G and -Q are independently from each other selected from —H, —CN, CF₃, and —Cl.

In a more preferred embodiment -G and -Q are independently from each other H, —CF₃, or CN.

In a even more preferred embodiment In a more preferred embodiment -G and -Q are independently from each other H, —CF₃, or —CN, whereas at least -G or -Q is —CF₃ or —CN.

In a preferred embodiment, the radiopharmaceutical compound labelled with $^{18}$F or $^{19}$F is selected from the following list, wherein U is a bombesin analog:

IIA-a-1  4-[18]Fluoro-3-cyano-benzoyl-Arg-Ava-Gln-Trp-Ala-Val-NMeGly-His-Sta-Leu-NH₂, IIA-a-2  4-[18]Fluoro-3-cyano-benzoyl-Arg-Ava-Gln-Trp-Ala-Val-Gly-His(Me)-Sta-Leu-NH₂, IIA-a-3  4-[18]Fluoro-3-cyano-benzoyl-Arg-Ava-Gln-Trp-Ala-Val-NMeGly-His(3Me)-Sta-Leu-NH₂, IIA-a-4 4-[18]Fluoro-3-cyano-benzoyl-1,4-cis-Achc-Gln-Trp-Ala-Val-Gly-His(3Me)-Sta-Leu-NH₂, IIA-a-5 4-[18]Fluoro-3-cyano-benzoyl-Gln-Trp-Ala-Val-Gly-His(3Me)-Sta-Leu-NH₂, IIA-a-6  4-[18]Fluoro-3-cyano-benzoyl-AOC-Gln-Trp-Ala-Val-Gly-His(3Me)-Sta-Leu-NH₂, IIA-a-7 4-[18]Fluoro-3-cyano-benzoyl-Ava-Gln-Trp-Ala-Val-NMeGly-His(3Me)-Sta-Cpa-NH₂, IIA-a-8 4-[18]Fluoro-3-cyano-benzoyl-Ava-Gln-Trp-Ala-Val-Gly-His(3Me)-FA4-Am,5-MeHpA-Leu-NH₂, IIA-a-9 4-[18]Fluoro-3-cyano-benzoyl-Ava-Gln-Trp-Ala-Val-Gly-His(3Me)-Sta-Leu-NH₂, IIA-a-10 4-[18]Fluoro-3-cyano-benzoyl-Lys(Me)2-βAla-Gln-Trp-Ala-Val-Gly-His(3Me)-Sta-Leu-NH₂, IIA-a-11 4-[18]Fluoro-3-cyano-benzoyl-Lys(Me)2-βAla-Gln-Trp-Ala-Val-Gly-His(3Me)-Sta-Leu-NH₂, IIA-a-12  4-[18]Fluoro-3-cyano-benzoyl-Arg-Ser-Gln-Trp-Ala-Val-Gly-His(3Me)-4-Am,5-MeHpA-Leu-NH₂, IIA-a-13  4-[18]Fluoro-3-cyano-benzoyl-Ser-Ser-Gln-Trp-Ala-Val-Gly-His(3Me)-4-Am,5-MeHpA-Leu-NH₂, IIA-a-14  4-[18]Fluoro-3-cyano-benzoyl-Lys(Me)2-Ser-Gln-Trp-Ala-Val-Gly-His(3Me)-4-Am,5-MeHpA-Leu-NH₂, IIA-a-15  4-[18]Fluoro-3-cyano-benzoyl-Arg-Ser-Gln-Trp-Ala-Val-Gly-His(3Me)-Sta-Leu-NH₂, IIA-a-16 4-[18]Fluoro-3-cyano-benzoyl-Lys(Me)2-βAla-Gln-Trp-Ala-Val-Gly-His(3Me)-4-Am,5-MeHpA-Leu-NH₂, IIA-a-17  4-[18]Fluoro-3-cyano-benzoyl-Ava-Gln-Trp-Ala-Val-Gly-His-4-Am,5-MeHpA-Leu-NH₂, IIA-a-18  4-[18]Fluoro-3-trifluoromethyl-benzoyl-Arg-Ava-Gln-Trp-Ala-Val-Gly-His(3Me)-Sta-LeuNH₂, IIA-a-19  4-[18]Fluoro-3-trifluoromethyl-benzoyl-Arg-Ava-Gln-Trp-Ala-Val-NMeGly-His(3Me)-Sta-Leu-NH₂, IIA-a-20 4-[18]Fluoro-3-trifluoromethyl-benzoyl-1,4-cis-Achc-Gln-Trp-Ala-Val-Gly-His(3Me)-Sta-Leu-NH₂, IIA-a-21  4-[18]Fluoro-3-trifluoromethyl-benzoyl-Gln-Trp-Ala-Val-Gly-His(3Me)-Sta-Leu-NH₂, IIA-a-22  4-[18]Fluoro-3-trifluoromethyl-benzoyl-Arg-βAla-Gln-Trp-Ala-Val-Gly-His(3Me)-4-Am,5-MeHpA-Leu-NH$_2$, IIB-a-23  4-[18]-Fluoro-3-cyano-benzoyl-Ava-Gln-Trp-Ala-Val-NMeGly-His(3Me)-4-Am,5-MeHpA-Cpa-NH$_2$, IIB-a-24  4-[18]-Fluoro-3-cyano-benzoyl-Ser-Ser-Gln-Trp-Ala-Val-Gly-His(3Me)-Sta-Leu-NH$_2$, IIB-a-25  4-[18]-Fluoro-3-cyano-benzoyl-DOA-Gln-Trp-Ala-Val-Gly-His(3Me)-Sta-Leu-NH$_2$, IIB-a-26  3,4-[18]-Difluorobenzoyl-Ava-Gln-Trp-Ala-Val-NMeGly-His-Sta-Leu-NH$_2$, IIB-a-27  3,4-[18]-Difluorobenzoyl-Ava-Gln-Trp-Ala-Val-NMeGly-His-FA02010-Cpa-NH$_2$, IIB-a-28  3,4-[18]-Difluorobenzoyl-Ava-Gln-Trp-Ala-Val-NMeGly-His-4-Am,5-MeHpA-tbuGly-NH$_2$, IIB-a-29  3,4-[18]-Difluorobenzoyl-Ava-Gln-Trp-Ala-Val-NMeGly-His(3Me)-Sta-Leu-NH$_2$, IIB-a-30  3,4-[18]-Difluorobenzoyl-Ava-Gln-Trp-Ala-Val-NMeGly-His(3Me)-Sta-tBuGly-NH$_2$, IIB-a-31  3,4-[18]-Difluorobenzoyl-Ava-Gln-Trp-Ala-Val-Gly-His(3Me)-Sta-Leu-NH$_2$, IIB-a-32  3,4-[18]-Difluorobenzoyl-Ava-Gln-Trp-Ala-Val-NMeGly-His(3Me)-4-Am,5-MeHpA-Leu-NH$_2$, IIB-a-33  3,4-[18]-Difluorobenzoyl-Ava-Gln-DTrp-Ala-Val-Gly-His-4-Am,5-MeHpA-tbuGly-NH$_2$, IIB-a-34  3,4-[18]-Difluorobenzoyl-Ava-Gln-DTrp-Ala-Val-Gly-His-4-Am-5-MeHxA-Cpa-NH$_2$, IIB-a-35  3,4-[18]-Difluorobenzoyl-Ava-Gln-Trp-Ala-Val-NMeGly-His(3Me)-Sta-Cpa-NH$_2$, IIB-a-36  3,4-[18]-Difluorobenzoyl-Ava-Gln-DTrp-Ala-Val-Gly-His-Sta-tbuAla-NH$_2$, IIB-a-37  3,4-[18]-Difluorobenzoyl-Arg-Ava-Gln-Trp-Ala-Val-NMeGly-His-Sta-Leu-NH$_2$, IIB-a-38 3,4-[18]-Difluorobenzoyl-Gln-Trp-Ala-Val-Gly-His(3Me)-Sta-Leu-NH$_2$, IIB-a-39  3,4-[18]-Difluorobenzoyl-Arg-Ava-Gln-Trp-Ala-Val-NMeGly-His(3Me)-Sta-Leu-NH$_2$, IIB-a-40  3,4-[18]-Difluorobenzoyl-Arg-Ava-Gln-Trp-Ala-Val-Gly-His(3Me)-Sta-Leu-NH$_2$, IIB-a-41  3,4-[18]-Difluorobenzoyl-Arg-βAla-Arg-Gln-Trp-Ala-Val-Gly-His(3Me)-Sta-Leu-NH$_2$, IIB-a-42  3,4-[18]-Difluorobenzoyl-Ava-Gln-Trp-Ala-Val-Gly-His(3Me)-Sta-Cpa-NH$_2$, IIB-a-43  3,4-[18]-Difluorobenzoyl-Ava-Gln-Trp-Ala-Val-Gly-His(3Me)-Sta-tBuGly-NH$_2$, IIB-a-44  3,4-[18]-Difluorobenzoyl-Arg-Arg-Gln-Trp-Ala-Val-NMeGly-His(3Me)-Sta-Leu-NH$_2$, IIB-a-45  3,4-[18]-Difluorobenzoyl-Arg-βAla-Gln-Trp-Ala-Val-NMeGly-His(3Me)-Sta-Leu-NH$_2$, IIB-a-46 3,4-[18]-Difluorobenzoyl-Gln-Trp-Ala-Val-Gly-His(3Me)-4-Am,5-MeHpA-Leu-NH$_2$, IIB-a-47  3,4-[18]-Difluorobenzoyl-Ava-Gln-Trp-Ala-Val-NMeGly-His(3Me)-4-Am,5-MeHpA-Cpa-NH$_2$, IIB-a-48  3,4-[18]-Difluorobenzoyl-Ava-Gln-Trp-Ala-Val-Gly-His(3Me)-4-Am,5-MeHpA-Leu-NH$_2$, IIB-a-49  3,4-[18]-Difluorobenzoyl-Ava-Gln-Trp-Ala-Val-Gly-NMeHis-4-Am,5-MeHpA-Cpa-NH$_2$, IIB-a-49  3,4-[18]-Difluorobenzoyl-Ava-Gln-Trp-Ala-Val-Gly-NMeHis(3Me)-4-Am,5-MeHpA-Leu-NH$_2$, IIB-a-50  3,4-[18]-Difluorobenzoyl-Ava-Gln-Trp-Ala-Val-Gly-NMeHis-4-Am,5-MeHpA-Leu-NH$_2$, IIB-a-51  3,4-[18]-Difluorobenzoyl-Ava-Gln-Trp-Ala-Val-NMeGly-His-AHMHxA-Leu-NH$_2$, IIB-a-52  3,4-[18]-Difluorobenzoyl-Ava-Gln-Trp-Ala-Val-βAla-NMeHis-Tha-Cpa-NH$_2$, IIB-a-53  3,4-[18]-Difluorobenzoyl-Ava-Gln-Trp-Ala-Val-βAla-NMeHis-Phe-Cpa-NH$_2$, IIB-a-54  3,4-[18]-Difluorobenzoyl-Ava-Gln-Trp-Ala-Val-βAla-NMeHis-Phe-Leu-NH$_2$, IIB-a-55  3,4-[18]-Difluorobenzoyl-Ava-Gln-Trp-Ala-Val-βAla-DHis-Phe-Leu-NH$_2$, IIB-a-56  3,4-[18]-Difluorobenzoyl-Ava-Gln-Trp-Ala-Val-βAla-His-βhLeu-Leu-NH$_2$, IIB-a-57  3,4-[18]-Difluorobenzoyl-Ava-Gln-Trp-Ala-Val-βAla-His-βhIle-Leu-NH$_2$, IIB-a-58  3,4-[18]-Difluorobenzoyl-Ava-Gln-Trp-Ala-Val-βAla-His-βhLeu-tbuGly-NH$_2$, IIB-a-59 3,4-[18-Difluorobenzoyl-Ava-Gln-Trp-Ala-Val-βAla-His(3Me)-Phe-Tha-NH$_2$, IIB-a-60  3,4-[18]-Difluorobenzoyl-Ava-Gln-Trp-Ala-Val-βAla-His(3Me)-Phe-Nle-NH$_2$, IIB-a-61  3,4-[18]-Difluorobenzoyl-Ava-Gln-Trp-Ala-Val-βAla-NMeHis-Phe-tbuGly-NH$_2$, IIB-a-62  3,4-[18]-Difluorobenzoyl-Ava-Gln-Trp-Ala-Val-βAla-NMeHis-Tha-tbuGly-NH$_2$, IIB-a-63  3,4-[18]-Difluorobenzoyl-Ava-Gln-Trp-Ala-Val-βAla-His(3Me)-Tha-tbuGly-NH$_2$, IIB-a-64  3,4-[18]-Difluorobenzoyl-Ava-Gln-Trp-Ala-Val-βAla-His(3Me)-Phe-Cpa-NH$_2$, IIB-a-65  3,4-[18]-Difluorobenzoyl-Ava-Gln-Trp-Ala-NMeVal-βAla-His-Phe-Leu-NH$_2$, IIB-a-66  3,4-[18]-Difluorobenzoyl-Ava-Gln-Trp-Ala-Val-βAla-His-NMePhe-Leu-NH$_2$, IIB-a-67  3,4-[18]-Difluorobenzoyl-Ava-Gln-DTrp-Ala-Val-βAla-His-Phe-Leu-NH$_2$, IIB-a-68  3,4-[18]-Difluorobenzoyl-Ava-Gln-Trp-DAla-Val-βAla-His-Phe-Leu-NH$_2$, IIB-a-69  3,4-[18]-Difluorobenzoyl-Ava-Gln-Trp-Ala-DVal-βAla-His-Phe-Leu-NH$_2$, IIB-a-70  3,4-[18]-Difluorobenzoyl-Ava-Gln-Trp-Ala-Val-βAla-His-DPhe-Leu-NH$_2$, IIB-a-71  3,4-[18]-Difluorobenzoyl-Ava-Gln-Trp-Ala-Val-βAla-His-βhIle-tbuGly-NH$_2$, IIB-a-72 4-[18]-Fluoro-3-cyano-phenylsulfonyl-Ava-Gln-Trp-Ala-Val-NMeGly-His-4-Am,5-MeHpA-Cpa-NH$_2$, IIB-a-73 4-[18]-Fluoro-3-cyano-phenylsulfonyl-Ava-Gln-Trp-Ala-Val-NMeGly-His-Sta-Cpa-NH$_2$, IIB-a-74 4-[18]-Fluoro-3-cyano-phenylsulfonyl-Ava-Gln-Trp-Ala-Val-NMeGly-His-Sta-tbuAla-NH$_2$, IIB-a-75 4-[18]-Fluoro-3-cyano-phenylsulfonyl-Ava-Gln-Trp-Ala-Val-NMeGly-His-4-Am,5-MeHpA-tbuAla-NH$_2$, 4-[18]Fluoro-3-cyano-benzoyl-(piperidyl-4-carbonyl)-Gln-Trp-Ala-Val-Gly-His(3Me)-Sta-Leu-NH$_2$, 4-[18]Fluoro-3-cyano-benzoyl-(piperazin-1-yl-acetyl)-Gln-Trp-Ala-Val-Gly-His(3Me)-Sta-Leu-NH$_2$, 4-[18]Fluoro-3-cyano-benzoyl-1,4-trans-Achc-Gln-Trp-Ala-Val-NMeGly-His-Sta-Leu-NH$_2$, IIB-a-1  4-[19]-Fluoro-3-cyano-benzoyl-Arg-Ava-Gln-Trp-Ala-Val-NMeGly-His-Sta-Leu-NH$_2$, IIB-a-2  4-[19]-Fluoro-3-cyano-benzoyl-Arg-Ava-Gln-Trp-Ala-Val-His(Me)-Sta-Leu-NH$_2$, IIB-a-3  4-[19]-Fluoro-3-cyano-benzoyl-Arg-Ava-Gln-Trp-Ala-Val-NMeGly-His(3Me)-Sta-Leu-NH$_2$, IIB-a-4  4-[19]-Fluoro-3-cyano-benzoyl-1,4-cis-Achc-Gln-Trp-Ala-Val-Gly-His(3Me)-Sta-Leu-NH$_2$, IIB-a-5 4-[19]-Fluoro-3-cyano-benzoyl-Gln-Trp-Ala-Val-Gly-His(3Me)-Sta-Leu-NH$_2$, IIB-a-6  4-[19]-Fluoro-3-cyano-benzoyl-AOC-Gln-Trp-Ala-Val-Gly-His(3Me)-Sta-Leu-NH$_2$, IIB-a-7  4-[19]-Fluoro-3-cyano-benzoyl-Ava-Gln-Trp-Ala-Val-NMeGly-His(3Me)-Sta-Cpa-NH$_2$, IIB-a-8   4-[19]-Fluoro-3-cyano-benzoyl-Ava-Gln-Trp-Ala-Val-Gly-His(3Me)-4-Am,5-MeHpA-Leu-NH$_2$,
IIB-a-9   4-[19]-Fluoro-3-cyano-benzoyl-Ava-Gln-Trp-Ala-Val-Gly-His(3Me)-Sta-Leu-NH$_2$,
IIB-a-10  4-[19]-Fluoro-3-cyano-benzoyl-Lys(Me)$_2$-βAla-Gln-Trp-Ala-Val-Gly-His(3Me)-Sta-Leu-NH$_2$,
IIB-a-11  4-[19]-Fluoro-3-cyano-benzoyl-Lys(Me)2-βAla-Gln-Trp-Ala-Val-Gly-His(3Me)-Sta-Leu-NH$_2$,
IIB-a-12  4-[19]-Fluoro-3-cyano-benzoyl-Arg-Ser-Gln-Trp-Ala-Val-Gly-His(3Me)-4-Am,5-MeHpA-Leu-NH$_2$,
IIB-a-13  4-[19]-Fluoro-3-cyano-benzoyl-Ser-Ser-Gln-Trp-Ala-Val-Gly-His(3Me)-4-Am,5-MeHpA-Leu-NH$_2$,
IIB-a-14  4-[19]-Fluoro-3-cyano-benzoyl-Lys(Me)2-Ser-Gln-Trp-Ala-Val-Gly-His(3Me)-4-Am,5-MeHpA-Leu-NH$_2$,
IIB-a-15  4-[19]-Fluoro-3-cyano-benzoyl-Arg-Ser-Gln-Trp-Ala-Val-Gly-His(3Me)-Sta-Leu-NH$_2$,
IIB-a-16  4-[19]-Fluoro-3-cyano-benzoyl-Lys(Me)2-βAla-Gln-Trp-Ala-Val-Gly-His(3Me)-4-Am,5-MeHpA-Leu-NH$_2$,
IIB-a-17  4-[19]-Fluoro-3-cyano-benzoyl-Ava-Gln-Trp-Ala-Val-Gly-His-4-Am,5-MeHpA-Leu-NH$_2$,
IIB-a-18  4-[19]-Fluoro-3-trifluoromethyl-benzoyl-Arg-Ava-Gln-Trp-Ala-Val-Gly-His(3Me)-Sta-Leu-NH$_2$,
IIB-a-19  4-[19]-Fluoro-3-trifluoromethyl-benzoyl-Arg-Ava-Gln-Trp-Ala-Val-NMeGly-His(3Me)-Sta-Leu-NH$_2$,
IIB-a-20  4-[19]-Fluoro-3-trifluoromethyl-benzoyl-1,4-cis-Achc-Gln-Trp-Ala-Val-Gly-His(3Me)-Sta-Leu-NH$_2$,
IIB-a-21  4-[19]-Fluoro-3-trifluoromethyl-benzoyl-Gln-Trp-Ala-Val-Gly-His(3Me)-Sta-Leu-NH$_2$,
IIB-a-22  4-[19]-Fluoro-3-trifluoromethyl-benzoyl-Arg-βAla-Gln-Trp-Ala-Val-Gly-His(3Me)-4-Am,5-MeHpA-Leu-NH$_2$,
IIB-a-23  4-[19]-Fluoro-3-cyano-benzoyl-Ava-Gln-Trp-Ala-Val-NMeGly-His(3Me)-4-Am,5-MeHpA-Cpa-NH$_2$,
IIB-a-24  4-[19]-Fluoro-3-cyano-benzoyl-Ser-Ser-Gln-Trp-Ala-Val-Gly-His(3Me)-Sta-Leu-NH$_2$,
IIB-a-25  4-[19]-Fluoro-3-cyano-benzoyl-DOA-Gln-Trp-Ala-Val-Gly-His(3Me)-Sta-Leu-NH$_2$,
IIB-a-26  3,4-[19]-Difluorobenzoyl-Ava-Gln-Trp-Ala-Val-NMeGly-His-Sta-Leu-NH$_2$,
IIB-a-27  3,4-[19]-Difluorobenzoyl-Ava-Gln-Trp-Ala-Val-NMeGly-His-FA02010-Cpa-NH$_2$,
IIB-a-28  3,4-[19]-Difluorobenzoyl-Ava-Gln-Trp-Ala-Val-NMeGly-His-4-Am,5-MeHpA-tbuGly-NH$_2$,
IIB-a-29  3,4-[19]-Difluorobenzoyl-Ava-Gln-Trp-Ala-Val-NMeGly-His(3Me)-Sta-Leu-NH$_2$,
IIB-a-30  3,4-[19]-Difluorobenzoyl-Ava-Gln-Trp-Ala-Val-NMeGly-His(3Me)-Sta-tBuGly-NH$_2$,
IIB-a-31  3,4-[19]-Difluorobenzoyl-Ava-Gln-Trp-Ala-Val-Gly-His(3Me)-Sta-Leu-NH$_2$,
IIB-a-32  3,4-[19]-Difluorobenzoyl-Ava-Gln-Trp-Ala-Val-NMeGly-His(3Me)-4-Am,5-MeHpA-Leu-NH$_2$)
IIB-a-33  3,4-[19]-Difluorobenzoyl-Ava-Gln-DTrp-Ala-Val-Gly-His-4-Am,5-MeHpA-tbuGly-NH$_2$,
IIB-a-34  3,4-[19]-Difluorobenzoyl-Ava-Gln-DTrp-Ala-Val-Gly-His-4-Am-5-MeHxA-Cpa-NH$_2$,
IIB-a-35  3,4-[19]-Difluorobenzoyl-Ava-Gln-Trp-Ala-Val-NMeGly-His(3Me)-Sta-Cpa-NH$_2$,
IIB-a-36  3,4-[19]-Difluorobenzoyl-Ava-Gln-DTrp-Ala-Val-Gly-His-Sta-tbuAla-NH$_2$,
IIB-a-37  3,4-[19]-Difluorobenzoyl-Arg-Ava-Gln-Trp-Ala-Val-NMeGly-His-Sta-Leu-NH$_2$,
IIB-a-38  3,4-[19]-Difluorobenzoyl-Gln-Trp-Ala-Val-Gly-His(3Me)-Sta-Leu-NH$_2$,
IIB-a-39  3,4-[19]-Difluorobenzoyl-Arg-Ava-Gln-Trp-Ala-Val-NMeGly-His(3Me)-Sta-Leu-NH$_2$,
IIB-a-40  3,4-[19]-Difluorobenzoyl-Arg-Ava-Gln-Trp-Ala-Val-Gly-His(3Me)-Sta-Leu-NH$_2$,
IIB-a-41  3,4-[19]-Difluorobenzoyl-Arg-βAla-Arg-Gln-Trp-Ala-Val-Gly-His(3Me)-Sta-Leu-NH$_2$,
IIB-a-42  3,4-[19]-Difluorobenzoyl-Ava-Gln-Trp-Ala-Val-Gly-His(3Me)-Sta-Cpa-NH$_2$,
IIB-a-43  3,4-[19]-Difluorobenzoyl-Ava-Gln-Trp-Ala-Val-Gly-His(3Me)-Sta-tBuGly-NH$_2$,
IIB-a-44  3,4-[19]-Difluorobenzoyl-Arg-Arg-Gln-Trp-Ala-Val-NMeGly-His(3Me)-Sta-Leu-NH$_2$,
IIB-a-45  3,4-[19]-Difluorobenzoyl-Arg-βAla-Gln-Trp-Ala-Val-NMeGly-His(3Me)-Sta-Leu-NH$_2$,
IIB-a-46  3,4-[19]-Difluorobenzoyl-Gln-Trp-Ala-Val-Gly-His(3Me)-4-Am,5-MeHpA-Leu-NH$_2$,
IIB-a-47  3,4-[19]-Difluorobenzoyl-Ava-Gln-Trp-Ala-Val-NMeGly-His(3Me)-4-Am,5-MeHpA-Cpa-NH$_2$,
IIB-a-48  3,4-[19]-Difluorobenzoyl-Ava-Gln-Trp-Ala-Val-Gly-His(3Me)-4-Am,5-MeHpA-Leu-NH$_2$,
IIB-a-49  3,4-[19]-Difluorobenzoyl-Ava-Gln-Trp-Ala-Val-Gly-NMeHis-4-Am,5-MeHpA-Cpa-NH$_2$,
IIB-a-49  3,4-[19]-Difluorobenzoyl-Ava-Gln-Trp-Ala-Val-Gly-NMeHis(3Me)-4-Am,5-MeHpA-Leu-NH$_2$,
IIB-a-50  3,4-[19]-Difluorobenzoyl-Ava-Gln-Trp-Ala-Val-Gly-NMeHis-4-Am,5-MeHpA-Leu-NH$_2$,
IIB-a-51  3,4-[19]-Difluorobenzoyl-Ava-Gln-Trp-Ala-Val-NMeGly-HIs-AHMHxA-Leu-NH$_2$,
IIB-a-52  3,4-[19]-Difluorobenzoyl-Ava-Gln-Trp-Ala-Val-βAla-NMeHis-Tha-Cpa-NH$_2$,
IIB-a-53  3,4-[19]-Difluorobenzoyl-Ava-Gln-Trp-Ala-Val-βAla-NMeHis-Phe-Cpa-NH$_2$,
IIB-a-54  3,4-[19]-Difluorobenzoyl-Ava-Gln-Trp-Ala-Val-βAla-NMeHis-Phe-Leu-NH$_2$,
IIB-a-55  3,4-[19]-Difluorobenzoyl-Ava-Gln-Trp-Ala-Val-βAla-DHis-Phe-Leu-NH$_2$,
IIB-a-56  3,4-[19]-Difluorobenzoyl-Ava-Gln-Trp-Ala-Val-βAla-His-BhLeu-Leu-NH$_2$,
IIB-a-57  3,4-[19]-Difluorobenzoyl-Ava-Gln-Trp-Ala-Val-βAla-His-BhIle-Leu-NH$_2$,
IIB-a-58  3,4-[19]-Difluorobenzoyl-Ava-Gln-Trp-Ala-Val-βAla-His-BhLeu-tbuGly-NH$_2$,
IIB-a-59  3,4-[19]-Difluorobenzoyl-Ava-Gln-Trp-Ala-Val-βAla-His(3Me)-Phe-Tha-NH$_2$,
IIB-a-60  3,4-[19]-Difluorobenzoyl-Ava-Gln-Trp-Ala-Val-βAla-His(3Me)-Phe-Nle-NH$_2$,
IIB-a-61  3,4-[19]-Difluorobenzoyl-Ava-Gln-Trp-Ala-Val-βAla-NMeHis-Phe-tbuGly-NH$_2$,
IIB-a-62  3,4-[19]-Difluorobenzoyl-Ava-Gln-Trp-Ala-Val-βAla-NMeHis-Tha-tbuGly-NH$_2$,
IIB-a-63  3,4-[19]-Difluorobenzoyl-Ava-Gln-Trp-Ala-Val-βAla-His(3Me)-Tha-tbuGly-NH$_2$,
IIB-a-64  3,4-[19]-Difluorobenzoyl-Ava-Gln-Trp-Ala-Val-βAla-His(3Me)-Phe-Cpa-NH$_2$,
IIB-a-65  3,4-[19]-Difluorobenzoyl-Ava-Gln-Trp-Ala-NMeVal-βAla-His-Phe-Leu-NH$_2$,
IIB-a-66  3,4-[19]-Difluorobenzoyl-Ava-Gln-Trp-Ala-Val-βAla-His-NMePhe-Leu-NH$_2$,
IIB-a-67  3,4-[19]-Difluorobenzoyl-Ava-Gln-DTrp-Ala-Val-βAla-His-Phe-Leu-NH$_2$,
IIB-a-68  3,4-[19]-Difluorobenzoyl-Ava-Gln-Trp-DAla-Val-βAla-His-Phe-Leu-NH$_2$, IIB-a-69   3,4-[19]-Difluorobenzoyl-Ava-Gln-Trp-Ala-DVal-βAla-His-Phe-Leu-NH$_2$, IIB-a-70   3,4-[19]-Difluorobenzoyl-Ava-Gln-Trp-Ala-Val-βAla-His-DPhe-Leu-NH$_2$, IIB-a-71   3,4-[19]-Difluorobenzoyl-Ava-Gln-Trp-Ala-Val-βAla-His-βhIle-tbuGly-NH$_2$, IIB-a-72  4-[19]-Fluoro-3-cyano-phenylsulfonyl-Ava-Gln-Trp-Ala-Val-NMeGly-His-4-Am,5-MeHpA-Cpa-NH$_2$, IIB-a-73  4-[19]-Fluoro-3-cyano-phenylsulfonyl-Ava-Gln-Trp-Ala-Val-NMeGly-His-Sta-Cpa-NH$_2$, IIB-a-74  4-[19]-Fluoro-3-cyano-phenylsulfonyl-Ava-Gln-Trp-Ala-Val-NMeGly-His-Sta-tbuAla-NH$_2$, IIB-a-75  4-[19]-Fluoro-3-cyano-phenylsulfonyl-Ava-Gln-Trp-Ala-Val-NMeGly-His-4-Am,5-MeHpA-tbuAla-NH$_2$.

4-[19]Fluoro-3-cyano-benzoyl-(piperidyl-4-carbonyl)-Gln-Trp-Ala-Val-Gly-His(3Me)-Sta-Leu-NH$_2$, 4-[19]Fluoro-3-cyano-benzoyl-(piperazin-1-yl-acetyl)-Gln-Trp-Ala-Val-Gly-His(3Me)-Sta-Leu-NH$_2$, 4-[19]Fluoro-3-cyano-benzoyl-1,4-trans-Achc-Gln-Trp-Ala-Val-NMeGly-His-Sta-Leu-NH$_2$, In a preferred embodiment, the radiopharmaceutical labelled with $^{18}$F or $^{19}$F is selected from the following list, wherein U is a somatostatin analog:

IIA-a-76:  4-[18]Fluoro-3-cyano-benzoyl-Ava-ε-c[Lys-(NMe)Phe-1Nal-D-Trp-Lys-Thr]

IIA-a-77:  4-[18]Fluoro-3-cyano-benzoyl-Ava-β-c[Dpr-Met-(NMe)Phe-Tyr-D-Trp-Lys]

IIB-a-76:  4-[19]Fluoro-3-cyano-benzoyl-Ava-ε-c[Lys-(NMe)Phe-1Nal-D-Trp-Lys-Thr]

IIB-a-77:  4-[19]Fluoro-3-cyano-benzoyl-Ava-β-c[Dpr-Met-(NMe) Phe-Tyr-D-Trp-Lys]

In a preferred embodiment, the radiopharmaceutical labelled with $^{18}$F or $^{19}$F is selected from the following list, wherein U is a neuropeptide Y$_1$ analog:

IIA-a-78: 4-[18]Fluoro-3-cyano-benzoyl-Ava-DCys-Leu-Ile-Thr-Arg-Cys-Arg-Tyr-NH$_2$ IIA-a-79: 4-[18]Fluoro-3-cyano-benzoyl-Ava-DCys-Leu-Ile-Val-Arg-Cys-Arg-Tyr-NH$_2$ IIA-a-78: 4-[19]Fluoro-3-cyano-benzoyl-Ava-DCys-Leu-Ile-Thr-Arg-Cys-Arg-Tyr-NH$_2$ IIA-a-79: 4-[19]Fluoro-3-cyano-benzoyl-Ava-DCys-Leu-Ile-Val-Arg-Cys-Arg-Tyr-NH$_2$ In a preferred embodiment, the radiopharmaceutical labelled with $^{18}$F or $^{19}$F is selected from the following list, wherein U is a small molecule:

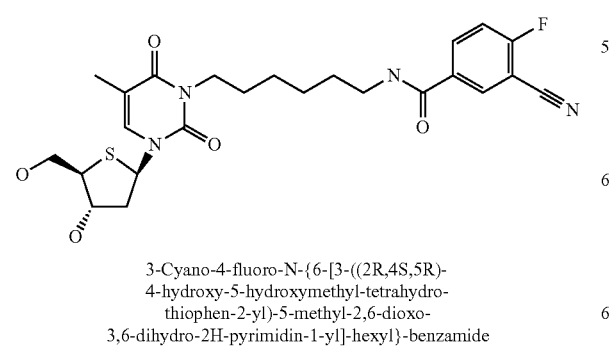

3-Cyano-4-fluoro-N-{6-[3-((2R,4S,5R)-4-hydroxy-5-hydroxymethyl-tetrahydro-thiophen-2-yl)-5-methyl-2,6-dioxo-3,6-dihydro-2H-pyrimidin-1-yl]-hexyl}-benzamide

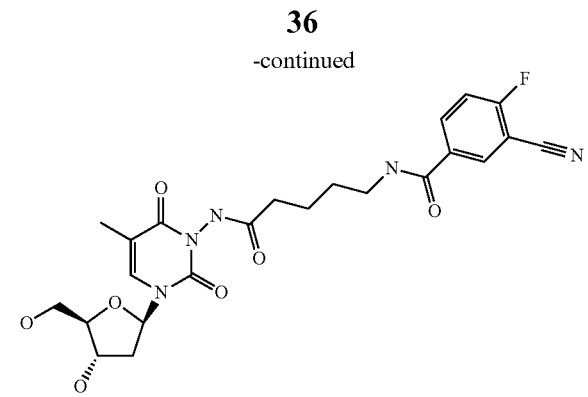

3-Cyano-4-fluoro-N-{4-[3-((2R,4S,5R)-4-hydroxy-5-hydroxymethyl-tetrahydro-furan-2-yl)-5-methyl-2,6-dioxo-3,6-dihydro-2H-pyrimidin-1-ylcarbamoyl]-butyl}-benzamide

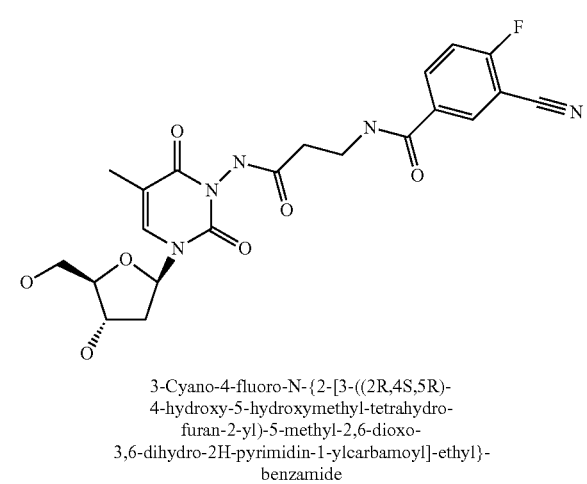

3-Cyano-4-fluoro-N-{2-[3-((2R,4S,5R)-4-hydroxy-5-hydroxymethyl-tetrahydro-furan-2-yl)-5-methyl-2,6-dioxo-3,6-dihydro-2H-pyrimidin-1-ylcarbamoyl]-ethyl}-benzamide

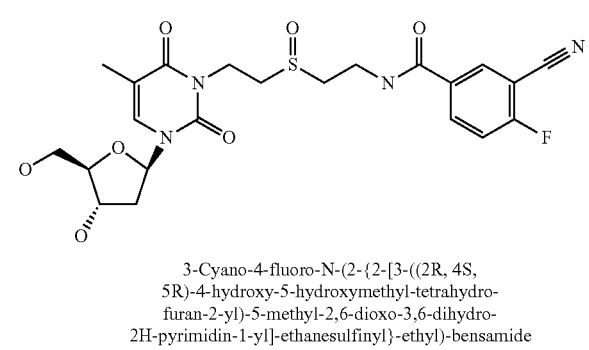

3-Cyano-4-fluoro-N-(2-{2-[3-((2R, 4S, 5R)-4-hydroxy-5-hydroxymethyl-tetrahydro-furan-2-yl)-5-methyl-2,6-dioxo-3,6-dihydro-2H-pyrimidin-1-yl]-ethanesulfinyl}-ethyl)-bensamide

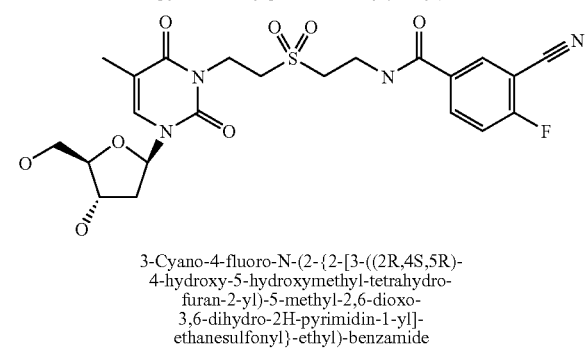

3-Cyano-4-fluoro-N-(2-{2-[3-((2R,4S,5R)-4-hydroxy-5-hydroxymethyl-tetrahydro-furan-2-yl)-5-methyl-2,6-dioxo-3,6-dihydro-2H-pyrimidin-1-yl]-ethanesulfonyl}-ethyl)-benzamide

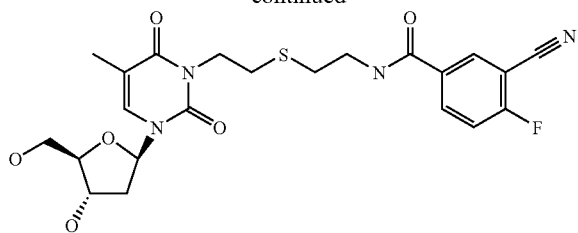

3-Cyano-4-fluoro-N-(2-{2-[3-((2R,4S,5R)-4-hydroxy-5-hydroxymethyl-tetrahydro-furan-2-yl)-5-methyl-2,6-dioxo-3,6-dihydro-2H-pyrimidin-1-yl]-ethylsulfanyl}-ethyl)-benzamide

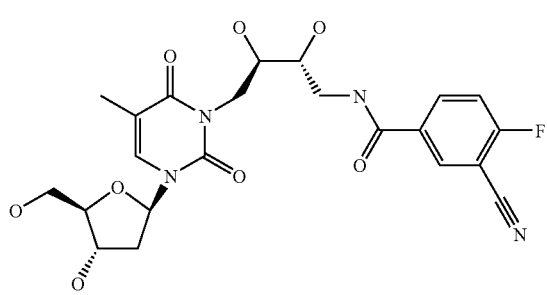

3-Cyano-N-({2R,3R)-2,3-dihydroxy-4-[3-((2R,4S,5R)-4-hydroxy-5-hydroxymethyl-tetrahydro-furan-2-yl)-5-methyl-2,6-dioxo-3,6-dihydro-2H-pyrimidin-1-yl]-butyl}-4-fluoro-benzamide

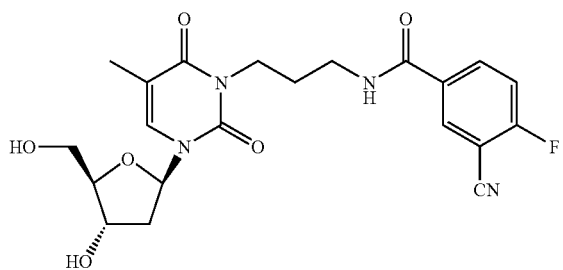

3-Cyano-4-[F]fluoro-N-(thymidinyl-propyl)-benzamide

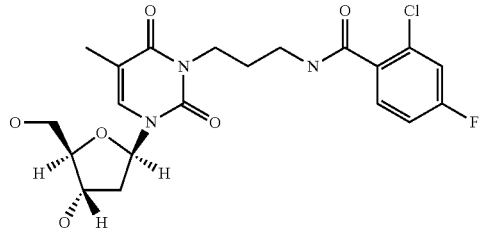

2-Chloro-4-fluoro-N-{3-[((2R,4S,5R)-4-hydroxy-5-hydroxymethyl-tetrahydro-furan-2-yl)-5-methyl-2,6-dioxo-3,6-dihydro-2H-pyrimidin-1-yl]-propyl}-benzamide

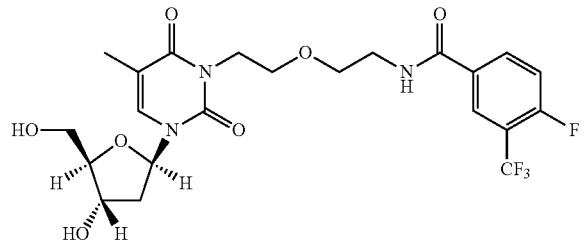 [SMILES: Cc1cn([C@H]2C[C@H](O)[C@@H](CO)O2)c(=O)n(CCOCCNC(=O)c2ccc(F)c(C#N)c2)c1=O]

3-Cyano-4-[F]fluoro-N-(2-[2-thymidinyl-ethoxy]-ethyl)-benzamide

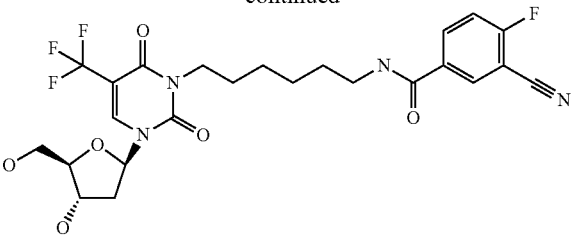

3-Cyano-4-fluoro-N-{6-[3-((2R,4S,5R)-4-hydroxy-5-hydroxymethyl-tetrahydro-furan-2-yl)-2,6-dioxo-5-trifluoromethyl-3,6-dihydro-2H-pyrimidin-1-yl]-hexyl}-benzamide

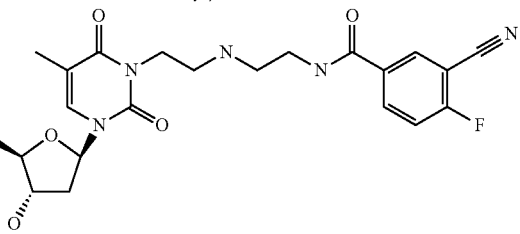

3-Cyano-4-fluoro-N-(2-{2-[3-((2R,4S,5R)-4-hydroxy-5-hydroxymethyl-tetrahydro-furan-2-yl)-5-methyl-2,6-dioxo-3-6-dihydro-2H-pyrimidin-1-yl]-ethylamino}-ethyl)-benzamide

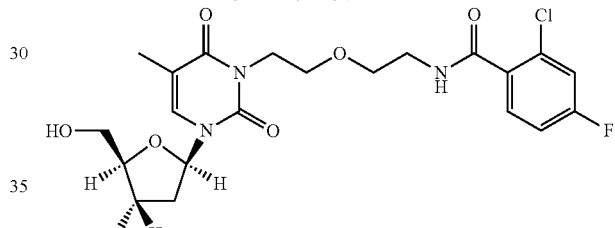

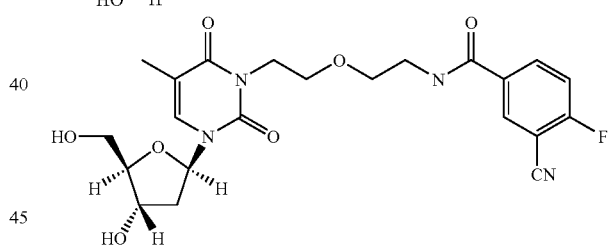

In a fourth aspect, the present invention also provides compositions comprising a compound having general chemical Formulae I or II or the pharmaceutically acceptable salts of inorganic or organic acids thereof, hydrates, complexes, esters, amides, solvates and prodrugs thereof and a pharmaceutically acceptable carrier, diluent, excipient or adjuvant. Pharmaceutically acceptable carriers, diluents, excipients or adjuvants may include any and all solvents, dispersion media, antibacterial and antifungal agents, isotonic agents, enzyme inhibitors, transfer ligands such as glucoheptonate, tartrate, citrate, or mannitol, and the like. Such compositions may be formulated as sterile, pyrogen-free, parenterally acceptable aqueous solution which may optionally be supplied in lyophilized form. The compositions of the invention may be provided as components of kits which may include buffers, additional vials, instructions for use, and the like.

In a fifth aspect, the present invention refers to a method of imaging diseases, the method comprising introducing into a patient a detectable quantity of a labeled compound having general chemical Formula A, wherein K=W, or a pharmaceutically acceptable salts of inorganic or organic acids thereof, hydrates, complexes, esters, amides, solvates and prodrugs thereof.

In a sixth aspect, the present invention provides a kit comprising a sealed vial containing a predetermined quantity of a compound having general chemical Formula I or the pharmaceutically acceptable salts of inorganic or organic acids thereof, hydrates, complexes, esters, amides, solvates and prodrugs thereof and optionally a pharmaceutically acceptable carrier, diluent, excipient or adjuvant.

In a seventh aspect of the invention, compounds according to Formula II, including compounds having general chemical Formulae IIA and IIB, are provided for use as medicament. Accordingly, the invention relates to compounds having general chemical Formula IIA for use as a positron emitting tomography (PET) diagnostic agent, wherein the fluorine isotope is $^{18}F$ and to compounds having general chemical Formula IIB for use as a precursor to prepare a positron emitting tomography (PET) diagnostic agent, wherein the fluorine isotope is $^{19}F$. More preferably, the invention relates to the use of compound having general chemical Formula I for the manufacture of compounds having general chemical Formula IIA as a diagnostic agent. Most preferably, the use is for imaging of tumors, imaging of inflammatory and/or neurodegenerative diseases, such as multiple sclerosis or Alzheimer's disease, or imaging of angiogenesis-associated diseases, such as growth of solid tumors, and rheumatoid arthritis.

In another aspect, the present invention relates to compound having general chemical Formula II for use in biological assays and chromatographic identification. More preferably, the invention relates to compounds having general chemical Formula IIB for use in biological assays and chromatographic identification, wherein the fluorine isotope is $^{19}F$. More preferably, the invention relates to the use of compounds having general chemical Formula I for the manufacture of compounds having general chemical Formula IIB as a measurement agent.

In another aspect of the invention compounds according to Formula II are provided for use as diagnostic imaging agent, preferably as imaging agent for PET applications.

In an eighth aspect of the invention, compounds having general chemical Formulae I or II of pharmaceutically acceptable salts of inorganic or organic acids thereof, hydrates, complexes, esters, amides, solvates and prodrugs thereof are provided for the use in manufacturing of a medicament, more specifically for the manufacture of a diagnostic imaging agent and most specifically for the manufacture of a diagnostic imaging agent for imaging tissue at a target site using the imaging agent.

The compounds of this invention are useful for the imaging of a variety of cancers including but not limited to: carcinoma such as bladder, breast, colon, kidney, liver, lung, including small cell lung cancer, esophagus, gall-bladder, ovary, pancreas, stomach, cervix, thyroid, prostate and skin, hematopoetic tumors of lymphoid and myeloid lineage, tumors of mesenchymal origin, tumors of central peripheral nervous systems, other tumors, including melanoma, seminoma, teratocarcinoma, osteosarcoma, xeroderma pigmentosum, keratoxanthoma, thyroid follicular cancer and Karposi's sarcoma.

Most preferably, the use is for only for imaging of tumors, but also for imaging of inflammatory and/or neurodegenerative diseases, such as multiple sclerosis or Alzheimer's disease, or imaging of angiogenesis-associated diseases, such as growth of solid tumors, and rheumatoid arthritis.

In a preferred embodiment, the bombesin analog is a peptide of sequence from Seq ID 1 to Seq ID 102 and preferably one of them, as far as the compound having general chemical Formula A comprises bombesin or bombesin analogs, this compound binds specifically to human GRP receptors present in prostate tumor, breast tumor and metastasis. More preferably the bombesin analog is additionally radiolabeled with a fluorine isotope (F) wherein F is $^{18}F$ or $^{19}F$. More preferably the bombesin analog is radiolabeled using the radiofluorination method of the present invention.

Therefore, according to a ninth aspect, the present invention refers to bombesin analogs that bind specifically to human GRP receptors present in prostate tumor, breast tumor and metastasis.

Further, the compounds having general chemical Formula II, in which W is $^{19}F$ or other non-radioactive ("cold") halogen elements may be used in biological assays and chromatographic identification. More preferably, the invention relates to the use of a compound having general chemical Formula I for the manufacture of a compound having general chemical Formula IIB as a measurement agent.

The radioactively labeled compounds according to Formula II provided by the invention may be administered intravenously in any pharmaceutically acceptable carrier, e.g., conventional medium such as an aqueous saline medium, or in blood plasma medium, as a pharmaceutical composition for intravenous injection. Such medium may also contain conventional pharmaceutical materials such as, for example, pharmaceutically acceptable salts to adjust the osmotic pressure, buffers, preservatives and the like. Among the preferred media are normal saline and plasma. Suitable pharmaceutical acceptable carriers are known to the person skilled in the art. In this regard reference can be made to e.g., Remington's Practice of Pharmacy, $11^{th}$ ed. and in J. of. Pharmaceutical Science & Technology, Vol. 52, No. 5, September-October, p. 238-311 see table page 240 to 311, both publication include herein by reference.

The concentration of the compound having general chemical Formula II and the pharmaceutically acceptable carrier, for example, in an aqueous medium, varies with the particular field of use. A sufficient amount is present in the pharmaceutically acceptable carrier when satisfactory visualization of the imaging target (e.g., a tumor) is achievable.

In accordance with the invention, the radiolabeled compounds having general chemical Formula II either as a neutral composition or as a salt with a pharmaceutically acceptable counter-ion are administered in a single unit injectable dose. Any of the common carriers known to those with skill in the art, such as sterile saline solution or plasma, can be utilized after radiolabelling for preparing the injectable solution to diagnostically image various organs, tumors and the like in accordance with the invention. Generally, the unit dose to be administered for a diagnostic agent has a radioactivity of about 0.1 mCi to about 100 mCi, preferably 1 mCi to 20 mCi. For a radiotherapeutic agent, the radioactivity of the therapeutic unit dose is about 10 mCi to 700 mCi, preferably 50 mCi to 400 mCi. The solution to be injected at unit dosage is from about 0.01 ml to about 30 ml. For diagnostic purposes after intravenous administration, imaging of the organ or tumor in vivo can take place in a matter of a few minutes. However, imaging takes place, if desired, in hours or even longer, after injecting into patients. In most instances, a sufficient amount of the administered dose will accumulate in the area to be imaged within about 0.1 of an hour to permit the taking of scintigraphic images. Any conventional method of scintigraphic imaging for diagnostic purposes can be utilized in accordance with this invention.

In a third aspect, the present invention refers to a method of preparing a compound having general chemical Formula II (method for fluorination and preferably radiofluorination) using an appropriate fluorination agent. The method comprises the (single) step of coupling a compound having general chemical Formula I with a fluorination agent, more preferably the fluorination agent is a radioactive or non-radioactive ("cold") fluorine isotope derivate. In the latter case the reagent to convert the compound having general chemical Formula I to the compound having general chemical Formula II is a fluorination agent. More preferably the compound having general chemical Formula II may thereafter be converted into a pharmaceutically acceptable salts of inorganic or organic acids thereof, hydrates, complexes, esters, amides, solvates and prodrugs thereof if desired. The reagents, solvents and conditions which can be used for this fluorination are common and well-known to the skilled person in the field. See, e.g., *J. Fluorine Chem.*, 27 (1985):117-191.

In a preferred embodiment of the method of preparing a compound having general chemical Formula A, wherein K=W comprises reacting a compound of general chemical Formula A, wherein K=$N^+(R^1)(R^2)(R^3)X^-$ with a fluorine isotope.

In a preferred embodiment of the method, the compound having general chemical Formula I and its pharmaceutically acceptable salts of inorganic or organic acids thereof, hydrates, complexes, esters, amides, solvates and prodrugs thereof is any preferred compound described above for obtaining any preferred compound having general chemical Formula II, more specifically any preferred compound having general chemical Formulae IIA and IIB, or pharmaceutically acceptable salt, hydrate, ester, amide, solvate or prodrug thereof as described above.

In a preferred method of preparing a compound having general chemical Formula II, the step of fluorination more preferably radiofluorination of a compound having general chemical Formula I is carried out at a temperature at or below 90° C.

In a preferred method of preparing a compound of Formula II, the step of fluorination more preferably radiofluorination of a compound of Formula I is carried out at a temperature selected from a range from 10° C. to 90° C.

In a preferred embodiment, the method of fluorination more preferably radiofluorination occurs at a reaction temperature of from room temperature to 80° C.

In a preferred method of preparing a compound of Formula II, the step of fluorination more preferably radiofluorination of a compound of Formula I is carried out at a temperature selected from a range from 10° C. to 70° C.

In a preferred method of preparing a compound of Formula II, the step of fluorination more preferably radiofluorination of a compound of Formula I is carried out at a temperature selected from a range from 30° C. to 60° C.

In a preferred method of preparing a compound of Formula II, the step of fluorination more preferably radiofluorination of a compound of Formula I is carried out at a temperature selected from a range from 45 to 55° C.

In a preferred method of preparing a compound of Formula II, the step of fluorination more preferably radiofluorination of a compound of Formula I is carried out at a temperature at 50° C.

More preferably, the radioactive fluorine isotope derivate is 4,7,13,16,21,24-Hexaoxa-1,10-diazabicyclo[8.8.8]-hexacosane K18F (crownether salt Kryptofix K18F), $K^{18}F$, $H^{18}F$, $KH^{18}F_2$, $Cs^{18}F$, $Na^{18}F$ or tetraalkylammonium salt of $^{18}F$ (e.g. [F-18]tetrabutylammonium fluoride). Most preferably, the a radioactive fluorine isotope derivate is $K^{18}F$, $H^{18}F$, or $KH^{18}F_2$.

In a preferred embodiment, the fluorination agent is a non-radioactive fluorine isotope. More preferably, the non-radioactive fluorine isotope is $^{19}F$ derivative, most preferably $^{19}F$.

In a preferred embodiment the solvents used in the present method may be DMF, DMSO, MeCN, DMA, DMAA, or mixture thereof, preferably the solvent is DMSO.

A new method is warranted in which the final product is prepared in a single step from the precursor. Only one purification step is necessary thereby the preparation can be accomplished in a short time (considering the half-life of $^{18}F$). In a typical prosthetic group preparation, very often temperatures of 100° C. and above are employed. The invention provides methods to accomplish the preparation at temperatures (80° C. or below) that preserve the biological properties of the final product. Additionally, single purification step is optionally carried out, thereby the preparation can be accomplished in a short time (considering the half-life of $^{18}F$).

In a tenth aspect the present invention refers to compounds having the general chemical Formula V:

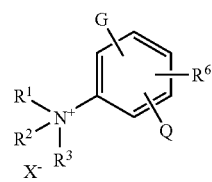

wherein $N^+(R^1)(R^2)(R^3)$, $X^-$, -G, and -Q, have the same meaning as depicted above for compounds having general chemical Formula I. This includes in particular all preferred embodiments mentioned above with regard to the residues and substituents $R^1$, $R^2$, $R^3$, $X^-$, -G, and -Q, and all residues used to define these residues and substituents, such as $R^4$, $R^5$ and the like;

$R^6$ is selected from the group comprising —S(O)$_2$—N(H)—CH$_2$—C(O)OH, —S(O)$_2$—N(Me)-CH$_2$—C(O)OH and C(O)OH.

In a preferred embodiment $R^6$ is selected from the group comprising —S(O)$_2$—N(Me)-CH$_2$—C(O)OH and C(O)OH.

In a more preferred embodiment $R^6$ is C(O)OH.

In a preferred embodiment of compounds of Formula V, -G and -Q are independently from each other selected from —H, —CN, CF$_3$, and —Cl.

In a more preferred embodiment of compounds of Formula V, -G and -Q are independently from each other H, —CF$_3$, or CN.

In a even more preferred embodiment of compounds of Formula V, -G and -Q are independently from each other H, —CF$_3$, or —CN, whereas at least one member of the group comprising -G or -Q is —CF$_3$ or —CN.

Preferred compounds of Formula V are selected from the group comprising

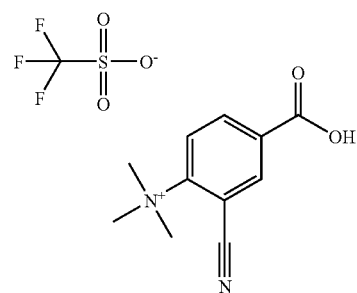

Trifluoro-methanesulfonate(4-carboxy-
2-cyano-phenyl)-trimethyl-ammonium;

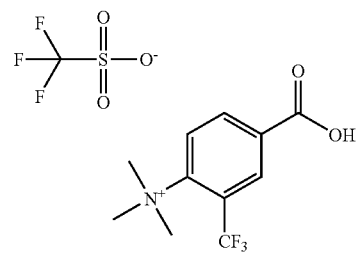

Trifluoro-methanesulfonate(4-carboxy-
2-trifluoromethyl-phenyl)-trimethyl-ammonium;

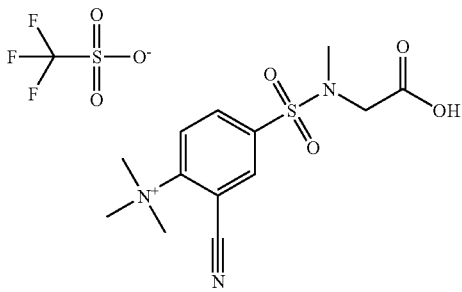

Trifluoro-methanesulfonate(4-(carboxymethyl-
methyl-sulfamoyl)-2-cyano-phenyl]-trimethyl-ammonium;

Compounds of Formula V are suited to be coupled to targeting agents towards compounds of Formula I which are starting materials for the radio labeling reaction towards compounds of Formula I or Formula A.

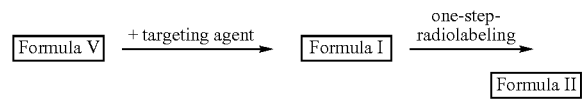

Formula A

In a eleventh aspect the present invention refers to a method to synthesize compounds of Formula I (Formula A) from compounds of Formula V.

Compounds of Formula V can be condensed to targeting agents equipped with or without a spacer to obtain compounds of Formula I as defined above (Formula A) by using typical condensing agents which are known to persons skilled in the art. Suited condensing agents are for example DCC, DIC and 4-(4,6-dimethoxy-1,3,5-triazin-2-yl)-4-methylpiperidinium tetrafluoroborate (J. Am. Chem. Soc. 2005, 127, 48, 16912-16920). Examples for such a reaction are depicted in scheme 3 and 4.

Example for Labeling:
First Example:

$^{18}$F-fluoride (up to 40 GBq) was azeotropically dried in the presence of Kryptofix 222 (5 mg in 1.5 ml MeCN) and cesium carbonate (2.3 mg in 0.5 ml water) by heating under a stream of nitrogen at 110-120° C. for 20-30 minutes. During this time 3×1 ml MeCN were added and evaporated. After drying, a solution of the precursor (2 mg) in 150 µl DMSO was added. The reaction vessel was sealed and heated at 50-70° C. for 5-15 mins to effect labeling. The reaction was cooled to room temperature and dilute with water (2.7 ml). The crude reaction mixture was analyzed using an analytical HPLC. The product was obtained by preparative radio HPLC to give to desired $^{18}$F labeled peptide.

Second Example:

Model compounds and peptides containing unnatural Histidine analogues $^{18}$F-fluoride (up to 100 GBq) was azeotropically dried in the presence of Kryptofix 222 (5 mg in 1.5 ml MeCN) and potassium carbonate (1 mg in 0.5 ml water) or cesium carbonate (2.3 mg in 0.5 ml water) by heating under nitrogen at 100-120° C. for 20-30 minutes. During this time 2–3×1 ml MeCN were added and evaporated under vacuum or with a stream of nitrogen. After drying, a solution of the precursor (100-300 µl of 0.0025-0.08M mg in DMSO) was added. The reaction vessel was sealed and heated at 50-90° C. for 5-15 mins to effect labeling. The crude reaction mixture was analyzed by HPLC. The product peak was confirmed by co-injection of the reaction mixture with the F19 cold standard. The reaction mixture was diluted with water (4 ml) and transferred to a semi-prep HPLC for purification. The product peak was collected diluted with water (10-20 ml) and immobilized on a C18 separation cartridge. The pure F18-labeled product was eluted from the cartridge with EtOH (1-2 ml).

Peptides Containing Natural Histidine $^{18}$F-fluoride (up to 100 GBq) was azeotropically dried in the presence of Kryptofix 222 (5 mg in 1.5 ml MeCN) and cesium carbonate (2.3 mg in 0.5 ml water) by heating under nitrogen at 100-120° C. for 20-30 minutes. During this time 2–3×1 ml MeCN were added and evaporated under vacuum or with a stream of nitrogen. After drying, a solution of the precursor (100-300 µl of 0.0025-0.08M mg in DMSO) was added. The reaction vessel was sealed and heated at 50-90° C. for 5-15 mins to effect labeling. The crude reaction mixture was analyzed by HPLC. The product peak was confirmed by co-injection of the reaction mixture with the F19 cold standard. The reaction mixture was diluted with water (4 ml) and transferred to a semi-prep HPLC for purification. The product peak was collected diluted with water (10-20 ml) and immobilized on a C18 separation cartridge. The pure F18-labeled product was eluted from the cartridge with EtOH (1-2 ml).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosure[s] of all applications, patents and publications, cited herein are incorporated by reference herein.

The following examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

General Method for the Preparation of Compounds

The peptide portion of the molecule -L-Y-U can be conveniently prepared according generally established techniques known in the art of peptide synthesis, such as solid-phase peptide synthesis. They are amenable Fmoc-solid phase peptide synthesis, employing alternate protection and deprotection. These methods are well documented in peptide literature. (Reference: "*Fmoc Solid Phase Peptide Synthesis*" *A practical approach*", Edited by W. C. Chan and P. D. White, Oxford University Press 2000) (For Abbreviations see Descriptions).

In the following two schematic examples are given of how to prepare a compound having general chemical Formula II using a compound having general chemical Formula I. The methods presented as schemes below are in principle suitable to generate compounds over the whole breadth of Formula II using compounds over the whole breadth of Formula I. The examples presented below are given merely to illustrate a way of labeling a compound having general chemical Formula I to arrive at a compound having general chemical Formula II and is not to be understood as to limit the invention to the methods exemplified herein.

Scheme 3 depicts an example of a synthetic route for forming a trimethylammonium substituted aromatic moiety containing peptide having general chemical Formula I and subsequent direct radiolabeling towards the corresponding $^{18}$F-labeled compound having general chemical formula II.

The synthesis starts with commercially available 2-Fluoro-5-formyl-benzonitrile (3) which is converted to the corresponding acid (4) by known oxidation methods, e.g., use of chromium reagents, manganese reagents or other typical reagents which are well-known to experts and which can be taken from, but are not limited to, the methods described and cited in the book: "*Modern oxidation methods*" by Jan-Erling Bäckvall, Wiley-VCH, 2004. A useful method is, e.g., the oxidation with sodium chlorite in phosphate-buffered tert-butanol solution.

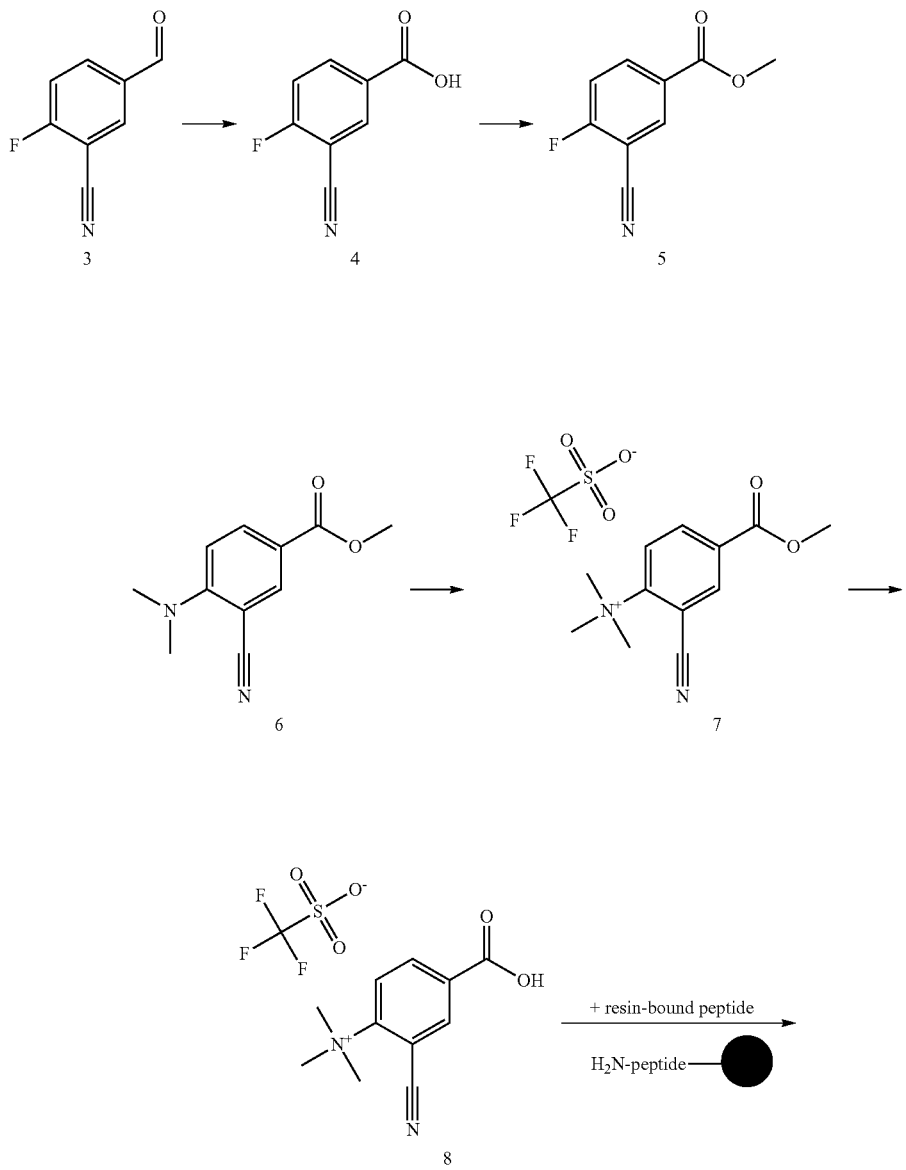

Scheme 3

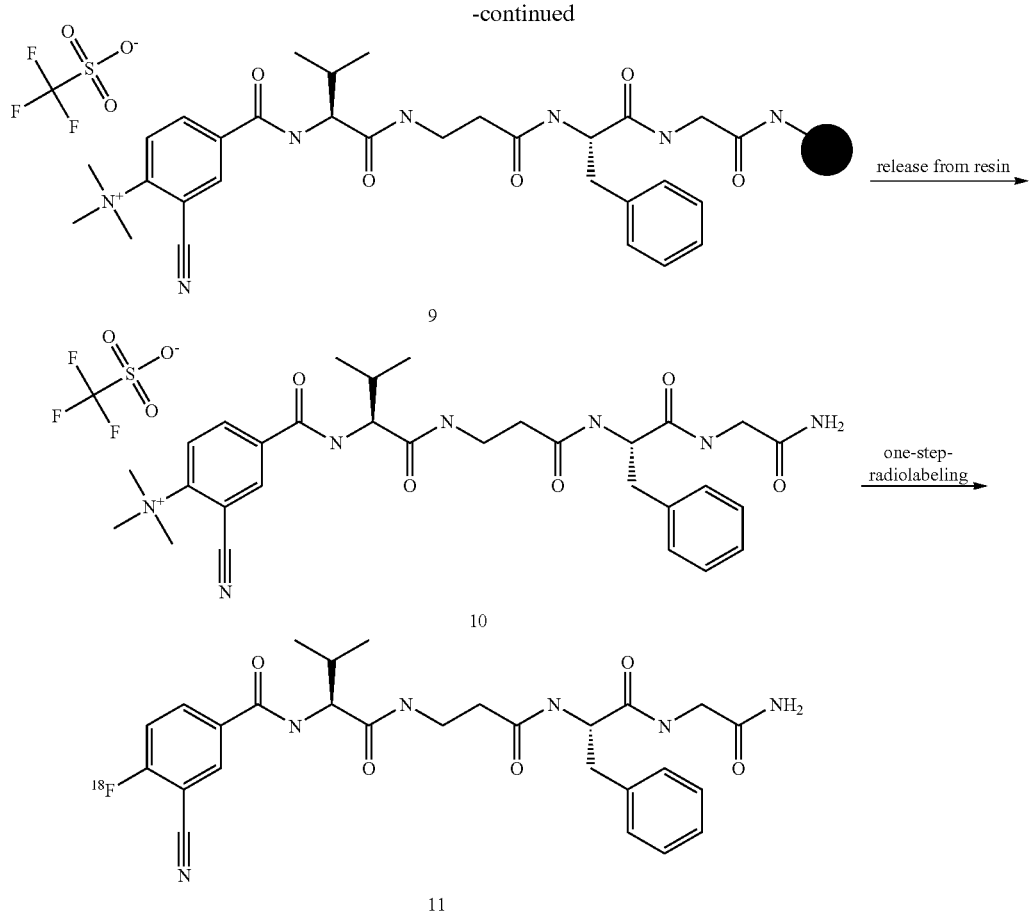

Acid (4) can be converted to the corresponding methyl ester with methanol and acetyl chloride (*Helv. Chim. Acta,* 2005, 88, 7:1630-1657). But the preparation of other alkyl esters (e.g., ethyl ester) and other esterification methods including variants under basic conditions are also possible and useful and are well known to experts. The displacement of fluoride (5) with dimethylamine or dimethylamine hydrochloride by nucleophilic aromatic substitution reaction can be carried out, e.g., in a suspension of DMSO and potassium carbonate (e.g., *Bioorg. Med. Chem. Lett.,* 10, 23, 2000:2603-2606). Useful other solvents can be selected from, but are not limited to, acetonitrile and DMF. The quarternisation of aniline (6) with methyl iodide, methyl triflate or other alkylating agents is carried out in boiling dichlormethane with normal or increased pressure (e.g., 1-10 bar). Other useful solvents for this reaction can be selected from, but are not limited to, acetone and dichloroethane. The crude product can be purified by reverse-phase column chromatography. The methyl ester (7) can be cleaved in boiling trifluoro acetic acid and water (*Bioorg. Med. Chem.,* 2003, 11:4189-4206) or under other acidic conditions. The acid (8) is coupled by solid phase synthesis (as shown in scheme 3) to solid-phase bound peptide to obtain amide (9) (or esters) by methods which are well known to experts. Typical condensating agents for those kinds of couplings are diisopropylcarbodiimid or dicyclohexylcarbodiimid, but also other condensating agents (see, e.g., Chan and White (*"Fmoc Solid Phase Peptide Synthesis—A Practical Approach"*), are possible. The resin-bound peptide is then cleaved from the resin by acidification to obtain liberated peptide (10). The cleavage is also possible by other appropriate methods which are very much dependent on the kind of linker. The methods of peptide cleavage from resin are very well known to experts and described in literature (e.g., Chan and White—*"Fmoc Solid Phase Peptide Synthesis—A Practical Approach"*). The purified peptide (10) is converted at 70° C.±45° C. with [$^{18}$F]potassium fluoride, potassium carbonate and Kryptofix (4,7,13,16,21,24-Hexaoxa-1,10-diaza-bicyclo[8.8.8]hexacosane) in dimethylsulfoxide to obtain the desired $^{18}$F-labeled peptide (11). The reagents and solvents which are used for this radiofluorination are common, well-known to experts since many years and described in many publications (e.g., *J. Fluorine Chem.,* 27 (1985):117-191). It was surprisingly found that the radiofluorination does take place and that the temperature can be decreased to <90° C. so that the peptide is not harmed or decomposed. The preferred temperature range for conducting the radioflurination of compounds according to Formula I is from 10° C. to 90° C. More preferred is the temperature range of 10° C. to 70° C. Even more preferred is the range of temperature from 35° C. to 65° C. Further preferred is a range of temperature from 45° C. to 55° C. Most preferred is a temperature of 50° C. for carrying out the radiofluorination of compounds having general chemical Formula I to arrive at compounds having general chemical Formula II.

Another example of a trimethyl ammonium derivative was prepared as shown in Scheme 4: Commercially available sulfonylchloride 12 was coupled with the secondary amine sarcosin methyl ester to the sulfonamide 13 in dichlormethane and diisopropyl ethyl amine to scavenge hydrogen chloride. Other useful solvents for this reaction can be, but are not limited to, DMF, THF, dioxane, dichloroethane, diethyl-ether and tert butyl ether. Other useful bases can be, but are not limited to, trimethylamine, N-methyl morpholine, NMP and sodium hydrogen carbonate.
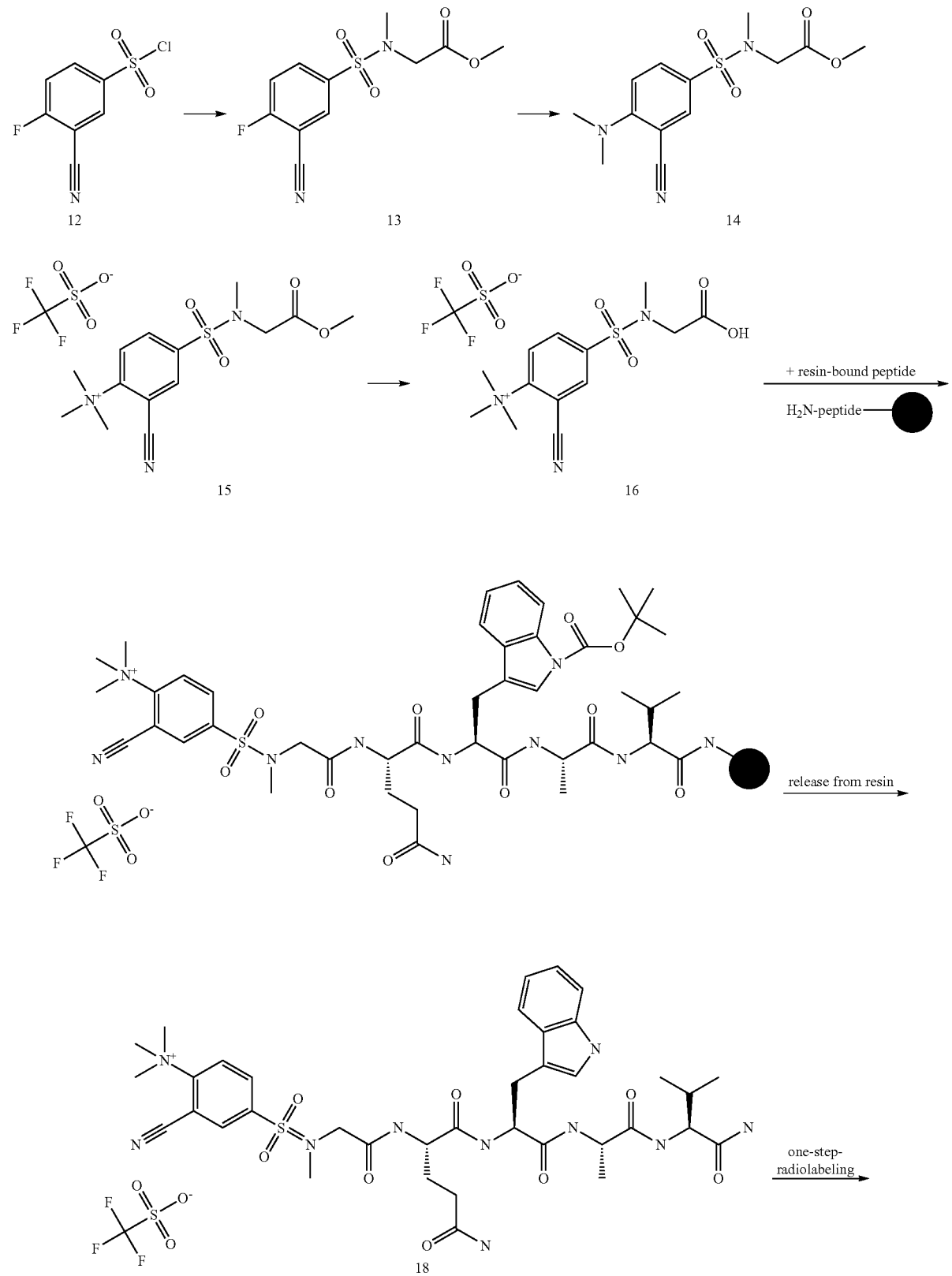

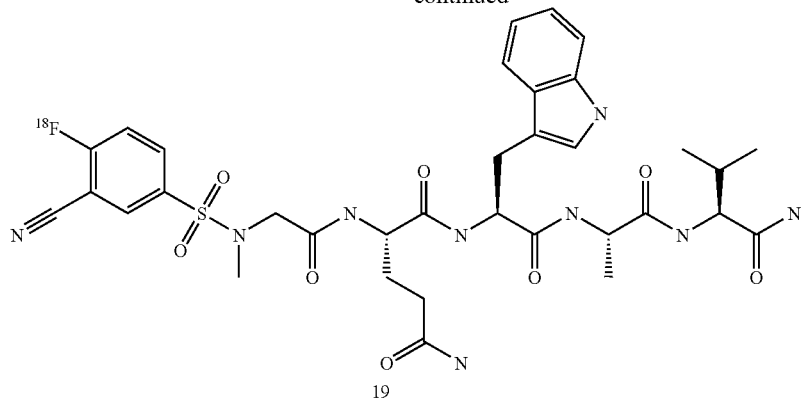

19

Sulfonamide 13 was then treated in an aromatic nucleophilic substitution reaction with dimethylammonium hydrochloride and potassium carbonate in dimethylsulfoxide to obtain dimethylaniline 14. The aniline derivative 14 was quarternized with methyltriflate or methyl iodide in dichloromethane or dichloroethane towards ammonium salt 15. The resulting ester 15 was cleaved under acidic conditions, e.g., in boiling trifluoro acetic acid and water (*Bioorg. Med. Chem.,* 2003, 11:4189-4206). The acid 16 was condensed to the resin-bound peptide by methods which are well known to experts. Typical condensating agents for those kinds of couplings are diisopropylcarbodiimid or dicyclohexylcarbodiimid, but also other condensating agents are possible and described. Examples are given in, but are not limited to, the methods described and cited in the book: Chan and White—"*Fmoc Solid Phase Peptide Synthesis—A Practical Approach*". The resin-bound trimethylammonium peptide 17 is then cleaved from the resin by acidification to obtain liberated peptide (18). The cleavage is also possible by other appropriate methods which are very much dependent on the kind of linker. The methods of peptide cleavage from resin are very well known to experts. Examples are given in, but are not limited to, the methods described and cited in the book: Chan and White—"*Fmoc Solid Phase Peptide Synthesis—A Practical Approach*". The purified peptide (18) is converted at 70° C.±45° C. with [$^{18}$F]potassium fluoride, potassium carbonate and Kryptofix (4,7,13,16,21,24-Hexaoxa-1,10-diaza-bicyclo [8.8.8]hexacosane) in dimethylsulfoxide to obtain the desired $^{18}$F-labeled peptide (19). The reagents and solvents which are used for this radiofluorination are common, well-known to experts and are described in many publications (e.g., *J. Fluorine Chem.,* 27 (1985):117-191). Beside potassium carbonate as base also tetraalkyl ammonium carbonate is possible. It was surprisingly found that the radiofluorination does take place at the given mild temperatures so that the peptide is not harmed or decomposed. The preferred temperature range for conducting the radiofluorination of compounds having general chemical Formula I is from 10° C. to 90° C. More preferred is the temperature range of 10° C. to 70° C. Even more preferred is the range of temperature from 35° C. to 65° C. Further preferred is a range of temperature from 45° C. to 55° C. Most preferred is a temperature of 50° C. for carrying out the radiofluorination of compounds according to Formula I to arrive at compounds according to Formula II.

More complex peptides can also be labeled directly in a one-step F-18 labeling procedure: The following fluorination-reaction (20→21; Scheme 5) is carried out in DMSO at 70° C. at 15 min reaction time.

Scheme 5

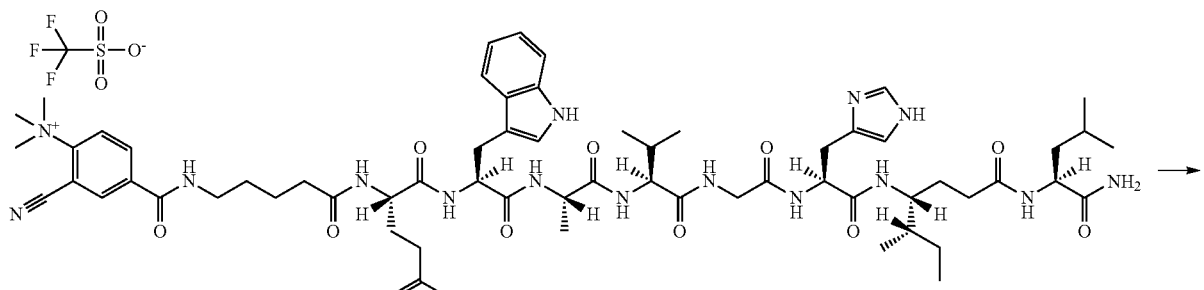

20

-continued

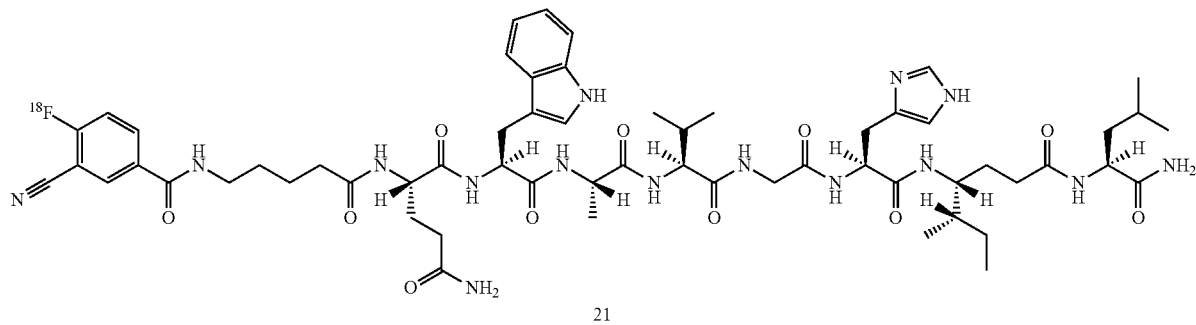

21

It is surprising that molecules with such a complex pattern of unprotected functionalities can be F-18 labeled easily under these mild conditions with high incorporation of F-18 fluoride. The chromatogram of FIG. 6 shows the desired product as peak in the radioactive version, whereas the non-radioactive standard co-elutes in the UV-chromatogram (HPLC chromatogram of reaction mixture with co-injection of the cold standard).

Another example for the F-18 labelling of complex peptides is shown in the following Scheme 6:

Again, the following HPLC-chromatogram represents the radioactive and the UV-version of the corresponding F-18 and F-19 fluoro-peptides (23 and 22), respectively. The Fluorination-reaction is also carried out in DMSO at 70° C. at 15 min reaction time. The respective chromatogram is shown in FIG. 7 (HPLC chromatogram of reaction mixture with co-injection of the cold standard).

The F-18 labeling of small molecules is also possible. For example compound 24 (WO 2007/16538 A2) can be condensed with trimethylammonium benzoic acid derivative 25

Scheme 6

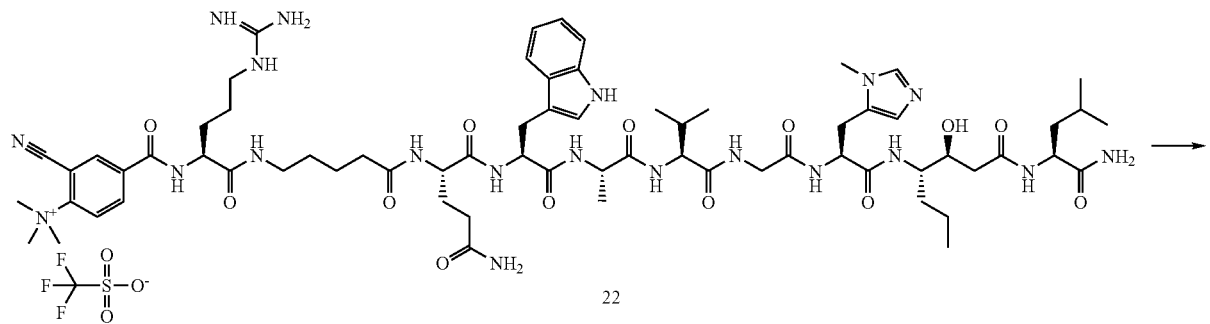

22

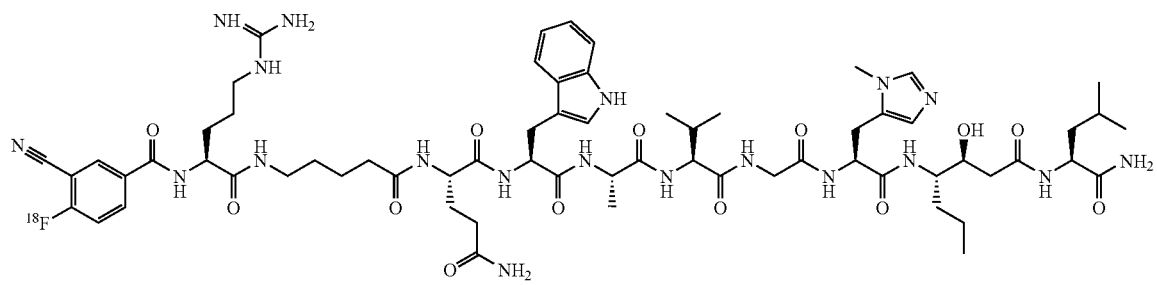

23 to obtain the precursor 26 for F-18 labeling (Scheme 7). The incorporation of F-18 fluoride is achieved to obtain F-18 labeled compound 27 (the corresponding non-radioactive reference standard is published (WO 2007/16538 A2)).

An example of the F-18 labeling of an oligonucleotide is shown in scheme 8. TTA1 (Nucleic Acids Research, 2004, Vol. 32, No. 19, 5757-5765) is equipped with a triimathylammonium derivative of Formula III by use of a triazine con- Scheme 7

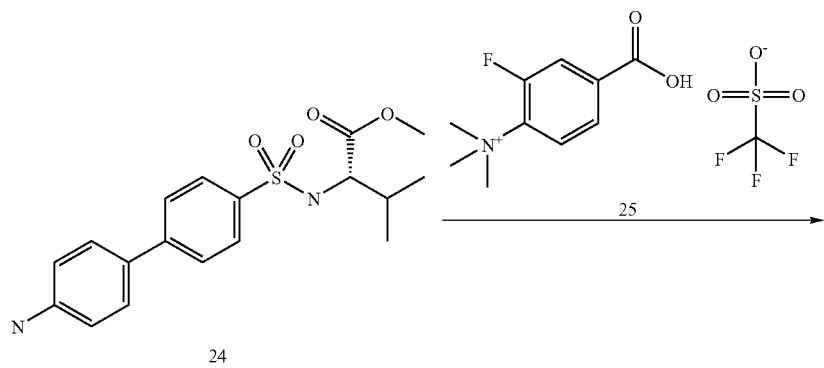

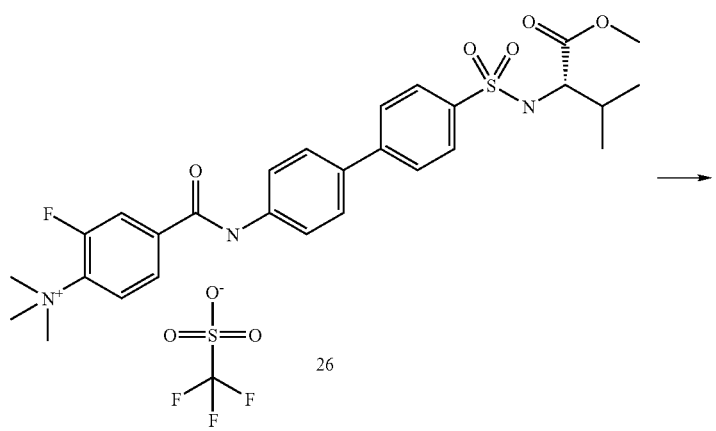

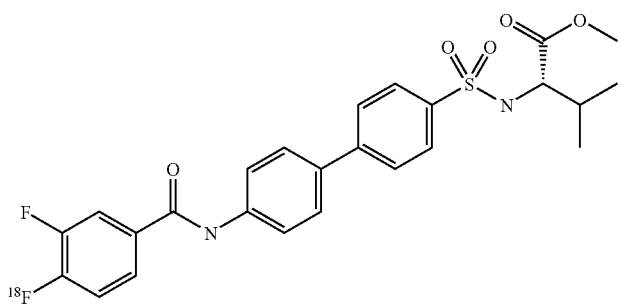

densating agent (J. Am. Chem. Soc. 2005, 127, 48, 16912-16920). The subsequent F-18 radiolabeling is obtained in reasonable yield, although the specific activity was relatively low due to the fact that the purification of the F-18 labeled compound is achieved under non-optimal circumstances.

FIG. 7 shows HPLC chromatograms of reaction mixture with co-injection of the cold standard.

FIG. 8 shows a tumor-tissue ratio of a Bombesin analog.

FIG. 9 shows HPLC chromatograms m of reaction mixture with co-injection of the cold standard.

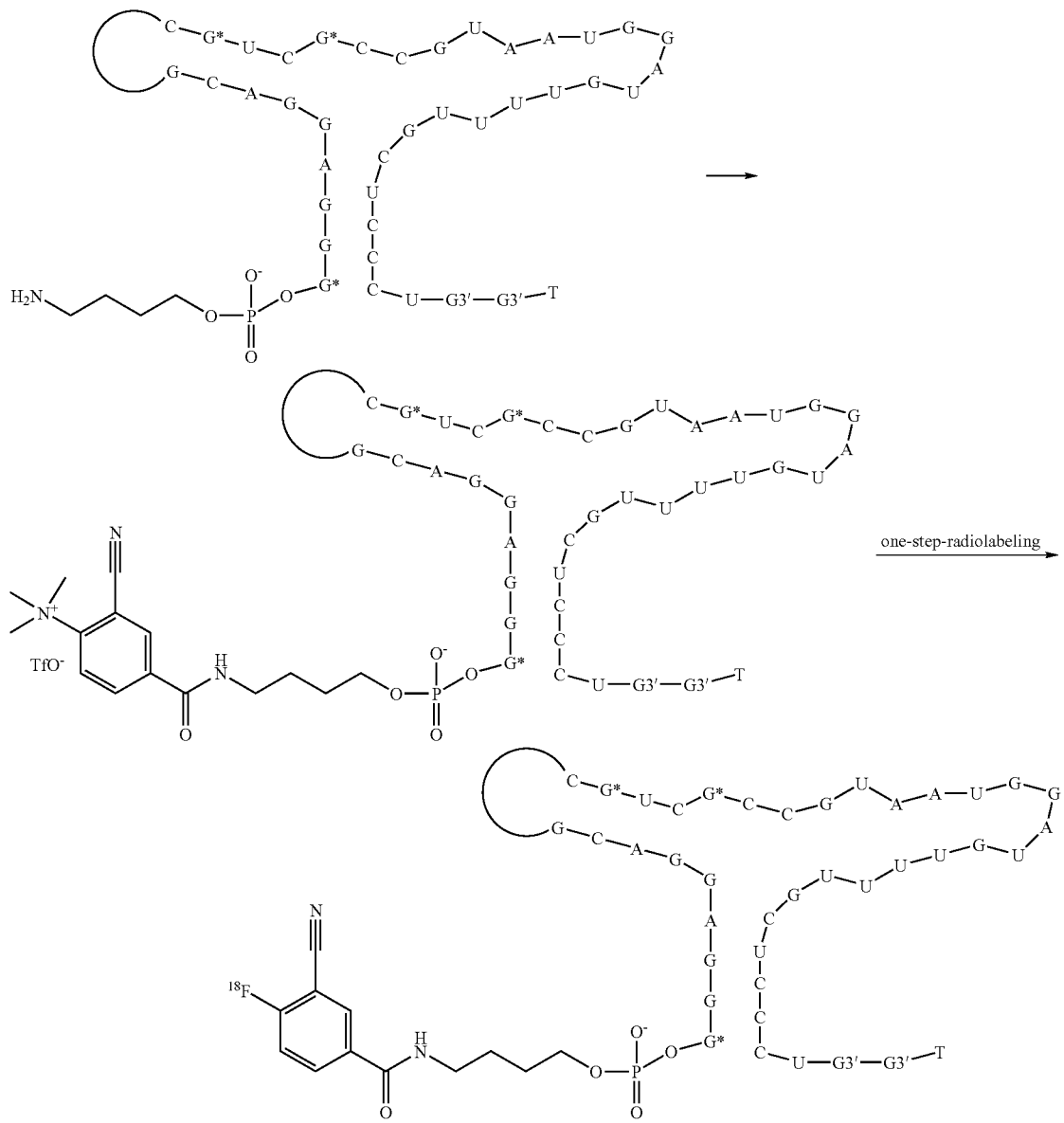

BRIEF DESCRIPTION OF THE DRAWINGS

FIG. 12a shows Table 1 and various small molecule targeting agents and the targets thereof.

FIG. 12b shows compounds in Table 1 (Ia-2 to Ia-12).

FIG. 12c shows compounds in Table 1 continued (Ia-13 to Ia-25).

FIG. 12*d* shows compounds in Table 2 (IIB-a-1 to IIB-a-13).

FIG. 12*e* shows compounds in Table 2 continued (IIB-a-14 to IIB-a-37).

FIG. 12*f* shows compounds in Table 2 continued (IIB-a-38 to IIB-a-60).

FIG. 12*g* shows compounds in Table 2 continued (IIB-a-61 to IIB-a-71).

FIG. 12*h* shows compounds in Table 2 continued (IIB-a-72 to IIB-a-75).

FIG. 12*i* shows compounds in Table 3 (IIA-a-2 to IIA-a-12).

FIG. 12*j* shows compounds in Table 3 continued (IIA-a-13 to IIA-a-22).

EXAMPLES

Example A

Synthesis $X^-N^+(R^1)(R^2)(R^3)$—$(C_6H_4(-G;-Q))$-L-Y-U (Ia)

Figure 1:
FIG. 1 shows an HPLC of Ia-1.
Figure 1:
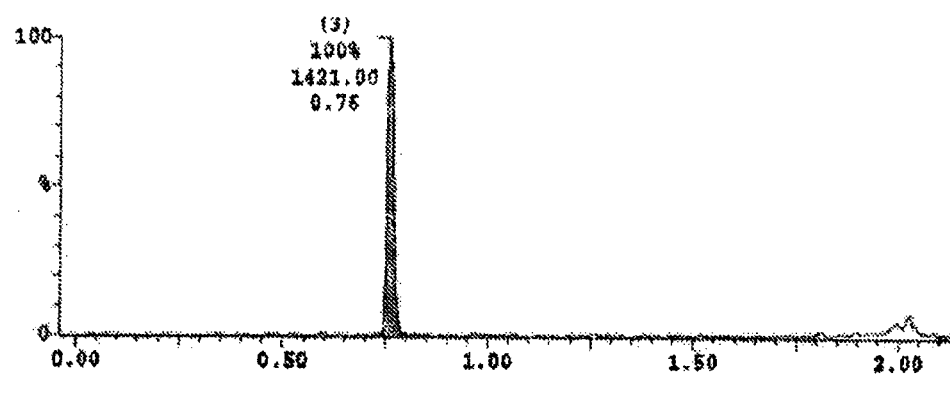

Synthesis of H-Y-U: Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support (e.g., Rink amide resin) with its amino group protected with an N-protecting agent, fluorenylmethoxycarbonyl (FMOC) group. The amino protecting group is removed with suitable deprotecting agent such as piperidine for FMOC and the next amino acid residue (in N-protected form) is added with a coupling agent such as dicyclohexylcarbodiimide (DCC), diisopropyl-cyclohexylcarbodiimide (DCCl), hydroxybenzotriazole (HOBt). Upon formation of a peptide bond, the reagents are washed from the support. After addition of the final residue of (Y), the peptide is attached to the solid support is ready for the coupling of $X^-N^+(R^1)(R^2)(R^3)$—$(C_6H_4(-G;-Q))$-L-OH.

Synthesis of $X^-N^+(R^1)(R^2)(R^3)$—$(C_6H_4(-G))$-L-Y-U (Ia)

Ia: L=CO, $X^-$=$CF_3SO_3^-$

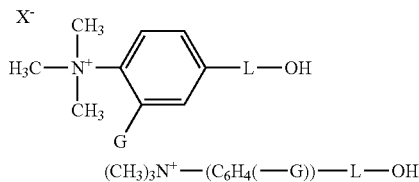

$(CH_3)_3N^+$—$(C_6H_4(—G))$—L—OH

-G=-CN, —$CF_3$, —F and others specified

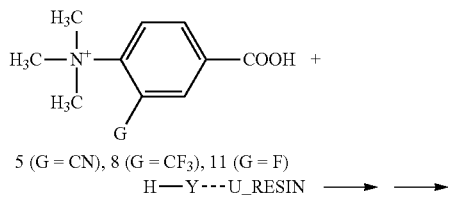

5 (G = CN), 8 (G = $CF_3$), 11 (G = F)

H—Y---U_RESIN →  →

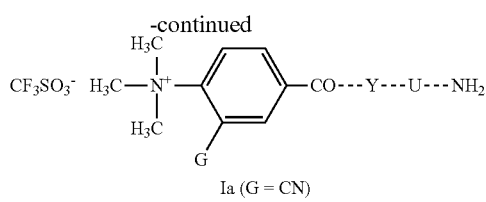

Ia (G = CN)

To a suspension of the resin -Y-U-RESIN in DMF (0.1 to 0.25 mmol), $X^-N^+(R^1)(R^2)(R^3)$—$(C_6H_4(-G))$-L-OH (5, 8 or 11, 2-4 equivalents) was added along with 4-(4,6-dimethoxy-1,3,5-triazin-2-yl)-4-methylmorpholinium tetrafluoroborate.

Example B describes the preparation of 5, 8 and 11.

After 3-8 hours, the resin was washed with DMF and dichloromethane. The peptide Ia) was isolated from the resin using TFA:diisopropylsilane:phenol:water cocktail with concomitant removal of the protecting groups of amino acids. The product was purified by HPLC using appropriate TFA:$H_2O$:0.1 TFA gradient using $C_{18}$-reverse phase column. The products were identified by mass spectra.

Ia-1: 4-(Trimethylammonium)-3-cyano-benzoyl-Arg-Ava-Gln-Trp-Ala-Val-NMeGly-His-Sta-Leu-$NH_2$: Molecular wt: Calculated: 1422.73, Found: 711.86 (($M^+$+1)/2)

Table 1; (FIGS. 12A-12C) lists all the trimethylammonium compounds precursors Ia-1 Ia-25 used for F-18 labeling Example B Preparation of $X^-N^+(R^1)(R^2)(R^3)$—$(C_6H_4(-G))$-L-OH 5 (G=-CN)

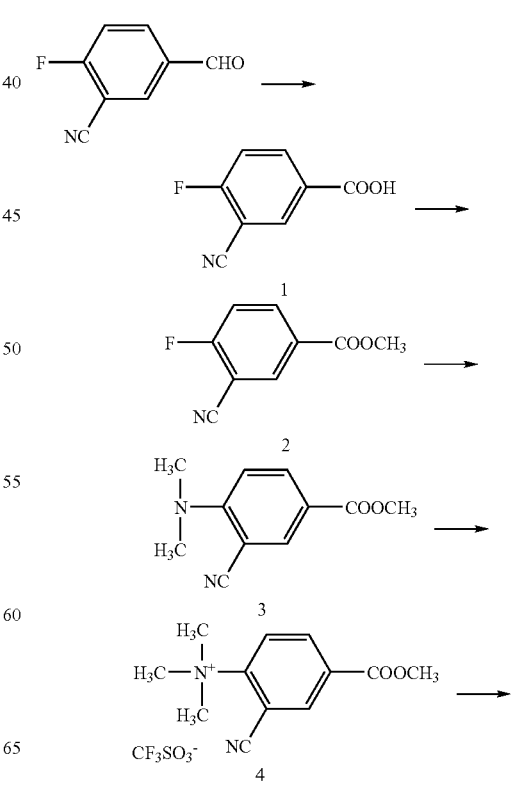

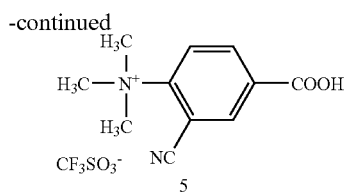

a) Synthesis of 3-Cyano-4-fluoro-benzoic acid

To a stirred solution of 15.0 g (97.6 mmol) 2-fluoro-5-formyl-benzonitrile (Aldrich), 150 ml dest. water and 630 ml t-butanol were added 40.8 g (361 mmol) sodium chlorite and 35.9 g (230 mmol) sodium hydrogen phosphate dihydrate. The reaction mixture was stirred over night and poured into a diluted aqueous hydrogen chloride solution (pH=3.5). The pH value was readjusted to pH=3.5 by aqueous hydrogen chloride. The aqueous solution was extracted trice with dichloromethane/isopropanol (10:1). The combined organic phases were dried (sodium sulfate) and concentrated. The residue was purified by extraction with sodium hydrogen carbonate solution and dichloromethane, acidification with aqueous solution and subsequent filtering. The solid crude product 1 was obtained in 90% yield (14.5 g, 87.8 mmol) and was used for the next step without purification. MS-ESI: 166 ($M^+$+1.77), Elementary analysis:

| Calculated: | C 58.19% | H 2.44% | F 11.51% | N 8.48% |
|---|---|---|---|---|
| Found: | C 58.81% | H 2.42% | F 11.41% | N 8.47% | b) Synthesis of 3-Cyano-4-fluoro-benzoic acid methyl ester 2

To a stirred suspension of 16.0 g (96.9 mmol) 1 and 161 ml methanol were added 30.4 g (387.6 mmol) acetyl chloride drop wisely at 0° C. The reaction mixture was stirred over night, filtered and concentrated. The residue was diluted with dichloromethane, washed with diluted sodium hydrogen carbonate solution, dried with sodium sulphate and concentrated. The residue was purified by column chromatography (hexane:ethylacetate). The desired product 2 was obtained in 78.1% yield (13.5 g; 75.7 mmol) MS-ESI: 180 ($M^+$+1, 57), Elementary analysis:

| Calculated: | C 60.34% | H 3.38% | F 10.60% | N 7.82% |
|---|---|---|---|---|
| Determined: | C 60.51% | H 3.39% | F 10.57% | N 7.80% | c) Synthesis of 3-Cyano-4-dimethylamino-benzoic acid methyl ester 3

To a stirred solution of 24.0 g (134 mmol) 2 and 240 ml dimethylsulphoxid were added 13.2 g (161 mmol) dimethylamine hydrochloride and 38.9 g (281 mmol) potassium carbonate. The reaction mixture was stirred over night and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude product 3 was obtained in 94% yield (25.7 g, 126 mmol) and was used for the next step without purification.

MS-ESI: 205 ($M^+$+1, 59),

Elementary analysis:

| Calculated: | C 64.69% | H 5.92% | N 13.72% |
|---|---|---|---|
| Found: | C 64.79% | H 5.95% | N 13.69% | d) Synthesis of (2-Cyano-4-methoxycarbonyl-phenyl)-trimethyl-ammonium trifluoro-methane-sulfonate 4

To a stirred solution of 6.16 g (30.2 mmol) 3 and 110 ml dichloromethane were added 50.0 g (302 mmol) methyltriflate (Aldrich) drop wisely. The reaction mixture was stirred over night and diethylether was added. After evaporation of one third of the solvent volume the desired compound precipitates and the rest of the solvent were decanted. The solid was washed extensively (ten times) with large amounts of diethylether. The solid was dried by use of oil pump vacuum and purified by (C-18) RP-column chromatography (acetonitril/water—gradient 1:99 to 80:20). The desired compound 4 was obtained in 69% yield (20.8 mmol, 7.68 g).

MS-ESI: 219 ($M^+$, 100),

Elementary analysis:

| Calculated: | C 42.39% | H 4.10% | F 15.47% | N 7.61% |
|---|---|---|---|---|
| Found: | C 42.42% | H 4.12% | F 15.41% | N 7.59% | e) Synthesis of Trifluoro-methanesulfonate(4-carboxy-2-cyano-phenyl)-trimethyl-ammonium 5

A solution of 4.01 g (10.9 mmol) 4, 95 ml dest. water and 95 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 5 was obtained in 93% yield (3.59 g, 10.1 mmol) and crude compound 5 was used for the next step without purification.

MS-ESI: 205 ($M^+$, 100),

Elementary analysis:

| Calculated: | C 40.68% | H 3.70% | F 16.09% | N 7.91% |
|---|---|---|---|---|
| Found: | C 40.72% | H 3.71% | F 16.06% | N 7.91% |

Preparation of RG-$L_1$-$B_1$-OH 8 (G=$CF_3$)

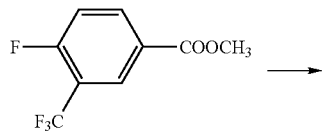

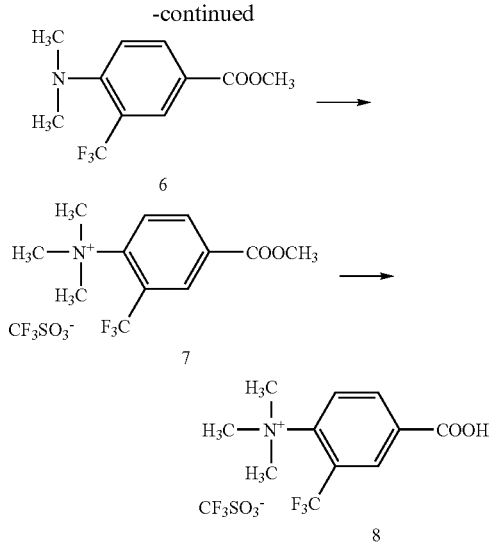

a) 4-Dimethylamino-2-trifluoromethyl-benzoic acid methyl ester 6

To a stirred solution of 4.48 g (22.5 mmol) 4-Fluoro-2-trifluoromethyl-benzoic acid methyl ester (Rarechem) and 60.0 ml dimethylsulfoxide were added 2.23 g (27.0 mmol) dimethylamine hydrochloride and 6.54 g (47.3 mmol) potassium carbonate. The reaction mixture was stirred for 8 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 6 was obtained in 72% yield (4.00 g, 16.2 mmol).

MS-ESI: 248 (M$^+$+1.78).

| Elementary analysis: | C 53.44% | H 4.89% | F 23.05% | N 5.67% |
|---|---|---|---|---|
| Found: | C 53.46% | H 4.91% | F 23.04% | N 5.64% | b) Trifluoro-methanesulfonate(4-methoxycarbonyl-3-trifluoromethyl-phenyl)-trimethyl-ammonium 7

To a stirred solution of 3.09 g (12.5 mmol) 6 and 50 ml dichloromethane were added 20.5 g (125 mmol) methyltriflate (Aldrich) drop wisely. The reaction mixture was refluxed for 2 days then cooled to room temperature. Diethylether was added. The desired compound precipitated and the solvent was decanted. The solid was washed extensively (ten times) with large amounts of diethylether. The solid was dried by use of oil pump vacuum and purified by (C-18) RP-column chromatography (acetonitrile/water-gradient 1:99 to 80:20). The desired compound 7 was obtained in 69% yield (3.55 g, 8.63 mmol).

MS-ESI: 262 (M$^+$, 87),

Elementary analysis:

| Calculated: | C 37.96% | H 3.68% | F 27.71% | N 3.41% |
|---|---|---|---|---|
| Determined: | C 38.01% | H 3.63% | F 27.69% | N 3.41% | c) Trifluoro-methanesulfonate(4-carboxy-3-trifluoromethyl-phenyl)-trimethylammonium 8

A solution of 2.84 g (6.92 mmol) 7, 60 ml dist. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 89% yield (2.45 g; 6.16 mmol) and crude compound 8 was used for the next step without purification.

MS-ESI: 248 (M$^+$, 59),

Elementary analysis:

| Calculated: | C 36.28% | H 3.30% | F 28.69% | N 3.53% |
|---|---|---|---|---|
| Determined: | C 36.30% | H 3.32% | F 28.67% | N 3.52% |

Preparation of X$^-$N$^+$(R$^1$)(R$^2$)(R$^3$)—(C$_6$H$_4$(-G))-L-OH 10 (-G=-F)

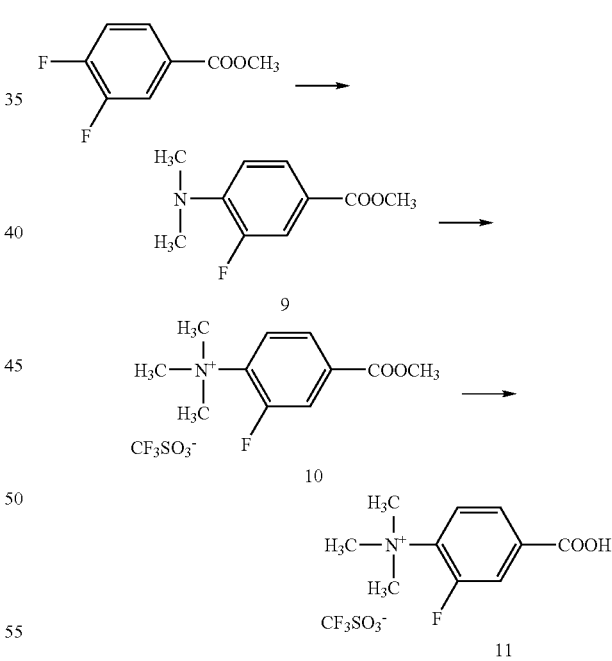

a) 3-Fluoro-4-dimethylamino-benzoic acid methyl ester 9

To a stirred solution of 38.7 g (225 mmol) 3.4-difluoro-benzoic acid methyl ester (Apollo) and 600 ml dimethylsulphoxide were added 22.3 g (270 mmol) dimethylamine hydrochloride and 65.4 g (473 mmol) potassium carbonate. The reaction mixture was stirred for 5 h at 55° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude product 9 was obtained in 71% yield (31.5 g, 160.0 mmol) and was used for the next step without purification.

MS-ESI: 198 (M$^+$+1, 72).

Elementary analysis:

| Calculated: | C 60.91% | H 6.13% | F 9.63% | N 7.10% |
|---|---|---|---|---|
| Found: | C 60.99% | H 6.15% | F 9.60% | N 7.07% | b) Synthesis of (2-fluoro-4-methoxycarbonyl-phenyl)-trimethyl-ammonium trifluoro-methane-sulfonate 10

To a stirred solution of 3.90 g (19.8 mmol) 9 and 70 ml dichloromethane were added 32.5 g (198 mmol) methyltriflate (Aldrich) drop wisely. The reaction mixture was stirred for 2.5 days at room temperature and diethylether was added. The desired compound precipitates and the solvent were decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 10 was obtained in 80% yield (5.72 g, 15.84 mmol).

MS-ESI: 212 (M$^+$, 76),

Elementary analysis:

| Calculated: | C | 39.89% | H | 4.18% | F | 21.03% | N | 3.88% |
|---|---|---|---|---|---|---|---|---|
| Found: | C | 39.93% | H | 4.20% | F | 21.01% | N | 3.84% | c) Synthesis of (4-carboxy-2-fluoro-phenyl)-trimethyl-ammonium trifluoro-methanesulfonate 11

A solution of 4.00 g (11.1 mmol) 10, 96 ml dest. water and 96 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 11 was obtained in 92% yield (3.54 g, 10.2 mmol) and crude compound 11 was used for the next step without purification.

MS-ESI: 198 (M$^+$, 76),

Elementary analysis:

| Calculated: | C | 38.04% | H | 3.77% | F | 21.88% | N | 4.03% |
|---|---|---|---|---|---|---|---|---|
| Found: | C | 38.10% | H | 3.79% | F | 21.81% | N | 4.00% |

Example C

Synthesis of F—(C$_6$H$_4$(-G))-L-Y-U (IIB-a)

For the identification $^{18}$F—(C$_6$H$_4$(-G))-L-Y-U, reference standards $^{19}$F—(C$_6$H$_4$(-G))-L-Y-U were prepared according to the scheme shown below.

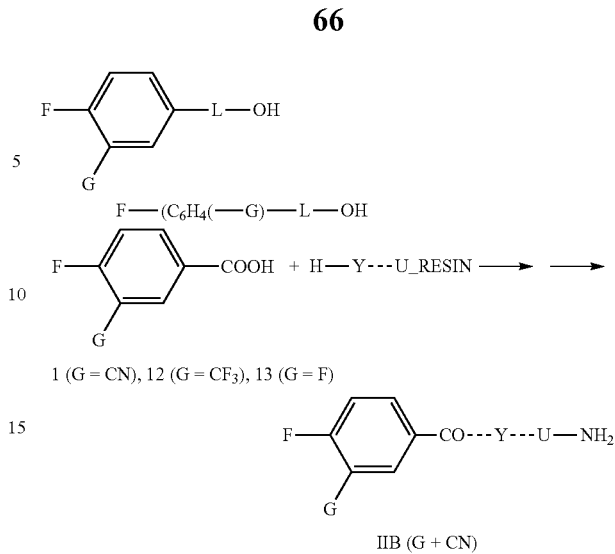

1 (G = CN), 12 (G = CF$_3$), 13 (G = F)

IIB (G + CN)

Compounds 1, 12 and 13 were purchased commercially.

Synthesis of H—Y-U-RESIN and coupling of $^{19}$F—(C$_6$H$_4$(-G))-L-OH were accomplished according to the methods described in Example A.

IIB-a-1: 4-[19]-Fluoro-3-cyano-benzoyl-Arg-Ava-Gln-Trp-Ala-Val-NMeGly-His-Sta-Leu-NH$_2$, Molecular Weight, Calculated: 1382.62, Found: 691.9 ((M$^+$+1)/2)

Table 2; (FIGS. 12D-12H) lists all the F-19 compounds (IIB-a-1 to IIB-a-25) prepared for the chromatographic identification for products resulting from Ia-1-Ia-25 used for F-18 labeling as well as binding affinities. The Table lists all other F-19 compounds used in the SA analysis for the selection of high affinity analogs. Measurement of binding constants is described in Example D.

Example D

In vitro binding affinity and specificity of Bombesin analogs for the human bombesin 2 receptor (GRPR) were assessed via a competitive receptor-binding assay using $^{125}$I-[Tyr$^4$]-Bombesin (Perkin Elmer; specific activity 81.4 TBq/mmol) as GRPR-specific radioligand. The assay was performed based on the scintillation proximity assay (SPA) technology (J. W. Carpenter et al, *Meth. Mol. Biol.*, 2002; 190:31-49) using GRPR-containing cell membranes (Perkin Elmer) and wheat germ agglutinin (WGA)-coated PVT beads (Amersham Bioscience).

Briefly, GRPR-containing membranes and WGA-PVT beads were mixed in assay buffer (50 mM Tris/HCl pH 7.2, 5 mM MgCl$_2$, 1 mM EGTA, Complete protease inhibitor (Roche Diagnostics GmbH) and 0.3% PEI) to give final concentrations of approximately 100 µg/ml protein and 40 mg/ml PVT-SPA beads. The ligand $^{125}$I-[Tyr$^4$]-Bombesin was diluted to 0.5 nM in assay buffer. The test compounds were dissolved in DMSO to give 1 mM stock solutions later on, they were diluted in assay buffer to 8 pM-1.5 µM.

The assay was then performed as follows: First, 10 µl of compound solution to be tested for binding were placed in white 384 well plates (Optiplate-384, Perkin-Elmer). At next, 20 µl GRPR/WGA-PVT bead mixture and 20 µl of the ligand solution were added. After 90 minutes incubation at room temperature, another 50 µl of assay buffer were added, the plate sealed and centrifuged for 10 min at 520×g at room temperature. Signals were measured in a TopCount (Perkin Elmer) for 1 min integration time per well. The IC$_{50}$ was calculated by nonlinear regression using the GraFit data analysis software (Erithacus Software Ltd.). Furthermore, the $K_I$ was calculated based on the $IC_{50}$ for test compound as well as the $K_D$ and the concentration of the ligand $^{125}$I-[Tyr$^4$]-Bombesin. Experiments were done with quadruple samples.

The Binding affinities measured for all the cold F-19 compounds are listed Table 2; (FIGS. 12D-12H).

Example E

General Radiolabeling Method

In a 5 mL Wheaton vial, $^{18}$F-fluoride (up to 40 GBq) was azeotropically dried in the presence of Kryptofix 222 (5 mg in 1.5 ml CH$_3$CN) and potassium carbonate (1 mg in 0.5 ml water) or cesium carbonate (2.3 mg in 0.5 ml water) by heating under a stream of nitrogen at 110-120° C. for 20-30 minutes. During this time 3×1 ml CH$_3$CN were added and evaporated. After drying, a solution of Ia-1 (2 mg) in 150 μl DMSO was added. The reaction vessel was sealed and heated at 50-70° C. for 5-15 mins to effect labeling. The reaction was cooled to room temperature and diluted with water (2.7 ml). The crude reaction mixture was analyzed using an analytical HPLC (Column Zorbax SB C18, 50×4.6 mm, 1.8μ, 2 ml/min, solvent A: H$_2$O, solvent B: MeCN, gradient: 5%-95% B in 7 min or Column Econosphere C18, 53×7 mm, 3 p, 3 ml/min (Alltech), solvent A: H$_2$O+0.1% TFA, solvent B: MeCN/Water 9/1+0.1% TFA, gradient: 5-95% B in 7 min. The F-18 labeled product IIA-a-1 was confirmed by co-injection with the cold F-19 fluoro standard (IIB-a-1) on the Econsphere analytical HPLC.

The product IIA-a-1 was obtained by preparative radio HPLC to give to desired F-18 labeled peptide.

Figure 2:
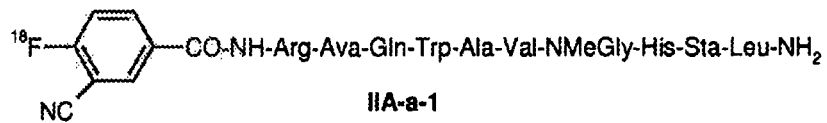
FIG. 2 shows an HPLC of IIA-a-1 and IIB-a-1.
Figure 2:
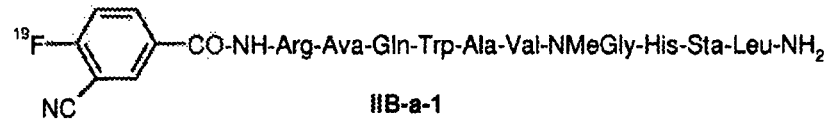
Figure 2:
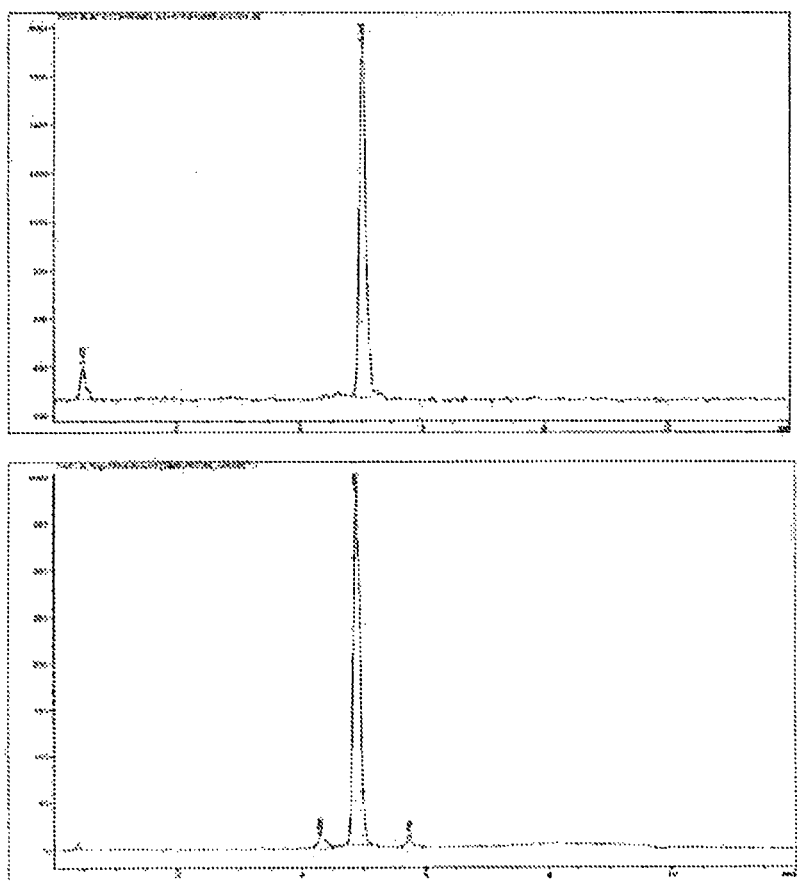

Conditions for HPLC according to FIG. 2:
Column: C-18, Gradient: A: 10 mM K$_2$HPO$_4$ pH: 9.04; B: 10 mM K$_2$HPO$_4$ pH: 9.04/ACN 3/7; Flow rate: 2 mL, 5% A to 95% B in 7 min. Retention time IIA-a-1—5.01 min. IIB-a-1—4.89 min.

In a similar manner, Compounds shown in Table 1; (FIGS. 12A-12C) (Ia-2 to Ia-22) were labeled with F-18 to yield F-18 labeled peptides, IIA-a-2 to IIA-a-22 (Table 3; FIGS. 12I-12J) respectively. The chromatographic behavior of IIA-a-2 to IIA-a-22 were compared with IIB-a-2 to IIB-a-22 respectively for complete characterization in rodent studies and imaging.

Human Serum Stability of IIA-a-1:

To qualify for pre-clinical and clinical use, it is necessary to establish the stability of the compounds in human serum. The compound a 70 μL of human serum containing the F-18 labeled peptide (5.89 MBq/mL) was incubated at 37° C. for 90 min. An aliquot was withdrawn at various intervals and the purity assessed by HPLC. Potassium hydrogen phosphate buffer system was used as a mobile phase to measure the stability of attached F-18 label.

Figure 3:
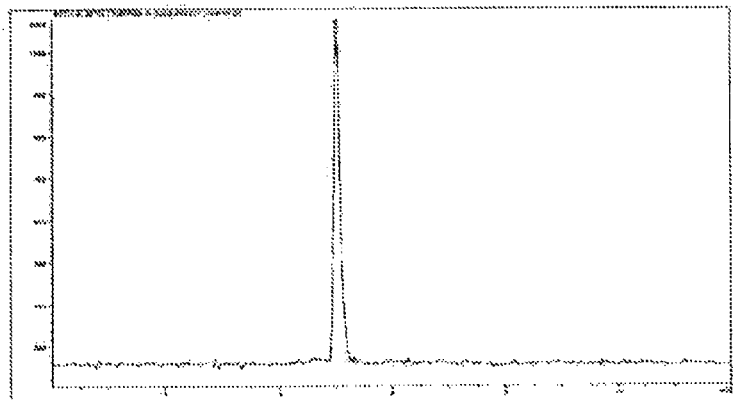
FIG. 3 shows HPLC chromatograms of reaction mixture with co-injection of the cold standard.
Figure 3:
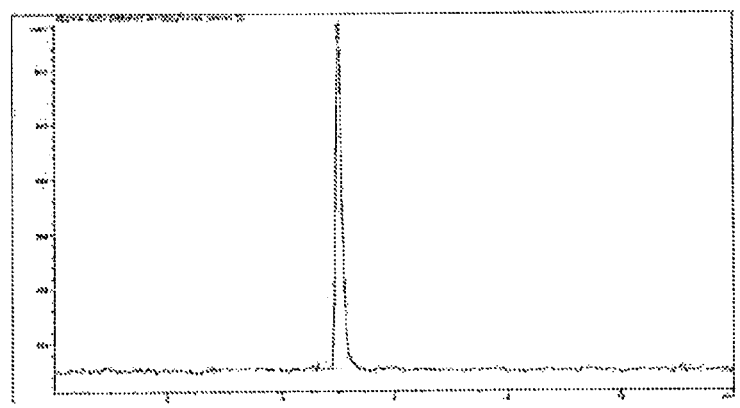
Figure 3:
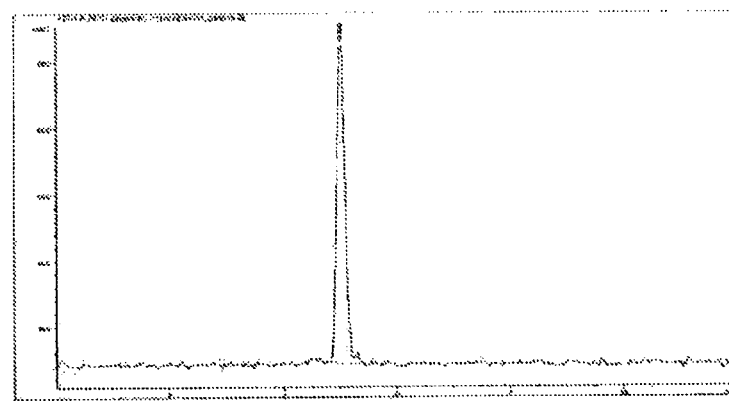

HPLC chromatograms are shown in FIG. 3. Conditions for HPLC: Column: C-18, Gradient: A: 10 mM K$_2$HPO$_4$ pH: 9.04; B: 10 mM K$_2$HPO$_4$ pH: 9.04/ACN 3/7; Flow rate: 2 mL, 5% A to 95% B in 7 min.

Trifluoroacetic acid system was used as a mobile phase to measure the stability of the entire molecule.

Figure 4:
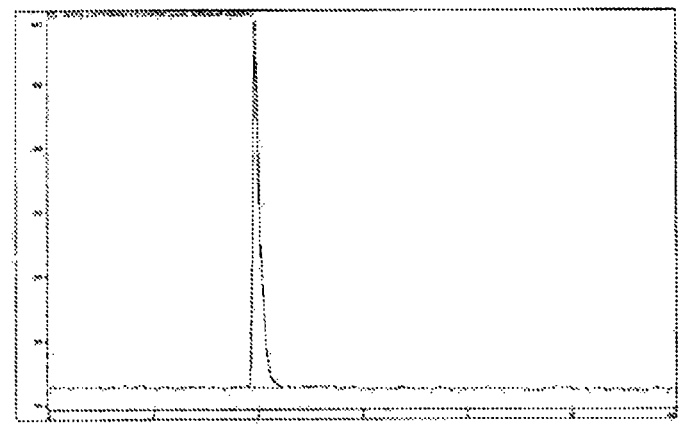
FIG. 4 shows HPLC chromatograms of reaction mixture with co-injection of the cold standard.
Figure 4:
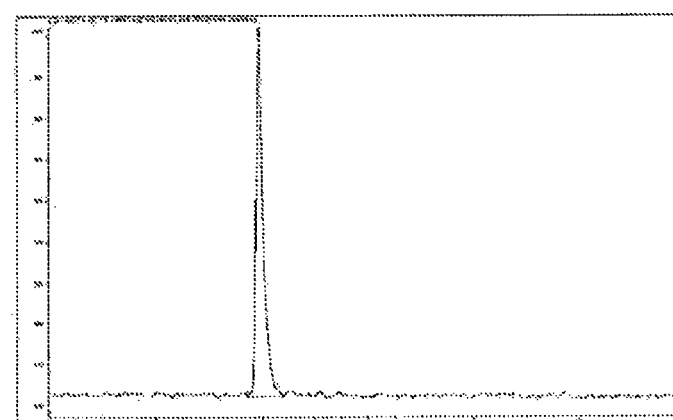
Figure 4:
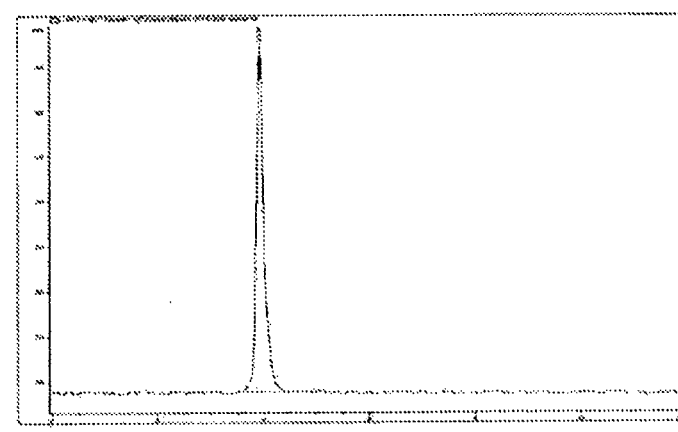

Column: C-18, Gradient: A: 10% CH$_3$CN: 90% H$_2$O, B: 90% CH$_3$CN: 10% H$_2$O containing 0.1% TFA (chromatograms in FIG. 4).

The above experiments clearly show that in the compounds of the present invention, the F-18 isotope and the [18]F—C$_6$H$_4$(-G,-Q)-L-Y—(IIA), targeting molecule of the invention are stable in human serum.

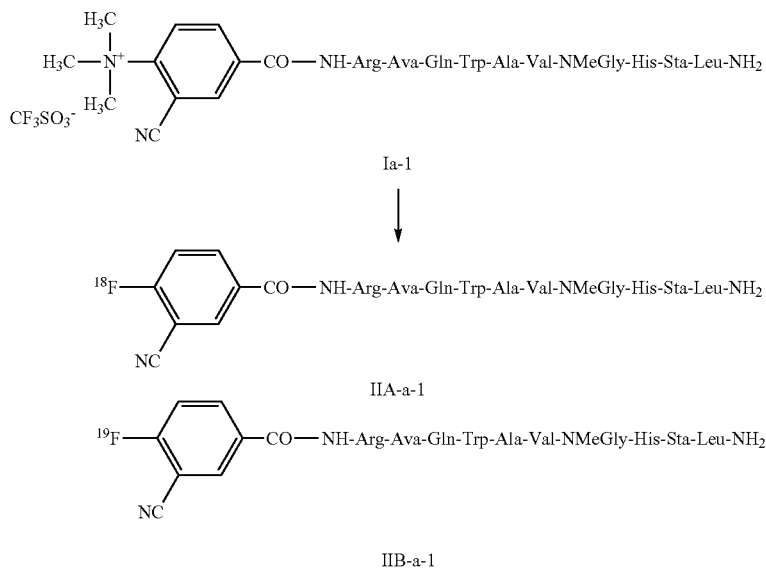

HPLC of Ia-1, IIA-a-1 and IIB-a-1 are shown in FIGS. 1 and 2.

Conditions for HPLC according to FIG. 1:
Column: C-18, Gradient: A: 10% CH$_3$CN: 90% H$_2$O, B: 90% CH$_3$CN: 10% H$_2$O containing 0.1% TFA (UPLC); Flow rate: 2 mL, 1% A to 99% B in 2 min.

In a similar manner, the compounds shown in Table 1; (FIGS. 12A-12C) (Ia-1 to Ia-22) were labelled with F-18 to yield F-18 labelled peptides, IIA-a-1 to IIA-a-22 (Table 3; FIGS. 12I-12J) respectively. The chromatographic behaviour of IIA-a-1 to IIA-a-22 were compared with IIB-a-1 to IIB-a-22 respectively for complete characterization in rodent studies and imaging.

Example 1 a) 2-Chloro-4-dimethylamino-benzoic acid methyl ester (1a)

To a stirred solution of 4.00 g (20.6 mmol) 2-chloro-4-fluoro-benzoic acid methyl ester (Apollo) and 60 ml dimethylsulphoxid were added 2.03 g (24.7 mmol) dimethylamine hydrochloride and 5.97 g (43.2 mmol) potassium carbonate. The reaction mixture was stirred over night and is reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude product 1a was obtained in 99% yield (4.36 g, 20.4 mmol) and was used for the next step without purification.

MS-ESI: 213/215 ($M^+$+1, 64/48).

Elementary analysis:

| Calculated: | C | 56.21% | H | 5.66% | N | 6.56% |
|---|---|---|---|---|---|---|
| Determined: | C | 56.39% | H | 5.67% | N | 6.54% | b) Synthesis of (3-chloro-4-methoxycarbonyl-phenyl)-trimethyl-ammonium trifluoro-methane-sulfonate (1b)

To a stirred solution of 4.49 g (21.0 mmol) Ia and 75 ml dichloromethane were added 34.5 g (210 mmol) methyltriflate (Aldrich) drop wisely. The reaction mixture was stirred for 2 days at room temperature. 17 g (10 mmol) methyltriflate (Aldrich) were added and the reaction mixture was stirred at 40° C. for 20 h. The reaction mixture was cooled to 20° C. and diethylether was added. The desired compound precipitates and the solvent was decanted and the solid was washed extensively (ten times) with large amounts of diethylether. The solid was dried by use of oil pump vacuum and purified by (C-18) RP-column chromatography (acetonitril/water-gradient 1:99 to 80:20). The desired compound 1b was obtained in 86% yield (6.86 g, 18.1 mmol).

MS-ESI: 228/230 ($M^+$, 81),

Elementary analysis:

| Calculated: | C | 38.15% | H | 4.00% | F | 15.09% | N | 3.71% |
|---|---|---|---|---|---|---|---|---|
| Determined: | C | 38.18% | H | 4.02% | F | 15.04% | N | 3.70% | c) Synthesis of (4-carboxy-3-chloro-phenyl)-trimethyl-ammonium trifluoro-methanesulfonate (1c)

A solution of 0.5 g (1.32 mmol) 1b, 12 ml dest. water and 12 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude 1c was obtained in 98% yield (471 mg, 1.3 mmol) and crude compound 1c was used for the next step without purification.

MS-ESI: 214/216 ($M^+$, 89/56),

Elementary analysis:

| Calculated: | C | 36.32% | H | 3.60% | F | 15.67% | N | 3.85% |
|---|---|---|---|---|---|---|---|---|
| Determined: | C | 36.37% | H | 3.63% | F | 15.61% | N | 3.83% | d) Synthesis of (4-Trimethylammonium-2-chloro-benzoyl)-Trp-Ala-Val-Leu-$NH_2$-triflate salt (1d)

To a stirred solution of 72.8 mg (0.2 mmol) 1c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Trp(Boc)-Ala-Val-Leu-$NH_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 69.4 mg (0.2 mmol) 1c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (1d) in 30.0% yield—16.2 mg (0.0195 mmol).

MS-ESI: 683/685 ($M^+$, 39/26)

e) Synthesis of [$^{18}$F]-(4-Fluoro-2-chloro-benzoyl)-Trp-Ala-Val-Leu-$NH_2$ (1e)

To a Wheaton vial (5 ml) charged with Kryptofix 222 (5 mg), potassium carbonate (1 mg in 500 μl water) and MeCN (1.5 ml) the fluorine containing water (316 MBq, 33 μl) were added. The solvent was removed by heating at 120° C. for 10 mins under a stream of nitrogen. Anhydrous MeCN (1 ml) was added and evaporated as before. This step was repeated again. A solution of 1d (2 mg) in anhydrous DMSO (300 μl) was added. After heating at 80° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 1e was confirmed by co-injection with the cold F-19 fluoro standard on the Econsphere analytical HPLC.

Example 2 a) Synthesis of 3-Cyano-4-fluoro-benzoic acid (2a)

To a stirred solution of 15.0 g (97.6 mmol) 2-fluoro-5-formyl-benzonitrile (Aldrich), 150 ml dest. water and 630 ml t-butanol were added 40.8 g (361 mmol) sodium chlorite and 35.9 g (230 mmol) sodium hydrogen phosphate dihydrate. The reaction mixture was stirred over night and poured into a diluted aqueous hydrogen chloride solution (pH=3.5). The pH value was readjusted to pH=3.5 by aqueous hydrogen chloride. The aqueous solution was extracted trice with dichloromethane/isopropanol (10:1). The combined organic phases were dried (sodium sulphate) and concentrated. The residue was purified by extraction with sodium hydrogen carbonate solution and dichloromethane, acidification with aqueous solution and subsequent filtering. The solid crude product 2a was obtained in 90% yield (14.5 g, 87.8 mmol) and was used for the next step without purification.

MS-ESI: 166 (M$^+$+1, 77),
Elementary analysis:

| Calculated: | C | 58.19% | H | 2.44% | F | 11.51% | N | 8.48% |
| Determined: | C | 58.81% | H | 2.42% | F | 11.41% | N | 8.47% | b) Synthesis of 3-Cyano-4-fluoro-benzoic acid methyl ester (2b)

To a stirred suspension of 16.0 g (96.9 mmol) 2a and 161 ml methanol were added 30.4 g (387.6 mmol) acetyl chloride drop wisely at 0° C. The reaction mixture was stirred over night, filtered and concentrated. The residue was diluted with dichloromethane, washed with diluted sodium hydrogen carbonate solution, dried with sodium sulphate and concentrated. The residue was purified by column chromatography (hexane:ethylacetate). The desired product 2b was obtained in 78.1% yield (13.5 g; 75.7 mmol)

MS-ESI: 180 (M$^+$+1, 57),
Elementary analysis:

| Calculated: | C | 60.34% | H | 3.38% | F | 10.60% | N | 7.82% |
| Determined: | C | 60.51% | H | 3.39% | F | 10.57% | N | 7.80% | c) Synthesis of 3-Cyano-4-dimethylamino-benzoic acid methyl ester (2c)

To a stirred solution of 24.0 g (134 mmol) 2b and 240 ml dimethylsulphoxid were added 13.2 g (161 mmol) dimethylamine hydrochloride and 38.9 g (281 mmol) potassium carbonate. The reaction mixture was stirred over night and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude product 2c was obtained in 94% yield (25.7 g, 126 mmol) and was used for the next step without purification.

MS-ESI: 205 (M$^+$+1, 59),
Elementary analysis:

| Calculated: | C | 64.69% | H | 5.92% | N | 13.72% |
| Determined: | C | 64.79% | H | 5.95% | N | 13.69% | d) Synthesis of (2-Cyano-4-methoxycarbonyl-phenyl)-trimethyl-ammonium trifluoro-methanesulfonate (2d)

To a stirred solution of 6.16 g (30.2 mmol) 2c and 110 ml dichloromethane were added 50.0 g (302 mmol) methyltriflate (Aldrich) drop wisely. The reaction mixture was stirred over night and diethylether was added. After evaporation of one third of the solvent volume the desired compound precipitates and the rest of the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 2d was obtained in 69% yield (20.8 mmol, 7.68 g).

MS-ESI: 219 (M$^+$, 100),
Elementary analysis:

| Calculated: | C | 42.39% | H | 4.10% | F | 15.47% | N | 7.61% |
| Determined: | C | 42.42% | H | 4.12% | F | 15.41% | N | 7.59% | e) Synthesis of Trifluoro-methanesulfonate(4-carboxy-2-cyano-phenyl)-trimethyl-ammonium; (2e)

A solution of 4.01 g (10.9 mmol) 2d, 95 ml dest. water and 95 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 2e was obtained in 93% yield (3.59 g, 10.1 mmol) and crude compound 2e was used for the next step without purification.

MS-ESI: 205 (M$^+$, 100),
Elementary analysis:

| Calculated: | C | 40.68% | H | 3.70% | F | 16.09% | N | 7.91% |
| Determined: | C | 40.72% | H | 3.71% | F | 16.06% | N | 7.91% | f) Synthesis of peptide (4-Trimethylammonium-3-cyano-benzoyl)-Arg-Ala-His(π-Me)-Leu-NH$_2$-triflate salt, (2f)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Arg(Pbf)-Ala-His(π-Me)-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (2f) in 27.0% yield—14.9 mg (0.0176 mmol).

MS-ESI: 698 (M$^+$, 100).

g) Synthesis of [$^{18}$F]-(4-Fluoro-3-cyano-benzoyl)-Arg-Ala-His(π-Me)-Leu-NH$_2$ (2g)

To a Wheaton vial (5 ml) charged with Kryptofix 222 (5 mg), potassium carbonate (1 mg in 500 μl water) and MeCN (1.5 ml) the fluorine containing water (356 MBq, 38 μl) were added. The solvent was removed by heating at 120° C. for 10 mins under a stream of nitrogen. Anhydrous MeCN (1 ml) was added and evaporated as before. This step was repeated again. A solution of 2f (2 mg) in anhydrous DMSO (300 μl) was added. After heating at 50° C. for 10 min. The crude reaction mixture was analyzed using an analytical HPLC (Column Zorbax SB C18, 50×4.6 mm, 1.8μ, 2 ml/min, solvent A: H$_2$O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product (2g) was confirmed by co-injection with the cold F-19 fluoro standard on the Econsphere analytical HPLC.

Example 3 a) 3-Fluoro-4-dimethylamino-benzoic acid methyl ester (3a)

To a stirred solution of 38.7 g (225 mmol) 3.4-difluoro-benzoic acid methyl ester (Apollo) and 600 ml dimethylsulphoxid were added 22.3 g (270 mmol) dimethylamine hydrochloride and 65.4 g (473 mmol) potassium carbonate. The reaction mixture was stirred for 5 h at 55° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude product 3a was obtained in 71% yield (31.5 g, 160.0 mmol) and was used for the next step without purification.

MS-ESI: 198 (M$^+$+1.72).

Elementary analysis:

| Calculated: | C 60.91% | H 6.13% | F 9.63% | N 7.10% |
|---|---|---|---|---|
| Determined: | C 60.99% | H 6.15% | F 9.60% | N 7.07% | b) Synthesis of (2-fluoro-4-methoxycarbonyl-phenyl)-trimethyl-ammonium trifluoro-methane-sulfonate (3b)

To a stirred solution of 3.90 g (19.8 mmol) 3a and 70 ml dichloromethane were added 32.5 g (198 mmol) methyltriflate (Aldrich) drop wisely. The reaction mixture was stirred for 2.5 days at room temperature and diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 3b was obtained in 80% yield (5.72 g, 15.84 mmol).

MS-ESI: 212 (M$^+$, 76),

Elementary analysis:

| Calculated: | C 39.89% | H 4.18% | F 21.03% | N 3.88% |
|---|---|---|---|---|
| Determined: | C 39.93% | H 4.20% | F 21.01% | N 3.84% | c) Synthesis of (4-carboxy-2-fluoro-phenyl)-trimethyl-ammonium trifluoro-methanesulfonate (3c)

A solution of 4.00 g (11.1 mmol) 3b, 96 ml dest. water and 96 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 3c was obtained in 92% yield (3.54 g, 10.2 mmol) and crude compound 3c was used for the next step without purification.

MS-ESI: 198 (M$^+$, 76),

Elementary analysis:

| Calculated: | C 38.04% | H 3.77% | F 21.88% | N 4.03% |
|---|---|---|---|---|
| Determined: | C 38.10% | H 3.79% | F 21.81% | N 4.00% | d) Synthesis of (4-Trimethylammonium-3-fluoro-benzoyl)-Gly-Thr-Tyr-Ala-NH$_2$-triflate salt (3d)

To a stirred solution of 69.4 mg (0.2 mmol) 3c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Gly-Thr(OtBu)-Tyr(OtBu)-Ala-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 69.4 mg (0.2 mmol) 3c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (3d) in 41.6% yield—20.0 mg (0.027 mmol).

MS-ESI: 590 (M$^+$, 100)

e) Synthesis of (3-Fluoro-4-[$^{18}$F]-fluoro-benzoyl)-Gly-Thr-Tyr-Ala-NH$_2$ (3e)

To a Wheaton vial (5 ml) charged with Kryptofix 222 (5 mg), potassium carbonate (1 mg in 500 μl water) and MeCN (1.5 ml) the fluorine containing water (405 MBq, 35 μl) were added. The solvent was removed by heating at 120° C. for 10 mins under a stream of nitrogen. Anhydrous MeCN (1 ml) was added and evaporated as before. This step was repeated again. A solution of 3d (2 mg) in anhydrous DMSO (300 μl) was added. After heating at 80° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econsphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 3e was confirmed by co-injection with the cold F-19 fluoro standard on the Econsphere analytical HPLC.

Example 4 a) 2-Fluoro-4-dimethylamino-benzoic acid methyl ester (4a)

To a stirred solution of 3.87 g (22.5 mmol) 2.4-difluoro-benzoic acid methyl ester (Apollo) and 60.0 ml dimethylsulphoxid were added 2.23 g (27.0 mmol) dimethylamine hydrochloride and 6.54 g (47.3 mmol) potassium carbonate. The reaction mixture was stirred for 5 h at 55° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 4a was obtained in 55% yield (2.44 g, 12.4 mmol).

MS-ESI: 198 (M$^+$+1, 86).
Elementary analysis:

| Calculated: | C 60.91% | H 6.13% | F 9.63% | N 7.10% |
|---|---|---|---|---|
| Determined: | C 60.95% | H 6.14% | F 9.59% | N 7.08% | b) Synthesis of (3-fluoro-4-methoxycarbonyl-phenyl)-trimethyl-ammonium trifluoro-methane-sulfonate (4b)

To a stirred solution of 2.46 g (12.5 mmol) 4a and 50 ml dichloromethane were added 20.5 g (125 mmol) methyltriflate (Aldrich) drop wisely. The reaction mixture was refluxed for 2 days. The solvent was carefully substituted by dichloroethan. The reaction mixture was refluxed for 2 days and then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 4b was obtained in 80% yield (3.61 g, 10.0 mmol).

MS-ESI: 212 (M$^+$, 77),
Elementary analysis:

| Calculated: | C 39.89% | H 4.18% | F 21.03% | N 3.88% |
|---|---|---|---|---|
| Determined: | C 39.94% | H 4.21% | F 21.00% | N 3.85% | c) Synthesis of (4-carboxy-3-fluoro-phenyl)-trimethyl-ammonium trifluoro-methanesulfonate (4c)

A solution of 2.50 g (6.92 mmol) 4b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 4c was obtained in 100% yield (2.40 g; 6.92 mmol) and crude compound 4c was used for the next step without purification.

MS-ESI: 198 (M$^+$, 76),
Elementary analysis:

| Calculated: | C 38.04% | H 3.77% | F 21.88% | N 4.03% |
|---|---|---|---|---|
| Determined: | C 38.09% | H 3.80% | F 21.82% | N 4.01% | d) Synthesis of (4-Trimethylammonium-2-fluoro-benzoyl)-Lys(N-dimethyl)-Ala-Gly-Leu-NH$_2$-triflate salt (4d)

To a stirred solution of 69.4 mg (0.2 mmol) 4c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Lys(N-dimethyl)-Ala-Gly-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 69.4 mg (0.2 mmol) 4c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (4d) in 45.0% yield—24.7 mg (0.0293 mmol).

MS-ESI: 596 (M$^+$, 100)

e) Synthesis of (2-Fluoro-4-[$^{18}$F]-fluoro-benzoyl)-Lys(N-dimethyl)-Ala-Gly-Leu-NH$_2$ (4e)

To a Wheaton vial (5 ml) charged with Kryptofix 222 (5 mg), potassium carbonate (1 mg in 500 μl water) and MeCN (1.5 ml) the fluorine containing water (385 MBq, 39 μl) were added. The solvent was removed by heating at 120° C. for 10 mins under a stream of nitrogen. Anhydrous MeCN (1 ml) was added and evaporated as before. This step was repeated again. A solution of 4d (2 mg) in anhydrous DMSO (300 μl) was added. After heating at 90° C. for 10 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econsphere C18, 53×7 mm, 3μ, 3 ml/min (Alltech), solvent A: H2O+0.1% TFA, solvent B: MeCN/

Water 9/1+0.1% TFA, gradient: 5-95% B in 7 mins. The F-18 labeled product 4e was confirmed by co-injection with the cold F-19 fluoro standard on the Econsphere analytical HPLC.

Example 5 a) 4-Dimethylamino-2.3-difluoro-benzoic acid methyl ester (5a)

To a stirred solution of 4.28 g (22.5 mmol) 2.3.4-Trifluoro-benzoic acid methyl ester (Apollo) and 60.0 ml dimethylsulphoxid were added 2.23 g (27.0 mmol) dimethylamine hydrochloride and 6.54 g (47.3 mmol) potassium carbonate. The reaction mixture was stirred for 5 h at 55° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 5a was obtained in 69% yield (3.34 g, 15.5 mmol).

MS-ESI: 216 ($M^+$+1, 81).

| Elementary analysis: | C 55.81% | H 5.15% | F 17.66% | N 6.51% |
|---|---|---|---|---|
| Determined: | C 55.90% | H 5.19% | F 17.63% | N 6.48% | b) Trifluoro-methanesulfonate(2,3-difluoro-4-methoxycarbonyl-phenyl)-trimethyl-ammonium (5b)

To a stirred solution of 2.69 g (12.5 mmol) 5a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 5b was obtained in 82% yield (3.88 g, 10.3 mmol).

MS-ESI: 230 ($M^+$, 34),
Elementary analysis:

| Calculated: | C 38.00% | H 3.72% | F 25.04% | N 3.69% |
|---|---|---|---|---|
| Determined: | C 38.04% | H 3.74% | F 25.00% | N 3.67% | c) Trifluoro-methanesulfonate(4-carboxy-2.3-difluoro-phenyl)-trimethyl-ammonium; (5c)

A solution of 2.63 g (6.92 mmol) 5b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 5c was obtained in 89% yield (2.24 g; 6.16 mmol) and crude compound 5c was used for the next step without purification.

MS-ESI: 216 ($M^+$, 77),

Elementary analysis:

| Calculated: | C 36.17% | H 3.31% | F 26.01% | N 3.83% |
|---|---|---|---|---|
| Determined: | C 36.21% | H 3.32% | F 26.00% | N 3.81% | d) Synthesis of (4-Trimethylammonium-2.3-difluoro-benzoyl)-Val-Arg-Ser-Gly-$NH_2$-triflate salt (5d)

To a stirred solution of 73 mg (0.2 mmol) 5c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-Arg(Pbf)-Ser(OtBu)-Gly-$NH_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 73 mg (0.2 mmol) 5c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (5d) in 39.5% yield—19.6 mg (0.0256 mmol).

MS-ESI: 616 ($M^+$, 100)

e) Synthesis of (2.3-Difluoro-4-[$^{18}$F]-fluoro-benzoyl)-Val-Arg-Ser-Gly-$NH_2$ (5e)

To a Wheaton vial (5 ml) charged with Kryptofix 222 (5 mg), potassium carbonate (1 mg in 500 µl water) and MeCN (1.5 ml) the fluorine containing water (319 MBq, 35 µl) were added. The solvent was removed by heating at 120° C. for 10 mins under a stream of nitrogen. Anhydrous MeCN (1 ml) was added and evaporated as before. This step was repeated again. A solution of 5d (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 5e was confirmed by co-injection with the cold F-19 fluoro standard on the Econsphere analytical HPLC.

Example 6 a) 4-Dimethylamino-2.6-difluoro-benzoic acid methyl ester (6a)

To a stirred solution of 4.28 g (22.5 mmol) 2,4,6-Trifluoro-benzoic acid methyl ester (Apollo) and 60.0 ml dimethylsulphoxid were added 2.23 g (27.0 mmol) dimethylamine hydrochloride and 6.54 g (47.3 mmol) potassium carbonate. The reaction mixture was stirred for 5 h at 55° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 6a was obtained in 74% yield (3.59 g, 16.7 mmol).

MS-ESI: 216 ($M^+$+1, 69).

| Elementary analysis: | C 55.81% | H 5.15% | F 17.66% | N 6.51% |
|---|---|---|---|---|
| Determined: | C 55.89% | H 5.18% | F 17.64% | N 6.49% | b) Trifluoro-methanesulfonate(2.6-difluoro-4-methoxycarbonyl-phenyl)-trimethyl-ammonium (6b)

To a stirred solution of 2.69 g (12.5 mmol) 6a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 6b was obtained in 78% yield (3.70 g, 9.75 mmol).

MS-ESI: 230 ($M^+$, 55),
Elementary analysis:

| Calculated: | C | 38.00% H | 3.72% F | 25.04% N | 3.69% |
|---|---|---|---|---|---|
| Determined: | C | 38.05% H | 3.73% F | 25.01% N | 3.68% | c) Trifluoro-methanesulfonate(4-carboxy-2.6-difluoro-phenyl)-trimethyl-ammonium; (6c)

A solution of 2.63 g (6.92 mmol) 6b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 6c was obtained in 92% yield (2.38 g; 6.37 mmol) and crude compound 6c was used for the next step without purification.

MS-ESI: 216 ($M^+$, 70),
Elementary analysis:

| Calculated: | C | 36.17% H | 3.31% F | 26.01% N | 3.83% |
|---|---|---|---|---|---|
| Determined: | C | 36.20% H | 3.33% F | 25.99% N | 3.82% | d) Synthesis of (4-Trimethylammonium-2.6-difluoro-benzoyl)-Gly-Pro-Phe-Val-$NH_2$-triflate salt (6d)

To a stirred solution of 73 mg (0.2 mmol) 6c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Gly-Pro-Phe-Val-$NH_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 73 mg (0.2 mmol) 6c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water: acetonitril gradient and 0.1% trifluoro acetic acid as co-solvent to obtain the desired product (6d) in 19.6% yield—9.75 mg (0.0127 mmol).

MS-ESI: 616 ($M^+$, 100)

e) Synthesis of (2.6-Difluoro-4-[$^{18}$F]-fluoro-benzoyl)-Gly-Pro-Phe-Val-$NH_2$ (6e)

To a Wheaton vial (5 ml) charged with Kryptofix 222 (5 mg), potassium carbonate (1 mg in 500 μl water) and MeCN (1.5 ml) the fluorine containing water (320 MBq, 37 μl) were added. The solvent was removed by heating at 120° C. for 10 mins under a stream of nitrogen. Anhydrous MeCN (1 ml) was added and evaporated as before. This step was repeated again. A solution of 6d (2 mg) in anhydrous DMSO (300 μl) was added. After heating at 90° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 6e was confirmed by co-injection with the cold F-19 fluoro standard on the Econsphere analytical HPLC.

Example 7 a) 2-Bromo-4-dimethylamino-benzoic acid methyl ester (7a)

To a stirred solution of 5.24 g (22.5 mmol) 2-Bromo-4-fluoro-benzoic acid methyl ester (Rarechemicals) and 60.0 ml dimethylsulphoxid were added 2.23 g (27.0 mmol) dimethylamine hydrochloride and 6.54 g (47.3 mmol) potassium carbonate. The reaction mixture was stirred for 11 h at 70° C. in an autoclave and was concentrated with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 7a was obtained in 70% yield (4.08 g, 15.8 mmol).

MS-ESI: 258/560 ($M^+$+1, 88/83).

| Elementary analysis: | C | 46.53% | H | 4.69% | N | 5.43% |
|---|---|---|---|---|---|---|
| Determined: | C | 46.60% | H | 4.71% | N | 5.42% | b) Trifluoro-methanesulfonate(3-bromo-4-methoxy-carbonyl-phenyl)-trimethyl-ammonium (7b)

To a stirred solution of 2.69 g (12.5 mmol) 7a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 7b was obtained in 69% yield (3.66 g, 8.63 mmol).

MS-ESI: 273/275 ($M^+$+1, 78/72),

Elementary analysis:

| Calculated: | C | 34.14% | H | 3.58% | F | 13.50% | N | 3.32% |
|---|---|---|---|---|---|---|---|---|
| Determined: | C | 34.17% | H | 3.59% | F | 13.47% | N | 3.31% | c) Trifluoro-methanesulfonate(3-bromo-4-carboxy-phenyl)-trimethyl-ammonium; (7c)

A solution of 2.92 g (6.92 mmol) 7b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 7c was obtained in 87% yield (2.46 g; 6.02 mmol) and crude compound 7c was used for the next step without purification.

MS-ESI: 258/260 ($M^+$, 64/59),

Elementary analysis:

| Calculated: | C | 32.37% | H | 3.21% | F | 13.96% | N | 3.43% |
|---|---|---|---|---|---|---|---|---|
| Determined: | C | 32.41% | H | 3.22% | F | 13.94% | N | 3.42% | d) Synthesis of (4-Trimethylammonium-2-bromo-benzoyl)-Gly-Phe-Ile-Gly-$NH_2$-triflate salt (7d)

To a stirred solution of 81.6 mg (0.2 mmol) 7c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Gly-Phe-Ile-Gly-NH2 (loading 0.68 mmol/g) which was prepared by standard protocol. The mixture was shaken intensively for 4 h. The mixture was filtered and washed with dimethylformamide. The coupling step was repeated. Thus, to a stirred solution of 81.6 mg (0.2 mmol) 7c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (7d) in 24.6% yield—12.5 mg (0.016 mmol).

MS-ESI: 633/635 ($M^+$, 100/88)

e) Synthesis of [$^{18}$F]-(2-Bromo-4-fluoro-benzoyl)-Gly-Phe-Ile-Gly-$NH_2$ (7e)

To a Wheaton vial (5 ml) charged with Kryptofix 222 (5 mg), potassium carbonate (1 mg in 500 µl water) and MeCN (1.5 ml) the fluorine containing water (336 MBq, 35 µl) were added. The solvent was removed by heating at 120° C. for 10 mins under a stream of nitrogen. Anhydrous MeCN (1 ml) was added and evaporated as before. This step was repeated again. A solution of 7d (2 mg) in anhydrous DMSO (300 µl) was added. After heating at 90° C. for 12 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 mL/min (Alltech), solvent A: H2O+0.1% TFA, solvent B: MeCN/Water 9/1+0.1% TFA, gradient: 5-95% B in 7 mins. The F-18 labeled product 7e was confirmed by co-injection with the cold F-19 fluoro standard on the Econsphere analytical HPLC.

Example 8 a) 4-Dimethylamino-2-nitro-benzoic acid methyl ester (8a)

To a stirred solution of 4.48 g (22.5 mmol) 4-fluoro-2-nitro-benzoic acid methyl ester (J. Fluorine Chem.; 63; 1-2; (1993); 25-30) and 60.0 ml dimethylsulphoxid were added 2.23 g (27.0 mmol) dimethylamine hydrochloride and 6.54 g (47.3 mmol) potassium carbonate. The reaction mixture was stirred for 7 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 8a was obtained in 61% yield (3.08 g, 13.7 mmol).

MS-ESI: 225 ($M^+$+1, 71).

| Elementary analysis: | C | 53.57% | H | 5.39% | N | 12.49% |
|---|---|---|---|---|---|---|
| Determined: | C | 53.60% | H | 5.40% | N | 12.47% | b) Trifluoro-methanesulfonate(4-methoxycarbonyl-3-nitro-phenyl)-trimethylammonium (8b)

To a stirred solution of 2.80 g (12.5 mmol) 8a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 8b was obtained in 45% yield (2.18 g, 5.63 mmol).

MS-ESI: 239 (M$^+$, 89),
Elementary analysis:

| Calculated: | C | 37.12% | H | 3.89% | F | 14.68% | N | 7.21% |
|---|---|---|---|---|---|---|---|---|
| Determined: | C | 37.15% | H | 3.90% | F | 14.67% | N | 7.19% | c) Trifluoro-methanesulfonate(4-carboxy-3-nitrophenyl)-trimethyl-ammonium (8c)

A solution of 2.68 g (6.92 mmol) 8b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 96% yield (2.48 g; 6.64 mmol) and crude compound 8c was used for the next step without purification.

MS-ESI: 225 (M$^+$, 66),
Elementary analysis:

| Calculated: | C | 35.30% | H | 3.50% | F | 15.23% | N | 7.48% |
|---|---|---|---|---|---|---|---|---|
| Determined: | C | 35.31% | H | 3.50% | F | 15.23% | N | 7.47% | d) Synthesis of (4-Trimethylammonium-2-nitro-benzoyl)-Ser-Thr-Val-Gly-NH$_2$-triflate salt (8d)

To a stirred solution of 75.0 mg (0.2 mmol) 8c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Ser(Ot-Bu)-Thr(OtBu)-Val-Gly-NH2 (loading 0.68 mmol/g) which was prepared by standard protocol. The mixture was shaken intensively for 4 h. The mixture was filtered and washed with dimethylformamide. The coupling step was repeated. Thus, to a stirred solution of 75.0 mg (0.2 mmol) 8c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (8d) in 35% yield (16.3 mg, 0.0228 mmol).

MS-ESI: 569 (M$^+$, 100)

e) Synthesis of [$^{18}$F]-(2-Nitro-4-fluoro-benzoyl)-Ser-Thr-Val-Gly-NH$_2$ (8e)

To a Wheaton vial (5 ml) charged with Kryptofix 222 (5 mg), potassium carbonate (1 mg in 500 μl water) and MeCN (1.5 ml) the fluorine containing water (376 MBq, 35 μl) was added. The solvent was removed by heating at 120° C. for 10 mins under a stream of nitrogen. Anhydrous MeCN (1 ml) was added and evaporated as before. This step was repeated again. A solution of 8d (2 mg) in anhydrous DMSO (300 μl) was added. After heating at 80° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 8e was confirmed by co-injection with the cold F-19 fluoro standard on the Econsphere analytical HPLC.

Example 9 a) 2-Cyano-4-dimethylamino-benzoic acid methyl ester (9a)

To a stirred solution of 4.03 g (22.5 mmol) 2-Cyano-4-fluoro-benzoic acid methyl ester (J. Med. Chem., 35; 24; (1992); 4613-4627) and 60.0 ml dimethylsulphoxid were added 2.23 g (27.0 mmol) dimethylamine hydrochloride and 6.54 g (47.3 mmol) potassium carbonate. The reaction mixture was stirred for 9 h at 60° C. in an autoclave and was concentrated with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 9a was obtained in 85% yield (3.90 g, 19.1 mmol).

MS-ESI: 205 (M$^+$+1, 81).

| Elementary analysis: | C | 64.69% | H | 5.92% | N | 13.72% |
|---|---|---|---|---|---|---|
| Determined: | C | 64.72% | H | 5.95% | N | 13.70% | b) Trifluoro-methanesulfonate(3-cyano-4-methoxycarbonyl-phenyl)-trimethylammonium; (9b)

To a stirred solution of 2.55 g (12.5 mmol) 9a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 9b was obtained in 78% yield (3.59 g, 9.75 mmol).

MS-ESI: 219 (M$^+$+1, 79),
Elementary analysis:

| Calculated: | C | 42.39% | H | 4.10% | F | 15.47% | N | 7.61% |
|---|---|---|---|---|---|---|---|---|
| Determined: | C | 42.41% | H | 4.11% | F | 15.42% | N | 7.60% | c) Trifluoro-methanesulfonate(4-carboxy-3-cyano-phenyl)-trimethyl-ammonium; (9c)

A solution of 2.55 g (6.92 mmol) 9b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 86% yield (2.10 g; 5.95 mmol) and crude compound 9c was used for the next step without purification.
MS-ESI: 205 ($M^+$, 76),
Elementary analysis:

| Calculated: | C | 40.68% | H | 3.70% | F | 16.09% | N | 7.91% |
|---|---|---|---|---|---|---|---|---|
| Determined: | C | 40.69% | H | 3.71% | F | 16.07% | N | 7.90% | d) Synthesis of (4-Trimethylammonium-2-cyano-benzoyl)-Arg-Val-Gly-Phe-$NH_2$-triflate salt (9d)

To a stirred solution of 71.0 mg (0.2 mmol) 9c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Arg(Pbf)-Val-Gly-Phe-$NH_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 71.0 mg (0.2 mmol) 9c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water: acetonitril gradient and 0.1% trifluoro acetic acid as co-solvent to obtain the desired product (9d) obtained in 38% yield (20.0 mg, 0.0247 mmol).
MS-ESI: 665 ($M^+$, 100)

e) Synthesis of [$^{18}F$]-(2-Cyano-4-fluoro-benzoyl)-Arg-Val-Gly-Phe-$NH_2$ (9e)

To a Wheaton vial (5 ml) charged with Kryptofix 222 (5 mg), potassium carbonate (1 mg in 500 μl water) and MeCN (1.5 ml) the fluorine containing water (309 MBq, 35 μl) was added. The solvent was removed by heating at 120° C. for 10 mins under a stream of nitrogen. Anhydrous MeCN (1 ml) was added and evaporated as before. This step was repeated again. A solution of 9d (2 mg) in anhydrous DMSO (300 μl) was added. After heating at 80° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 9e was confirmed by co-injection with the non-radioactive F-19 fluoro standard on the Econsphere analytical HPLC.

Example 10 a) 4-Dimethylamino-3-methanesulfonyl-benzoic acid methyl ester (10a)

To a stirred solution of 5.23 g (22.5 mmol) 4-Fluoro-3-methanesulfonyl-benzoic acid methyl ester (J. Med. Chem.; 40; 13; 1997; 2017-2034) and 60.0 ml dimethylsulphoxid were added 2.23 g (27.0 mmol) dimethylamine hydrochloride and 6.54 g (47.3 mmol) potassium carbonate. The reaction mixture was stirred for 7 h at 60° C. in an autoclave and was concentrated with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 10a was obtained in 56% yield (3.24 g, 12.6 mmol).
MS-ESI: 258 ($M^+$+1, 81).

| Elementary analysis: | C | 51.35% | H | 5.88% | N | 5.44% |
|---|---|---|---|---|---|---|
| Determined: | C | 51.37% | H | 5.90% | N | 5.42% | b) Trifluoro-methanesulfonate(2-methanesulfonyl-4-methoxycarbonyl-phenyl)-trimethyl-ammonium, (10b)

To a stirred solution of 3.22 g (12.5 mmol) 10a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 10b was obtained in 58% yield (3.05 g, 7.25 mmol).
MS-ESI: 272 ($M^+$, 88),
Elementary analysis:

| Calculated: | C | 37.05% | H | 4.31% | F | 13.52% | N | 3.32% |
|---|---|---|---|---|---|---|---|---|
| Determined: | C | 37.09% | H | 4.33% | F | 13.50% | N | 3.31% | c) Trifluoro-methanesulfonate(4-carboxy-2-methane-sulfonyl-phenyl)-trimethylammonium; (10c)

A solution of 2.91 g (6.92 mmol) 10b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 96% yield (2.70 g; 6.64 mmol) and crude compound 10c was used for the next step without purification.

MS-ESI: 258 (M+, 93),
Elementary analysis:

| Calculated: | C | 35.38% | H | 3.96% | F | 13.99% | N | 3.44% |
|---|---|---|---|---|---|---|---|---|
| Determined: | C | 35.39% | H | 3.96% | F | 13.97% | N | 3.44% | d) Synthesis of (4-Trimethylammonium-3-methane-sulfonyl-benzoyl)-Gly-Phe-Val-Leu-NH$_2$-triflate salt (10d)

To a stirred solution of 81.0 mg (0.2 mmol) 10c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Gly-Phe-Val-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 81.0 mg (0.2 mmol) 10c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (10d) in 33% yield—17.7 mg (0.021 mmol).

MS-ESI: 675 (M+, 100)

e) Synthesis of [$^{18}$F]-(3-Methanesulfonyl-4-fluoro-benzoyl)-Gly-Phe-Val-Leu-NH$_2$ (10e)

To a Wheaton vial (5 ml) charged with Kryptofix 222 (5 mg), potassium carbonate (1 mg in 500 μl water) and MeCN (1.5 ml) the fluorine containing water (399 MBq, 35 μl) was added. The solvent was removed by heating at 120° C. for 10 mins under a stream of nitrogen. Anhydrous MeCN (1 ml) was added and evaporated as before. This step was repeated again. A solution of 10d (2 mg) in anhydrous DMSO (300 μl) was added. After heating at 80° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 10e was confirmed by co-injection with the non-radioactive F-19 fluoro standard on the Econsphere analytical HPLC.

Example 11 a) 4-Dimethylamino-3-nitro-benzoic acid methyl ester (11a)

To a stirred solution of 4.48 g (22.5 mmol) 4-Fluoro-3-nitro-benzoic acid methyl ester (Bioorg. Med. Chem.; 6; 8; 1998; 1185-1208) and 60.0 ml dimethylsulphoxid were added 2.23 g (27.0 mmol) dimethylamine hydrochloride and 6.54 g (47.3 mmol) potassium carbonate. The reaction mixture was stirred for 8 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 11a was obtained in 69% yield (3.48 g, 15.5 mmol).

MS-ESI: 225 (M++1, 74).

| Elementary analysis: | C | 53.57% | H | 5.39% | N | 12.49% |
|---|---|---|---|---|---|---|
| Determined: | C | 53.62% | H | 5.42% | N | 12.46% | b) Trifluoro-methanesulfonate(4-methoxycarbonyl-2-nitro-phenyl)-trimethylammonium (11b)

To a stirred solution of 2.80 g (12.5 mmol) 11a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 11b was obtained in 71% yield (3.44 g, 8.88 mmol).

MS-ESI: 239 (M+, 82),
Elementary analysis:

| Calculated: | C | 37.12% | H | 3.89% | F | 14.68% | N | 7.21% |
|---|---|---|---|---|---|---|---|---|
| Determined: | C | 37.14% | H | 3.91% | F | 14.67% | N | 7.20% | c) Trifluoro-methanesulfonate(4-carboxy-2-nitro-phenyl)-trimethyl-ammonium (11c)

A solution of 2.68 g (6.92 mmol) 11b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 93% yield (2.41 g; 6.44 mmol) and crude compound 11c was used for the next step without purification.

MS-ESI: 225 (M+, 66),
Elementary analysis:

| Calculated: | C | 35.30% | H | 3.50% | F | 15.23% | N | 7.48% |
|---|---|---|---|---|---|---|---|---|
| Determined: | C | 35.32% | H | 3.51% | F | 15.21% | N | 7.46% | d) Synthesis of (4-Trimethylammonium-3-nitro-benzoyl)-Thr-Val-Phe-Leu-NH$_2$-triflate salt (11d)

To a stirred solution of 75.0 mg (0.2 mmol) 11c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Thr(OtBu)-Val-Phe-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 75.0 mg (0.2 mmol) 11c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (11d) in 56% yield (30.1 mg, 0.0364 mmol).

MS-ESI: 686 (M$^+$, 100)

e) Synthesis of [$^{18}$F]-(3-Nitro-4-fluoro-benzoyl)-Thr-Val-Phe-Leu-NH$_2$ (11e)

To a Wheaton vial (5 ml) charged with Kryptofix 222 (5 mg), potassium carbonate (1 mg in 500 µl water) and MeCN (1.5 ml) the fluorine containing water (344 MBq, 35 µl) was added. The solvent was removed by heating at 120° C. for 10 mins under a stream of nitrogen. Anhydrous MeCN (1 ml) was added and evaporated as before. This step was repeated again. A solution of 11d (2 mg) in anhydrous DMSO (300 µl) was added. After heating at 65° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 11e was confirmed by co-injection with the non-radioactive F-19 fluoro standard on the Econsphere analytical HPLC.

Example 12 a) 4-Dimethylamino-3-trifluoromethyl-benzoic acid methyl ester (12a)

To a stirred solution of 4.48 g (22.5 mmol) 4-Fluoro-3-trifluoromethyl-benzoic acid methyl ester (Rarechem) and 60.0 ml dimethylsulphoxid were added 2.23 g (27.0 mmol) dimethylamine hydrochloride and 6.54 g (47.3 mmol) potassium carbonate. The reaction mixture was stirred for 8 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 12a was obtained in 72% yield (4.00 g, 16.2 mmol).

MS-ESI: 248 (M$^+$+1, 100).

| Elementary analysis: | C | 53.44% | H | 4.89% | F | 23.05% | N | 5.67% |
|---|---|---|---|---|---|---|---|---|
| Determined: | C | 53.48% | H | 4.90% | F | 23.03% | N | 5.65% | b) Trifluoro-methanesulfonate(4-methoxycarbonyl-2-trifluoromethyl-phenyl)-trimethyl-ammonium (12b)

To a stirred solution of 3.09 g (12.5 mmol) 12a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 12b was obtained in 69% yield (3.55 g, 8.63 mmol).

MS-ESI: 262 (M$^+$, 67),

Elementary analysis:

| Calculated: | C | 37.96% | H | 3.68% | F | 27.71% | N | 3.41% |
|---|---|---|---|---|---|---|---|---|
| Determined: | C | 38.00% | H | 3.62% | F | 27.68% | N | 3.40% | c) Trifluoro-methanesulfonate(4-carboxy-2-trifluoromethyl-phenyl)-trimethyl-ammonium (12c)

A solution of 2.84 g (6.92 mmol) 12b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 89% yield (2.45 g; 6.16 mmol) and crude compound 12c was used for the next step without purification.

MS-ESI: 248 (M$^+$, 100),

Elementary analysis:

| Calculated: | C | 36.28% | H | 3.30% | F | 28.69% | N | 3.53% |
|---|---|---|---|---|---|---|---|---|
| Determined: | C | 36.29% | H | 3.31% | F | 28.67% | N | 3.51% | d) Synthesis of (4-Trimethylammonium-3-trifluormethyl-benzoyl)-Val-βAla-Phe-Gly-NH$_2$-triflate salt (12d)

To a stirred solution of 79.4 mg (0.2 mmol) 12c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Phe-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 79.4 mg (0.2 mmol) 12c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water: acetonitril gradient and 0.1% trifluoro acetic acid as co-solvent to obtain the desired product (12d) in 21.5% yield—10.9 mg (0.014 mmol).

MS-ESI: 636 ($M^+$, 100)

e) Synthesis of [$^{18}$F]-(3-Trifluormethyl-4-fluoro-benzoyl)-Val-βAla-Phe-Gly-$NH_2$ (12e)

To a Wheaton vial (5 ml) charged with Kryptofix 222 (5 mg), potassium carbonate (1 mg in 500 µl water) and MeCN (1.5 ml) the fluorine containing water (356 MBq, 35 µl) was added. The solvent was removed by heating at 120° C. for 10 mins under a stream of nitrogen. Anhydrous MeCN (1 ml) was added and evaporated as before. The step was repeated again. A solution of 12d (2 mg) in anhydrous DMSO (300 µl) was added. After heating at 50° C. for 18 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: $H_2O$+0.1% TFA, solvent B: MeCN/Water 9/1+0.1% TFA, gradient: 5-95% B in 7 mins. The F-18 labeled product 12e was confirmed by co-injection with the non-radioactive F-19 fluoro standard on the Econsphere analytical HPLC.

Example 13 a) 4-Dimethylamino-2-trifluoromethyl-benzoic acid methyl ester (13a)

To a stirred solution of 4.48 g (22.5 mmol) 4-Fluoro-2-trifluoromethyl-benzoic acid methyl ester (Rarechem) and 60.0 ml dimethylsulphoxid were added 2.23 g (27.0 mmol) dimethylamine hydrochloride and 6.54 g (47.3 mmol) potassium carbonate. The reaction mixture was stirred for 8 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 13a was obtained in 72% yield (4.00 g, 16.2 mmol).

MS-ESI: 248 ($M^+$+1, 78).

| Elementary analysis: | C | 53.44% | H | 4.89% | F | 23.05% | N | 5.67% |
|---|---|---|---|---|---|---|---|---|
| Determined: | C | 53.46% | H | 4.91% | F | 23.04% | N | 5.64% | b) Trifluoro-methanesulfonate(4-methoxycarbonyl-3-trifluoromethyl-phenyl)-trimethyl-ammonium (13b)

To a stirred solution of 3.09 g (12.5 mmol) 13a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 13b was obtained in 69% yield (3.55 g, 8.63 mmol).

MS-ESI: 262 ($M^+$, 87),
Elementary analysis:

| Calculated: | C | 37.96% | H | 3.68% | F | 27.71% | N | 3.41% |
|---|---|---|---|---|---|---|---|---|
| Determined: | C | 38.01% | H | 3.63% | F | 27.69% | N | 3.41% | c) Trifluoro-methanesulfonate(4-carboxy-3-trifluoromethyl-phenyl)-trimethylammonium (13c)

A solution of 2.84 g (6.92 mmol) 13b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 89% yield (2.45 g; 6.16 mmol) and crude compound 13c was used for the next step without purification.

MS-ESI: 248 ($M^+$, 59),
Elementary analysis:

| Calculated: | C | 36.28% | H | 3.30% | F | 28.69% | N | 3.53% |
|---|---|---|---|---|---|---|---|---|
| Determined: | C | 36.30% | H | 3.32% | F | 28.67% | N | 3.52% | d) Synthesis of (4-Trimethylammonium-2-trifluormethyl-benzoyl)-Val-βAla-His(π-Me)-Gly-$NH_2$-triflate salt (13d)

To a stirred solution of 79.4 mg (0.2 mmol) 13c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-His(π-Me)-Gly-$NH_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 79.4 mg (0.2 mmol) 13c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (13d).

MS-ESI: 640 ($M^+$, 100)

e) Synthesis of ([$^{18}$F]-4-Fluoro-2-trifluormethyl-benzoyl)-Val-βAla-His(π-Me)-Gly-NH$_2$ (13e)

To a Wheaton vial (5 ml) charged with Kryptofix 222 (5 mg), potassium carbonate (1 mg in 500 µl water) and MeCN (1.5 ml) the fluorine containing water (321 MBq, 35 µl) was added. The solvent was removed by heating at 120° C. for 10 mins under a stream of nitrogen. Anhydrous MeCN (1 ml) was added and evaporated as before. This step was repeated again. A solution of 13d (2 mg) in anhydrous DMSO (300 µl) was added. After heating at 75° C. for 20 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 13e was confirmed by co-injection with the non-radioactive F-19 fluoro standard on the Econsphere analytical HPLC.

Example 14 a) 4-Fluoro-3-trifluoromethoxy-benzoic acid methyl ester (14a)

To a stirred suspension of 21.2 g (96.9 mmol) 4-Fluoro-3-trifluoromethoxy-benzoic acid (JRD-Fluoro) and 161 ml methanol were added 30.4 g (387.6 mmol) acetyl chloride drop wisely at 0° C. The reaction mixture was stirred over night, filtered and concentrated. The residue was diluted with dichloromethane, washed with diluted sodium hydrogen carbonate solution, dried with sodium sulphate and concentrated. The residue was purified by column chromatography (hexane:ethylacetate). The desired product 14a was obtained in 75% yield (17.3 g; 72.7 mmol)

MS-ESI: 239 (M$^+$+1, 66),
Elementary analysis:

| | | | | | | | |
|---|---|---|---|---|---|---|---|
| Calculated: | C | 45.39% | H | 2.54% | F | 31.91% | |
| Determined: | C | 45.41% | H | 2.52% | F | 31.89% | | b) 4-Dimethylamino-3-trifluoromethoxy-benzoic acid methyl ester (14b)

To a stirred solution of 5.36 g (22.5 mmol) 14a and 60.0 ml dimethylsulphoxid were added 2.23 g (27.0 mmol) dimethylamine hydrochloride and 6.54 g (47.3 mmol) potassium carbonate. The reaction mixture was stirred for 8 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 14b was obtained in 69% yield (4.09 g, 15.5 mmol).

MS-ESI: 264 (M$^+$+1, 100).

| | | | | | | | |
|---|---|---|---|---|---|---|---|
| Elementary analysis: | C | 50.20% | H | 4.60% | F | 21.65% | N 5.32% |
| Determined: | C | 50.22% | H | 4.61% | F | 21.64% | N 5.31% | c) Trifluoro-methanesulfonate(4-methoxycarbonyl-2-trifluoromethoxy-phenyl)-trimethyl-ammonium (14c)

To a stirred solution of 3.29 g (12.5 mmol) 14b and 50 ml dichloroethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 14c was obtained in 57% yield (3.06 g, 7.13 mmol).

MS-ESI: 278 (M$^+$, 82),
Elementary analysis:

| | | | | | | | |
|---|---|---|---|---|---|---|---|
| Calculated: | C | 36.54% | H | 3.54% | F | 26.68% | N 3.28% |
| Determined: | C | 36.56% | H | 3.56% | F | 27.67% | N 3.26% | d) Trifluoro-methanesulfonate(4-carboxy-2-trifluoromethoxy-phenyl)-trimethylammonium (14d)

A solution of 2.95 g (6.92 mmol) 14c, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 94% yield (2.68 g; 6.50 mmol) and crude compound 14d was used for the next step without purification.

MS-ESI: 264 (M$^+$, 100),
Elementary analysis:

| | | | | | | | |
|---|---|---|---|---|---|---|---|
| Calculated: | C | 34.87% | H | 3.17% | F | 27.58% | N 3.39% |
| Determined: | C | 34.89% | H | 3.19% | F | 27.56% | N 3.38% | e) Synthesis of (4-Trimethylammonium-3-trifluoromethoxy-benzoyl)-Val-βAla-Phe-Gly-NH$_2$-triflate salt (14e)

To a stirred solution of 82.6 mg (0.2 mmol) 14d in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Phe-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 82.6 mg (0.2 mmol) 14d in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether.

The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (14e) in 28% yield—14.6 mg (0.0182 mmol).

MS-ESI: 653 (M$^+$, 100)

f) Synthesis of ([$^{18}$F]-4-Fluoro-3-trifluoromethoxy-benzoyl)-Val-βAla-Phe-Gly-NH$_2$ (14f)

To a Wheaton vial (5 ml) charged with Kryptofix 222 (5 mg), potassium carbonate (1 mg in 500 µl water) and MeCN (1.5 ml) the fluorine containing water (321 MBq, 35 µl) was added. The solvent was removed by heating at 120° C. for 10 mins under a stream of nitrogen. Anhydrous MeCN (1 ml) was added and evaporated as before. This step was repeated again. A solution of 14e (2 mg) in anhydrous DMSO (300 µl) was added. After heating at 65° C. for 10 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econsphere C18, 53×7 mm, 3µ, 3 ml/min (Alltech), solvent A: H$_2$O+0.1% TFA, solvent B: MeCN/Water 9/1+0.1% TFA, gradient: 5-95% B in 7 mins. The F-18 labeled product 14f was confirmed by co-injection with the non-radioactive F-19 fluoro standard on the Econsphere analytical HPLC.

Example 15 a) 5-Dimethylamino-2-trifluoromethyl-benzoic acid methyl ester (15a)

To a stirred solution of 4.48 g (22.5 mmol) 5-Fluoro-2-trifluoromethyl-benzoic acid methyl ester (Rarechem) and 60.0 ml dimethylsulphoxid were added 2.23 g (27.0 mmol) dimethylamine hydrochloride and 6.54 g (47.3 mmol) potassium carbonate. The reaction mixture was stirred for 8 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 15a was obtained in 72% yield (4.00 g, 16.2 mmol).

MS-ESI: 248 (M$^+$+1, 100).

| Elementary analysis: | C | 53.44% | H | 4.89% | F | 23.05% | N | 5.67% |
|---|---|---|---|---|---|---|---|---|
| Determined: | C | 53.45% | H | 4.90% | F | 23.05% | N | 5.65% | b) Trifluoro-methanesulfonate(3-methoxycarbonyl-4-trifluoromethyl-phenyl)-trimethyl-ammonium (15b)

To a stirred solution of 3.09 g (12.5 mmol) 15a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 15b was obtained in 69% yield (3.55 g, 8.63 mmol).

MS-ESI: 262 (M$^+$, 100),
Elementary analysis:

| Calculated: | C | 37.96% | H | 3.68% | F | 27.71% | N | 3.41% |
|---|---|---|---|---|---|---|---|---|
| Determined: | C | 38.00% | H | 3.69% | F | 27.68% | N | 3.40% | c) Trifluoro-methanesulfonate(3-carboxy-4-trifluoromethyl-phenyl)-trimethyl-ammonium (15c)

A solution of 2.84 g (6.92 mmol) 15b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 89% yield (2.45 g; 6.16 mmol) and crude compound 15c was used for the next step without purification.

MS-ESI: 248 (M$^+$, 45),
Elementary analysis:

| Calculated: | C | 36.28% | H | 3.30% | F | 28.69% | N | 3.53% |
|---|---|---|---|---|---|---|---|---|
| Determined: | C | 36.31% | H | 3.31% | F | 28.68% | N | 3.51% | d) Synthesis of (5-Trimethylammonium-2-trifluormethyl-benzoyl)-Val-βAla-Trp-Gly-NH$_2$-triflate salt (15d)

To a stirred solution of 79.4 mg (0.2 mmol) 15c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Trp(N-Boc)-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 79.4 mg (0.2 mmol) 15c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (15d) in 26% yield—13.9 mg (0.017 mmol).

MS-ESI: 675 (M$^+$, 100)

e) Synthesis of ([$^{18}$F]-5-Fluoro-2-trifluormethyl-benzoyl)-Val-βAla-Trp-Gly-NH$_2$ (15e)

To a Wheaton vial (5 ml) charged with Kryptofix 222 (5 mg), potassium carbonate (1 mg in 500 µl water) and MeCN (1.5 ml) the fluorine containing water (316 MBq, 33 µl) was added. The solvent was removed by heating at 120° C. for 10 mins under a stream of nitrogen. Anhydrous MeCN (1 ml) was added and evaporated as before. This step was repeated again. A solution of 15d (2 mg) in anhydrous DMSO (300 µl) was added. After heating at 75° C. for 18 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 15e was confirmed by co-injection with the non-radioactive F-19 fluoro standard on the Econsphere analytical HPLC.

Example 16 a) 2-Bromo-5-dimethylamino-benzoic acid methyl ester (16a)

To a stirred solution of 5.24 g (22.5 mmol) 2-Bromo-5-fluoro-benzoic acid methyl ester (Rarechemicals) and 60.0 ml dimethylsulphoxid were added 2.23 g (27.0 mmol) dimethylamine hydrochloride and 6.54 g (47.3 mmol) potassium carbonate. The reaction mixture was stirred for 11 h at 70° C. in an autoclave and was concentrated with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 16a was obtained in 70% yield (4.08 g, 15.8 mmol).

MS-ESI: 258/560 (M$^+$+1, 90/81).

| Elementary analysis: | C | 46.53% H | 4.69% N | 5.43% |
|---|---|---|---|---|
| Determined: | C | 46.59% H | 4.72% N | 5.41% | b) Trifluoro-methanesulfonate(4-bromo-3-methoxy-carbonyl-phenyl)-trimethylammonium (16b)

To a stirred solution of 2.69 g (12.5 mmol) 16a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 16b was obtained in 79% yield (4.17 g, 9.88 mmol).

MS-ESI: 272/274 (M$^+$, 89/80),
Elementary analysis:

| Calculated: | C | 34.14% H | 3.58% F | 13.50% N | 3.32% |
|---|---|---|---|---|---|
| Determined: | C | 34.16% H | 3.60% F | 13.48% N | 3.30% | c) Trifluoro-methanesulfonate(4-bromo-3-carboxy-phenyl)-trimethyl-ammonium (16c)

A solution of 2.92 g (6.92 mmol) 16b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 16c was obtained in 87% yield (2.46 g; 6.02 mmol) and crude compound 16c was used for the next step without purification.

MS-ESI: 258/260 (M$^+$, 78/69),
Elementary analysis:

| Calculated: | C | 32.37% H | 3.21% F | 13.96% N | 3.43% |
|---|---|---|---|---|---|
| Determined: | C | 32.40% H | 3.22% F | 13.95% N | 3.41% | d) Synthesis of (5-Trimethylammonium-2-bromo-benzoyl)-Val-βAla-Arg-Gly-NH$_2$-triflate salt (16d)

To a stirred solution of 81.4 mg (0.2 mmol) 16c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Arg(Pbf)-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 81.4 mg (0.2 mmol) 16c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (16d) in 52% yield (27.2 mg, 0.0338 mmol).

MS-ESI: 655/657 (M$^+$, 100/82)

e) Synthesis of [$^{18}$F]-(2-Bromo-5-fluoro-benzoyl)-Val-βAla-Arg-Gly-NH$_2$ (16e)

To a Wheaton vial (5 ml) charged with Kryptofix 222 (5 mg), potassium carbonate (1 mg in 500 µl water) and MeCN (1.5 ml) the fluorine containing water (334 MBq, 35 µl) was added. The solvent was removed by heating at 120° C. for 10 mins under a stream of nitrogen. Anhydrous MeCN (1 ml) was added and evaporated as before. This step was repeated again. A solution of 16d (2 mg) in anhydrous DMSO (300 µl) was added. After heating at 90° C. for 20 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 16e was confirmed by co-injection with the non-radioactive F-19 fluoro standard on the Econsphere analytical HPLC.

Example 17 a) 5-Dimethylamino-2-methanesulfonyl-benzoic acid methyl ester (17a)

To a stirred solution of 5.23 g (22.5 mmol) 5-Fluoro-2-methanesulfonyl-benzoic acid methyl ester (J. Med. Chem.; 40; 13; 1997; 2017-2034) and 60.0 ml dimethylsulphoxid were added 2.23 g (27.0 mmol) dimethylamine hydrochloride and 6.54 g (47.3 mmol) potassium carbonate. The reaction mixture was stirred for 7 h at 60° C. in an autoclave and was concentrated with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 17a was obtained in 56% yield (3.24 g, 12.6 mmol).

MS-ESI: 257 ($M^+$+1, 75).

| Elementary analysis: | C | 51.35% | H | 5.88% | N | 5.44% |
|---|---|---|---|---|---|---|
| Determined: | C | 51.37% | H | 5.88% | N | 5.42% | b) Trifluoro-methanesulfonate(4-methanesulfonyl-3-methoxycarbonyl-phenyl)-trimethyl-ammonium (17b)

To a stirred solution of 3.22 g (12.5 mmol) 17a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 17b was obtained in 58% yield (3.05 g, 7.25 mmol).

MS-ESI: 272 ($M^+$, 69),
Elementary analysis:

| Calculated: | C | 37.05% | H | 4.31% | F | 13.52% | N | 3.32% |
|---|---|---|---|---|---|---|---|---|
| Determined: | C | 37.07% | H | 4.33% | F | 13.48% | N | 3.31% | c) Trifluoro-methanesulfonate(3-carboxy-4-methane-sulfonyl-phenyl)-trimethyl-ammonium; (17c)

A solution of 2.91 g (6.92 mmol) 17b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 96% yield (2.70 g; 6.64 mmol) and crude compound 17c was used for the next step without purification.

MS-ESI: 258 ($M^+$+1, 69),
Elementary analysis:

| Calculated: | C | 35.38% | H | 3.96% | F | 13.99% | N | 3.44% |
|---|---|---|---|---|---|---|---|---|
| Determined: | C | 35.40% | H | 3.97% | F | 13.96% | N | 3.43% | d) Synthesis of (5-Trimethylammonium-2-methane-sulfonyl-benzoyl)-Val-βAla-Arg-Gly-$NH_2$-triflate salt (17d)

To a stirred solution of 81.0 mg (0.2 mmol) 17c in 1.5 ml dichloromethane and 0.25 ml dimethylformamid was added 65 mg (0.5 mmol) diisopropylethylamin and 0.031 ml (0.2 mmol) diisopropylcarbodiimide. The solution was added to 0.065 mmol Rink-resin-bound H-Val-βAla-Arg(Pbf)-Gly-$NH_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 81.0 mg (0.2 mmol) 17c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (17d) in 33% yield (17.2 g, 0.0214 mmol).

MS-ESI: 656 ($M^+$, 100)

e) Synthesis of [$^{18}$F]-(2-Methanesulfonyl-5-fluoro-benzoyl)-Val-βAla-Arg-Gly-$NH_2$ (17e)

To a Wheaton vial (5 ml) charged with Kryptofix 222 (5 mg), potassium carbonate (1 mg in 500 µl water) and MeCN (1.5 ml) the fluorine containing water (366 MBq, 35 µl) was added. The solvent was removed by heating at 120° C. for 10 mins under a stream of nitrogen. Anhydrous MeCN (1 ml) was added and evaporated as before. This step was repeated again. A solution of 17d (2 mg) in anhydrous DMSO (300 µl) was added. After heating at 70° C. for 18 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 17e was confirmed by co-injection with the non-radioactive F-19 fluoro standard on the Econsphere analytical HPLC.

Example 18 a) 2-Chloro-5-dimethylamino-benzoic acid methyl ester (18a)

To a stirred solution of 4.00 g (20.6 mmol) 2-Chloro-5-fluoro-benzoic acid methyl ester (Rarechem) and 60 ml dimethylsulphoxid were added 2.03 g (24.7 mmol) dimethylamine hydrochloride and 5.97 g (43.2 mmol) potassium carbonate. The reaction mixture was stirred over night and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude product 18a was obtained in 99% yield (4.46 g, 20.9 mmol) and was used for the next step without purification.

MS-ESI: 213/215 ($M^+$+1, 78/53).

Elementary analysis:

| Calculated: | C | 56.21% | H | 5.66% | N | 6.56% |
|---|---|---|---|---|---|---|
| Determined: | C | 56.29% | H | 5.68% | N | 6.55% | b) Synthesis of (4-chloro-3-methoxycarbonyl-phenyl)-trimethyl-ammonium trifluoro-methane-sulfonate (18b)

To a stirred solution of 4.49 g (21.0 mmol) 18a and 75 ml dichloromethane were added 34.5 g (21.0 mmol) methyltriflate (Aldrich) drop wisely. The reaction mixture was stirred for 2 days at room temperature. 17 g (10 mmol) methyltriflate (Aldrich) were added and the reaction mixture was stirred at 40° C. for 20 h. The reaction mixture was cooled to 20° C. and diethylether was added. The desired compound precipitates and the solvent was decanted and the solid was washed extensively (ten times) with large amounts of diethylether. The solid was dried by use of oil pump vacuum and purified by (C-18) RP-column chromatography (acetonitril/water-gradient 1:99 to 80:20). The desired compound 18b was obtained in 86% yield (6.78 g, 18.1 mmol).

MS-ESI: 227/229 ($M^+$, 78/21),

Elementary analysis:

| Calculated: | C | 38.15% | H | 4.00% | F | 15.09% | N | 3.71% |
|---|---|---|---|---|---|---|---|---|
| Determined: | C | 38.17% | H | 4.03% | F | 15.05% | N | 3.70% | c) Synthesis of (3-carboxy-4-chloro-phenyl)-trimethyl-ammonium trifluoro-methanesulfonate (18c)

A solution of 0.5 g (1.32 mmol) 18b, 12 ml dest. water and 12 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 18c was obtained in 98% yield (471 mg, 1.3 mmol) and crude compound 18c was used for the next step without purification.

MS-ESI: 214/216 ($M^+$, 89/51),

Elementary analysis:

| Calculated: | C | 36.32% | H | 3.60% | F | 15.67% | N | 3.85% |
|---|---|---|---|---|---|---|---|---|
| Determined: | C | 36.37% | H | 3.63% | F | 15.61% | N | 3.83% | d) Synthesis of (5-Trimethylammonium-2-chloro-benzoyl)-Val-βAla-Arg-Gly-$NH_2$-triflate salt (18d)

To a stirred solution of 73.0 mg (0.2 mmol) 18c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Arg(Pbf)-Gly-$NH_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 73.0 mg (0.2 mmol) 18c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (18d) in 31% yield—15.3 mg (0.020 mmol).

MS-ESI: 611/613 ($M^+$+1, 100/41).

e) Synthesis of [$^{18}$F]-(5-Fluoro-2-chloro-benzoyl)-Val-βAla-Arg-Gly-$NH_2$ (18e)

To a Wheaton vial (5 ml) charged with Kryptofix 222 (5 mg), potassium carbonate (1 mg in 500 μl water) and MeCN (1.5 ml) the fluorine containing water (384 MBq, 35 μl) was added. The solvent was removed by heating at 120° C. for 10 mins under a stream of nitrogen. Anhydrous MeCN (1 ml) was added and evaporated as before. This step was repeated again. A solution of 18d (2 mg) in anhydrous DMSO (300 μl) was added. After heating at 80° C. for 20 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 18e was confirmed by co-injection with the non-radioactive F-19 fluoro standard on the Econsphere analytical HPLC.

Example 19 a) 5-Dimethylamino-2-nitro-benzoic acid methyl ester (19a)

To a stirred solution of 4.48 g (22.5 mmol) 5-Fluoro-5-nitro-benzoic acid methyl ester (Rarechem) and 60.0 ml dimethylsulphoxid were added 2.23 g (27.0 mmol) dimethylamine hydrochloride and 6.54 g (47.3 mmol) potassium carbonate. The reaction mixture was stirred for 8 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 19a was obtained in 69% yield (3.49 g, 15.5 mmol).

MS-ESI: 225 (M$^+$+1, 52).

| Elementary analysis: | C | 53.57% | H | 5.39% | N | 12.49% |
|---|---|---|---|---|---|---|
| Determined: | C | 53.61% | H | 5.40% | N | 12.47% | b) Trifluoro-methanesulfonate(3-methoxycarbonyl-4-nitro-phenyl)-trimethylammonium (19b)

To a stirred solution of 2.80 g (12.5 mmol) 19a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 19b was obtained in 71% yield (3.44 g, 8.88 mmol).

MS-ESI: 239 (M$^+$, 69),
Elementary analysis:

| Calculated: | C | 37.12% | H | 3.89% | F | 14.68% | N | 7.21% |
|---|---|---|---|---|---|---|---|---|
| Determined: | C | 37.14% | H | 3.91% | F | 14.66% | N | 7.20% | c) Trifluoro-methanesulfonate(3-carboxy-4-nitro-phenyl)-trimethyl-ammonium (19c)

A solution of 2.46 g (6.92 mmol) 19b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 93% yield (2.41 g; 6.44 mmol) and crude compound 19c was used for the next step without purification.

MS-ESI: 225 (M$^+$, 96),
Elementary analysis:

| Calculated: | C | 35.30% | H | 3.50% | F | 15.23% | N | 7.48% |
|---|---|---|---|---|---|---|---|---|
| Determined: | C | 35.34% | H | 3.52% | F | 15.23% | N | 7.47% | d) Synthesis of (2-Nitro-5-trimethylammonium-benzoyl)-Val-βAla-Phe-Gly-NH$_2$-triflate salt (19d)

To a stirred solution of 75.0 mg (0.2 mmol) 19c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Phe-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 75.0 mg (0.2 mmol) 19c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent 19d was obtained in 42% yield (20.8 mg, 0.0273 mmol).

MS-ESI: 614 (M$^+$, 100).

e) Synthesis of [$^{18}$F]-(5-Fluoro-2-nitro-benzoyl)-Val-βAla-Phe-Gly-NH$_2$ (19e)

To a Wheaton vial (5 ml) charged with Kryptofix 222 (5 mg), potassium carbonate (1 mg in 500 μl water) and MeCN (1.5 ml) the fluorine containing water (311 MBq, 35 μl) was added. The solvent was removed by heating at 120° C. for 10 mins under a stream of nitrogen. Anhydrous MeCN (1 ml) was added and evaporated as before. This step was repeated again. A solution of 19d (2 mg) in anhydrous DMSO (300 μl) was added. After heating at 70° C. for 12 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 19e was confirmed by co-injection with the non-radioactive F-19 fluoro standard on the Econsphere analytical HPLC.

Example 20 a) 2-Chloro-4-dimethylamino-5-methanesulfonyl-benzoic acid methyl ester (20a)

To a stirred solution of 6.00 g (22.5 mmol) 2-Chloro-4-fluoro-5-methanesulfonyl-benzoic acid methyl ester (J. Med. Chem.; 40; 13; 1997; 2017-2034) and 60.0 ml dimethylsulphoxid were added 2.23 g (27.0 mmol) dimethylamine hydrochloride and 6.54 g (47.3 mmol) potassium carbonate. The reaction mixture was stirred for 15 h at 65° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 20a was obtained in 59% yield (3.87 g, 13.3 mmol).

MS-ESI: 292/294 (M$^+$+1, 69/23).

| Elementary analysis: | C | 45.29% | H | 4.84% | N | 4.80% |
|---|---|---|---|---|---|---|
| Determined: | C | 45.31% | H | 4.86% | N | 4.78% | b) Trifluoro-methanesulfonate(5-chloro-2-methane-sulfonyl-4-methoxycarbonyl-phenyl)-trimethyl-ammonium (20b)

To a stirred solution of 3.65 g (12.5 mmol) 20a and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 20b was obtained in 58% yield (3.31 g, 7.25 mmol).

MS-ESI: 307 (M$^+$, 100),
Elementary analysis:

| Calculated: | C | 34.25% | H | 3.76% | F | 12.50% | N | 3.07% |
|---|---|---|---|---|---|---|---|---|
| Determined: | C | 34.24% | H | 3.80% | F | 12.47% | N | 3.06% | c) Trifluoro-methanesulfonate(4-carboxy-5-chloro-2-methanesulfonyl-phenyl)-trimethylammonium (20c)

A solution of 3.16 g (6.92 mmol) 20b, 60 ml dest. water and 60 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 83% yield (2.53 g; 5.74 mmol) and crude compound 20c was used for the next step without purification.

MS-ESI: 293 (M$^+$, 48),
Elementary analysis:

| Calculated: | C | 32.62% | H | 3.42% | F | 12.90% | N | 3.17% |
|---|---|---|---|---|---|---|---|---|
| Determined: | C | 32.64% | H | 3.44% | F | 12.89% | N | 3.16% | d) Synthesis of (2-Chloro-5-methanesulfonyl-4-trimethylammonium-benzoyl)-Val-βAla-Phe-Gly-NH$_2$-triflate salt (20d)

To a stirred solution of 88.4 mg (0.2 mmol) 20c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Phe-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 88.4 mg (0.2 mmol) 20c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound H-Val-βAla-Phe-Gly-NH$_2$ and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent. The desired compound 20d was obtained in 43% yield (23.2 mg, 280 mmol).

MS-ESI: 681/683 (M$^+$, 100).

e) Synthesis of [$^{18}$F]-(2-Chloro-4-fluoro-5-methanesulfonyl-benzoyl)-Val-βAla-Phe-Gly-NH$_2$ (20e)

To a Wheaton vial (5 ml) charged with Kryptofix 222 (5 mg), potassium carbonate (1 mg in 500 μl water) and MeCN (1.5 ml) the fluorine containing water (322 MBq, 35 μl) was added. The solvent was removed by heating at 120° C. for 10 mins under a stream of nitrogen. Anhydrous MeCN (1 ml) was added and evaporated as before. This step was repeated again. A solution of 20d (2 mg) in anhydrous DMSO (300 μl) was added. After heating at 90° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 20e was confirmed by co-injection with the non-radioactive F-19 fluoro standard on the Econsphere analytical HPLC.

Example 21 a) Synthesis of 2-Cyano-5-fluoro-benzoic acid methyl ester (21a)

To a stirred suspension of 16.0 g (96.9 mmol) 2-Cyano-5-fluoro-benzoic acid (Apollo) and 161 ml methanol were added 30.4 g (387.6 mmol) acetyl chloride drop wisely at 0° C. The reaction mixture was stirred over night, filtered and concentrated. The residue was diluted with dichloromethane, washed with diluted sodium hydrogen carbonate solution, dried with sodium sulphate and concentrated. The residue was purified by column chromatography (hexane:ethylacetate). The desired product 21a was obtained in 86.0 yield (14.9 g; 83.3 mmol)

MS-ESI: 180 (M$^+$+1,100),
Elementary analysis:

| Calculated: | C | 60.34% | H | 3.38% | F | 10.60% | N | 7.82% |
|---|---|---|---|---|---|---|---|---|
| Determined: | C | 60.41% | H | 3.39% | F | 10.58% | N | 7.79% | b) Synthesis of 2-Cyano-5-dimethylamino-benzoic acid methyl ester (21b)

To a stirred solution of 4.03 g (22.5 mmol) 21a and 60.0 ml dimethylsulphoxid were added 2.23 g (27.0 mmol) dimethylamine hydrochloride and 6.54 g (47.3 mmol) potassium carbonate. The reaction mixture was stirred for 15 h at 65° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 21b was obtained in 89.0% yield (4.09 g, 20.0 mmol).

MS-ESI: 205 (M$^+$+1, 100),

Elementary analysis:

| Calculated: | C | 64.69% | H | 5.92% | N | 13.72% |
|---|---|---|---|---|---|---|
| Determined: | C | 64.75% | H | 5.94% | N | 13.68% | c) Trifluoro-methanesulfonate(4-cyano-3-methoxy-carbonyl-phenyl)-trimethylammonium (21c)

To a stirred solution of 2.55 g (12.5 mmol) 21b and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 21c was obtained in 88% yield (4.05 g, 11.0 mmol).

MS-ESI: 219 (M$^+$, 71),

Elementary analysis:

| Calculated: | C | 42.39% | H | 4.10% | F | 15.47% | N | 7.61% |
|---|---|---|---|---|---|---|---|---|
| Determined: | C | 42.41% | H | 4.13% | F | 15.45% | N | 7.60% | d) Synthesis of Trifluoro-methanesulfonate(3-carboxy-4-cyano-phenyl)-trimethyl-ammonium (21d)

A solution of 4.01 g (10.9 mmol) 21c, 95 ml dest. water and 95 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 21d was obtained in 96% yield (3.70 g, 10.5 mmol) and crude compound 21d was used for the next step without purification.

MS-ESI: 205 (M$^+$, 76),

Elementary analysis:

| Calculated: | C | 40.68% | H | 3.70% | F | 16.09% | N | 7.91% |
|---|---|---|---|---|---|---|---|---|
| Determined: | C | 40.70% | H | 3.72% | F | 16.07% | N | 7.90% | e) Synthesis of peptide(5-Trimethylammonium-2-cyano-benzoyl)-Val-βAla-Arg-Gly-NFI$_2$-triflate salt (21e)

To a stirred solution of 70.8 mg (0.2 mmol) 21d in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Arg(Pbf)-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 21d in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water: acetonitril gradient and 0.1% trifluoro acetic acid as co-solvent. The desired compound 21e was obtained in 38% yield (18.6 mg, 0.0247 mmol).

MS-ESI: 603 (M$^+$, 100), f) Synthesis of [$^{18}$F]-(5-Fluoro-2-cyano-benzoyl)-Val-βAla-Arg-Gly-NH$_2$ (21f)

To a Wheaton vial (5 ml) charged with Kryptofix 222 (5 mg), potassium carbonate (1 mg in 500 μl water) and MeCN (1.5 ml) the fluorine containing water (345 MBq, 35 μl) was added. The solvent was removed by heating at 120° C. for 10 mins under a stream of nitrogen. Anhydrous MeCN (1 ml) was added and evaporated as before. This step was repeated again. A solution of 21e (2 mg) in anhydrous DMSO (300 μl) was added. After heating at 90° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 21f was confirmed by co-injection with the non-radioactive F-19 fluoro standard on the Econsphere analytical HPLC.

Example 22 a) Synthesis of 2-Chloro-4,5-difluoro-benzoic acid methyl ester (22a)

To a stirred suspension of 5.0 g (26 mmol) 2-Chloro-4,5-difluoro-benzoic acid (Apollo) and 50 ml methanol were added 7.41 ml (104 mmol) acetyl chloride drop wisely at 0° C. The reaction mixture was stirred over night, filtered and concentrated. The residue was diluted with dichloromethane, washed with diluted sodium hydrogen carbonate solution, dried with sodium sulphate and concentrated. The residue was purified by column chromatography (hexane:ethylacetate). The desired product 22a was obtained in 84% yield (4.51 g, 21.8 mmol).

MS-ESI: 207/209 (M$^+$+1, 64/22).

Elementary analysis:

| Calculated: | C | 46.51% | H | 2.44% | F | 18.39% |
|---|---|---|---|---|---|---|
| Determined: | C | 46.59% | H | 2.46% | F | 18.35% | b) 2-Chloro-4-dimethylamino-5-fluoro-benzoic acid methyl ester (22b)

To a stirred solution of 23.1 g (112 mmol) 22a and 231 ml dimethylsulphoxid were added 10.0 g (123 mmol) dimethylamine hydrochloride and 32.4 g (234 mmol) potassium carbonate. The reaction mixture was stirred for 24 h at 60° C. in an autoclave and was reduced with high vacuum rotation evaporator at 65° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude was purified by column chromatography and the desired product 22b was obtained in 89.5% yield (23.1 g 100 mmol).

MS-ESI: 232/234 ($M^+$+1, 55/18).

Elementary analysis:

| Calculated: | C 51.85% | H 4.79% | F 8.20% | N 6.05% |
|---|---|---|---|---|
| Determined: | C 51.89% | H 4.81% | F 8.18% | N 6.03% | c) Trifluoro-methanesulfonate(5-chloro-2-fluoro-4-methoxycarbonyl-phenyl)-trimethyl-ammonium (22c)

To a stirred solution of 7.06 g (30.5 mmol) 22b and 100 ml dichloroethane were added 50 g (305 mmol) methyltriflate (Aldrich) drop wisely. The reaction mixture was stirred for 24 hours at 90° C. and then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 22c was obtained in 91.1% yield (11.0 g; 27.8 mmol).

MS-ESI: 246/248 ($M^+$, 100/32).

| Calculated: | C 36.42% | H 3.57% | F 19.20% | N 3.54% |
|---|---|---|---|---|
| Determined: | C 36.46% | H 3.58% | F 19.18% | N 3.51% | d) Synthesis of Trifluoro-methanesulfonate(4-carboxy-5-chloro-2-fluoro-phenyl)-trimethyl-ammonium (22d)

A solution of 2.0 g (5.05 mmol) 22c, 45 ml dest. water and 45 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude product 22d was obtained and crude compound 22d was used for the next step without purification. The desired crude compound 22d was obtained in 76% yield (1.46 g, 3.84 mmol).

MS-ESI: 232/234 ($M^+$, 68/21).

| Calculated: | C 34.61% | H 3.17% | F 19.91% | N 3.67% |
|---|---|---|---|---|
| Determined: | C 34.66% | H 3.19% | F 19.94% | N 3.66% | e) Synthesis of peptide(4-Trimethylammonium-2-chloro-5-fluoro-benzoyl)-Val-βAla-Phe-Gly-$NH_2$-triflate salt (22e)

To a stirred solution of 76 mg (0.2 mmol) 22d in 1.5 ml dichloromethane and 0.25 ml dimethylformamid were added 0.031 ml (0.2 mmol) diisopropylcarbodiimid. The solution was added to 0.065 mmol Rink-resin-bound H-Val-βAla-Phe-Gly-$NH_2$ (loading 0.68 mmol/g) which was prepared by standard protocol. The mixture was shaken intensively for 4 h. The mixture was filtered and washed with dimethylformamide The coupling step was repeated. Thus, to a stirred solution of 76 mg (0.2 mmol) 22d in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound H-Val-βAla-Phe-Gly-$NH_2$ and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain 22e in 37% yield (18.6 mg, 0.0241 mmol).

MS-ESI: 620/622 ($M^+$, 100/34).

f) Synthesis of [$^{18}$F]-(4-Trimethylammonium-2-chloro-5-fluoro-benzoyl)-Val-βAla-Phe-Gly-$NH_2$ (22f)

To a Wheaton vial (5 ml) charged with Kryptofix 222 (5 mg), potassium carbonate (1 mg in 500 µl water) and MeCN (1.5 ml) the fluorine containing water (319 MBq, 33 µl) was added. The solvent was removed by heating at 120° C. for 10 mins under a stream of nitrogen. Anhydrous MeCN (1 ml) was added and evaporated as before. This step was repeated again. A solution of 22e (2 mg) in anhydrous DMSO (300 µl) was added. After heating at 90° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 22f was confirmed by co-injection with the non-radioactive F-19 fluoro standard on the Econsphere analytical HPLC.

Example 23

Synthesis of (4-Trimethylammonium-3-cyano-benzoyl)-Gly-Tyr-βAla-Val-$NH_2$, (23a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Gly-Tyr(OtBu)-βAla-Val-$NH_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 23a in 40% yield (19.8 mg (0.0176 mmol)).
MS-ESI: 609 ($M^+$, 67).

Synthesis of [$^{18}$F]-4-Fluoro-3-cyano-benzoyl)-Gly-Tyr-βAla-Val-NH$_2$, (23b)

To a Wheaton vial (5 ml) charged with Kryptofix 222 (5 mg), potassium carbonate (1 mg in 500 μl water) and MeCN (1.5 ml) the fluorine containing water (356 MBq, 35 μl) was added. The solvent was removed by heating at 120° C. for 10 mins under a stream of nitrogen. Anhydrous MeCN (1 ml) was added and evaporated as before. This step was repeated again. A solution of 23a (2 mg) in anhydrous DMSO (300 μl) was added. After heating at 50° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 23b was confirmed by co-injection with the non-radioactive F-19 fluoro standard on the Econsphere analytical HPLC.

Example 24

Synthesis of (4-Trimethylammonium-3-cyano-benzoyl)-Ava-His(π-Me)-Sta-Leu-NH$_2$-triflate salt, (24a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Ava-His(π-Me)-Sta-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 24a in 38% yield (21.6 mg (0.023 mmol)).
MS-ESI: 727 ($M^+$, 77).

Synthesis of [$^{18}$F]-4-Fluoro-3-cyano-benzoyl)-Ava-His(π-Me)-Sta-Leu-NH$_2$, (24b)

To a Wheaton vial (5 ml) charged with Kryptofix 222 (5 mg), potassium carbonate (1 mg in 500 μl water) and MeCN (1.5 ml) the fluorine containing water (377 MBq, 35 μl) was added. The solvent was removed by heating at 120° C. for 10 mins under a stream of nitrogen. Anhydrous MeCN (1 ml) was added and evaporated as before. This step was repeated again. A solution of 24a (2 mg) in anhydrous DMSO (300 μl) was added. After heating at 50° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 24b was confirmed by co-injection with the non-radioactive F-19 fluoro standard on the Econsphere analytical HPLC.

Example 25

Synthesis of (4-Trimethylammonium-3-cyano-benzoyl)-N-MeGly-His(π-Me)-Sta-Leu-NH$_2$-triflate salt, (25a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H—N-MeGly-His(Tr)-Sta-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 25a in 29% yield (16.0 mg (0.0189 mmol)).
MS-ESI: 698 ($M^+$, 75).

Synthesis of [$^{18}$F]-4-Fluoro-3-cyano-benzoyl)-N-MeGly-His(π-Me)-Sta-Leu-NH$_2$, (25b)

To a Wheaton vial (5 ml) charged with Kryptofix 222 (5 mg), potassium carbonate (1 mg in 500 μl water) and MeCN (1.5 ml) the fluorine containing water (382 MBq, 35 μl) was added. The solvent was removed by heating at 120° C. for 10 mins under a stream of nitrogen. Anhydrous MeCN (1 ml) was added and evaporated as before. This step was repeated again. A solution of 25a (2 mg) in anhydrous DMSO (300 μl) was added. After heating at 50° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 25b was confirmed by co-injection with the non-radioactive F-19 fluoro standard on the Econsphere analytical HPLC.

Example 26

Synthesis of (4-Trimethylammonium-3-cyano-benzoyl)-Val-βAla-Arg-Gly-NH$_2$-triflate salt, (26a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Arg(Pbf)-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 26a in 47% yield (20.3 mg, 0.0305 mmol). (19.5 mg (0.026 mmol)).
MS-ESI: 603 (M$^+$, 100).

Synthesis of [$^{18}$F]-4-Fluoro-3-cyano-benzoyl)-Val-βAla-Arg-Gly-NH$_2$, (26b)

To a Wheaton vial (5 ml) charged with Kryptofix 222 (5 mg), potassium carbonate (1 mg in 500 µl water) and MeCN (1.5 ml) the fluorine containing water (344 MBq, 35 µl) was added. The solvent was removed by heating at 120° C. for 10 mins under a stream of nitrogen. Anhydrous MeCN (1 ml) was added and evaporated as before. This step was repeated again. A solution of 26a (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 26b was confirmed by co-injection with the non-radioactive F-19 fluoro standard on the Econsphere analytical HPLC.

Example 27

Synthesis of (4-Trimethylammonium-3-cyano-benzoyl)-Val-βAla-His(II-Me)-Gly-NH$_2$ triflate salt, (27a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-His(II-Me)-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 27a in 33% yield (16.0 mg (0.0215 mmol)).
MS-ESI: 597 (M$^+$, 100).

Synthesis of [$^{18}$F]-4-Fluoro-3-cyano-benzoyl)-Val-βAla-His(π-Me)-Gly-NH$_2$, (27b)

Figure 5:
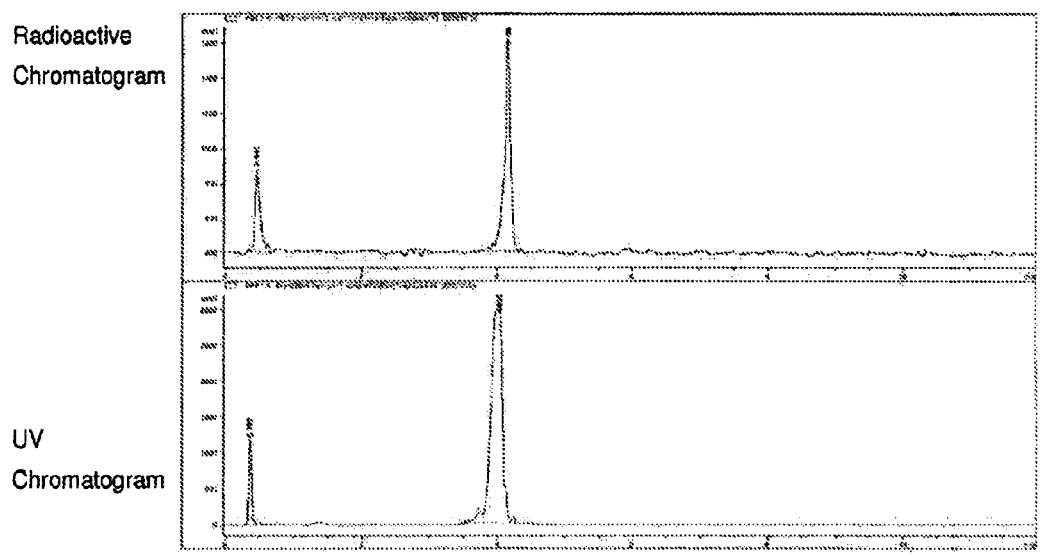
FIG. 5 shows HPLC chromatograms of reaction mixture with co-injection of the cold standard.
Figure 6:
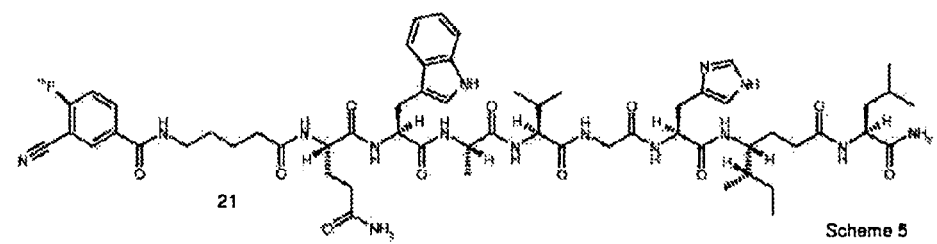
FIG. 6 shows HPLC chromatograms of reaction mixture with co-injection of the cold standard.
Figure 6:
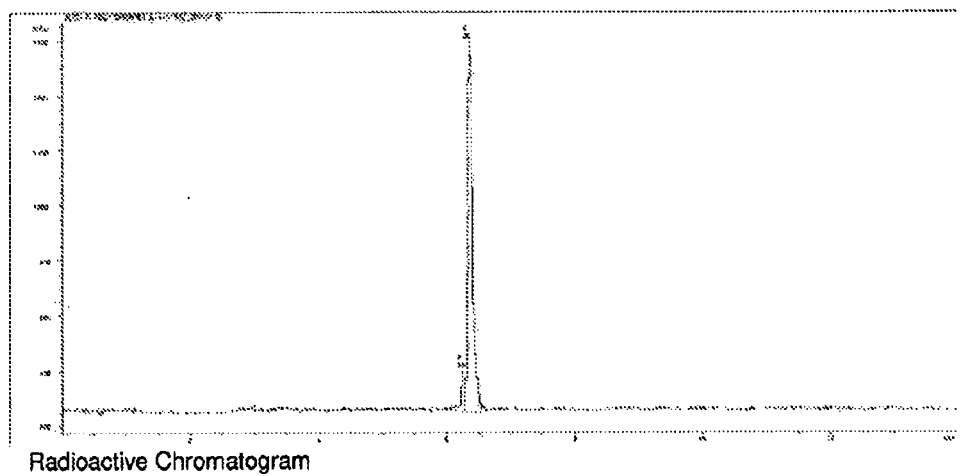
Figure 6:
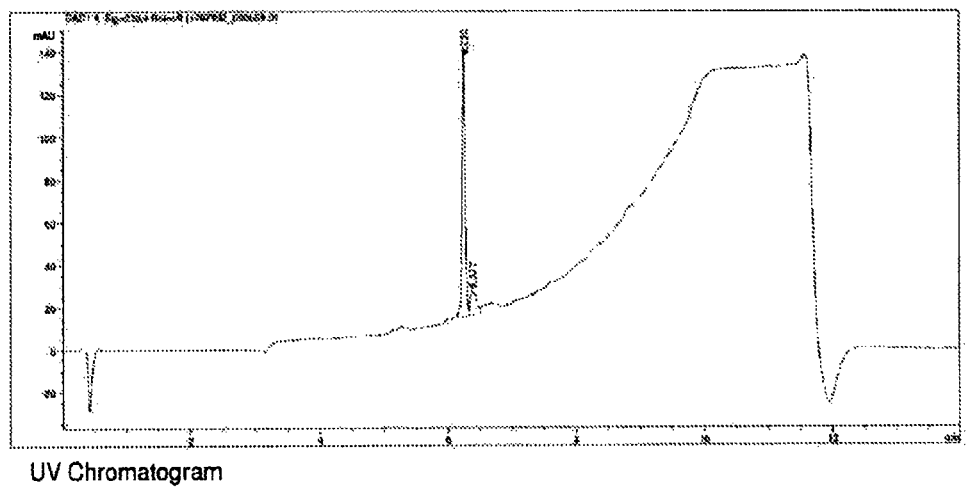
Figure 7:
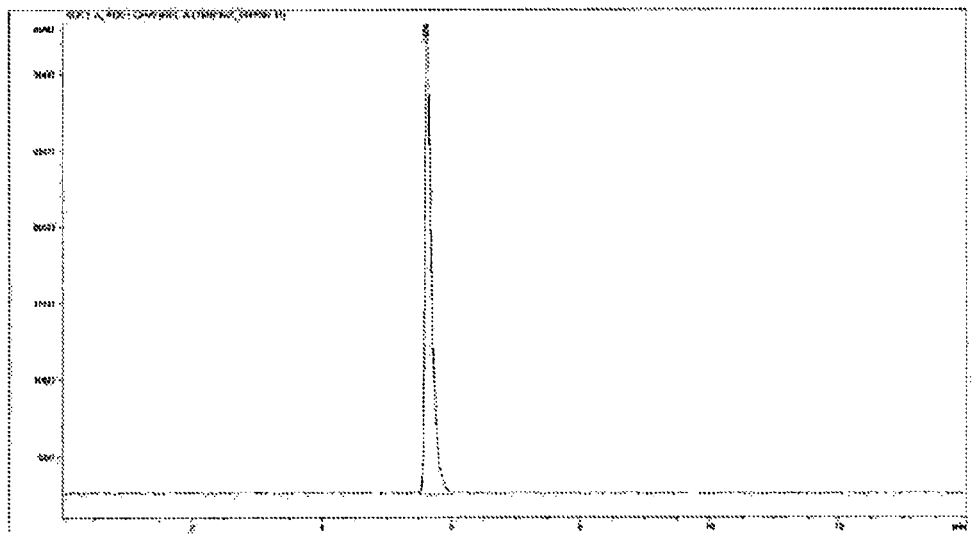
Figure 7:
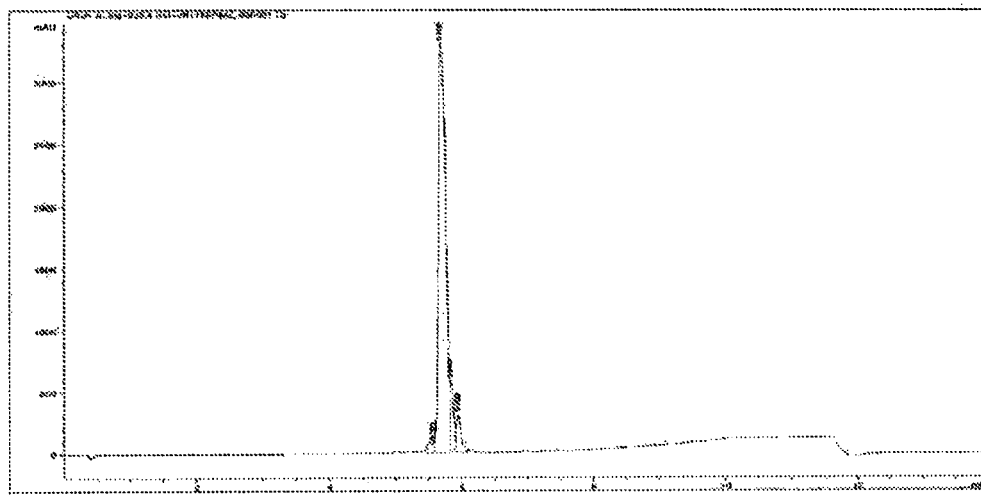

To a Wheaton vial (5 ml) charged with Kryptofix 222 (5 mg), potassium carbonate (1 mg in 500 µl water) and MeCN (1.5 ml) the fluorine containing water (367 MBq, 35 µl) was added. The solvent was removed by heating at 120° C. for 10 mins under a stream of nitrogen. Anhydrous MeCN (1 ml) was added and evaporated as before. This step was repeated again. A solution of 27a (2 mg) in anhydrous DMSO (300 µl) was added. After heating at 50° C. for 15 min the crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 27b was confirmed by co-injection with the non-radioactive F-19 fluoro standard on the Econsphere analytical HPLC (FIG. 5; HPLC chromatogram of reaction mixture with co-injection of the cold standard).

Example 28

Synthesis of (4-Trimethylammonium-3-cyano-benzoyl)-Val-βAla-His(π-Me)-Leu-NH$_2$ triflate salt, (28a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-His(π-Me)-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 28a in 57% yield (29.8 mg (0.037 mmol)).

MS-ESI: 654 ($M^+$, 100).

Synthesis of [$^{18}$F]-4-Fluoro-3-cyano-benzoyl)-Val-βAla-His(π-Me)-Leu-NH$_2$, (28b)

To a Wheaton vial (5 ml) charged with Kryptofix 222 (5 mg), potassium carbonate (1 mg in 500 μl water) and MeCN (1.5 ml) the fluorine containing water (356 MBq, 35 μl) was added. The solvent was removed by heating at 120° C. for 10 mins under a stream of nitrogen. Anhydrous MeCN (1 ml) was added and evaporated as before. This step was repeated again. A solution of 28a (2 mg) in anhydrous DMSO (300 μl) was added. After heating at 50° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econsphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 28b was confirmed by co-injection with the non-radioactive F-19 fluoro standard on the Econsphere analytical HPLC.

Example 29

Synthesis of (4-Trimethylammonium-3-cyano-benzoyl)-Val-βAla-Phe-Gly-NH$_2$ triflate salt, (29a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Phe-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 29a in 46% yield (22.2 mg (0.0299 mmol)).

MS-ESI: 593 ($M^+$, 100).

Synthesis of [$^{18}$F]-(4-Fluoro-3-cyano-benzoyl)-Val-βAla-Phe-Gly-NH$_2$, (29b)

To a Wheaton vial (5 ml) charged with Kryptofix 222 (5 mg), potassium carbonate (1 mg in 500 μl water) and MeCN (1.5 ml) the fluorine containing water (333 MBq, 35 μl) was added. The solvent was removed by heating at 120° C. for 10 mins under a stream of nitrogen. Anhydrous MeCN (1 ml) was added and evaporated as before. This step was repeated again. A solution of 29a (2 mg) in anhydrous DMSO (300 μl) was added. After heating at 50° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econsphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 29b was confirmed by co-injection with the non-radioactive F-19 fluoro standard on the Econsphere analytical HPLC.

Example 30

Synthesis of (4-Trimethylammonium-3-cyano-benzoyl)-Val-βAla-Trp-Gly-NH$_2$-triflate salt, (30a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Trp(Boc)-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 30a in 41% yield (20.8 mg (0.021 mmol)).

MS-ESI: 632 ($M^+$, 100).

Synthesis of [$^{18}$F]-4-Fluoro-3-cyano-benzoyl)-Val-βAla-Trp-Gly-NH$_2$, (30b)

To a Wheaton vial (5 ml) charged with Kryptofix 222 (5 mg), potassium carbonate (1 mg in 500 μl water) and MeCN (1.5 ml) the fluorine containing water (368 MBq, 35 μl) was added. The solvent was removed by heating at 120° C. for 10 mins under a stream of nitrogen. Anhydrous MeCN (1 ml) was added and evaporated as before. This step was repeated again. A solution of 30a (2 mg) in anhydrous DMSO (300 μl) was added. After heating at 50° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econsphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 30b was confirmed by co-injection with the non-radioactive F-19 fluoro standard on the Econsphere analytical HPLC.

Example 31

Synthesis of (4-Trimethylammonium-3-cyano-benzoyl)-Val-βAla-Tyr-Gly-NH₂ triflate salt, (31a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Tyr(OtBu)-Gly-NH₂ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 31a in 36% yield (17.7 mg (0.0234 mmol)).

MS-ESI: 609 (M⁺, 100).

Synthesis of [¹⁸F]-4-Fluoro-3-cyano-benzoyl)-Val-βAla-Tyr-Gly-NH₂, (31b)

To a Wheaton vial (5 ml) charged with Kryptofix 222 (5 mg), potassium carbonate (1 mg in 500 μl water) and MeCN (1.5 ml) the fluorine containing water (339 MBq, 35 μl) was added. The solvent was removed by heating at 120° C. for 10 mins under a stream of nitrogen. Anhydrous MeCN (1 ml) was added and evaporated as before. This step was repeated again. A solution of 31a (2 mg) in anhydrous DMSO (300 μl) was added. After heating at 50° C. for 15 min. The crude reaction mixture was analyzed using an analytical HPLC (Column Zorbax SB C18, 50×4.6 mm, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 31b was confirmed by co-injection with the non-radioactive F-19 fluoro standard on the Econsphere analytical HPLC.

Example 32 a) Synthesis of (4-Trimethylammonium-3-trifluormethyl-benzoyl)-Val-βAla-His(π-Me)-Gly-NH₂-triflate salt (32a)

To a stirred solution of 79.4 mg (0.2 mmol) 12c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-His(π-Me)-Gly-NH₂ (loading 0.68 mmol/g) which was prepared by standard protocol. The mixture was shaken intensively for 4 h. The mixture was filtered and washed with dimethylformamide. The coupling step was repeated. Thus, to a stirred solution of 79.4 mg (0.2 mmol) 12c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (32a) in 59% yield (24.2 mg (0.0384 mmol)).

MS-ESI: 598 (M⁺, 88)

b) Synthesis of [¹⁸F]-4-Fluoro-3-cyano-benzoyl)-Val-βAla-His(π-Me)-Gly-NH₂, (32b)

To a Wheaton vial (5 ml) charged with Kryptofix 222 (5 mg), potassium carbonate (1 mg in 500 μl water) and MeCN (1.5 ml) the fluorine containing water (318 MBq, 35 μl) was added. The solvent was removed by heating at 120° C. for 10 mins under a stream of nitrogen. Anhydrous MeCN (1 ml) was added and evaporated as before. This step was repeated again. A solution of 32a (2 mg) in anhydrous DMSO (300 μl) was added. After heating at 50° C. for 15 min. The crude reaction mixture was analyzed using an analytical HPLC (Column Zorbax SB C18, 50×4.6 mm, 1.8μ, 2 ml/min, solvent A: H2O, solvent B: MeCN, gradient: 5%-95% B in 7 mins or Column Econosphere C18, 53×7 mm, 3μ, 3 ml/min (Alltech), solvent A: H2O+0.1% TFA, solvent B: MeCN/Water 9/1+0.1% TFA, gradient: 5-95% B in 7 mins. The F-18 labeled product 32b was confirmed by co-injection with the non-radioactive F-19 fluoro standard on the Econsphere analytical HPLC.

Example 33 a) Synthesis of (4-Trimethylammonium-3-cyano-benzoyl)-Val-βAla-Lys-Gly-NH₂-triflate salt (33a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Lys(Boc)-Gly-NH₂ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 33a in 52% yield (24.5 mg (0.0338 mmol)).
MS-ESI: 575 (M+, 100).

b) Synthesis of [$^{18}$F]-4-Fluoro-3-cyano-benzoyl)-Val-βAla-Lys-Gly-NH$_2$, (33b)

To a Wheaton vial (5 ml) charged with Kryptofix 222 (5 mg), potassium carbonate (1 mg in 500 µl water) and MeCN (1.5 ml) the fluorine containing water (301 MBq, 35 µl) was added. The solvent was removed by heating at 120° C. for 10 mins under a stream of nitrogen. Anhydrous MeCN (1 ml) was added and evaporated as before. This step was repeated again. A solution of 33a (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 33b was confirmed by co-injection with the non-radioactive F-19 fluoro standard on the Econsphere analytical HPLC.

Example 34 a) Synthesis of (4-Trimethylammonium-3-cyano-benzoyl)-Val-βAla-Met-Gly-NH$_2$-triflate salt (34a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-Met-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed peptide resin and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product 34a in 37% yield (17.4 mg (0.024 mmol)).
MS-ESI: 577 (M+, 100).

b) Synthesis of [$^{18}$F]-4-Fluoro-3-cyano-benzoyl)-Val-βAla-Met-Gly-NH$_2$, (34b)

To a Wheaton vial (5 ml) charged with Kryptofix 222 (5 mg), potassium carbonate (1 mg in 500 µl water) and MeCN (1.5 ml) the fluorine containing water (383 MBq, 35 µl) was added. The solvent was removed by heating at 120° C. for 10 mins under a stream of nitrogen. Anhydrous MeCN (1 ml) was added and evaporated as before. This step was repeated again. A solution of 34a (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 34b was confirmed by co-injection with the non-radioactive F-19 fluoro standard on the Econsphere analytical HPLC.

Example 35 a) Synthesis of (3-Cyano-4-fluoro-benzenesulfonyl)-methyl-amino]-acetic acid methyl ester (35a)

To a suspension of 6.90 g (0.05 mol) sarcosin hydrochloride and 19.5 g (0.15 mol) diisopropylethyl amin in 70.0 ml dichloromethane were added 11.5 g (0.055 mol) 3-cyano-4-fluoro-benzenesulfonyl chloride (Aldrich) in 50.0 ml dichloromethane dropwisely at 0° C. The suspension was stirred for 4 h. The suspension was poured on 150 ml stirred ice/water mixture. The water phase was separated and extracted twice with dichlormethane. The combined dichloromethane phases were washed twice with diluted hydrogen chloride solution and subsequently with sodium hydrogen carbonate solution, dried with sodium sulphate and concentrated. The oily crude product 35a was purified by column chromatography (hexane:ethylacetate). The desired product 35a was obtained in 58.2% yield (8.32 g; 29.1 mmol)
MS-ESI: 287 (M++1, 100).

| Elementary analysis: | C 46.15% | H 3.87% | F 6.64% | N 9.79% |
|---|---|---|---|---|
| Determined: | C 46.16% | H 3.88% | F 6.65% | N 9.80% | b) Synthesis of (3-Cyano-4-dimethylamino-benzenesulfonyl)-methyl-amino]-acetic acid methyl ester (35b)

To a stirred solution of 5.72 g (20.0 mmol) 35a and 60 ml dimethylsulphoxid were added 2.03 g (24.7 mmol) dimethylamine hydrochloride and 5.97 g (43.2 mmol) potassium carbonate. The reaction mixture was stirred over night and was reduced with high vacuum rotation evaporator at 60° C. The residue was diluted with dichloromethane, washed twice with water. The combined water phases were extracted with dichloromethane. The combined dichloromethane phases were washed with diluted sodium hydrogen carbonate solution, dried with sodium sulphate and concentrated. The oily crude product 35b was obtained in 95% yield (5.92 g, 19.9 mmol) and was used for the next step without purification.
MS-ESI: 312 (M++1, 100).

| Elementary analysis: | C 50.15% | H 5.50% | N 13.50% |
|---|---|---|---|
| Determined: | C 50.18% | H 5.52% | N 13.48% | c) Synthesis of Trifluoro-methanesulfonate[2-cyano-4-(methoxycarbonylmethyl-methyl-sulfamoyl)-phenyl]-trimethyl-ammonium (35c)

To a stirred solution of 3.89 g (12.5 mmol) 35b and 50 ml dichloromethane were added 20.5 g (125 mmol) methyltriflate (Aldrich) drop wisely. The reaction mixture was refluxed for 2 days then cooled to room temperature. Diethylether was added. The desired compound precipitates and the solvent was decanted. The solid was washed extensively (ten times) with large amounts of diethylether. The solid was dried by use of oil pump vacuum and purified by (C-18) RP-column chromatography (acetonitril/water-gradient 1:99 to 80:20). The desired compound 35c was obtained in 43% yield (2.55 g, 5.375 mmol).

MS-ESI: 326 (M$^+$, 100).

| Elementary analysis: | C 37.89% | H 4.24% | F 11.99% | N 8.84% |
|---|---|---|---|---|
| Determined: | C 37.92% | H 4.26% | F 11.96% | N 8.86% | d) Trifluoro-methanesulfonate[4-(carboxymethyl-methyl-sulfamoyl)-2-cyano-phenyl]-trimethyl-ammonium (35d)

A solution of 2.38 g (5.0 mmol) 35c, 50 ml dest. water and 50 ml trifluoroacetic acid was refluxed for 2 days. The reaction mixture was evaporated, dried by use of oil pump vacuum over night and treated with diethyl ether. The resulting solid was filtered, washed extensively with diethyl ether and dried by oil pump vacuum. The solid crude was obtained in 79% yield (1.82 g; 3.95 mmol) and crude compound 35d was used for the next step without purification.

MS-ESI: 312 (M$^+$, 100).

| Elementary analysis: | C 36.44% | H 3.93% | F 12.35% | N 9.11% |
|---|---|---|---|---|
| Determined: | C 36.47% | H 3.95% | F 12.33% | N 9.10% | e) Synthesis of (4-Trimethylammonium-3-cyano-benzenesulfonyl)-Gly-Val-βAla-His(π-Me)-Gly-NH$_2$-triflate salt (35e)

To a stirred solution of 82.4 mg (0.2 mmol) 35d in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.065 mmol Rink-resin-bound H-Val-βAla-His(π-Me)-Gly-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 82 mg (0.2 mmol) 35d in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water:acetonitril gradient and 0.1% trifluoro acetic acid as co-solvent to obtain the desired product (35e) in 55% yield—30.5 mg (0.036 mmol).

MS-ESI: 705 (M$^+$, 100).

f) Synthesis of [$^{18}$F]-(4-Fluoro-3-cyano-benzene-sulfonyl)-Val-βAla-His(π-Me)-Gly-NH$_2$-triflate salt (35f)

To a Wheaton vial (5 ml) charged with Kryptofix 222 (5 mg), potassium carbonate (1 mg in 500 µl water) and MeCN (1.5 ml) the fluorine containing water (344 MBq, 33 µl) was added. The solvent was removed by heating at 120° C. for 10 mins under a stream of nitrogen. Anhydrous MeCN (1 ml) was added and evaporated as before. This step was repeated again. A solution of 35e (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 35f was confirmed by co-injection with the non-radioactive F-19 fluoro standard on the Econsphere analytical HPLC.

Example 36 a) Synthesis of N-(4-Trimethylammonium-3-cyano-benzoyl)-6-fluoro-dopamin-triflate salt (36a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was stirred for 20 min and 34 mg (0.2 mmol) symphatomimetic 6-fluoro-dopamin (J. Fluorine Chem.; 74; 1; 1995; 113-122, CAS Nr. 71144-39-3) was added. The reaction mixture was stirred intensively for 8 h. The reaction mixture was evaporated in vacuum, diluted with dichloromethane:iso-propanol mixture (10:1) and washed twice with water. The combined water phases were extracted with dichloromethane. The combined organic phases were washed with brine, dried with sodium sulphate and concentrated. The oily crude was purified by RP column chromatography (water:acetonitril gradient) and the desired product 36a was obtained in 44% yield (45 mg, 0.088 mmol).

MS-ESI: 358 (M$^+$, 100).

| Elementary analysis: | C 47.34% | H 4.17% | F 14.98% | N 8.28% |
|---|---|---|---|---|
| Determined: | C 47.36% | H 4.19% | F 14.97% | N 8.27% | b) Synthesis of [$^{18}$F]-N-(4-Fluoro-3-cyano-benzoyl)-6-fluoro-dopamin-triflate salt (36b)

To a Wheaton vial (5 ml) charged with Kryptofix 222 (5 mg), potassium carbonate (1 mg in 500 µl water) and MeCN (1.5 ml) the fluorine containing water (356 MBq, 35 µl) was added. The solvent was removed by heating at 120° C. for 10 mins under a stream of nitrogen. Anhydrous MeCN (1 ml) was added and evaporated as before. This step was repeated again. A solution of 36a (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/

Water 9/1+0.1% TFA, gradient: 5-95% B in 7 mins. The F-18 labeled product 36b was confirmed by co-injection with the non-radioactive F-19 fluoro standard on the Econsphere analytical HPLC.

Example 37 a) Synthesis of N-(4-Trimethylammonium-3-cyano-benzoyl)-didemethyltamoxifen-triflate salt (37a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was stirred for 20 min and 0.2 mmol estrogen antagonist didemethyltamoxifen (J. Pharm. Sci.; 82; 9; (1993); 927-933, CAS Nr. 80234-20-4) was added. The reaction mixture was stirred intensively for 8 h. The reaction mixture was evaporated in vacuum, diluted with dichloromethane and washed twice with water. The combined water phases were extracted with dichloromethane. The combined dichloromethane phases were washed with brine, dried with sodium sulphate and concentrated. The oily crude was purified by column chromatography and the desired product 37b was obtained in 56% yield (76 mg, 0.112 mmol)

MS-ESI: 531 (M+, 100).

| Elementary analysis: | C 63.61% | H 5.34% | F 8.38% | N 6.18% |
|---|---|---|---|---|
| Determined: | C 63.64% | H 5.35% | F 8.37% | N 6.17% | b) Synthesis of [$^{18}$F]-N-(4-Fluoro-3-cyano-benzoyl) didemethyltamoxifen (37b)

To a Wheaton vial (5 ml) charged with Kryptofix 222 (5 mg), potassium carbonate (1 mg in 500 µl water) and MeCN (1.5 ml) the fluorine containing water (337 MBq, 35 µl) was added. The solvent was removed by heating at 120° C. for 10 mins under a stream of nitrogen. Anhydrous MeCN (1 ml) was added and evaporated as before. This step was repeated again. A solution of 37a (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 37b was confirmed by co-injection with the non-radioactive F-19 fluoro standard on the Econsphere analytical HPLC.

Example 38 a) Synthesis of N-(4-Trimethylammonium-3-cyano-benzoyl)-alaphen-triflate salt (38a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was stirred for 20 min and 49 mg (0.2 mmol) alaphen (Pharm. Chem. J. (Engl. Transl.); 9; 3; (1975); p. 158; CAS Nr. 15269-42-8) was added. The reaction mixture was stirred intensively for 8 h. The reaction mixture was evaporated in vacuum, diluted with dichloromethane:isopropanol mixture (10:1) and washed twice with water. The combined water phases were extracted with dichloromethane. The combined dichloromethane phases were washed with brine, dried with sodium sulphate and concentrated. The oily crude was purified by RP column chromatography and the desired product 38a was obtained in 64% yield (77 mg, 0.13 mmol).

MS-ESI: 394 (M+, 100)

| Elementary analysis: | C 53.38% | H 5.84% | F 11.01% | N 8.12% |
|---|---|---|---|---|
| Determined: | C 53.41% | H 5.85% | F 11.00% | N 8.11% | b) Synthesis of [$^{18}$F]-N-(4-Fluoro-3-cyano-benzoyl) alaphen (38b)

To a Wheaton vial (5 ml) charged with Kryptofix 222 (5 mg), potassium carbonate (1 mg in 500 µl water) and MeCN (1.5 ml) the fluorine containing water (364 MBq, 35 µl) was added. The solvent was removed by heating at 120° C. for 10 mins under a stream of nitrogen. Anhydrous MeCN (1 ml) was added and evaporated as before. This step was repeated again. A solution of 38a (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 38b was confirmed by co-injection with the non-radioactive F-19 fluoro standard on the Econsphere analytical HPLC.

Example 39 a) Synthesis of 3-Cyano-4-(trimethylammonium)-benzoyl-Ava-Gln-Trp-Ala-Val-Gly-His-(4-amino-5-methyl-heptanoic acid)-Leu-NH$_2$ trifluoracetic acid salt (39a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.025 mmol Rink-resin-bound H-Ava-Gln-Trp-Ala-Val-Gly-His-(4-amino-5-methyl-heptanoic acid)-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water: acetonitril gradient and 0.1% trifluoro acetic acid as co-solvent. The desired compound 39 was obtained in 35% yield (12.2 mg, 0.012 mmol).

MS-ESI: 1237 (M$^+$, 100), b) "Synthesis of 3-cyano-4-[18F]fluorobenzoyl-Ava-Gln-Trp-Ala-Val-Gly-His-(4-amino-5-methyl-heptanoic acid)-Leu-NH$_2$ (39b)

labeled product was confirmed by co-injection with the F-19 cold standard on an analytical HPLC (Column ACE 3μ C18 50×4.6 mm, 1 mL/min (Agilent), solvent A: H$_2$O+0.1% TFA, solvent B: MeCN/Water 9/1+0.1% TFA, gradient: 0% for 2 min, then 0% B to 95% B in 7 mins).

Example 40 a) Synthesis of 3-Cyano-4-(trimethylammonium)-benzoyl-Arg-Ava-Gln-Trp-Ala-Val-Gly-His(πMe)-Sta-Leu-NH$_2$ trifluoracetic acid salt (40a) (SEQ ID NO: 414)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.025 mmol Rink-resin-bound H-Arg-Ava-Gln-Trp-Ala-Val-Gly-His(πMe)-Sta-Leu-NH$_2$ (SEQ ID NO: 415) (loading 0.68 mmol/g) which was prepared by standard protocol. The mixture was shaken intensively for 4 h. The mixture was

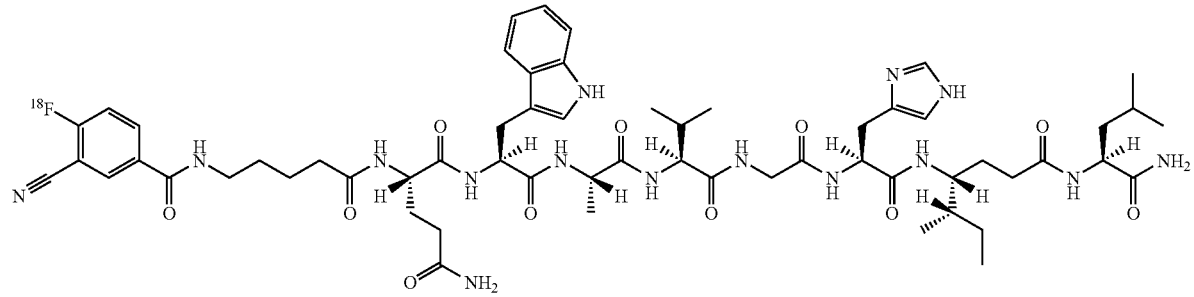 [SMILES: CC[C@H](C)[C@@H](CCC(=O)N[C@@H](CC(C)C)C(N)=O)NC(=O)[C@H](Cc1c[nH]cn1)NC(=O)CNC(=O)[C@@H](NC(=O)[C@H](C)NC(=O)[C@H](Cc1c[nH]c2ccccc12)NC(=O)[C@H](CCC(N)=O)NC(=O)CCCCNC(=O)c1ccc([18F])c(C#N)c1)C(C)C]

18F-fluoride (2475 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. A solution of 3-cyano-4-trimethylammoniumbenzoyl-Ava-Gln-Trp-Ala-Val-Gly-His-(4-amino-5-methyl-heptanoic acid)-Leu-NH$_2$ trifluoroacetate salt (2 mg) (which was synthesized by standard solid phase Fmoc-peptide methods described and cited, e.g., in the book: Chan and White—"Fmoc Solid Phase Peptide Synthesis—A Practical Approach") in anhydrous DMSO (150 μl) was added. After heating at 70° C. for 15 min. The reaction mixture was transferred to a vial containing water (4 ml). The reaction vial washed with 150 μl DMSO and this was also transferred to the vial containing water. This solution was transferred to a semi-prep HPLC (column: ACE 5μ C18, 250×10 mm, solvent A: H$_2$O+0.1% TFA, solvent B: MeCN/Water 9/1+0.1% TFA, gradient: 30% B for 5 min at 2 ml/min, then 30-70% B in 10 mins at 3 mL/min) and the desired F18 product peak was collected (253 MBq, 20.4% d.c.). The F-18 filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water: acetonitril gradient and 0.1% trifluoro acetic acid as co-solvent. The desired compound 40a was obtained in 28% yield (10.8 mg, 0.007 mmol).

MS-ESI: 1423 (M$^+$, 100), b) Synthesis of 3-Cyano-4-[18F]fluorobenzoyl-Arg-Ava-Gln-Trp-Ala-Val-Gly-His(πMe)-Sta-Leu-NH$_2$ (40b) (SEQ ID NO: 416)

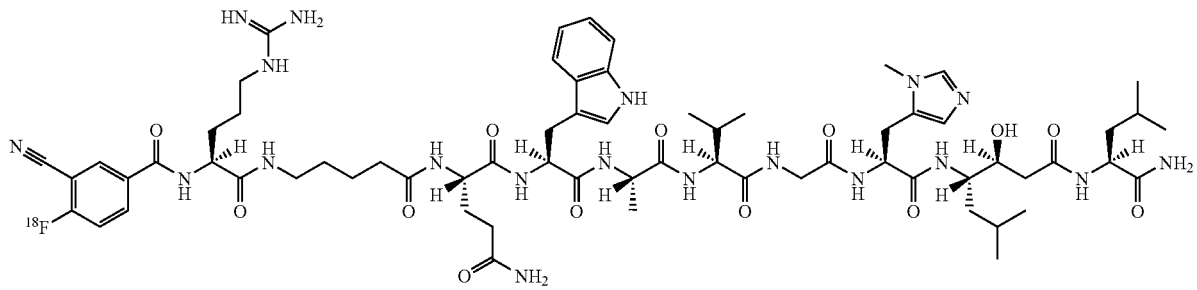 [SMILES: CC(C)C[C@H](NC(=O)C[C@H](O)[C@H](CC(C)C)NC(=O)[C@H](Cc1cncn1C)NC(=O)CNC(=O)[C@@H](NC(=O)[C@H](C)NC(=O)[C@H](Cc1c[nH]c2ccccc12)NC(=O)[C@H](CCC(N)=O)NC(=O)CCCCNC(=O)[C@H](CCCNC(=N)N)NC(=O)c1ccc([18F])c(C#N)c1)C(C)C)C(N)=O]

$^{18}$F-fluoride (2475 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. A solution of 3-cyano-4-trimethylammoniumbenzoyl-Arg-Ava-Gln-Trp-Ala-Val-Gly-His(3Me)-Sta-Leu-NH$_2$ trifluoroacetate salt (2 mg) (which was synthesized by standard solid phase Fmoc-peptide methods described and cited, e.g., in the book: Chan and White—"Fmoc Solid Phase Peptide Synthesis—A Practical Approach") in anhydrous DMSO (150 μl) was added. After heating at 70° C. for 15 min. The reaction mixture was transferred to a vial containing water (4 ml). The reaction vial washed with 150 μl DMSO and this was also transferred to the vial containing water. This solution was transferred to a semi-prep HPLC (column: ACE 5μ C18, 250×10 mm, solvent A: H$_2$O+0.1% TFA, solvent B: MeCN/Water 9/1+0.1% TFA, gradient: 30% B for 5 min at 2 ml/min, then 30-70% B in 10 mins at 3 ml/min) and the desired F18 product peak was collected (144 MBq, 11.5% d.c.). The F-18 labeled product was confirmed by co-injection with the F-19 cold standard on an analytical HPLC (Column ACE 3μ C18 50×4.6 mm, 1 ml/min (Agilent), solvent A: H2O+0.1% TFA, solvent B: MeCN/Water 9/1+0.1% TFA, gradient: 0% for 2 min, then 0% B to 95% B in 7 mins).

Example 41 a) Synthesis of 3-Cyano-4-(trimethylammonium)-benzoyl-Arg-βAla-Gln-Trp-Ala-Val-Gly-His(3Me)-Sta-Leu-NH$_2$ trifluoracetic acid salt (41a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.025 mmol Rink-resin-bound H-Arg-βAla-Gln-Trp-Ala-Val-Gly-His(3Me)-Sta-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water: acetonitril gradient and 0.1% trifluoro acetic acid as co-solvent. The desired compound 41a was obtained in 24% yield (9.0 mg, 0.006 mmol).

MS-ESI: 1394 (M$^+$, 100)

b) Synthesis of 3-cyano-4-[18F]fluorobenzoyl-Arg-βAla-Gln-Trp-Ala-Val-Gly-His(3Me)-Sta-Leu-NH$_2$ (41b)

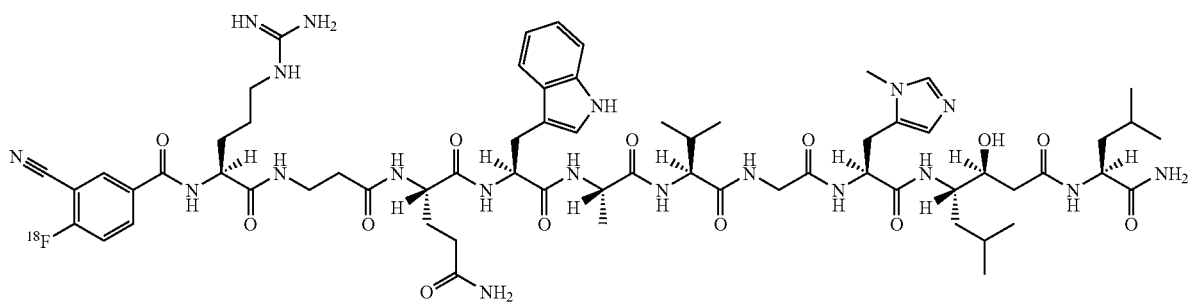 [SMILES: CC(C)C[C@H](NC(=O)C[C@H](O)[C@H](CC(C)C)NC(=O)[C@H](Cc1cncn1C)NC(=O)CNC(=O)[C@@H](NC(=O)[C@H](C)NC(=O)[C@H](Cc1c[nH]c2ccccc12)NC(=O)[C@H](CCC(N)=O)NC(=O)CCNC(=O)[C@H](CCCNC(=N)N)NC(=O)c1ccc([18F])c(C#N)c1)C(C)C)C(N)=O]

$^{18}$F-fluoride (1419 MBq) was azeotropically dried in the presence of Kryptofix 222 (5 mg in 1.5 ml MeCN) and potassium carbonate (1 mg in 0.5 ml water) by heating under nitrogen at 120° C. for 30 minutes. During this time 2×1 ml MeCN were added and evaporated. A solution of 3-cyano-4-trimethylammoniumbenzoyl-Arg-βAla-Gln-Trp-Ala-Val-Gly-His(3Me)-Sta-Leu-NH2 trifluoroacetate salt (2 mg)

preparative RP-18 HPLC-MS with a water:acetonitril gradient and 0.1% trifluoro acetic acid as co-solvent. The desired compound 42a was obtained in 32% yield (11.1 mg, 0.008 mmol).

MS-ESI: 1267 (M$^+$, 100)

b) Synthesis of 3-cyano-4-[18F]-fluorobenzoyl-Ava-Gln-Trp-Ala-Val-Gly-His(3Me)-Sta-Leu-NH$_2$ (42b)

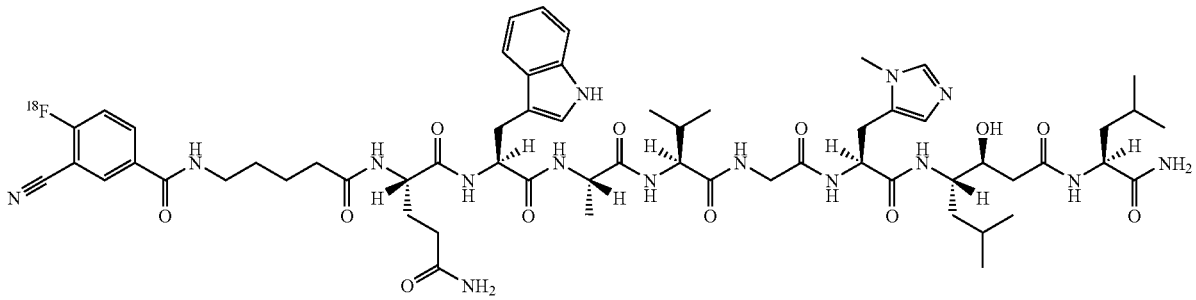 [SMILES: CC(C)C[C@H](NC(=O)C[C@H](O)[C@H](CC(C)C)NC(=O)[C@H](Cc1cncn1C)NC(=O)CNC(=O)[C@@H](NC(=O)[C@H](C)NC(=O)[C@H](Cc1c[nH]c2ccccc12)NC(=O)[C@H](CCC(N)=O)NC(=O)CCCCNC(=O)c1ccc([18F])c(C#N)c1)C(C)C)C(N)=O]

(which was synthesized by standard solid phase Fmoc-peptide methods described and cited, e.g., in the book: Chan and White—"Fmoc Solid Phase Peptide Synthesis—A Practical Approach") in anhydrous DMSO (150 μl) was added. After heating at 50° C. for 15 min. The reaction mixture was diluted with water (4 ml) and transferred to a semi-prep HPLC (column: Zorbax Bonus 5μ C18, 250×9.2 mm, solvent A: H2O+ 0.1% TFA, solvent B: MeCN/Water 9/1+0.1% TFA, gradient: 29-34% B in 20 mins at 3 ml/min) and the desired F18 product peak was collected (150 MBq, 21.1% d.c.). The F-18 labeled product was confirmed by co-injection with the F-19 cold standard on an analytical HPLC (Column Zorbax Bonus 5μ C18 250×4.6 mm, 1 ml/min (Agilent), solvent A: H2O+0.1% TFA, solvent B: MeCN/Water 9/1+0.1% TFA, gradient: 29% B to 34% B in 20 mins).

Example 42 a) Synthesis of 3-Cyano-4-(trimethylammonium)-benzoyl-Ava-Gln-Trp-Ala-Val-Gly-His(3Me)-Sta-Leu-NH$_2$ trifluoracetic acid salt (42a)

To a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.025 mmol Rink-resin-bound H-Arg-βAla-Gln-Trp-Ala-Val-Gly-His(3Me)-Sta-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 70.8 mg (0.2 mmol) 2e in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by 18F-fluoride (869 MBq) was azeotropically dried in the presence of Kryptofix 222 (5 mg in 1.5 ml MeCN) and potassium carbonate (1 mg in 0.5 ml water) by heating under nitrogen at 120° C. for 30 minutes. During this time 2×1 ml MeCN were added and evaporated. A solution of 3-cyano-4-trimethylammoniumbenzoyl-Ava-Gln-Trp-Ala-Val-Gly-His(3Me)-Sta-Leu-NH2 trifluoroacetate salt (2 mg) (which was synthesized by standard solid phase Fmoc-peptide methods described and cited, e.g., in the book: Chan and White—"Fmoc Solid Phase Peptide Synthesis—A Practical Approach") in anhydrous DMSO (150 μl) was added. After heating at 50° C. for 15 min. The reaction mixture was diluted with water (4 ml) and transferred to a semi-prep HPLC (column: Zorbax Bonus 5μ C18, 250×9.2 mm, solvent A: H2O+ 0.1% TFA, solvent B: MeCN/Water 9/1+0.1% TFA, gradient: 34-38% B in 20 mins at 3 ml/min) and the desired F18 product peak was collected (184 MBq, 37.8% d.c.). The F-18 labeled product was confirmed by co-injection with the F-19 cold standard on an analytical HPLC (Column Zorbax Bonus 5μ C18 250×4.6 mm, 1 ml/min (Agilent), solvent A: H2O+0.1% TFA, solvent B: MeCN/Water 9/1+0.1% TFA, gradient: 34% B to 38% B in 20 mins).

Example 43 a) Synthesis of 3-Trifluormethyl-4-(trimethylammonium)-benzoyl-Arg-Ava-Gln-Trp-Ala-Val-NMeGly-His(3Me)-Sta-Leu-NH$_2$ (43a)

To a stirred solution of 79.4 mg (0.2 mmol) 12c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to 0.025 mmol Rink-resin-bound H-Arg-βAla-Gln-Trp-Ala-Val-Gly-His(3Me)-Sta-Leu-NH$_2$ (loading 0.68 mmol/g) which was prepared by standard protocol. The mixture was shaken intensively for 4 h. The mixture was filtered and washed with dimethylformamide. The coupling step was repeated. Thus, to a stirred solution of 79.4 mg (0.2 mmol) 12c in 1.5 ml dichloromethane and 0.25 ml dimethylformamid was added 65 mg (0.5 mmol) diisopropylethylamin and 0.031 ml (0.2 mmol) diisopropylcarbodiimid. The solution was added to the washed Rink-resin-bound peptide and the mixture was again shaken intensively for 4 h. The mixture was filtered and washed extensively with dimethylformamide and dichloromethane. The resin was treated with a mixture of 0.85 ml trifluoroacetic acid, 0.05 ml distilled water, 0.05 ml phenol, 0.05 ml triisopropylsilane for 3 h. The mixture was added in ca. 9 ml ice cold methyl tert-butyl ether. The solid was separated by centrifugation. Water was added to the solid and the supernatant was liophylized. The residue was purified by preparative RP-18 HPLC-MS with a water: acetonitril gradient and 0.1% trifluoro acetic acid as co-solvent. The desired compound 43a was obtained in 29% yield (11.5 mg, 0.0072 mmol).

MS-ESI: 1480 (M+, 100)

b) Synthesis of 3-trifluoromethyl-4-[18F]-fluorobenzoyl-Arg-Ava-Gln-Trp-Ala-Val-NMeGly-His(3Me)-Sta-Leu-NH$_2$ (43b)

stirred for 30 min at room temperature. A solution of 794 mg (2 mmol) 12c, 650 mg (5 mmol) diisopropylethylamin and 0.31 ml (2.0 mmol) diisopropylcarbodiimid which was strirred in 8 ml DMF was added. The reaction mixture was stirred for 4 hours at room temperature and reduced with high vacuum rotation evaporator at 65° C. The residue was diluted with diethyl ether and filtered. The filter cake solid was purified by RP column chromatography (MeCN:water) to obtain 44a in 25% yield (163 mg, 0.25 mmol) after lyophilisation.

MS-ESI: 505 (M+, 100)

Elementary analysis:

| Calculated: | C | 55.04% | H | 4.31% | N | 8.56% |
| Determined: | C | 55.02% | H | 4.32% | N | 8.55% |

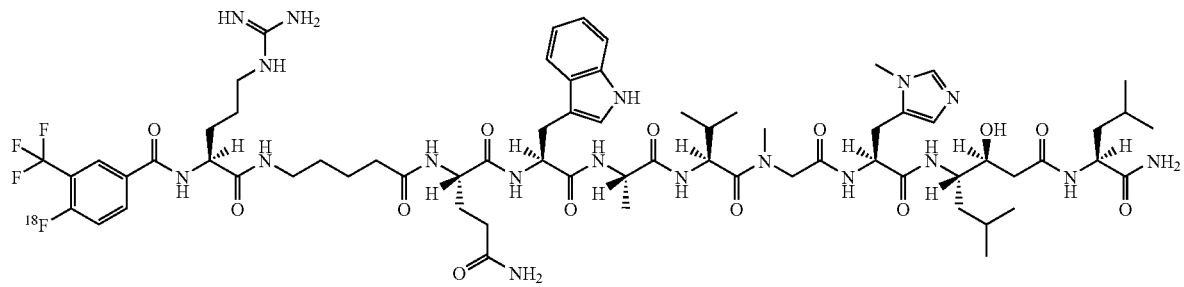 [SMILES: CC(C)C[C@H](NC(=O)C[C@H](O)[C@H](CC(C)C)NC(=O)[C@H](Cc1cncn1C)NC(=O)CN(C)C(=O)[C@@H](NC(=O)[C@H](C)NC(=O)[C@H](Cc1c[nH]c2ccccc12)NC(=O)[C@H](CCC(N)=O)NC(=O)CCCCNC(=O)[C@H](CCCNC(=N)N)NC(=O)c1ccc([18F])c(C(F)(F)F)c1)C(C)C)C(N)=O]

18F-fluoride (835 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. A solution of 3-trifluoromethyl-4-trimethylammoniumbenzoyl-Arg-Ava-Gln-Trp-Ala-Val-NMeGly-His(3Me)-Sta-Leu-NH$_2$ trifluoroacetate salt (2 mg) (which was synthesized by standard solid phase Fmoc-peptide methods described and cited, e.g., in the book: Chan and White—"Fmoc Solid Phase Peptide Synthesis—A Practical Approach") in anhydrous DMSO (150 µl) was added. After heating at 70° C. for 15 min the reaction mixture was diluted with water (4 ml) and transferred to a semi-prep HPLC (column: ACE 5µ C18 250×10 mm, solvent A: H$_2$O+0.1% TFA, solvent B: MeCN/Water 9/1+0.1% TFA, gradient: 20% for 2 min, then 20-60% B in 20 mins at 3 ml/min) and the desired F18 product peak was collected (78 MBq, 29.0% d.c.). The F-18 labeled product was confirmed by co-injection with the F-19 cold standard on an analytical HPLC (Column ACE C18, 50×4.6 mm, 3µ, 2 ml/min, solvent A: 10 mM K$_2$HPO$_4$ in H$_2$O, solvent B: 10 mM K$_2$HPO$_4$ in MeCN/H$_2$O (7:3), gradient: 5%-95% B in 7 mins).

Example 44 a) Synthesis of Trifluoro-methanesulfonate[4-(1-benzyl-2,3-dihydro-1H-pyrrolo[2,3-b]quinolin-4-ylcarbamoyl)-2-trifluoromethyl-phenyl]trimethyl-ammonium (44a)

To a suspension 30 mg (1.3 mmol) sodium hydride in 2 ml dry THF 275 mg (1 mmol) 1-Benzyl-2,3-dihydro-1H-pyrrolo [2,3-b]quinolin-4-ylamine (J. Med. Chem. 2004, 47, 1413) in 1 ml dry THF were added drop wisely. The solution was b) Synthesis of [F-19]-N-(1-Benzyl-2,3-dihydro-1H-pyrrolo[2,3-b]quinolin-4-yl)-4-fluoro-3-trifluoromethyl-benzamide (44b)

To a Wheaton vial (5 ml) charged with Kryptofix 222 (5 mg), potassium carbonate (1 mg in 500 µl water) and MeCN (1.5 ml) the fluorine containing water (364 MBq, 35 µl) was added. The solvent was removed by heating at 120° C. for 10 mins under a stream of nitrogen. Anhydrous MeCN (1 ml) was added and evaporated as before. This step was repeated again. A solution of 44a (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 44b was confirmed by co-injection with the non-radioactive F-19 fluoro standard (J. Med. Chem. 2004, 47, 1413-1422) on the Econsphere analytical HPLC.

Example 45 a) Synthesis of trimethyl-(2-nitro-4-{2-[(2-pyridin-2-yl-quinoline-4-carbonyl)-amino]-ethylcarbamoyl}-phenyl)trifluoro-methanesulfonate ammonium salt (45a)

To a solution of 328 mg (1 mmol) 2-[(2-Pyridin-2-yl-quinoline-4-carbonyl)-amino]-ethyl-ammonium chloride (Tetrahedron, (2004), 8729-8738) and 325 mg (2.5 mmol) diisopropylethylamine was added a solution of 748 mg (2 mmol) 12c, 650 mg (5 mmol) diisopropylethylamin and 0.31 ml (2.0 mmol) diisopropylcarbodiimid which was strirred in 8 ml DMF 20 min before. The reaction mixture wast stirred for 20 hours and was concentrated in vacuum. The residue was treated with diethyl ether—the supernatant was decanted and the solid was solved in water-acetonitrile. The product was purified by RP-column chromatography. The desired product 45a was obtained in 31% yield (201 mg, 0.31 mmol).

MS-ESI: 500 (M+, 100)

Elementary analysis:

| Calculated: | C | 51.85% | H | 4.20% | N | 12.96% |
|---|---|---|---|---|---|---|
| Determined: | C | 51.86% | H | 4.19% | N | 12.95% | b) Synthesis of [F-18]-2-Pyridin-2-yl-quinoline-4-carboxylic acid[2-(4-fluoro-3-nitro-benzoylamino)-ethyl]-amide (45b)

To a Wheaton vial (5 ml) charged with Kryptofix 222 (5 mg), potassium carbonate (1 mg in 500 µl water) and MeCN (1.5 ml) the fluorine containing water (387 MBq, 35 µl) was added. The solvent was removed by heating at 120° C. for 10 mins under a stream of nitrogen. Anhydrous MeCN (1 ml) was added and evaporated as before. This step was repeated again. A solution of 45a (2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H2O, solvent B: MeCN, gradient: 5%-95% B in 7 mins or Column Econsphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 45b was confirmed by co-injection with the non-radioactive F-19 fluoro standard (Tetrahedron 60 (2004) 8729-8738) on the Econsphere analytical HPLC.

Example 46 a) Synthesis of Trifluoro-methanesulfonate{2-fluoro-4-[4'-((S)-1-methoxycarbonyl-2-methyl-propylsulfamoyl)-biphenyl-4-ylcarbamoyl]-phenyl}-trimethyl-ammonium (46a)

To a solution of 362 mg (1 mmol) (S)-2-(4'-Amino-biphenyl-4-sulfonylamino)-3-methyl-butyric acid methyl ester (WO2007/16538A2) and 325 mg (2.5 mmol) diisopropylethylamine was added a solution of 694 mg (2 mmol) 3c, 650 mg (5 mmol) diisopropylethylamin and 0.31 ml (2.0 mmol) diisopropylcarbodiimid which was strirred for 20 min in 8 ml DMF before. The reaction mixture was stirred for 20 hours and was concentrated in vacuum. The residue was treated with diethyl ether; the supernatant was decanted and the solid crode product was solved in water-acetonitrile. The product was purified by RP-column chromatography. The desired product 46a was obtained in 38% yield (263 mg, 0.38 mmol).

MS-ESI: 543 (M+, 100)

Elementary analysis:

| Calculated: | C | 50.36% | H | 4.81% | N | 6.07% |
|---|---|---|---|---|---|---|
| Determined: | C | 50.38% | H | 4.80% | N | 6.07% | b) Synthesis of [F-18]-(S)-2-[4'-(3,4-Difluoro-benzoylamino)-biphenyl-4-sulfonylamino]-3-methyl-butyric acid methyl ester (46b)

To a Wheaton vial (5 ml) charged with Kryptofix 222 (5 mg), potassium carbonate (1 mg in 500 µl water) and MeCN (1.5 ml) the fluorine containing water (321 MBq, 35 µl) was added. The solvent was removed by heating at 120° C. for 10 mins under a stream of nitrogen. Anhydrous MeCN (1 ml) was added and evaporated as before. This step was repeated again. A solution of 46a (2 mg) in anhydrous DMSO (300 µl) was added. After heating at 50° C. for 15 min. The crude reaction mixture was analyzed using an analytical HPLC (Column Zorbax SB C18, 50×4.6 mm, 2 ml/min, solvent A: H2O, solvent B: MeCN, gradient: 5%-95% B in 7 mins or Column Econosphere C18, 53×7 mm, 3µ, 3 ml/min (Alltech), solvent A: H2O+0.1% TFA, solvent B: MeCN/Water 9/1+0.1% TFA, gradient: 5-95% B in 7 mins. The F-18 labeled product 46b was confirmed by co-injection with the non-radioactive F-19 fluoro standard (Tetrahedron 60 (2004) 8729-8738) on the Econsphere analytical HPLC.

Example 47

Synthesis of [F-18](4-fluoro-3-cyano-benzoyl)-TTA1 (47)

To a stirred solution of 70.8 mg (0.2 mmol) 2e in 0.25 ml acetonitril was added 33 mg (0.25 mmol) diisopropylethylamin and 66 mg (0.2 mmol) 4-(4,6-dimethoxy-1,3,5-triazin-2-yl)-4-methylpiperidinium tetrafluoroborate (J. Am. Chem. Soc. 2005, 127, 48, 16912-16920). The reaction was stirred for 40 min. Five microliters of the reaction solution were added without further purification to 1.2 mg (100 nmol) TTA1 (Nucleic Acids Research, 2004, Vol. 32, No. 19, 5757-5765) dissolved in 20 µl buffer (pH ~7). A solution of citric acid was added (pH ~6). After incubation for 1 hr at 37° C., the product was purified by spin-filtration using a spin filter with a 10 kDa cut-off membrane (Microcon® MY-10, Amicon bioseparations). The residue on the filter was washed three times with acidified water (pH ~6-citric acid). The purity was determined by HPLC analyses.

To a Wheaton vial (5 ml) charged with Kryptofix 222 (5 mg), potassium carbonate (1 mg in 500 µl water) and MeCN (1.5 ml) the fluorine containing water (316 MBq, 33 µl) were added. The solvent was removed by heating at 120° C. for 10 mins under a stream of nitrogen. Anhydrous MeCN (1 ml) was added and evaporated as before. This step was repeated again.

The above mentioned TTA1-trimethylammonium-solution was added. After heating at 80° C. for 15 min. The crude reaction mixture was analyzed using an analytical HPLC (Column Zorbax SB C18, 50×4.6 mm, 1.8µ, 2 ml/min, solvent A: H₂O, solvent B: MeCN, gradient: 0.1%-25% B in 7 mins or Column Econosphere C18, 53×7 mm, 3µ, 3 ml/min (Alltech), solvent A: H₂O+0.1% TFA, solvent B: MeCN/Water 1/1+0.1% TFA, gradient: 0.1-25% B in 7 mins. The F-18 labeled product was approached by co-injection with the cold F-19 fluoro standard on the Econsphere analytical HPLC.

Example A1

Radiosynthesis of Methyl 3-Cyano-4-[$^{18}$F]fluorobenzoate

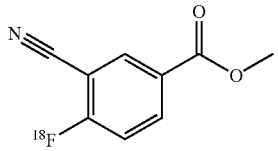

$^{18}$F-fluoride (63 MBq) was azeotropically dried in the presence of Kryptofix 222 (5 mg in 1.5 ml MeCN) and potassium carbonate (1 mg in 0.5 ml water) by heating under nitrogen at 120° C. for 30 minutes. During this time 2×1 ml MeCN were added and evaporated. After drying, a 0.04M solution of methyl 3-cyano-4-trimethylammoniumbenzoate triflate salt in 300 μl DMSO was added. The reaction vessel was sealed and heated at 50° C. for 15 mins to effect labeling. The crude reaction mixture was analyzed using an analytical HPLC (Column ACE C18, 50×4.6 mm, 3μ, 2 ml/min, solvent A: 10 mM K$_2$HPO$_4$ in H$_2$O, solvent B: 10 mM K$_2$HPO$_4$ in MeCN/H$_2$O (7:3), gradient: 5%-95% B in 7 mins), the incorporation yield was 93.5%. The F-18 labeled product was confirmed by co-injection with the F-19 cold standard on an analytical HPLC (Column Altech Econsphere C18 RP, 53×7 mm, 3μ, 3 ml/min (Agilent), solvent A: H$_2$O+0.1% TFA, solvent B: MeCN/Water 9/1+0.1% TFA, gradient: 5% B to 95% B in 7 mins).

Example B1

Radiosynthesis of Methyl 3-Trifluoromethyl-4-[$^{18}$F]fluorobenzoate

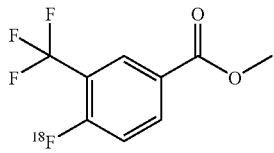

$^{18}$F-fluoride (73 MBq) was azeotropically dried in the presence of Kryptofix 222 (5 mg in 1.5 ml MeCN) and potassium carbonate (1 mg in 0.5 ml water) by heating under nitrogen at 120° C. for 30 minutes. During this time 2×1 ml MeCN were added and evaporated. After drying, a 0.04M solution of methyl 3-trifluoromethyl-4-trimethylammoniumbenzoate triflate salt in 300 μl DMSO was added. The reaction vessel was sealed and heated at 50° C. for 15 mins to effect labeling. The crude reaction mixture was analyzed using an analytical HPLC (Column ACE C18, 50×4.6 mm, 3μ, 2 mVmin, solvent A: 10 mM K$_2$HPO$_4$ in H$_2$O, solvent B: 10 mM K$_2$HPO$_4$ in MeCN/H$_2$O (7:3), gradient: 5%-95% B in 7 mins), the incorporation yield was 86.6%. The F-18 labeled product was confirmed by co-injection with the F-19 cold standard on an analytical HPLC (Column Zorbax SB, 50×4.6 mm, 1.8μ, 3 ml/min (Agilent), solvent A: H$_2$O+0.1% TFA, solvent B: MeCN/Water 9/1+0.1% TFA, gradient: 5% B to 95% B in 7 mins).

Example C1

Radiosynthesis of Methyl 2-Chloro-4-[$^{18}$F]fluorobenzoate

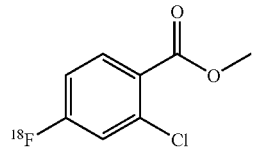

$^{18}$F-fluoride (307 MBq) was azeotropically dried in the presence of Kryptofix 222 (5 mg in 1.5 ml MeCN) and potassium carbonate (1 mg in 0.5 ml water) by heating under nitrogen at 120° C. for 30 minutes. During this time 2×1 ml MeCN were added and evaporated. After drying, a solution of 1 mg methyl 2-chloro-4-trimethylammoniumbenzoate triflate salt in 100 μl DMSO was added. The reaction vessel was sealed and heated at 50° C. for 15 mins to effect labeling. The crude reaction mixture was analyzed using an analytical HPLC (Column ACE C18, 50×4.6 mm, 3μ, 2 ml/min, solvent A: 10 mM K$_2$HPO$_4$ in H$_2$O, solvent B: 10 mM K$_2$HPO$_4$ in MeCN/H$_2$O (7:3), gradient: 5%-95% B in 7 mins), the incorporation yield was 70.0%. The F-18 labeled product was confirmed by co-injection with the F-19 cold standard on an analytical HPLC (Column Zorbax SB, 250×4.6 mm, 5μ, 1 mL/min (Agilent), solvent A: H$_2$O+0.1% TFA, solvent B: MeCN/Water 9/1+0.1% TFA, gradient: 5% B to 95% B in 7 mins).

Figure 9:
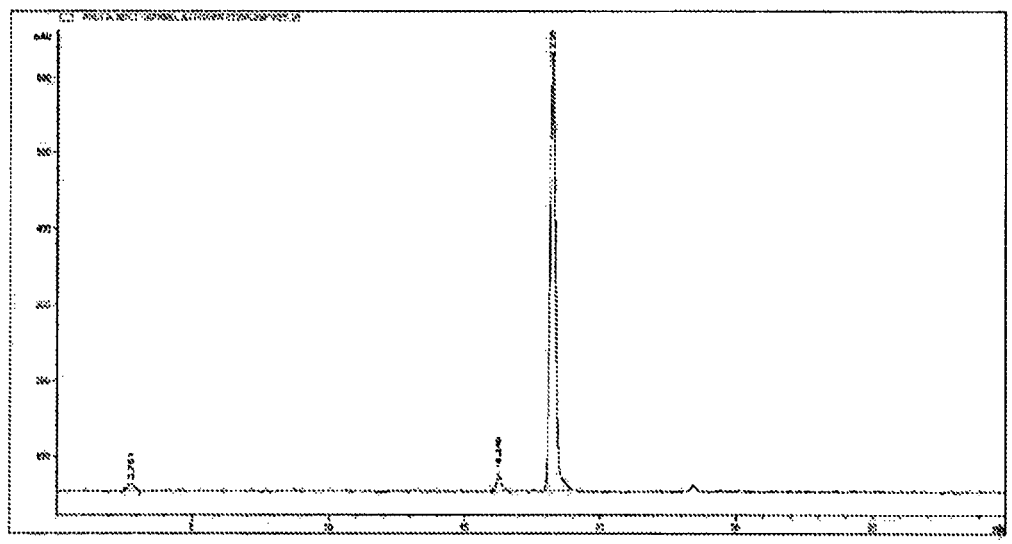
Figure 9:
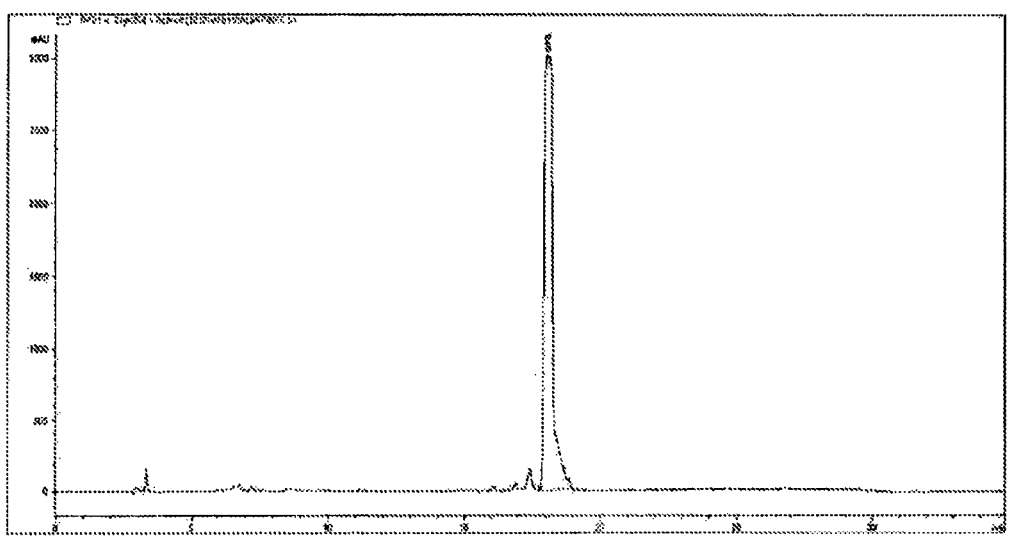

FIG. 9: HPLC chromatogram of reaction mixture with co-injection of the cold standard

Example D1

Radiosynthesis of Methyl 2-Fluoro-4-[$^{18}$F]fluorobenzoate

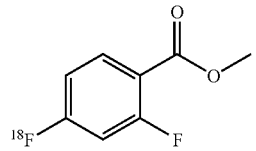

$^{18}$F-fluoride (839 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. After drying, a solution of 1 mg methyl 2-fluoro-4-trimethylammoniumbenzoate triflate salt in 100 μl DMSO was added. The reaction vessel was sealed and heated at 70° C. for 15 mins to effect labeling. The crude reaction mixture was analyzed using an analytical HPLC (Column ACE C18, 50×4.6 mm, 3μ, 2 ml/min, solvent A: 10 mM K$_2$HPO$_4$ in H$_2$O, solvent B: 10 mM K$_2$HPO$_4$ in MeCN/H$_2$O (7:3), gradient: 5%-95% B in 7 mins), the incorporation yield was 86.1%. The F-18 labeled product was confirmed by co-injection with the F-19 cold standard on an analytical HPLC (Column Zorbax SB, 250×4.6 mm, 5μ, 1 mL/min (Agilent), solvent A: H₂O+0.1% TFA, solvent B: MeCN/Water 9/1+0.1% TFA, gradient: 5% B to 95% B in 7 mins).

Example E

Radiosynthesis of Methyl 3-Fluoro-4-[$^{18}$F]fluorobenzoate

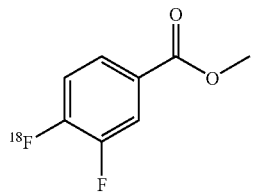

$^{18}$F-fluoride (751 MBq) was azeotropically dried in the presence of Kryptofix 222 (5 mg in 1.5 ml MeCN) and potassium carbonate (1 mg in 0.5 ml water) by heating under nitrogen at 120° C. for 30 minutes. During this time 2×1 ml MeCN were added and evaporated. After drying, a solution of 1 mg methyl 3-fluoro-4-trimethylammoniumbenzoate triflate salt in 100 μl DMSO was added. The reaction vessel was sealed and heated at 50° C. for 15 mins to effect labeling. The crude reaction mixture was analyzed using an analytical HPLC (Column Zorbax SB C18, 50×4.6 mm, 1.8μ, 2 ml/min, solvent A: H₂O, solvent B: water, gradient: 5%-95% B in 7 mins), the incorporation yield was 85.4%.

Example F1

Radiosynthesis of Methyl (3-Cyano-4-[$^{18}$F]fluorobenzenesulfonylamino)-acetate

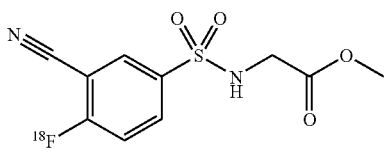 [SMILES: COC(=O)CNS(=O)(=O)c1ccc([18F])c(C#N)c1]

$^{18}$F-fluoride (123 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. After drying, a solution of 1 mg methyl (3-cyano-4-trimethylammoniumbenzenesulfonylamino)-acetate triflate salt in 300 μl DMSO was added. The reaction vessel was sealed and heated at 70° C. for 15 mins to effect labeling. The crude reaction mixture was analyzed using an analytical HPLC (Column ACE C18, 50×4.6 mm, 3μ, 2 ml/min, solvent A: 10 mM K₂HPO₄ in H₂O, solvent B: 10 mM K₂HPO₄ in MeCN/H₂O (7:3), gradient: 5%-95% B in 7 mins), the incorporation yield was 77.6%.

Example G1

Radiosynthesis of 3-cyano-4-[$^{18}$F]fluorobenzoyl-D-Ala-D-Phe-NH₂

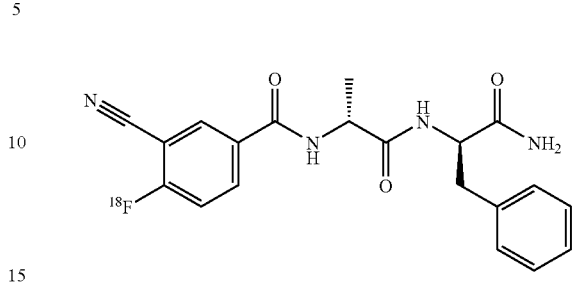

To a Wheaton vial (5 ml) charged with Kryptofix 222 (5 mg), potassium carbonate (1 mg in 500 μl water) and MeCN (1.5 ml) the fluorine containing water (1160 MBq, 80 μl) were added. The solvent was removed by heating at 120° C. for 10 mins under a stream of nitrogen. Anhydrous MeCN (1 ml) was added and evaporated as before. This step was repeated again. A solution of 3-cyano-4-trimethylammoniumbenzoyl-D-Ala-D-Phe-NH₂ trifluoroacetate salt (2 mg) in anhydrous DMSO (300 μl) was added. After heating at 50° C. for 15 min. The reaction was cooled to room temperature and dilute with water (2.7 ml). The crude reaction mixture was analyzed using an analytical HPLC (Column ACE C18, 50×4.6 mm, 3μ, 2 ml/min, solvent A: 10 mM K₂HPO₄ in H₂O, solvent B: 10 mM K₂HPO₄ in MeCN/H₂O (7:3), gradient: 5%-95% B in 7 mins). The product was obtained by preparative radio HPLC to give 301 MBq (51% d.c.) [column: Phenomenex Luna C18, 250×10 mm, 5μ, solvent A: H₂O+0.1% TFA, solvent B: MeCN/Water 9/1+0.1% TFA, gradient: 5% B for 5 min at 2 ml/min, 5% B for 1 min at 3 ml/min, then 5-60% B in 19 mins at 3 ml/min].

Example H1

Radiosynthesis of 3-cyano-4-[$^{18}$F]fluorobenzoyl-Val-βAla-Phe-Gly-NH₂

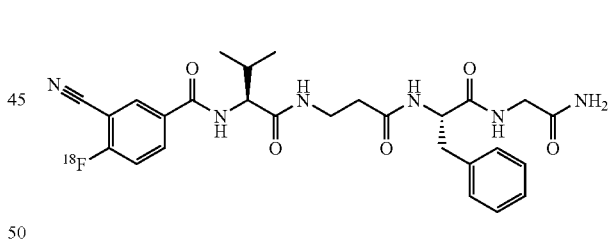

To a Wheaton vial (5 ml) charged with Kryptofix 222 (5 mg), potassium carbonate (1 mg in 500 μl water) and MeCN (1.5 ml) the fluorine containing water (454 MBq, 50 μl) were added. The solvent was removed by heating at 120° C. for 10 mins under a stream of nitrogen. Anhydrous MeCN (1 ml) was added and evaporated as before. This step was repeated again. A solution of 3-cyano-4-trimethylammoniumbenzoyl-Val-Ala-Phe-Gly-NH₂ trifluoroacetate salt (2 mg) in anhydrous DMSO (300 μl) was added. After heating at 50° C. for 15 min. The crude reaction mixture was analyzed using an analytical HPLC (Column Zorbax SB C18, 50×4.6 mm, 1.8μ, 2 ml/min, solvent A: H₂O, solvent B: MeCN, gradient: 5%-95% B in 7 mins or Column Econosphere C18, 53×7 mm, 3μ, 3 ml/min (Alltech), solvent A: H₂O+0.1% TFA, solvent B: MeCN/Water 9/1+0.1% TFA, gradient: 5-95% B in 7 mins). The F-18 labeled product was confirmed by co-injection with the F-19 cold standard on the Econsphere analytical HPLC.

Example I1

Radiosynthesis of 3-cyano-4-[18F]fluorobenzoyl-Val-βAla-Ara-Gly-NH₂

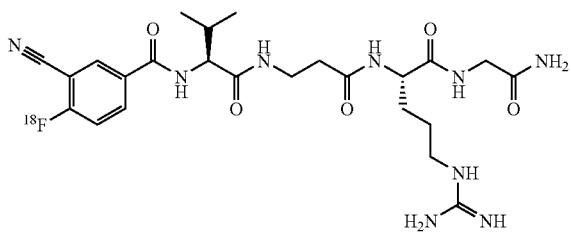 [SMILES: CC(C)[C@H](NC(=O)c1ccc([18F])c(C#N)c1)C(=O)NCCC(=O)N[C@@H](CCCNC(=N)N)C(=O)NCC(N)=O]

To a Wheaton vial (5 ml) charged with Kryptofix 222 (5 mg), potassium carbonate (1 mg in 500 µl water) and MeCN (1.5 ml) the fluorine containing water (316 MBq, 33 µl) were added. The solvent was removed by heating at 120° C. for 10 mins under a stream of nitrogen. Anhydrous MeCN (1 ml) was added and evaporated as before. This step was repeated again. A solution of 3-cyano-4-trimethylammoniumbenzoyl-Val-βAla-Arg-Gly-NH₂ (SEQ ID NO: 24) trifluoroacetate salt (ZK6005341, 2 mg) in anhydrous DMSO (300 µl) was added. After heating at 50° C. for 15 min. The crude reaction mixture was analyzed using an analytical HPLC (Column Zorbax SB C18, 50×4.6 mm, 1.8µ, 2 ml/min, solvent A: H₂O, solvent B: MeCN, gradient: 5%-95% B in 7 mins or Column Econosphere C18, 53×7 mm, 3µ, 3 ml/min (Alltech), solvent A: H₂O+0.1% TFA, solvent B: MeCN/Water 9/1+0.1% TFA, gradient: 5-95% B in 7 mins.

Example J1

Radiosynthesis of 3-cyano-4-[¹⁸F]fluorobenzoyl-Val-βAla-His(Me)-Gly-NH₂

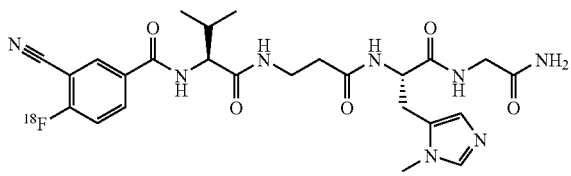 [SMILES: CC(C)[C@H](NC(=O)c1ccc([18F])c(C#N)c1)C(=O)NCCC(=O)N[C@@H](Cc1cncn1C)C(=O)NCC(N)=O]

¹⁸F-fluoride (123 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. After drying, a solution of 3-cyano-4-trimethylammoniumbenzoyl-Val-βAla-Arg-Gly-NH₂ (SEQ ID NO: 26) trifluoroacetate salt (ZK6012623, 2 mg) in anhydrous DMSO (300 µl) was added. After heating at 70° C. for 5 min. The crude reaction mixture was analyzed using an analytical HPLC (Column ACE C18, 50×4.6 mm, 3µ, 2 ml/min, solvent A: 10 mM K₂HPO₄ in H₂O, solvent B: 10 mM K₂HPO₄ in MeCN/H₂O (7:3), gradient: 5%-95% B in 7 mins), the incorporation yield was 77.0%. The F-18 labeled product was confirmed by co-injection with the F-19 cold standard on the same analytical column for analyzing the reaction mixture.

Figure 10:
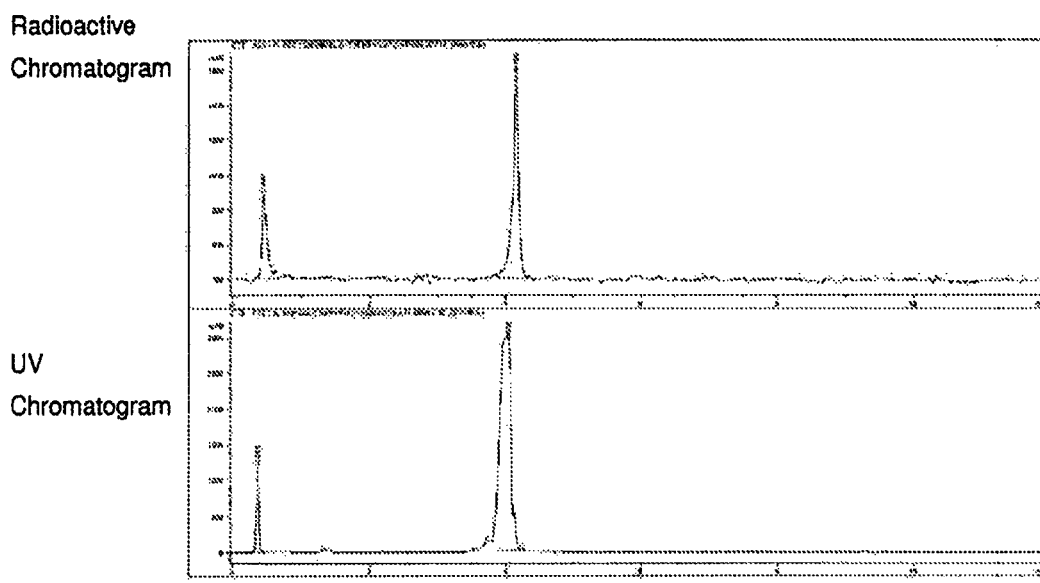
FIG. 10 shows HPLC chromatograms of reaction mixture with co-injection of the cold standard.

FIG. 10: HPLC chromatogram of reaction mixture with co-injection of the cold standard

Example K1

Radiosynthesis of 3-cyano-4-[¹⁸F]fluorobenzoyl-Ava-Gln-Trp-Ala-Val-Gly-His-FA01010-Leu-NH₂

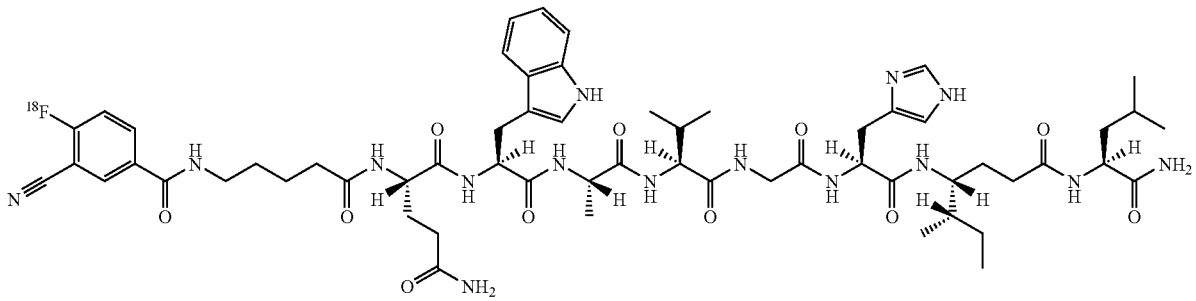 [SMILES: CC[C@H](C)[C@@H](CCC(=O)N[C@@H](CC(C)C)C(N)=O)NC(=O)[C@H](Cc1c[nH]cn1)NC(=O)CNC(=O)[C@@H](NC(=O)[C@H](C)NC(=O)[C@H](Cc1c[nH]c2ccccc12)NC(=O)[C@H](CCC(N)=O)NC(=O)CCCCNC(=O)c1ccc([18F])c(C#N)c1)C(C)C]

¹⁸F-fluoride (2475 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. A solution of 3-cyano-4-trimethylammoniumbenzoyl-Ava-Gln-Trp-Ala-Val-Gly-His-FA01010-Leu-NH₂ trifluoroacetate salt (2 mg) in anhydrous DMSO (150 µl) was added. After heating at 70° C. for 15 min. The reaction mixture was transferred to a vial containing water (4 ml). The reaction vial washed with 150 µl DMSO and this was also transferred to the vial containing water. This solution was transferred to a semi-prep HPLC (column: ACE 5µ C18, 250×10 mm, solvent A: H₂O+0.1% TFA, solvent B: MeCN/Water 9/1+0.1% TFA, gradient: 30% B for 5 min at 2 ml/min, then 30-70% B in 10 mins at 3 ml/min) and the desired F18 product peak was collected (253 MBq, 20.4% d.c.). The F-18 labeled product was confirmed by co-injection with the F-19 cold standard on an analytical HPLC (Column ACE 3µ C18 50×4.6 mm, 1 ml/min (Agilent), solvent A: H₂O+0.1% TFA, solvent B: MeCN/Water 9/1+0.1% TFA, gradient: 0% for 2 min, then 0% B to 95% B in 7 mins).

Figure 11:
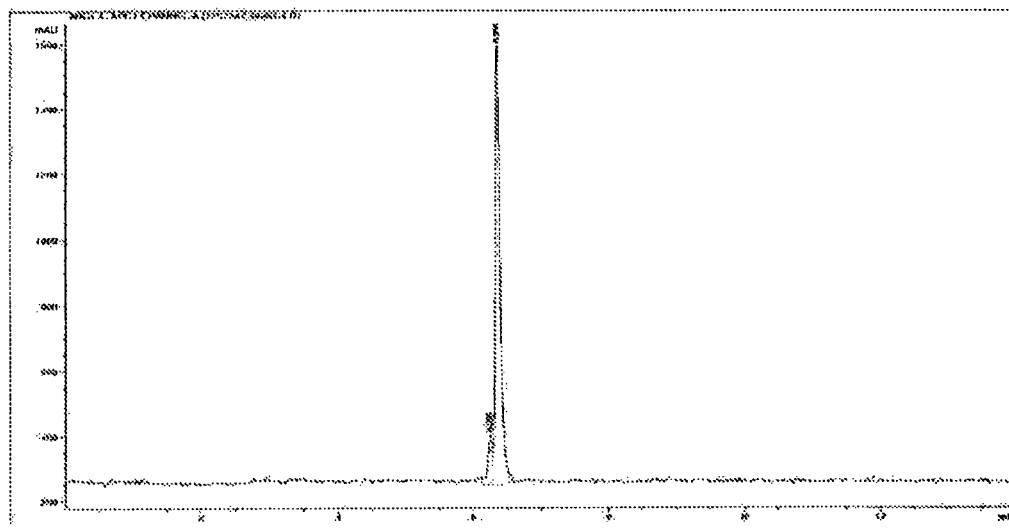
FIG. 11: shows HPLC chromatograms of reaction mixture with co-injection of the cold standard.
Figure 11:
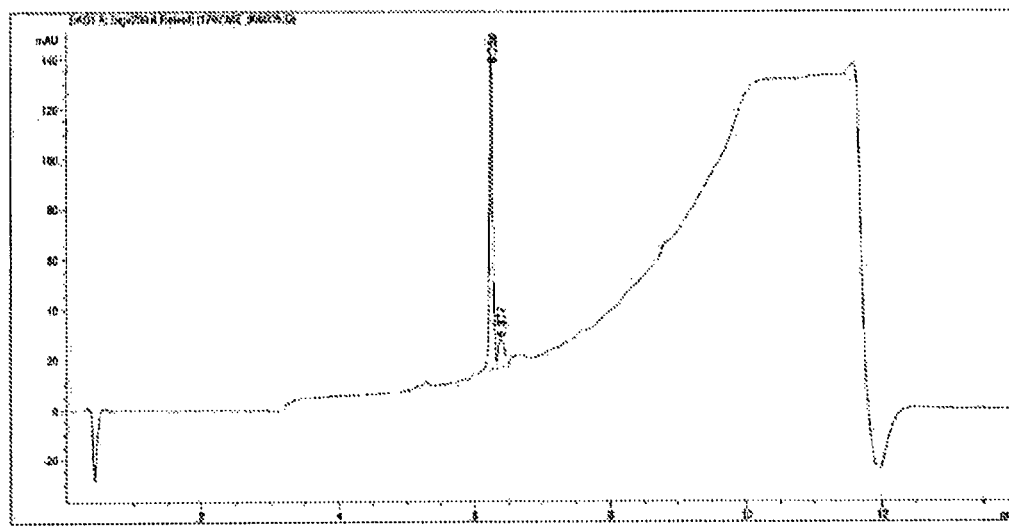

FIG. 11: HPLC chromatogram of reaction mixture with co-injection of the cold standard

Example L1

Radiosynthesis of 3-cyano-4-[¹⁸F]fluorobenzoyl-Arg-Ava-Gln-Trp-Ala-Val-Gly-His(3Me)-Sta-Leu-NH₂

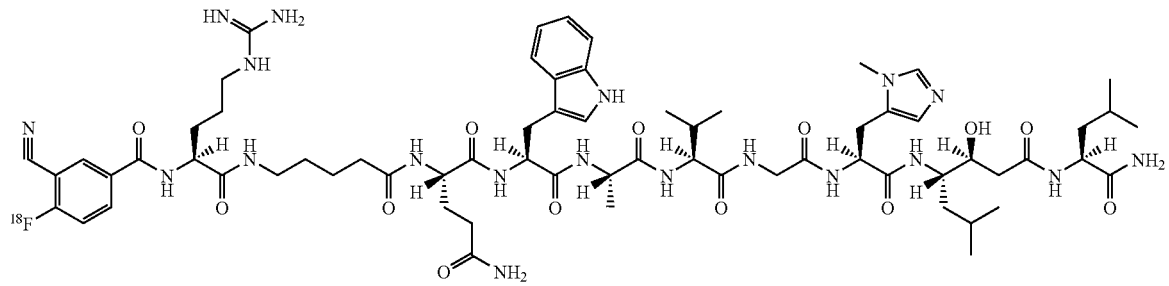 [SMILES: CC(C)C[C@H](NC(=O)C[C@H](O)[C@H](CC(C)C)NC(=O)[C@H](Cc1cncn1C)NC(=O)CNC(=O)[C@@H](NC(=O)[C@H](C)NC(=O)[C@H](Cc1c[nH]c2ccccc12)NC(=O)[C@H](CCC(N)=O)NC(=O)CCCCNC(=O)[C@H](CCCNC(=N)N)NC(=O)c1ccc([18F])c(C#N)c1)C(C)C)C(N)=O]

¹⁸F-fluoride (2475 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. A solution of 3-cyano-4-trimethylammoniumbenzoyl-Arg-Ava-Gln-Trp-Ala-Val-Gly-His(3Me)-Sta-Leu-NH₂ trifluoroacetate salt (2 mg) in anhydrous DMSO (150 µl) was added. After heating at 70° C. for 15 min. The reaction mixture was transferred to a vial containing water (4 ml). The reaction vial washed with 150 µl DMSO and this was also transferred to the vial containing water. This solution was transferred to a semi-prep HPLC (column: ACE 5µ C18, 250×10 mm, solvent A: H₂O+0.1% TFA, solvent B: MeCN/Water 9/1+0.1% TFA, gradient: 30% B for 5 min at 2 ml/min, then 30-70% B in 10 mins at 3 ml/min) and the desired F18 product peak was collected (144 MBq, 11.5% d.c.). The F-18 labeled product was confirmed by co-injection with the F-19 cold standard on an analytical HPLC (Column ACE 3µ C18 50×4.6 mm, 1 ml/min (Agilent), solvent A: H₂O+0.1% TFA, solvent B: MeCN/Water 9/1+0.1% TFA, gradient: 0% for 2 min, then 0% B to 95% B in 7 mins).

Figure 12:
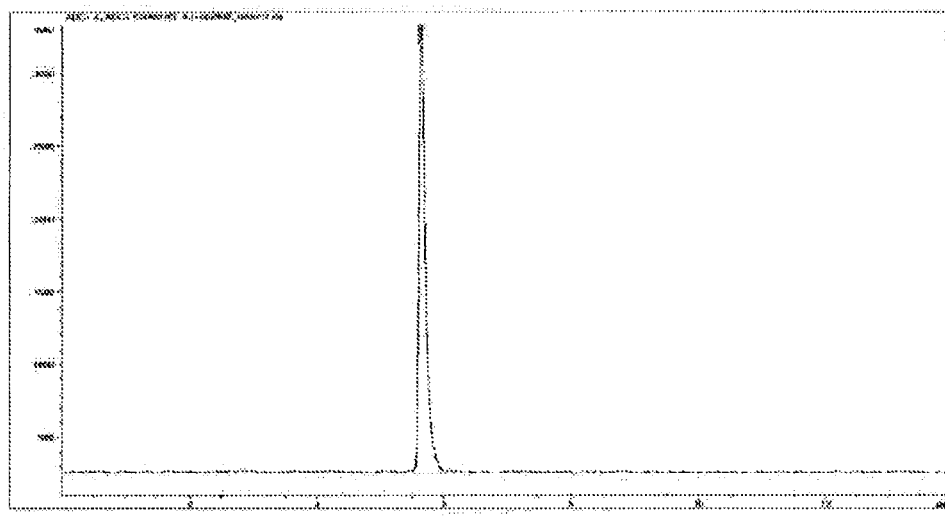
FIG. 12: shows HPLC chromatograms of reaction mixture with co-injection of the cold standard.
Figure 12:
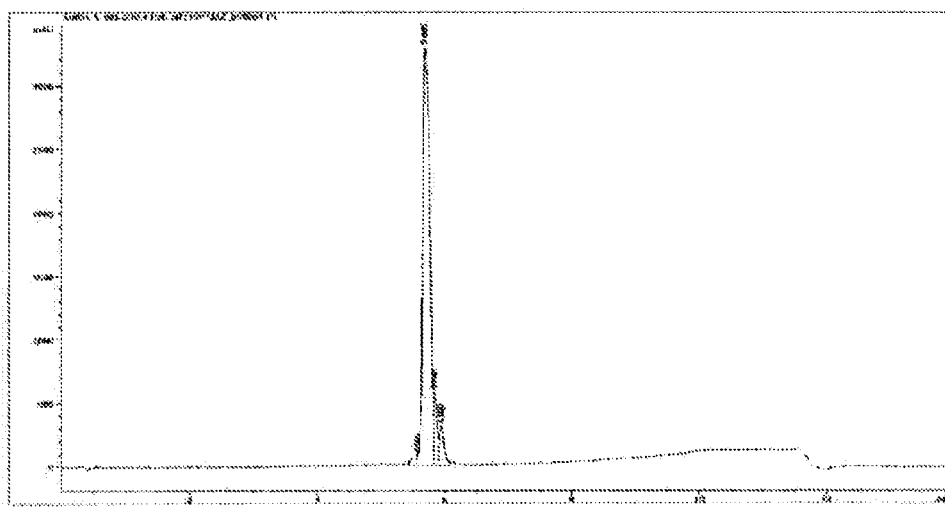

FIG. 12:HPLC chromatogram of reaction mixture with co-injection of the cold standard ¹⁸F-fluoride (1419 MBq) was azeotropically dried in the presence of Kryptofix 222 (5 mg in 1.5 ml MeCN) and potassium carbonate (1 mg in 0.5 ml water) by heating under nitrogen at 120° C. for 30 minutes. During this time 2×1 ml MeCN were added and evaporated. A solution of 3-cyano-4-trimethylammoniumbenzoyl-Arg-βAla-Gln-Trp-Ala-Val-Gly-His(3Me)-Sta-Leu-NH₂ trifluoroacetate salt (2 mg) in anhydrous DMSO (150 µl) was added. After heating at 50° C. for 15 min. The reaction mixture was diluted with water (4 ml) and transferred to a semi-prep HPLC (column: Zorbax Bonus 5µ C18, 250×9.2 mm, solvent A: H₂O+0.1% TFA, solvent B: MeCN/Water 9/1+0.1% TFA, gradient: 29-34% B in 20 mins at 3 ml/min) and the desired F18 product peak was collected (150 MBq, 21.1% d.c.). The F-18 labeled product was confirmed by co-injection with the F-19 cold standard on an analytical HPLC (Column Zorbax Bonus 5µ C18 250×4.6 mm, 1 ml/min (Agilent), solvent A: H₂O+0.1% TFA, solvent B: MeCN/Water 9/1+0.1% TFA, gradient: 29% B to 34% B in 20 mins).

Example M1

Radiosynthesis of 3-cyano-4-[¹⁸F]fluorobenzoyl-Ara-βAla-Gln-Trp-Ala-Val-Gly-His(3Me)-Sta-Leu-NH₂

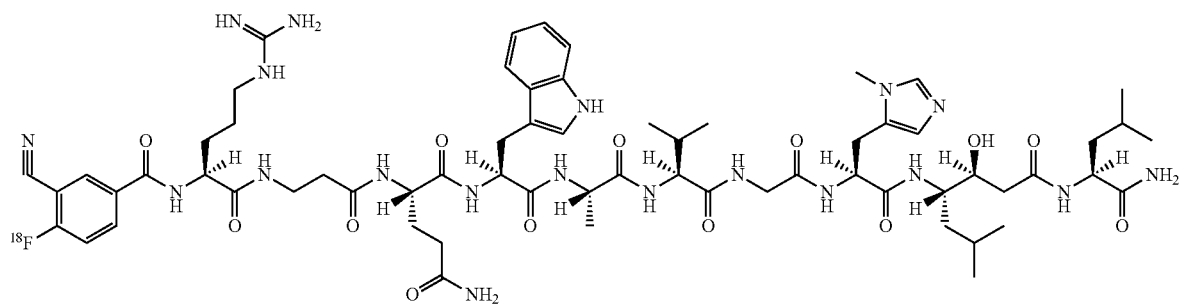 [SMILES: CC(C)C[C@H](NC(=O)C[C@H](O)[C@H](CC(C)C)NC(=O)[C@H](Cc1cncn1C)NC(=O)CNC(=O)[C@@H](NC(=O)[C@H](C)NC(=O)[C@H](Cc1c[nH]c2ccccc12)NC(=O)[C@H](CCC(N)=O)NC(=O)CCNC(=O)[C@H](CCCNC(=N)N)NC(=O)c1ccc([18F])c(C#N)c1)C(C)C)C(N)=O]

Example N1

Radiosynthesis of 3-cyano-4-[$^{18}$F]-fluorobenzoyl-Ava-Gln-Trp-Ala-Val-Gly-His(3Me)-Sta-Leu-NH$_2$

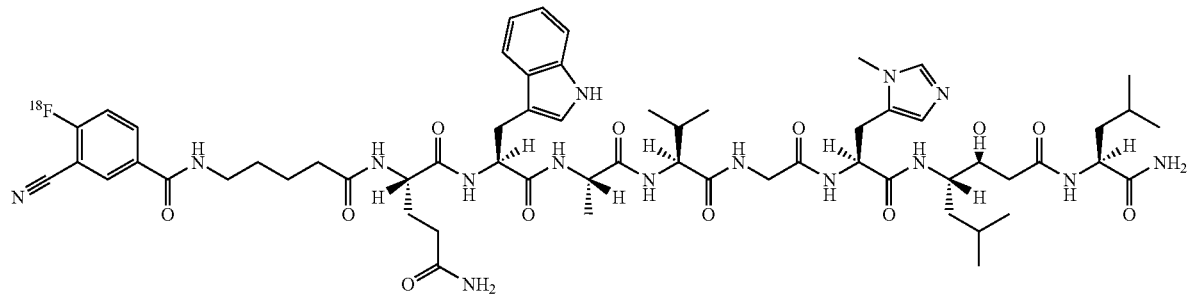 [SMILES: CC(C)C[C@H](NC(=O)C[C@H](O)[C@H](CC(C)C)NC(=O)[C@H](Cc1cncn1C)NC(=O)CNC(=O)[C@@H](NC(=O)[C@H](C)NC(=O)[C@H](Cc1c[nH]c2ccccc12)NC(=O)[C@H](CCC(N)=O)NC(=O)CCCCNC(=O)c1ccc([18F])c(C#N)c1)C(C)C)C(N)=O]

$^{18}$F-fluoride (869 MBq) was azeotropically dried in the presence of Kryptofix 222 (5 mg in 1.5 ml MeCN) and potassium carbonate (1 mg in 0.5 ml water) by heating under nitrogen at 120° C. for 30 minutes. During this time 2×1 ml MeCN were added and evaporated. A solution of 3-cyano-4-trimethylammoniumbenzoyl-Ava-Gln-Trp-Ala-Val-Gly-His(3Me)-Sta-Leu-NH$_2$ trifluoroacetate salt (2 mg) in anhydrous DMSO (150 μl) was added. After heating at 50° C. for 15 min. The reaction mixture was diluted with water (4 ml) and transferred to a semi-prep HPLC (column: Zorbax Bonus 5μ C18, 250×9.2 mm, solvent A: H$_2$O+0.1% TFA, solvent B: MeCN/Water 9/1+0.1% TFA, gradient: 34-38% B in 20 mins at 3 ml/min) and the desired F18 product peak was collected (184 MBq, 37.8% d.c.). The F-18 labeled product was confirmed by co-injection with the F-19 cold standard on an analytical HPLC (Column Zorbax Bonus 5μ C18 250×4.6 mm, 1 ml/min (Agilent), solvent A: H$_2$O+0.1% TFA, solvent B: MeCN/Water 9/1+0.1% TFA, gradient: 34% B to 38% B in 20 mins).

$^{18}$F-fluoride (835 MBq) was azeotropically dried in the presence of Kryptofix 222 (5 mg in 1.5 ml MeCN) and cesium carbonate (2.3 mg in 0.5 ml water) by heating under nitrogen at 120° C. for 30 minutes. During this time 2×1 ml MeCN were added and evaporated. A solution of 3-trifluoromethyl-4-trimethylammoniumbenzoyl-Arg-Ava-Gln-Trp-Ala-Val-NMeGly-His(3Me)-Sta-Leu NH$_2$ trifluoroacetate salt (2 mg) in anhydrous DMSO (150 μl) was added. After heating at 70° C. for 15 min. The reaction mixture was diluted with water (4 ml) and transferred to a semi-prep HPLC (column: ACE 5μ C18 250×10 mm, solvent A: H$_2$O+0.1% TFA, solvent B: MeCN/Water 9/1+0.1% TFA, gradient: 20% for 2 min, then 20-60% B in 20 mins at 3 ml/min) and the desired F18 product peak was collected (78 MBq, 29.0% d.c.). The F-18 labeled product was confirmed by co-injection with the F-19 cold standard on an analytical HPLC (Column ACE C18, 50×4.6 mm, 3μ, 2 ml/min, solvent A: 10 mM K$_2$HPO$_4$ in H$_2$O, solvent B: 10 mM K$_2$HPO$_4$ in MeCN/H$_2$O (7:3), gradient: 5%-95% B in 7 mins).

Example O1

Radiosynthesis of 3-trifluoromethyl-4-[$^{18}$F]-fluorobenzoyl-Arg-Ava-Gln-Trp-Ala-Val-NMeGly-His(3Me)-Sta-Leu-NH$_2$

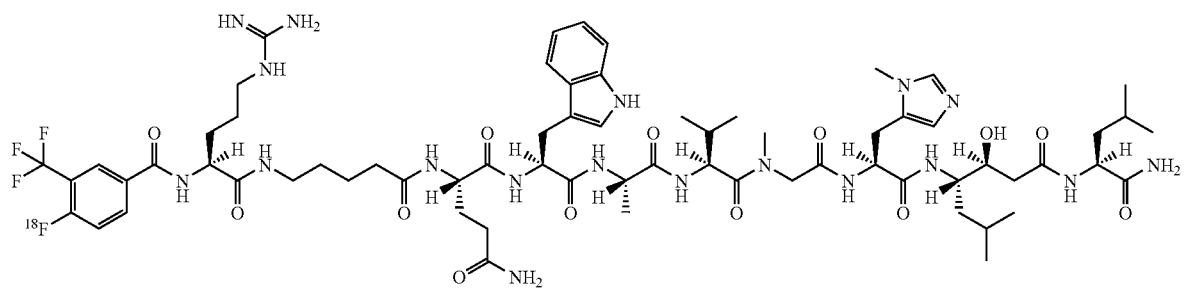 [SMILES: CC(C)C[C@H](NC(=O)C[C@H](O)[C@H](CC(C)C)NC(=O)[C@H](Cc1cncn1C)NC(=O)CN(C)C(=O)[C@@H](NC(=O)[C@H](C)NC(=O)[C@H](Cc1c[nH]c2ccccc12)NC(=O)[C@H](CCC(N)=O)NC(=O)CCCCNC(=O)[C@H](CCCNC(=N)N)NC(=O)c1ccc([18F])c(C(F)(F)F)c1)C(C)C)C(N)=O]

Generic Structure of 3-Cyano Activated Bombesin Peptides Precursors

| Precursor | Sequence |
|---|---|
| | Ava-Gln-Trp-Ala-Val-NMeGly-His(3Me)-Sta-Cpa-NH2 |
| | Ava-Gln-Trp-Ala-Val-Gly-His(3Me)-FA2010-Leu-NH2 |
| | Ava-Gln-Trp-Ala-Val-Gly-His(3Me)-Sta-Leu-NH2 |
| | Arg-βAla-Gln-Trp-Ala-Val-Gly-His(3Me)-Sta-Leu-NH2 |
| | Lys(Me)2-βAla-Gln-Trp-Ala-Val-Gly-His(3Me)-Sta-Leu-NH2 |
| | Arg-Ser-Gln-Trp-Ala-Val-Gly-His(3Me)-FA02010-Leu-NH2 |
| | Ser-Ser-Gln-Trp-Ala-Val-Gly-His(3Me)-FA02010-Leu-NH2 |
| | Lys(Me)2-Ser-Gln-Trp-Ala-Val-Gly-His(3Me)-FA02010-Leu-NH2 |
| | Arg-Ser-Gln-Trp-Ala-Val-Gly-His(3Me)-Sta-Leu-NH2 |
| | Lys(Me)2-βAla-Gln-Trp-Ala-Val-Gly-His(3Me)-FA02010-Leu-NH2 |
| | Ava-Gln-Trp-Ala-Val-Gly-His-FA02010-Leu-NH2 |
| | Arg-Ava-Gln-Trp-Ala-Val-NMeGly-His-Sta-Leu-NH2 |
| | Arg-Ava-Gln-Trp-Ala-Val-Gly-His(3Me)-Sta-Leu-NH2 |
| | Arg-Ava-Gln-Trp-Ala-Val-NMeGly-His(3Me)-Sta-Leu-NH2 |
| | 1,4-cis-Achc-Gln-Trp-Ala-Val-Gly-His(3Me)-Sta-Leu-NH2 |
| | Ava-Gln-Trp-Ala-Val-Gly-His(3Me)-Sta-Cpa-NH2 |
| | Ava-Gln-Trp-Ala-Val-NMeGly-His(3Me)-FA02010-Cpa-NH2 |
| | Dioxa-Gln-Trp-Ala-Val-Gly-His(3Me)-Sta-Leu-NH2 |
| | Ser-Ser-Gln-Trp-Ala-Val-Gly-His(3Me)-Sta-Leu-NH2 |

Generic Structure of 3-Cyano Activated Bombesin Peptides Labeled with F-18

| F18 labeled | Sequence |
|---|---|
| | Ava-Gln-Trp-Ala-Val-NMeGly-His(3Me)-Sta-Cpa-NH2 |
| | Ava-Gln-Trp-Ala-Val-Gly-His(3Me)-FA1010-Leu-NH2 |
| | Ava-Gln-Trp-Ala-Val-Gly-His(3Me)-Sta-Leu-NH2 |
| | Arg-βAla-Gln-Trp-Ala-Val-Gly-His(3Me)-Sta-Leu-NH2 |
| | Lys(Me)2-βAla-Gln-Trp-Ala-Val-Gly-His(3Me)-Sta-Leu-NH2 |
| | Arg-Ser-Gln-Trp-Ala-Val-Gly-His(3Me)-FA02010-Leu-NH2 |
| | Ser-Ser-Gln-Trp-Ala-Val-Gly-His(3Me)-FA02010-Leu-NH2 |
| | Lys(Me)2-Ser-Gln-Trp-Ala-Val-Gly-His(3Me)-FA02010-Leu-NH2 |
| | Arg-Ser-Gln-Trp-Ala-Val-Gly-His(3Me)-Sta-Leu-NH2 |
| | Lys(Me)2-βAla-Gln-Trp-Ala-Val-Gly-His(3Me)-FA02010-Leu-NH2 |
| | Ava-Gln-Trp-Ala-Val-Gly-His-FA02010-Leu-NH2 |
| | Arg-Ava-Gln-Trp-Ala-Val-NMeGly-His-Sta-Leu-NH2 |
| | Arg-Ava-Gln-Trp-Ala-Val-Gly-His(3Me)-Sta-Leu-NH2 |
| | Arg-Ava-Gln-Trp-Ala-Val-NMeGly-His(3Me)-Sta-Leu-NH2 |
| | 1,4-cis-Achc-Gln-Trp-Ala-Val-Gly-His(3Me)-Sta-Leu-NH2 |
| | Ava-Gln-Trp-Ala-Val-Gly-His(3Me)-Sta-Cpa-NH2 |
| | Ava-Gln-Trp-Ala-Val-NMeGly-His(3Me)-FA02010-Cpa-NH2 |
| | Dioxa-Gln-Trp-Ala-Val-Gly-His(3Me)-Sta-Leu-NH2 |
| | Ser-Ser-Gln-Trp-Ala-Val-Gly-His(3Me)-Sta-Leu-NH2 |

Generic Structure of 3-Trifluoromethyl Activated Bombesin Peptides Precursors

| Precursor | Sequence |
|---|---|
| | Arg-βAla-Gln-Trp-Ala-Val-Gly-His(3Me)-FA02010-Leu-NH2 |
| | Arg-Ava-Gln-Trp-Ala-Val-NMeGly-His-Sta-Leu-NH2 |
| | Arg-Ava-Gln-Trp-Ala-Val-NMeGly-His(3Me)-Sta-Leu-NH2 |
| | Gln-Trp-Ala-Val-Gly-His(3Me)-Sta-Leu-NH2 |

Generic Structure of 3-Trifluoromethyl Activated Bombesin Peptides Labeled with F-18

| F18 labeled | Sequence |
|---|---|
| | Arg-βAla-Gln-Trp-Ala-Val-Gly-His(3Me)-FA02010-Leu-NH2 |
| | Arg-Ava-Gln-Trp-Ala-Val-NMeGly-His-Sta-Leu-NH2 |
| | Arg-Ava-Gln-Trp-Ala-Val-NMeGly-His(3Me)-Sta-Leu-NH2 |
| | Gln-Trp-Ala-Val-Gly-His(3Me)-Sta-Leu-NH2 |

Aminoacid abbreviations

All natural amino acids were represented by 3-letter codes. Unless otherwise stated all the aminoacids have L-configurations.

Sta—Statine
His(3Me)—3-methylhisitidine

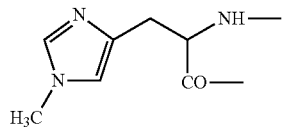

Figure 13:
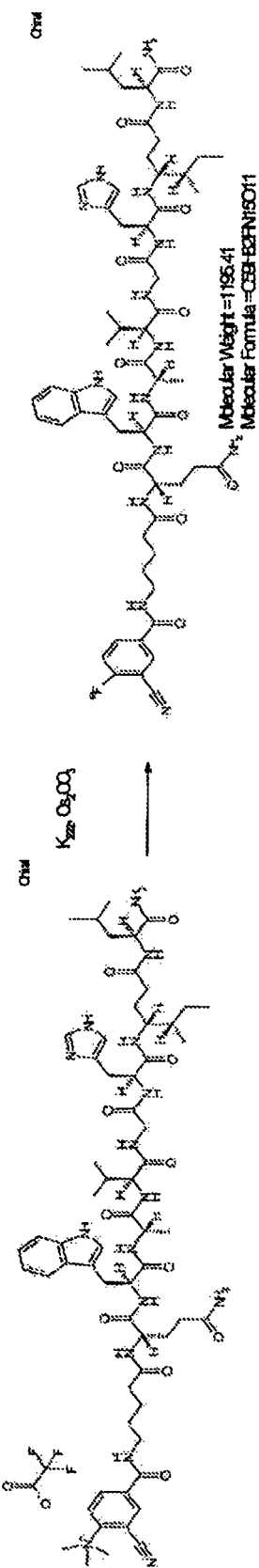
FIG. 13 shows a Bombesin analog.

Ava—5-aminovaleric acid
AOC—8-aminooctanoic acid
tBuGly—t-butylglycine
tBuAla—t-butylalanine
BhLeu—β-homoleucine
BhIle—β-homoisoleucine
Lys(Me)$_2$—ε-N,N-dimethyllysine
DOA—3,6-dioxa-8-aminooctanoic acid
4-Am-5-MeHpA—4-amino-5-methylheptanoic acid
4-Am-5-MeHxA—4-amino-5-methylhexanoic acid
1,4-cis-ACHC—1,4-cis-aminocyclohexamecarboxylic acid
AHMHxA—(3R,4S)-4-amino-3-hydroxy-5-methylhexanoic acid
Biodistribution of F-18-Bombesin Analog
see FIG. 13
wherein Bombesin analogue is Gln-Trp-Ala-Val-Gly-His-FA01010-Leu-NH2
Radiolabeling of this bombesin analogue with F-18 was carried out via the method. The radiochemical yield was approx. 27% (decay corrected) giving 76 MBq in 50 μl ethanol with a radiochemical purity of >99% by HPLC and a specific activity of ~480 GBq/mmol.
Nude mice bearing human prostate cancer PC-3 were injected with 100 μl radioactive peptide dissolved in PBS containing 135 kBq per animal. For blocking 100 μg unlabeled gastrin-releasing peptide was co-injected. One hour post injection the animals were sacrificed and organs dissected for counting in a gamma-counter. Values are expressed as percent of the injected dose per gram organ weight.

|  | 1 h<br>% ID/g | 1 h Blocking<br>% ID/g |
|---|---|---|
| Tumor (% ID/g) | 1.00 ± 0.01 | 0.18 ± 0.03 |
| Blood (% ID/g) | 0.05 ± 0.01 | 0.12 ± 0.00 |
| Muscle (% ID/g) | 0.02 ± 0.00 | 0.03 ± 0.02 |
| Pancreas (% ID/g) | 0.34 ± 0.03 | 0.10 ± 0.02 |
| Liver (% ID/g) | 0.35 ± 0.13 | 0.39 ± 0.05 |
| Kidneys (% ID/g) | 0.24 ± 0.02 | 0.71 ± 0.12 |
| Tumor/Tissue-Ratios |  |  |
| T/Blood | 21.03 ± 11.92 | 1.57 ± 0.22 |
| T/Muscle | 59.99 ± 29.53 | 6.31 ± 3.27 |

It can be seen that $^{18}$F-labelled bombesin analog accumulates in tumor and the targeting agent $^{18}$F-labelled bombesin is specific since the blocking values are low in case of tumor and inchanged for the other tissue.

Figure 8:
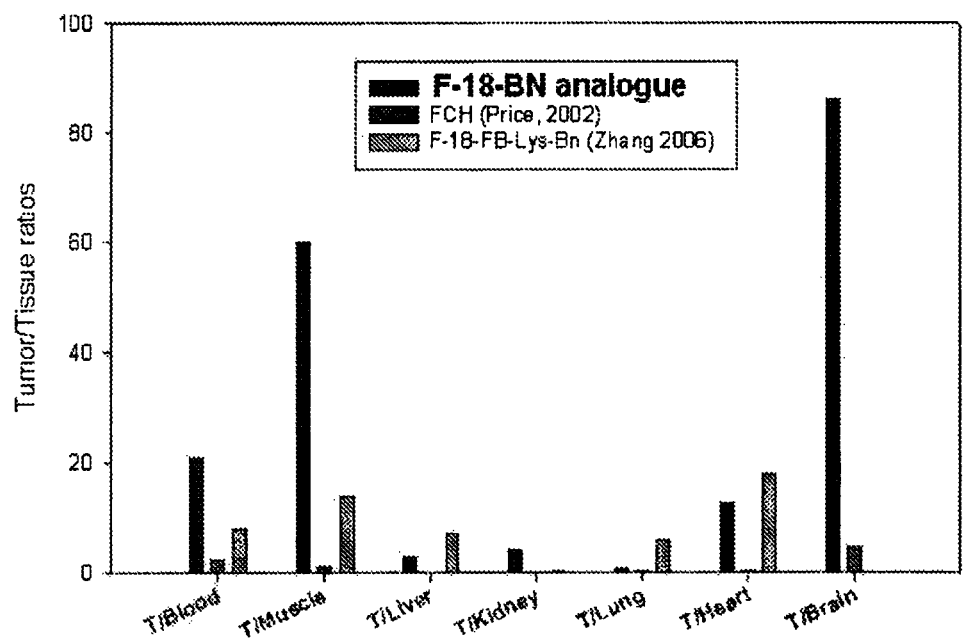

Comparison of $^{18}$F-Labelled Bombesin Analogs
Protocol as above
Table 1; (FIGS. 12A-12C)
Table 1; (FIGS. 12A-12C) shows biodistribution in Nude mice bearing human prostate cancer PC-3 were injected with 100 μl radioactive peptide dissolved in PBS containing 135 kBq per animal.
Bombesin Analogs for PET: Comparison with 18F-Choline (FCH) and 18F-FB-Lys-BN
FIG. 8 shows that tumor-tissue ratio of Bombesin analog Gln-Trp-Ala-Val-Gly-His-FA01010-Leu-NH2 is 2.5 time higher than the tumor-tissue ratio of 18F-choline (FCH) and 18F-FB-Lys-BN.

Synthesis of H-Y-E: Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support (e.g., Rink amide resin) with its amino group protected with an N-protecting agent, fluorenylmethoxycarbonyl (FMOC) group. The amino protecting group is removed with suitable deprotecting agent such as piperidine for FMOC and the next amino acid residue (in N-protected form) is added with a coupling agents such as dicyclohexylcarbodiimide (DCC), di-isopropyl-cyclohexylcarbodiimide (DCCI), hydroxybenzotriazole (HOBt). Upon formation of a peptide bond, the reagents are washed from the support. After addition of the final residue of (Y), the peptide is attached to the solid support is ready for the coupling of RG-L$_1$-B$_1$-OH.

It is understood that the examples and embodiments described herein are for illustrative purpose only and that various modifications and changes in light thereof as well as combinations of features described in this application will be suggested to persons skilled in the art and are to be included within the spirit and purview of the described invention and within the scope of the appended claims. From the foregoing description, one skilled in the art can easily ascertain the essential characteristics of this invention and, without departing from the spirit and scope thereof, can make various changes and modifications.

The entire disclosures of all applications, patents and publications, cited herein and of corresponding European application No. 06090166.7, filed Sep. 8, 2006, European application No. 07090079.0, filed Apr. 23, 2007, and U.S. Provisional Application Ser. No. 60/845,163, filed Sep. 18, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of Formula A

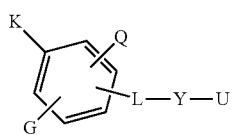

A wherein
- -G is selected from —C≡N and —CF$_3$, wherein the respective substituent can be in ortho, para or meta position in respect of the K group,
- -Q is hydrogen,
- -L- is —CO— or —SO$_2$—,
- Y is a bond or a spacer, wherein (a) the spacer is Arg-Ser, Arg-Ava, Lys(Me)2-β-ala, Lys(Me)2-ser, Arg-β-ala, Ser-Ser, Ser-Thr, Arg-Thr, S-alkylcysteine, cysteic acid, thioalkylcysteine (S—S-alkyl) or

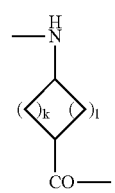

wherein k and l are independently selected in the range of from 0 to 4, or (b) the spacer is a non-amino acid moiety selected from the group consisting of —NH—(CH$_2$)$_p$—CO—, wherein p is an integer of from 2 to 10, —NH—(CH$_2$—CH$_2$—O)$_q$—CH$_2$—CH$_2$—CO—, wherein q is an integer of from 0 to 5, —NH-cycloalkyl-CO— wherein cycloalkyl is selected from C$_5$-C$_8$ cycloalkyl, and —NH-heterocycloalkyl-(CH$_2$)$_v$—CO— wherein heterocycloalkyl is selected from C$_5$-C$_8$ heterocycloalkyl containing carbon atoms and 1, 2, 3 or 4 oxygen, nitrogen or sulfur heteroatoms and v is an integer of from 1 to 4, U is a targeting agent comprising
  (a) a peptide selected from the group consisting of somatostatin, somatostatin receptor specific peptides, neuropeptide Y, neuropeptide Y$_1$, bombesin, gastrin, gastrin releasing peptide, epidermal growth factor (EGF of various origin), insulin growth factor (IGF) and IGF-1, integrins ($\alpha_3\beta_1$, $\alpha_v\beta_3$, $\alpha_v\beta_5$, $\alpha$IIb$_3$), LHRH agonists and antagonists, transforming growth factors, particularly TGF-$\alpha$; angiotensin; cholecystokinin receptor peptides, cholecystokinin (CCK); neurotensin, thyrotropin releasing hormone, pituitary adenylate cyclase activating peptide (PACAP), chemokines, substrates and inhibitors for cell surface matrix metalloproteinase, prolactin, tumor necrosis factor, interleukins (IL-1, IL-2, IL-4 or IL-6), interferons, and vasoactive intestinal peptide (VIP);
  (b) a peptide selected from the group consisting of peptides having sequence III or IV:
    AA$_1$-AA$_2$-AA$_3$-AA$_4$-AA$_5$-AA$_6$-AA$_7$-AA$_8$-NT$_1$T$_2$ (type A) III, with:
      T$_1$=T$_2$=H or
      T$_1$=H, T$_2$=OH or
      T$_1$=CH$_3$, T$_2$=OH
      AA$_1$=Gln, Asn, Phe(4-CO—NH$_2$)
      AA$_2$=Trp, D-Trp
      AA$_3$=Ala, Ser, Val
      AA$_4$=Val, Ser, Thr
      AA$_5$=Gly, (N-Me)Gly
      AA$_6$=His, His(3-Me), (N-Me)His, (N-Me)His(3-Me)
      AA$_7$=Sta, Statine analogs and isomers, 4-Am,5-MeHpA, 4-Am,5-MeHxA, $\gamma$-substituted amino acids
      AA$_8$=Leu, Cpa, Cba, CpnA, Cha, t-buGly, tBuAla, Met, Nle, iso-Bu-Gly; or
    AA$_1$-AA$_2$-AA$_3$-AA$_4$-AA$_5$-AA$_6$-AA$_7$-AA$_8$-NT$_1$T$_2$ (type B) IV, with:
      T$_1$=T$_2$=H or
      T$_1$=H, T$_2$=OH or
      T$_1$=CH$_3$, T$_2$=OH
      AA$_1$=Gln, Asn or Phe(4-CO—NH$_2$)
      AA$_2$=Trp, D-Trp
      AA$_3$=Ala, Ser, Val
      AA$_4$=Val, Ser. Thr
      AA$_5$=$\beta$Ala, $\beta^2$- and $\beta^3$-amino acids as shown herein after

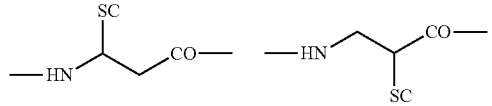

wherein SC represents a side chain found in proteinogenic amino acids and homologs of proteinogenic amino acids,
      AA$_6$=His, His(3-Me), (N-Me)His, (N-Me)His(3-Me)
      AA$_7$=Phe, Tha, Nal,
      AA$_8$=Leu, Cpa, Cba, CpnA, Cha, t-buGly, tBuAla, Met, Nle, iso-Bu-Gly; or
  (c) wherein U is a NR$^7$-peptide, —(CH$_2$)$_{n'}$-peptide, —O—(CH$_2$)$_{n'}$-peptide or —S—(CH$_2$)$_{n'}$-peptide, wherein
    n' is an integer of from 1 to 6,
    R$^7$ is hydrogen or unbranched or branched alkyl and the peptide is defined in (a) or (b);

X$^-$ is CF$_3$S(O)$_2$O$^-$, C$_4$F$_9$S(O)$_2$O$^-$, iodide anion, bromide anion, chloride anion, perchlorate anion (ClO$_4^-$), phosphate anion, trifluoroacetate anion (CF$_3$—C(O)O$^-$), or the anion of another salt of an inorganic or organic acid, K is N$^+$(R$^1$)(R$^2$)(R$^3$)X$^-$ or W,
  wherein
    R$^1$, R$^2$ and R$^3$ are each methyl, and
    W is $^{18}$F, or a pharmaceutically acceptable salt of an inorganic or organic acid thereof.

2. The compound according claim 1, wherein X$^-$ is CF$_3$—C(O)O$^-$, CF$_3$S(O)$_2$O$^-$ or C$_4$F$_9$S(O)$_2$O$^-$.

3. The compound according to claim 1, wherein X$^-$ is F$_3$—C(O)O$^-$ or CF$_3$S(O)$_2$O$^-$.

4. The compound according to claim 1, wherein Y is Arg-Ser, Arg-Ava, Lys(Me)2-$\beta$-ala, Lys (Me)2-ser, Arg-$\beta$-ala, Ser-Ser, Ser-Thr, Arg-Thr, S-alkylcysteine, Cysteic acid, thioalkylcysteine (S—S-Alkyl) or

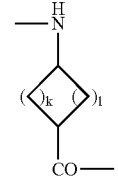

wherein k and l are independently selected in the range of from 0 to 4.

5. The compound according to claim 1, wherein -Y- is a non-amino acid moiety selected from the group consisting of
  —NH—(CH$_2$)$_p$—CO—, wherein p is an integer of from 2 to 10,
  —NH—(CH$_2$—CH$_2$—O)$_q$—CH$_2$—CH$_2$—CO—, wherein q is an integer of from 0 to 5,
  —NH-cycloalkyl-CO— wherein cycloalkyl is selected from C$_5$-C$_8$ cycloalkyl, and
  —NH-heterocycloalkyl-(CH$_2$)$_v$—CO— wherein heterocycloalkyl is selected from C$_5$-C$_8$ heterocycloalkyl containing carbon atoms and 1, 2, 3 or 4 oxygen, nitrogen or sulfur heteroatoms and v is an integer of from 1 to 4.

6. The compound according to claim 1, wherein U is selected from the group consisting of somatostatin, somatostatin receptor specific peptides, neuropeptide Y, neuropeptide Y$_1$, bombesin, gastrin, gastrin releasing peptide, epidermal growth factor (EGF of various origin), insulin growth factor (IGF) and IGF-1, integrins ($\alpha_3\beta_1$, $\alpha_v\beta_3$, $\alpha_v\beta_5$, $\alpha$IIb$_3$), LHRH agonists and antagonists, transforming growth factors, particularly TGF-$\alpha$; angiotensin; cholecystokinin receptor peptides, cholecystokinin (CCK); neurotensin, thyrotropin releasing hormone, pituitary adenylate cyclase activating peptide (PACAP), chemokines, substrates and inhibitors for cell surface matrix metalloproteinase, prolactin, tumor necrosis factor, interleukins (IL-1, IL-2, IL-4 or IL-6), interferons, and vasoactive intestinal peptide (VIP).

7. The compound according to claim 1, wherein U is selected from the group consisting of bombesin, somatostatin and neuropeptide $Y_1$.

8. The compound according to claim 1, wherein U is selected from the group consisting of peptides having sequence III or IV:

$AA_1$-$AA_2$-$AA_3$-$AA_4$-$AA_5$-$AA_6$-$AA_7$-$AA_8$-$NT_1T_2$ (type A) III, with:
$T_1=T_2=H$ or
$T_1=H$, $T_2=OH$ or
$T_1=CH_3$, $T_2=OH$;
$AA_1$=Gln, Asn, Phe(4-CO—$NH_2$)
$AA_2$=Trp, D-Trp
$AA_3$=Ala, Ser, Val
$AA_4$=Val, Ser, Thr
$AA_5$=Gly, (N-Me)Gly
$AA_6$=His, His(3-Me), (N-Me)His, (N-Me)His(3-Me)
$AA_7$=Sta, Statine analogs and isomers, 4-Am,5-MeHpA, 4-Am,5-MeHxA, γ-substituted amino acids
$AA_8$=Leu, Cpa, Cba, CpnA, Cha, t-buGly, tBuAla, Met, Nle, iso-Bu-Gly $AA_1$-$AA_2$-$AA_3$-$AA_4$-$AA_5$-$AA_6$-$AA_7$-$AA_8$-$NT_1T_2$ (type B) IV, with:
$T_1=T_2=H$ or $T_1=H$, $T_2=OH$ or $T_1=CH_3$, $T_2=OH$
$AA_1$=Gln, Asn or Phe(4-CO—$NH_2$)
$AA_2$=Trp, D-Trp
$AA_3$=Ala, Ser, Val
$AA_4$=Val, Ser. Thr
$AA_5$=βAla, $β^2$- and $β^3$-amino acids as shown herein after

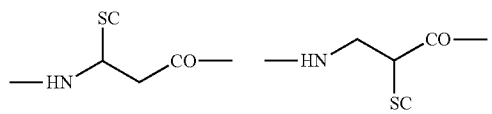

wherein SC represents a side chain found in proteinogenic amino acids and homologs of proteinogenic amino acids,
$AA_6$=His, His(3-Me), (N-Me)His, (N-Me)His(3-Me)
$AA_7$=Phe, Tha, Nal,
$AA_8$=Leu, Cpa, Cba, CpnA, Cha, t-buGly, tBuAla, Met, Nle, iso-Bu-Gly.

9. The compound according to claim 1, wherein U is a $NR^7$-peptide, or —$(CH_2)_{n'}$-peptide, —O—$(CH_2)_{n'}$-peptide or —S—$(CH_2)_{n'}$-peptide, wherein n' is an integer of from 1 to 6, and wherein $R^7$ is hydrogen or unbranched or branched alkyl.

10. The compound according to claim 9, wherein $R^7$ is hydrogen or unbranched or branched $C_1$-$C_6$ alkyl.

11. The compound according to claim 9, wherein $R^7$ is hydrogen or methyl.

12. A compound selected from
Ia-1: 4-(Trimethylammonium)-3-cyano-benzoyl-Arg-Ava-Gln-Trp-Ala-Val-NMeGly-His-Sta-Leu-$NH_2$ (SEQ ID NO: 103),
Ia-2: 4-(Trimethylammonium)-3-cyano-benzoyl-Arg-Ava-Gln-Trp-Ala-Val-Gly-His(Me)-Sta-Leu-$NH_2$ (SEQ ID NO: 109),
Ia-3: 4-(Trimethylammonium)-3-cyano-benzoyl-Arg-Ava-Gln-Trp-Ala-Val-NMeGly-His(3Me)-Sta-Leu-$NH_2$ (SEQ ID NO: 110),
Ia-4: 4-(Trimethylammonium)-3-cyano-benzoyl-1,4-cis-Achc-Gln-Trp-Ala-Val-Gly-His(3Me)-Sta-Leu-$NH_2$ (SEQ ID NO: 111),
Ia-5: 4-(Trimethylammonium)-3-cyano-benzoyl-Gln-Trp-Ala-Val-Gly-His(3Me)-Sta-Leu-$NH_2$ (SEQ ID NO: 112),
Ia-6: 4-(Trimethylammonium)-3-cyano-benzoyl-AOC-Gln-Trp-Ala-Val-Gly-His(3Me)-Sta-Leu-$NH_2$ (SEQ ID NO: 113),
Ia-7: 4-(Trimethylammonium)-3-cyano-benzoyl-Ava-Gln-Trp-Ala-Val-NMeGly-His(3Me)-Sta-Cpa-$NH_2$ (SEQ ID NO: 114),
Ia-8: 4-(Trimethylammonium)-3-cyano-benzoyl-Ava-Gln-Trp-Ala-Val-Gly-His(3Me)-4-Am,5-MeHpA-Leu-$NH_2$ (SEQ ID NO: 115),
Ia-9: 4-(Trimethylammonium)-3-cyano-benzoyl-Ava-Gln-Trp-Ala-Val-Gly-His(3Me)-Sta-Leu-$NH_2$ (SEQ ID NO: 116),
Ia-10: 4-(Trimethylammonium)-3-cyano-benzoyl-Lys(Me)2-βAla-Gln-Trp-Ala-Val-Gly-His(3Me)-Sta-Leu-$NH_2$ (SEQ ID NO: 117),
Ia-11: 4-(Trimethylammonium)-3-cyano-benzoyl-Lys(Me)2-βAla-Gln-Trp-Ala-Val-Gly-His(3Me)-Sta-Leu-$NH_2$ (SEQ ID NO: 118),
Ia-12: 4-(Trimethylammonium)-3-cyano-benzoyl-Arg-Ser-Gln-Trp-Ala-Val-Gly-His(3Me)-4-Am,5-MeHpA-Leu-$NH_2$ (SEQ ID NO: 119),
Ia-13: 4-(Trimethylammonium)-3-cyano-benzoyl-Ser-Ser-Gln-Trp-Ala-Val-Gly-His(3Me)-4-Am,5-MeHpA-Leu-$NH_2$ (SEQ ID NO: 120),
Ia-14: 4-(Trimethylammonium)-3-cyano-benzoyl-Lys(Me)2-Ser-Gln-Trp-Ala-Val-Gly-His(3Me)-4-AM-5-MeHpA-Leu-$NH_2$ (SEQ ID NO: 121),
Ia-15: 4-(Trimethylammonium)-3-cyano-benzoyl-Arg-Ser-Gln-Trp-Ala-Val-Gly-His(3Me)-Sta-Leu-$NH_2$ (SEQ ID NO: 122),
Ia-16: 4-(Trimethylammonium)-3-cyano-benzoyl-Lys(Me)2-βAla-Gln-Trp-Ala-Val-Gly-His(3Me)-4-Am,5-MeHpA-Leu-$NH_2$ (SEQ ID NO: 123),
Ia-17: 4-(Trimethylammonium)-3-cyano-benzoyl-Ava-Gln-Trp-Ala-Val-Gly-His-4-Am,5-MeHpA- -Leu-$NH_2$ (SEQ ID NO: 124),
Ia-18: 4-(Trimethylammonium)-3-trifluoromethyl-benzoyl-Arg-Ava-Gln-Trp-Ala-Val-Gly-His(3Me)-Sta-Leu-$NH_2$ (SEQ ID NO: 125),
Ia-19: 4-(Trimethylammonium)-3-trifluoromethyl-benzoyl-Arg-Ava-Gln-Trp-Ala-Val-NMeGly-His(3Me)-Sta-Leu-$NH_2$ (SEQ ID NO: 126),
Ia-20: 4-(Trimethylammonium)-3-trifluoromethyl-benzoyl-1,4-cis-Achc-Gln-Trp-Ala-Val-Gly-His(3Me)-Sta-Leu-$NH_2$ (SEQ ID NO: 127),
Ia-21: 4-(Trimethylammonium)-3-trifluoromethyl-benzoyl-Gln-Trp-Ala-Val-Gly-His(3Me)-Sta-Leu-$NH_2$ (SEQ ID NO: 128),
Ia-22: 4-(Trimethylammonium)-3-trifluoromethyl-benzoyl-Arg-βAla-Gln-Trp-Ala-Val-Gly-His(3Me)-4-Am, 5-MeHpA-Leu-$NH_2$ (SEQ ID NO: 129),
Ia-23: 4-(Trimethylammonium)-3-cyano-benzoyl-Ava-Gln-Trp-Ala-Val-NMeGly-His(3Me)-4-Am,5-MeHpA-Cpa-$NH_2$ (SEQ ID NO: 130),
Ia-24: 4-(Trimethylammonium)-3-cyano-benzoyl-Ser-Ser-Gln-Trp-Ala-Val-Gly-His(3Me)-Sta-Leu-$NH_2$ (SEQ ID NO: 131), Ia-25: 4-(Trimethylammonium)-3-cyano-benzoyl-DOA-Gln-Trp-Ala-Val-Gly-His(3Me)Sta-Leu-NH$_2$ (SEQ ID NO: 132), Ia-66: 4-(Trimethylammonium)-3-cyano-benzoyl-Ava-ε-c[Lys-(NMe)Phe-1Nal-D-Trp-Lys-Thr] (SEQ ID NO: 133)

Ia-67: 4-(Trimethylammonium)-3-cyano-benzoyl-Ava-β-c[Dpr-Met-(NMe)Phe-Tyr-D-Trp-Lys] (SEQ ID NO: 134)

Ia-68: 4-(Trimethylammonium)-3-cyano-benzoyl-Ava-DCys-Leu-Ile-Thr-Arg-Cys-Arg-Tyr-NH$_2$] (SEQ ID NO: 135) or Ia-69: 4-(Trimethylammonium)-3-cyano-benzoyl-Ava-DCys-Leu-Ile-Val-Arg-Cys-Arg-Tyr-NH$_2$] (SEQ ID NO: 136).

13. A compound selected from the group consisting of

IIA-a-1: 4-[18]Fluoro-3-cyano-benzoyl-Arg-Ava-Gln-Trp-Ala-Val-NMeGly-His-Sta-Leu-NH$_2$ (SEQ ID NO: 137), IIA-a-2: 4-[18]Fluoro-3-cyano-benzoyl-Arg-Ava-Gln-Trp-Ala-Val-Gly-His(Me)-Sta-Leu-NH$_2$ (SEQ ID NO: 138), IIA-a-3: 4-[18]Fluoro-3-cyano-benzoyl-Arg-Ava-Gln-Trp-Ala-Val-NMeGly-His(3Me)-Sta-Leu-NH$_2$ (SEQ ID NO: 139), IIA-a-4: 4-[18]Fluoro-3-cyano-benzoyl-1,4-cis-Achc-Gln-Trp-Ala-Val-Gly-His(3Me)-Sta-Leu-NH$_2$ (SEQ ID NO: 140), IIA-a-5: 4-[18]Fluoro-3-cyano-benzoyl-Gln-Trp-Ala-Val-Gly-His(3Me)-Sta-Leu-NH$_2$ (SEQ ID NO: 141), IIA-a-6: 4-[18]Fluoro-3-cyano-benzoyl-AOC-Gln-Trp-Ala-Val-Gly-His(3Me)-Sta-Leu-NH$_2$ (SEQ ID NO: 142), IIA-a-7: 4-[18]Fluoro-3-cyano-benzoyl-Ava-Gln-Trp-Ala-Val-NMeGly-His (3Me)-Sta-Cpa-NH$_2$ (SEQ ID NO: 143), IIA-a-8: 4-[18]Fluoro-3-cyano-benzoyl-Ava-Gln-Trp-Ala-Val-Gly-His(3Me)-FA4-Am,5-MeHpA-Leu-NH$_2$ (SEQ ID NO: 144), IIA-a-9: 4-[18]Fluoro-3-cyano-benzoyl-Ava-Gln-Trp-Ala-Val-Gly-His(3Me)-Sta-Leu-NH$_2$ (SEQ ID NO: 145), IIA-a-10: 4-[18]Fluoro-3-cyano-benzoyl-Lys(Me)2-βAla-Gln-Trp-Ala-Val-Gly-His(3Me)-Sta-Leu-NH$_2$ (SEQ ID NO: 146), IIA-a-11: 4-[18]Fluoro-3-cyano-benzoyl-Lys(Me)2-βAla-Gln-Trp-Ala-Val-Gly-His(3Me)-Sta-Leu-NH$_2$ (SEQ ID NO: 147), IIA-a-12: 4-[18]Fluoro-3-cyano-benzoyl-Arg-Ser-Gln-Trp-Ala-Val-Gly-His(3Me)-4-Am,5-MeHpA-Leu-NH$_2$ (SEQ ID NO: 148), IIA-a-13: 4-[18]Fluoro-3-cyano-benzoyl-Ser-Ser-Gln-Trp-Ala-Val-Gly-His(3Me)-4-Am,5-MeHpA-Leu-NH$_2$ (SEQ ID NO: 149), IIA-a-14: 4-[18]Fluoro-3-cyano-benzoyl-Lys(Me)2-Ser-Gln-Trp-Ala-Val-Gly-His(3Me)-4-Am,5-MeHpA-Leu-NH$_2$ (SEQ ID NO: (SEQ ID NO: 150), IIA-a-15: 4-[18]Fluoro-3-cyano-benzoyl-Arg-Ser-Gln-Trp-Ala-Val-Gly-His(3Me)-Sta-Leu-NH$_2$ (SEQ ID NO: 151), IIA-a-16: 4-[18]Fluoro-3-cyano-benzoyl-Lys(Me)2-βAla-Gln-Trp-Ala-Val-Gly-His(3Me)-4-Am,5-Me-HpA-Leu-NH$_2$ (SEQ ID NO: 152), IIA-a-17: 4-[18]Fluoro-3-cyano-benzoyl-Ava-Gln-Trp-Ala-Val-Gly-His-4-Am,5-MeHpA-Leu-NH$_2$ (SEQ ID NO: 153), IIA-a-18: 4-[18]Fluoro-3-trifluoromethyl-benzoyl-Arg-Ava-Gln-Trp-Ala-Val-Gly-His(3Me)-Sta-LeuNH$_2$ (SEQ ID NO: 154), IIA-a-19: 4-[18]Fluoro-3-trifluoromethyl-benzoyl-Arg-Ava-Gln-Trp-Ala-Val-NMeGly-His(3Me)-Sta-Leu-NH$_2$ (SEQ ID NO: 155), IIA-a-20: 4-[18]Fluoro-3-trifluoromethyl-benzoyl-1,4-cis-Achc-Gln-Trp-Ala-Val-Gly-His(3Me)-Sta-Leu-NH$_2$ (SEQ ID NO: 156), IIA-a-21: 4-[18]Fluoro-3-trifluoromethyl-benzoyl-Gln-Trp-Ala-Val-Gly-His(3Me)-Sta-Leu-NH$_2$ (SEQ ID NO: 157), IIA-a-22: 4-[18]Fluoro-3-trifluoromethyl-benzoyl-Arg-βAla-Gln-Trp-Ala-Val-Gly-His(3Me)-4-Am,5-Me-HpA-Leu-NH$_2$ (SEQ ID NO: 158), 4-[18]Fluoro-3-cyano-benzoyl-(piperidyl-4-carbonyl)-Gln-Trp-Ala-Val-Gly-His(3Me)-Sta-Leu-NH$_2$ (SEQ ID NO: 213), 4-[18]Fluoro-3-cyano-benzoyl-(piperazin-1-yl-acetyl)-Gln-Trp-Ala-Val-Gly-His(3Me)-Sta-Leu-NH$_2$ (SEQ ID NO: 214), 4-[18]Fluoro-3-cyano-benzoyl-1,4-trans-Achc-Gln-Trp-Ala-Val-NMeGly-His-Sta-Leu-NH$_2$ (SEQ ID NO: 215), IIA-a-76: 4-[18]Fluoro-3-cyano-benzoyl-Ava-ε-c[Lys-(NMe)Phe-1Nal-D-Trp-Lys-Thr] (SEQ ID NO: 295)

IIA-a-77: 4-[18]Fluoro-3-cyano-benzoyl-Ava-β-c[Dpr-Met-(NMe)Phe-Tyr-D-Trp-Lys] (SEQ ID NO: 296)

IIA-a-78: 4-[18]Fluoro-3-cyano-benzoyl-Ava-DCys-Leu-Ile-Thr-Arg-Cys-Arg-Tyr-NH$_2$ (SEQ ID NO: 299) and IIA-a-79: 4-[18]Fluoro-3-cyano-benzoyl-Ava-DCys-Leu-Ile-Val-Arg-Cys-Arg-Tyr-NH$_2$ (SEQ ID NO: 300).

14. A compound of Formula A

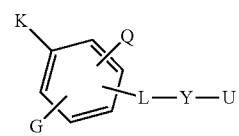

A wherein

-G is —C≡N or —CF$_3$, wherein the respective substituent —C≡N or CF$_3$ can be in ortho, para or meta position in respect of the K group, -Q is hydrogen, -L- is —CO— or —SO$_2$—, Y is a bond or a spacer, wherein (a) the spacer is Arg-Ser, Arg-Ava, Lys(Me)2-β-ala, Lys(Me)2-ser, Arg-β-ala, Ser-Ser, Ser-Thr, Arg-Thr, S-alkylcysteine, cysteic acid, thioalkylcysteine (S—S-alkyl) or

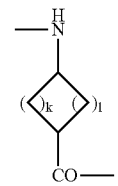

wherein k and l are independently selected in the range of from 0 to 4, or (b) the spacer is a non-amino acid moiety selected from the group consisting of
- —NH—(CH$_2$)$_p$—CO—, wherein p is an integer of from 2 to 10,
- —NH—(CH$_2$—CH$_2$—O)$_q$—CH$_2$—CH$_2$—CO—, wherein q is an integer of from 0 to 5,
- —NH-cycloalkyl-CO— wherein cycloalkyl is selected from C$_5$-C$_8$ cycloalkyl, and
- —NH-heterocycloalkyl-(CH$_2$)$_v$—CO— wherein heterocycloalkyl is selected from C$_5$-C$_8$ heterocycloalkyl containing carbon atoms and 1, 2, 3 or 4 oxygen, nitrogen or sulfur heteroatoms and v is an integer of from 1 to 4, X$^-$ is CF$_3$S(O)$_2$O$^-$, C$_4$F$_9$S(O)$_2$O$^-$, iodide anion, bromide anion, chloride anion, perchlorate anion (ClO$_4^-$), phosphate anion, trifluoroacetate anion (CF$_3$—C(O)O$^-$), or the anion of another salt of an inorganic or organic acid, K is N$^+$(R$^1$)(R$^2$)(R$^3$)X$^-$ or W, wherein R$^1$, R$^2$ and R$^3$ are each methyl, and W is a fluorine isotope, and U is selected from the group consisting of

| | |
|---|---|
| Gln-Trp-Ala-Val-NMeGly-His-Sta-Leu-NH$_2$ | SEQ ID NO: 1 |
| Gln-Trp-Ala-Val-Gly-His(Me)-Sta-Leu-NH$_2$ | SEQ ID NO: 2 |
| Gln-Trp-Ala-Val-NMeGly-His(3Me)-Sta-Leu-NH$_2$ | SEQ ID NO: 3 |
| Gln-Trp-Ala-Val-Gly-His(3Me)-Sta-Leu-NH$_2$ | SEQ ID NO: 4 |
| Gln-Trp-Ala-Val-NMeGly-His(3Me)-Sta-Cpa-NH$_2$ | SEQ ID NO: 7 |
| Gln-Trp-Ala-Val-Gly-His(3Me)-4-Am,5-MeHpA-Leu-NH$_2$ | SEQ ID NO: 8 |
| Gln-Trp-Ala-Val-Gly-His(3Me)-4-Am,5-MeHpA-Leu-NH$_2$ | SEQ ID NO: 12 |
| Gln-Trp-Ala-Val-Gly-His-4-Am,5-MeHpA-Leu-NH$_2$ | SEQ ID NO: 17 |
| Gln-Trp-Ala-Val-NMeGly-His(3Me)-4-Am,5-MeHpA-Cpa-NH$_2$ | SEQ ID NO: 23 |
| Gln-Trp-Ala-Val-NMeGly-His-FA02010-Cpa-NH$_2$ | SEQ ID NO: 27 |
| Gln-Trp-Ala-Val-NMeGly-His-4-Am,5-MeHpA-tbuGly-NH$_2$ | SEQ ID NO: 28 |
| Gln-Trp-Ala-Val-NMeGly-His(3Me)-Sta-tBuGly-NH$_2$ | SEQ ID NO: 30 |
| Gln-Trp-Ala-Val-NMeGly-His(3Me)-4-Am,5-MeHpA-Leu-NH$_2$ | SEQ ID NO: 32 |
| Gln-DTrp-Ala-Val-Gly-His-4-Am,5-MeHpA-tbuGly-NH$_2$ | SEQ ID NO: 33 |
| Gln-DTrp-Ala-Val-Gly-His-4-Am-5-MeHxA-Cpa-NH$_2$ | SEQ ID NO: 34 |
| Gln-Trp-Ala-Val-NMeGly-His(3Me)-Sta-Cpa-NH$_2$ | SEQ ID NO: 35 |
| Gln-DTrp-Ala-Val-Gly-His-Sta-tbuAla-NH$_2$ | SEQ ID NO: 36 |
| Gln-Trp-Ala-Val-Gly-His(3Me)-Sta-Cpa-NH$_2$ | SEQ ID NO: 42 |
| Gln-Trp-Ala-Val-Gly-His(3Me)-Sta-tBuGly-NH$_2$ | SEQ ID NO: 43 |
| Gln-Trp-Ala-Val-Gly-His(3Me)-4-Am,5-MeHpA-Leu-NH$_2$ | SEQ ID NO: 46 |
| Gln-Trp-Ala-Val-Gly-His(3Me)-4-Am,5-MeHpA-Leu-NH$_2$ | SEQ ID NO: 48 |
| Gln-Trp-Ala-Val-Gly-NMeHis-4-Am,5-MeHpA-Cpa-NH$_2$ | SEQ ID NO: 49 |
| Gln-Trp-Ala-Val-Gly-NMeHis(3Me)-4-Am,5-MeHpA-Leu-NH$_2$ | SEQ ID NO: 47 |
| Gln-Trp-Ala-Val-Gly-NMeHis-4-Am,5-MeHpA-Leu-NH$_2$ | SEQ ID NO: 50 |
| Gln-Trp-Ala-Val-NMeGly-HIs-AHMHxA-Leu-NH$_2$ | SEQ ID NO: 51 |
| Gln-Trp-Ala-Val-βAla-NMeHis-Tha-Cpa-NH$_2$ | SEQ ID NO: 52 |
| Gln-Trp-Ala-Val-βAla-NMeHis-Phe-Cpa-NH$_2$ | SEQ ID NO: 53 |
| Gln-Trp-Ala-Val-βAla-NMeHis-Phe-Leu-NH$_2$ | SEQ ID NO: 54 |
| Gln-Trp-Ala-Val-βAla-DHis-Phe-Leu-NH$_2$ | SEQ ID NO: 55 |
| Gln-Trp-Ala-Val-βAla-His-βhLeu-Leu-NH$_2$ | SEQ ID NO: 56 |
| Gln-Trp-Ala-Val-βAla-His-βhIle-Leu-NH$_2$ | SEQ ID NO: 57 |
| Gln-Trp-Ala-Val-βAla-His-βhLeu-tbuGly-NH$_2$ | SEQ ID NO: 58 |
| Gln-Trp-Ala-Val-βAla-His(3Me)-Phe-Tha-NH$_2$ | SEQ ID NO: 59 |
| Gln-Trp-Ala-Val-βAla-His(3Me)-Phe-Nle-NH$_2$ | SEQ ID NO: 60 |
| Gln-Trp-Ala-Val-βAla-NMeHis-Phe-tbuGly-NH$_2$ | SEQ ID NO: 61 |
| Gln-Trp-Ala-Val-βAla-NMeHis-Tha-tbuGly-NH$_2$ | SEQ ID NO: 62 |
| Gln-Trp-Ala-Val-βAla-His(3Me)-Tha-tbuGly-NH$_2$ | SEQ ID NO: 63 |
| Gln-Trp-Ala-Val-βAla-His(3Me)-Phe-Cpa-NH$_2$ | SEQ ID NO: 64 |
| Gln-Trp-Ala-NMeVal-βAla-His-Phe-Leu-NH$_2$ | SEQ ID NO: 65 |
| Gln-Trp-Ala-Val-βAla-His-NMePhe-Leu-NH$_2$ | SEQ ID NO: 66 |
| Gln-DTrp-Ala-Val-βAla-His-Phe-Leu-NH$_2$ | SEQ ID NO: 67 |
| Gln-Trp-DAla-Val-βAla-His-Phe-Leu-NH$_2$ | SEQ ID NO: 68 |
| Gln-Trp-Ala-DVal-βAla-His-Phe-Leu-NH$_2$ | SEQ ID NO: 69 |
| Gln-Trp-Ala-Val-βAla-His-DPhe-Leu-NH$_2$ | SEQ ID NO: 70 |

-continued

| | |
|---|---|
| Gln-Trp-Ala-Val-βAla-His-βhIle-tbuGly-NH₂ | SEQ ID NO: 71 |
| Gln-Trp-Ala-Val-NMeGly-His-4-Am,5-MeHpA-Cpa-NH₂ | SEQ ID NO: 72 |
| Gln-Trp-Ala-Val-NMeGly-His-Sta-Cpa-NH₂ | SEQ ID NO: 73 |
| Gln-Trp-Ala-Val-NMeGly-His-Sta-tbuAla-NH₂ | SEQ ID NO: 74 |
| Gln-Trp-Ala-Val-NMeGly-His-4-Am,5-MeHpA-tbuAla-NH₂ | SEQ ID NO: 75 |
| Gln-Trp-Ala-Val-His(Me)-Sta-Leu-NH₂ | SEQ ID NO: 77 |
| Gln-Trp-Ala-Val-Gly-His(3Me)-FA4-Am,5-MeHpA-Leu-NH₂ | SEQ ID NO: 82 |
| Gln-Trp-Ala-Val-Gly-His(3Me)-4-Am,5-MeHpA-Leu-NH₂ | SEQ ID NO: 90 |
| Gln-Trp-Ala-Val-Gly-His-4-Am,5-MeHpA-Leu-NH₂ | SEQ ID NO: 91 |
| Gln-Trp-Ala-Val-Gly-His(3Me)-4-Am-5-MeHpA-4-amino-5-methyl-heptanoic acid-Leu-NH₂ and | SEQ ID NO: 101 |
| Gln-Trp-Ala-Val-NMeGly-His(3Me)-4-Am-5-MeHpA-4-amino-5-methyl-heptanoic acid-Cpa-NH₂, | SEQ ID NO: 102 | or a pharmaceutically acceptable salt of an inorganic or organic acid thereof.

15. A method of preparing a compound of claim 1 having chemical Formula A, wherein K=W, and W is fluorine isotope $^{18}$F, according to claim 1, wherein a compound having general chemical Formula A, wherein K=—N$^+$(R$^1$)(R$^2$)(R$^3$)X$^-$, is labelled with a said fluorine isotope.

16. The method according to claim 15, comprising the step of coupling a compound having chemical Formula A, wherein K=—N$^+$(R$^1$)(R$^2$)(R$^3$)X$^-$, with a fluorine isotope $^{18}$F to form a compound having general chemical Formula A, wherein K=W, and W is fluorine isotope $^{18}$F, and
wherein K, R$^1$, R$^2$, R$^3$ and X$^-$ are as defined.

17. A composition comprising a compound of claim 1 having chemical Formula A, wherein K=—N$^+$(R$^1$)(R$^2$)(R$^3$)X$^-$ or W, and W is fluorine isotope $^{18}$F, according to claim 1, and a pharmaceutically acceptable carrier, diluent, adjuvant or excipient.

18. A method of diagnostic imaging, comprising introducing into a patient a detectable quantity of a labelled compound of claim 1 having chemical Formula A, wherein K=W, and W is fluorine isotope $^{18}$F, according to claim 1, or of a pharmaceutically acceptable salt of an inorganic or organic acid thereof.

19. A kit comprising a sealed vial containing a predetermined quantity of a compound of claim 1 having chemical Formula A, wherein K=—N$^+$(R$^1$)(R$^2$)(R$^3$)X$^-$, according to claim 1, or a pharmaceutically acceptable salt of an inorganic or organic acid thereof.

20. A peptide sequence selected from

| | |
|---|---|
| Gln-Trp-Ala-Val-NMeGly-His-Sta-Leu-NH₂ | SEQ ID NO: 1 |
| Gln-Trp-Ala-Val-Gly-His(Me)-Sta-Leu-NH₂ | SEQ ID NO: 2 |
| Gln-Trp-Ala-Val-NMeGly-His(3Me)-Sta-Leu-NH₂ | SEQ ID NO: 3 |
| Gln-Trp-Ala-Val-Gly-His(3Me)-Sta-Leu-NH₂ | SEQ ID NO: 4 |
| Gln-Trp-Ala-Val-NMeGly-His(3Me)-Sta-Cpa-NH₂ | SEQ ID NO: 7 |
| Gln-Trp-Ala-Val-Gly-His(3Me)-4-Am,5-MeHpA-Leu-NH₂ | SEQ ID NO: 8 |
| Gln-Trp-Ala-Val-Gly-His(3Me)-4-Am,5-MeHpA-Leu-NH₂ | SEQ ID NO: 12 |
| Gln-Trp-Ala-Val-Gly-His-4-Am,5-MeHpA-Leu-NH₂ | SEQ ID NO: 17 |
| Gln-Trp-Ala-Val-NMeGly-His(3Me)-4-Am,5-MeHpA-Cpa-NH₂ | SEQ ID NO: 23 |
| Gln-Trp-Ala-Val-NMeGly-His-FA02010-Cpa-NH₂ | SEQ ID NO: 27 |
| Gln-Trp-Ala-Val-NMeGly-His-4-Am,5-MeHpA-tbuGly-NH₂ | SEQ ID NO: 28 |
| Gln-Trp-Ala-Val-NMeGly-His(3Me)-Sta-tBuGly-NH₂ | SEQ ID NO: 30 |
| Gln-Trp-Ala-Val-NMeGly-His(3Me)-4-Am,5-MeHpA-Leu-NH₂ | SEQ ID NO: 32 |
| Gln-DTrp-Ala-Val-Gly-His-4-Am,5-MeHpA-tbuGly-NH₂ | SEQ ID NO: 33 |
| Gln-DTrp-Ala-Val-Gly-His-4-Am-5-MeHxA-Cpa-NH₂ | SEQ ID NO: 34 |
| Gln-Trp-Ala-Val-NMeGly-His(3Me)-Sta-Cpa-NH₂ | SEQ ID NO: 35 |
| Gln-DTrp-Ala-Val-Gly-His-Sta-tbuAla-NH₂ | SEQ ID NO: 36 |
| Gln-Trp-Ala-Val-Gly-His(3Me)-Sta-Cpa-NH₂ | SEQ ID NO: 42 |
| Gln-Trp-Ala-Val-Gly-His(3Me)-Sta-tBuGly-NH₂ | SEQ ID NO: 43 |
| Gln-Trp-Ala-Val-Gly-His(3Me)-4-Am,5-MeHpA-Leu-NH₂ | SEQ ID NO: 46 |
| Gln-Trp-Ala-Val-Gly-His(3Me)-4-Am,5-MeHpA-Leu-NH₂ | SEQ ID NO: 48 |
| Gln-Trp-Ala-Val-Gly-NMeHis-4-Am,5-MeHpA-Cpa-NH₂ | SEQ ID NO: 49 |
| Gln-Trp-Ala-Val-Gly-NMeHis(3Me)-4-Am,5-MeHpA-Leu-NH₂ | SEQ ID NO: 47 |
| Gln-Trp-Ala-Val-Gly-NMeHis-4-Am,5-MeHpA-Leu-NH₂ | SEQ ID NO: 50 |
| Gln-Trp-Ala-Val-NMeGly-HIs-AHMHxA-Leu-NH₂ | SEQ ID NO: 51 |
| Gln-Trp-Ala-Val-βAla-NMeHis-Tha-Cpa-NH₂ | SEQ ID NO: 52 |
| Gln-Trp-Ala-Val-βAla-NMeHis-Phe-Cpa-NH₂ | SEQ ID NO: 53 |
| Gln-Trp-Ala-Val-βAla-NMeHis-Phe-Leu-NH₂ | SEQ ID NO: 54 |
| Gln-Trp-Ala-Val-βAla-DHis-Phe-Leu-NH₂ | SEQ ID NO: 55 |

| Sequence | SEQ ID NO |
|---|---|
| Gln-Trp-Ala-Val-βAla-His-βhLeu-Leu-NH₂ | SEQ ID NO: 56 |
| Gln-Trp-Ala-Val-βAla-His-βhIle-Leu-NH₂ | SEQ ID NO: 57 |
| Gln-Trp-Ala-Val-βAla-His-βhLeu-tbuGly-NH₂ | SEQ ID NO: 58 |
| Gln-Trp-Ala-Val-βAla-His(3Me)-Phe-Tha-NH₂ | SEQ ID NO: 59 |
| Gln-Trp-Ala-Val-βAla-His(3Me)-Phe-Nle-NH₂ | SEQ ID NO: 60 |
| Gln-Trp-Ala-Val-βAla-NMeHis-Phe-tbuGly-NH₂ | SEQ ID NO: 61 |
| Gln-Trp-Ala-Val-βAla-NMeHis-Tha-tbuGly-NH₂ | SEQ ID NO: 62 |
| Gln-Trp-Ala-Val-βAla-His(3Me)-Tha-tbuGly-NH₂ | SEQ ID NO: 63 |
| Gln-Trp-Ala-Val-βAla-His(3Me)-Phe-Cpa-NH₂ | SEQ ID NO: 64 |
| Gln-Trp-Ala-NMeVal-βAla-His-Phe-Leu-NH₂ | SEQ ID NO: 65 |
| Gln-Trp-Ala-Val-βAla-His-NMePhe-Leu-NH₂ | SEQ ID NO: 66 |
| Gln-DTrp-Ala-Val-βAla-His-Phe-Leu-NH₂ | SEQ ID NO: 67 |
| Gln-Trp-DAla-Val-βAla-His-Phe-Leu-NH₂ | SEQ ID NO: 68 |
| Gln-Trp-Ala-DVal-βAla-His-Phe-Leu-NH₂ | SEQ ID NO: 69 |
| Gln-Trp-Ala-Val-βAla-His-DPhe-Leu-NH₂ | SEQ ID NO: 70 |
| Gln-Trp-Ala-Val-βAla-His-βhIle-tbuGly-NH₂ | SEQ ID NO: 71 |
| Gln-Trp-Ala-Val-NMeGly-His-4-Am,5-MeHpA-Cpa-NH₂ | SEQ ID NO: 72 |
| Gln-Trp-Ala-Val-NMeGly-His-Sta-Cpa-NH₂ | SEQ ID NO: 73 |
| Gln-Trp-Ala-Val-NMeGly-His-Sta-tbuAla-NH₂ | SEQ ID NO: 74 |
| Gln-Trp-Ala-Val-NMeGly-His-4-Am,5-MeHpA-tbuAla-NH₂ | SEQ ID NO: 75 |
| Gln-Trp-Ala-Val-His(Me)-Sta-Leu-NH₂ | SEQ ID NO: 77 |
| Gln-Trp-Ala-Val-Gly-His(3Me)-FA4-Am,5-MeHpA-Leu-NH₂ | SEQ ID NO: 82 |
| Gln-Trp-Ala-Val-Gly-His(3Me)-4-Am,5-MeHpA-Leu-NH₂ | SEQ ID NO: 90 |
| Gln-Trp-Ala-Val-Gly-His-4-Am,5-MeHpA-Leu-NH₂ | SEQ ID NO: 91 |
| Gln-Trp-Ala-Val-Gly-His(3Me)-4-Am-5-MeHpA-4-amino-5-methyl-heptanoic acid-Leu-NH₂ or | SEQ ID NO: 101 |
| Gln-Trp-Ala-Val-NMeGly-His(3Me)-4-Am-5-MeHpA-4-amino-5-methyl-heptanoic acid-Cpa-NH₂. | SEQ ID NO: 102 |

21. The compound of claim 5, wherein v is an integer 1 or 2.

22. A compound of claim 14, wherein W is $^{18}$F.

23. A method of claim 18, wherein the diagnostic imaging is by positron emission tomography (PET).

* * * * *